(12) United States Patent
Laurent et al.

(10) Patent No.: US 9,796,716 B2
(45) Date of Patent: Oct. 24, 2017

(54) SELECTIVE INHIBITORS OF TEC AND SRC PROTEIN KINASE FAMILIES

(71) Applicant: Pharmascience, Inc., Montreal (CA)

(72) Inventors: Alain Laurent, Montreal (CA); Yannick Rose, Montreal (CA); James B. Jaquith, Montreal (CA)

(73) Assignee: PHARMASCIENCE, INC., Montreal (CA)

( * ) Notice: Subject to any disclaimer, the term of this patent is extended or adjusted under 35 U.S.C. 154(b) by 0 days.

(21) Appl. No.: 14/404,497

(22) PCT Filed: May 28, 2013

(86) PCT No.: PCT/CA2013/000513
§ 371 (c)(1),
(2) Date: Nov. 28, 2014

(87) PCT Pub. No.: WO2013/177668
PCT Pub. Date: Dec. 5, 2013

(65) Prior Publication Data
US 2015/0191473 A1    Jul. 9, 2015

(30) Foreign Application Priority Data

May 31, 2012 (CA) ..................................... 2779184
Apr. 17, 2013 (CA) ..................................... 2813299

(51) Int. Cl.
*C07D 487/04* (2006.01)
*A61K 31/519* (2006.01)
*A61P 29/00* (2006.01)
*A61P 35/00* (2006.01)
*A61P 19/02* (2006.01)

(52) U.S. Cl.
CPC ................................ *C07D 487/04* (2013.01)

(58) Field of Classification Search
CPC ........................... C07D 487/04; A61K 31/519
See application file for complete search history.

(56) References Cited

U.S. PATENT DOCUMENTS 7,514,444 B2    4/2009   Honigberg et al.

FOREIGN PATENT DOCUMENTS

| CA | 2385769 A1 | 3/2001 |
|---|---|---|
| CA | 2440724 A1 | 10/2002 |
| CN | 103787839 A | 5/2014 |
| WO | WO 0119829 | * 9/2000 |
| WO | WO 01/19829 | * 3/2001 |
| WO | 02/076989 A1 | 10/2002 |
| WO | 02/080926 A1 | 10/2002 |

OTHER PUBLICATIONS

Berge et al., "Pharmaceutical salts", J. Pharm. Sci. 66(1): 1-19, 1977.
Bradshaw, "The Src, Syk, and Tec family kinases: distinct types of molecular switches", Cellular Signalling 22: 1175-1184, 2010.
Herman et al., "Bruton tyrosine kinase represents a promising therapeutic target for treatment of chronic lymphocytic leukemia and is effectively targeted by PCI-32765", Blood 117(23): 6287-6289, 2011.
Honigberg et al., "The Bruton tyrosine kinase inhibitor PCI-32765 blocks B-cell activation and is efficacious in models Of autoimmune disease and B-cell malignancy", PNAS 107(29): 13075-13080, 2010.
Kim et al., "Src kinases as therapeutic targets for cancer", Nat. Rev. Clin. Oncol. 6: 587-595, 2009.
Liu et al., "Antiarthritis effect of a novel Bruton's tyrosine kinase (BTK) inhibitor in rat collagen-induced arthritis and mechanism-based pharmacokinetic/pharmacodynamic modeling: relationships between inhibition of BTK phosphorylation and efficacy", J. Pharm. Exp. Ther. 338(1): 154-163, 2011.
Liu et al., "Significant species difference in amide hydrolysis of GDC-0834, a novel potent and selective Bruton's tyrosine kinase inhibitor", Drug Metab. Dispos. 39(10): 1840-1849, 2011.
Martin et al., "Update on lymphocyte specific kinase inhibitors: a patent survey", Expert Opin. Ther. Pat. 20: 1573-1593, 2010.
Mellor et al., "Cardiotoxicity associated with targeting kinase pathways in cancer", Toxicological Sciences 120(1): 14-32, 2011.
Tan et al., "Markers in the epidermal growth factor receptor pathway and skin toxicity during erlotinib treatment", Ann. Oncol. 19: 185-190, 2008.
Bendele, "Animal models of rheumatoid arthritis", J. Musculoskel. Neuron Interact 1(4): 377-385, 2001.
Braselmann, et al., "R406, an Orally Available Spleen Tyrosine Kinase Inhibitor Blocks Fc Receptor Signaling and Reduces Immune Complex-Mediated Inflammation", J. Pharmacol. Exp. Ther. 319(3): 998-1008, 2006.
Dheng, et al., Biochem. Pharmacol. 22(23): 3099-3108, 1973.
Plowman, et al., "Receptor Tyrosine Kinases as Targets for Drug Intervention", DN&P 7(6): 334-339, 1994.
Trentham, et al., "Autoimmunity to Type II Collagen: an Experimental Model of Arthritis", J. Exp. Med. 146: 857-868, 1977.

\* cited by examiner

*Primary Examiner* — Susanna Moore
(74) *Attorney, Agent, or Firm* — Troutman Sanders LLP

(57) ABSTRACT

The present invention relates to a novel family of inhibitors of protein kinases. In particular, the present invention relates to inhibitors of the members of the Tec and Src protein kinase families. In one embodiment, the inhibitors of the invention are encompassed by Formula 1:

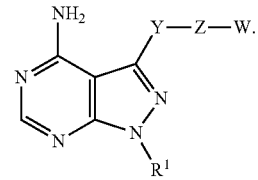

Formula 1

20 Claims, No Drawings

SELECTIVE INHIBITORS OF TEC AND SRC PROTEIN KINASE FAMILIES

CROSS REFERENCE TO RELATED APPLICATIONS

The present application claims the benefit of priority to PCT International Application No. PCT/CA13/00513 filed 28 May 2013, which claims the benefit of priority to CA Application No. 2,813,299 filed 17 Apr. 2013 and CA Application No. 2,779,184 filed 31 May 2012; each of which is incorporated herein by reference in its entirety.

FIELD OF INVENTION

The present invention relates to a novel family of inhibitors of protein kinases. In particular, the present invention relates to inhibitors of the members of the Tec and Src protein kinase families.

BACKGROUND OF THE INVENTION

Protein kinases are a large group of intracellular and transmembrane signaling proteins in eukaryotic cells. These enzymes are responsible for transfer of the terminal (gamma) phosphate from ATP to specific amino acid residues of target proteins. Phosphorylation of specific tyrosine, serine or threonine amino acid residues in target proteins can modulate their activity leading to profound changes in cellular signaling and metabolism. Protein kinases can be found in the cell membrane, cytosol and organelles such as the nucleus and are responsible for mediating multiple cellular functions including metabolism, cellular growth and division, cellular signaling, modulation of immune responses, and apoptosis. The receptor tyrosine kinases are a large family of cell surface receptors with protein tyrosine kinase activity that respond to extracellular cues and activate intracellular signaling cascades (Plowman et al. (1994) DN&P, 7(6):334-339).

Aberrant activation or excessive expression of various protein kinases are implicated in the mechanism of multiple diseases and disorders characterized by benign and malignant proliferation, excess angiogenesis, as well as diseases resulting from inappropriate activation of the immune system. Thus, inhibitors of select kinases or kinase families are expected to be useful in the treatment of cancer, autoimmune diseases, and inflammatory conditions including, but not limited to: solid tumors, hematological malignancies, arthritis, graft versus host disease, lupus erythematosus, psoriasis, colitis, illeitis, multiple sclerosis, uveitis, coronary artery vasculopathy, systemic sclerosis, atherosclerosis, asthma, transplant rejection, allergy, dermatomyositis, pemphigus and the like.

Examples of kinases that can be targeted to modulate disease include receptor tyrosine kinases such as members of the platelet-derived growth factor receptor (PDGFR), vascular endothelial growth factor receptor (VEGFR) families and intracellular proteins such as members of the Syk, SRC, and Tec families of kinases.

Tec kinases are non-receptor tyrosine kinases predominantly, but not exclusively, expressed in cells of hematopoietic origin (Bradshaw J M. Cell Signal. 2010, 22:1175-84). The Tec family includes Tec, Bruton's tyrosine kinase (Btk), inducible T-cell kinase (Itk), resting lymphocyte kinase (Rlk/Txk), and bone marrow-expressed kinase (Bmx/Etk). Btk is a Tec family kinase which is important in B-cell receptor signaling. Btk is activated by Src-family kinases and phosphorylates PLC gamma leading to effects on B-cell function and survival. Additionally, Btk is important in signal transduction in response to immune complex recognition by macrophage, mast cells and neutrophils. Btk inhibition is also important in survival of lymphoma cells (Herman, SEM. Blood 2011, 117:6287-6289) suggesting that inhibition of Btk may be useful in the treatment of lymphomas.

cSRC is the prototypical member of the SRC family of tyrosine kinases which includes Lyn, Fyn, Lck, Hck, Fgr, Blk, Syk, Yrk, and Yes. cSRC is critically involved in signaling pathways involved in cancer and is often overexpressed in human malignancies (Kim L C, Song L, Haura E B. Nat Rev Clin Oncol. 2009 6(10):587-9). The role of cSRC in cell adhesion, migration and bone remodeling strongly implicate this kinase in the development and progression of bone metastases. cSRC is also involved in signaling downstream of growth factor receptor tyrosine kinases and regulates cell cycle progression suggesting that cSRC inhibition would impact cancer cell proliferation. Additionally, inhibition of SRC family members may be useful in treatments designed to modulate immune function. SRC family members, including Lck, regulate T-cell receptor signal transduction which leads to gene regulation events resulting in cytokine release, survival and proliferation. Thus, inhibitors of Lck have been keenly sought as immunosuppressive agents with potential application in graft rejection and T-cell mediated autoimmune disease (Martin et al. Expert Opin Ther Pat. 2010, 20:1573-93).

Inhibition of kinases using small molecule inhibitors has successfully led to several approved therapeutic agents used in the treatment of human conditions. Herein, we disclose a novel family of kinase inhibitors. Further, we demonstrate that modifications in compound substitution can influence kinase selectivity and therefore the biological function of that agent.

PCT Publication Nos. WO02/080926 and WO02/76986 disclose pyrazolopyrimidines as therapeutic agents. Btk is included in a long list of biologically un-related kinases. No evidence of kinase inhibition or cellular activity was disclosed in WO02/080926 and exemplification centers on amide and sulfonamide derivatives with a limited subset of unsubstituted 4-phenoxyphenyl derivatives.

U.S. Pat. No. 7,514,444 discloses inhibitors of Btk. Compound 13 (PCI-32765) of this patent has been reported to show ATP competitive binding to a wide range of kinases including Btk, Lck, Lyn, cSRC, Jak, EGFR, KDR and others (Honigberg, L. A, et al, The Bruton tyrosine kinase inhibitor PCI-32765 blocks B-cell activation and is efficacious in models of autoimmune disease and B-cell malignancy, PNAS vol. 107 no. 29, 13075-13080). Specifically for Btk, the acrylamide functionality of compound 13 is reported to covalently bind the thiol moiety of Cys481, which is situated adjacent to the ATP binding pocket of Btk, thus inducing "sustained" inhibition of Btk. However, compound 13 also inhibits various kinases which also feature a Cys adjacent to the ATP binding pocket, such as Bmx, Tec, Txk, Itk, EGFR, ErbB2, ErbB4, Jak3 and Blk. Covalent binding to any of these kinases may diminish the selective nature of this approach.

GDC-0834 belongs to a structurally unrelated family of compounds which were recently reported to demonstrate significant Btk selectivity (Liu L., et al, Antiarthritis effect of a novel Bruton's tyrosine kinase (BTK) inhibitor in rat collagen-induced arthritis and mechanism-based pharmacokinetic/pharmacodynamic modeling: relationships between inhibition of BTK phosphorylation and efficacy. J Pharmacol Exp Ther. 2011 July; 338(1):154-63). GDC-0834 was active in several animal models of autoimmune disease. However, this compound failed in Phase 1 clinical trials as a result of human specific metabolism (Liu L, et al, Significant species difference in amide hydrolysis of GDC-0834, a novel potent and selective Bruton's tyrosine kinase inhibitor, Drug Metab Dispos. 2011 October; 39(10): 1840-9).

Inhibition of EGFR has been related to the induction of severe rash with multiple clinical compounds (Tan A R, et al, Markers in the epidermal growth factor receptor pathway and skin toxicity during erlotinib treatment. Ann Oncol. 2008 January; 19(1):185-90). Similarly, inhibition of KDR (VEGFR2) has been clinically related to hypertension (Howard R. Mellor, et al., Cardiotoxicity Associated with Targeting Kinase Pathways in Cancer, Toxicological Sciences 120(1), 14-32 (2011). Therefore, the development of Btk inhibitors which demonstrated greater kinase selectivity could potentially be useful in various B-cell related indications which require acute and/or chronic dosing regimens, such as cancer, inflammatory and autoimmune diseases.

The present invention relates to a family of potent and selective, non-covalent Btk inhibitors which demonstrate cellular activity, oral exposure and activity in animal models of inflammation and autoimmune disease. Kinase selectivity and cellular potency are related to specific substitution patterns on the compounds. Synthetic methods are disclosed which provide compounds on multi-gram scale.

SUMMARY OF THE INVENTION

The present invention relates to a novel family of kinase inhibitors. Compounds of this class have been found to have inhibitory activity against members of the Tec and Scr protein kinase families.

One aspect of the present invention is directed to a compound of Formula 1:

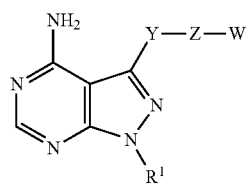

Formula 1 wherein
$R^1$ is selected from the group consisting of:
1) hydrogen,
2) alkyl,
3) heteroalkyl,
4) carbocyclyl,
5) heterocyclyl,
6) —C(O)$R^4$, wherein the alkyl, heteroalkyl, carbocyclyl and heterocyclyl may be further substituted by the groups consisting of:
1) hydroxy,
2) alkoxy,
3) alkyl,
4) —OC(O)$R^4$,
5) —OC(O)N$R^5R^6$,
6) —C(O)$R^4$,
7) —C(O)N$R^5R^6$,
8) —N$R^5R^6$,
9) —N$R^2$C(O)$R^4$,
10) —N$R^2$S(O)$_nR^4$,
11) —N$R^2$C(O)N$R^5R^6$;

Y is selected from:

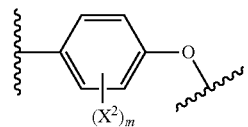

Z is selected from:

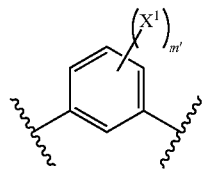

Wherein Y—Z—W is selected from:

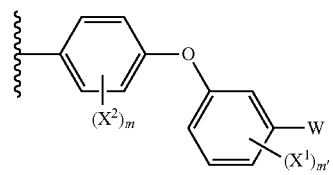

$X^1$ and $X^2$ are independently selected from hydrogen, halogen or cyano;
n is an integer from 0 to 2;
m is an integer from 0 to 2;
m' is an integer from 0 to 2;
W is independently selected from:
1) alkyl,
2) aralkyl,
3) heteroaralkyl,
4) —O$R^3$,
5) —OC(O)$R^4$,
6) —OC(O)N$R^5R^6$,
7) —CH$_2$O—$R^4$,
8) —N$R^5R^6$,
9) —N$R^2$C(O)$R^4$,
10) —N$R^2$S(O)$_nR^4$,
11) —N$R^2$C(O)N$R^5R^6$;
wherein the alkyl, aralkyl and heteroaralkyl may be further substituted;
$R^2$ is selected from hydrogen or alkyl;
$R^3$ is selected from substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, substituted or unsubstituted aralkyl or substituted or unsubstituted heteroaralkyl;
$R^4$ is selected from substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, substituted or unsubstituted aralkyl or substituted or unsubstituted heteroaralkyl;
$R^5$ and $R^6$ are independently selected from hydrogen, alkyl, alkenyl, alkynyl, heteroalkyl, carbocyclyl, heterocyclyl, aryl, heteroaryl or $R^5$ and $R^6$ can be fused to form a 3 to 8 membered heterocyclyl ring system.

Preferred embodiment includes compounds of Formula 1 where W is selected from —$OR^3$ and $R^3$ is selected from substituted or unsubstituted aralkyl, or substituted or unsubstituted heteroaralkyl.

Preferred embodiment includes compounds of Formula 1 where W is selected from the group consisting of:

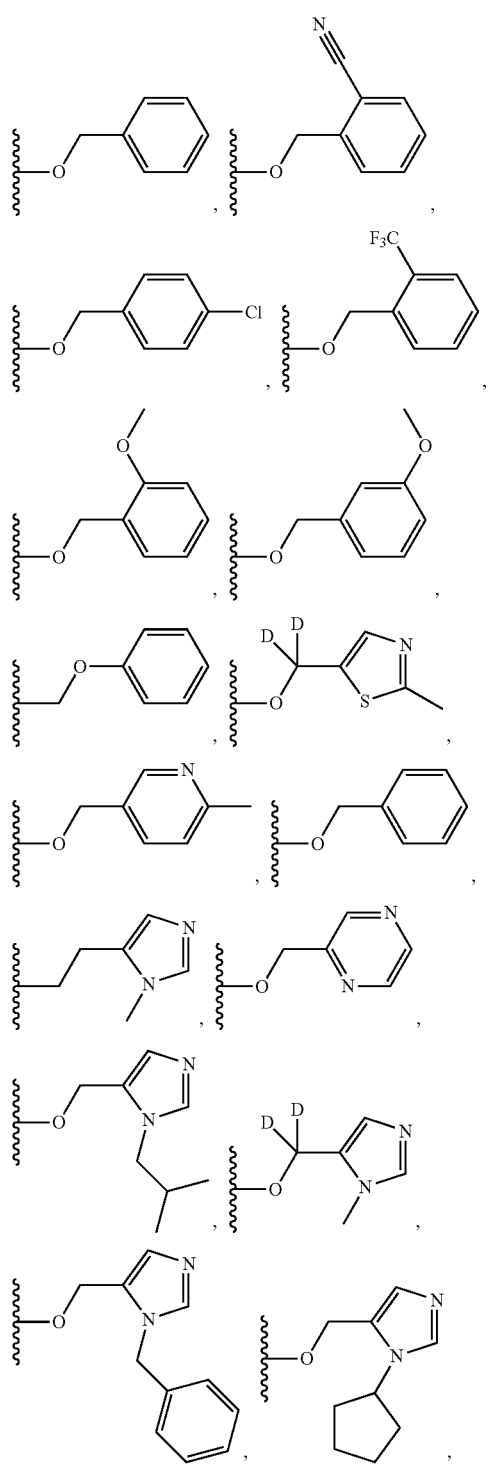

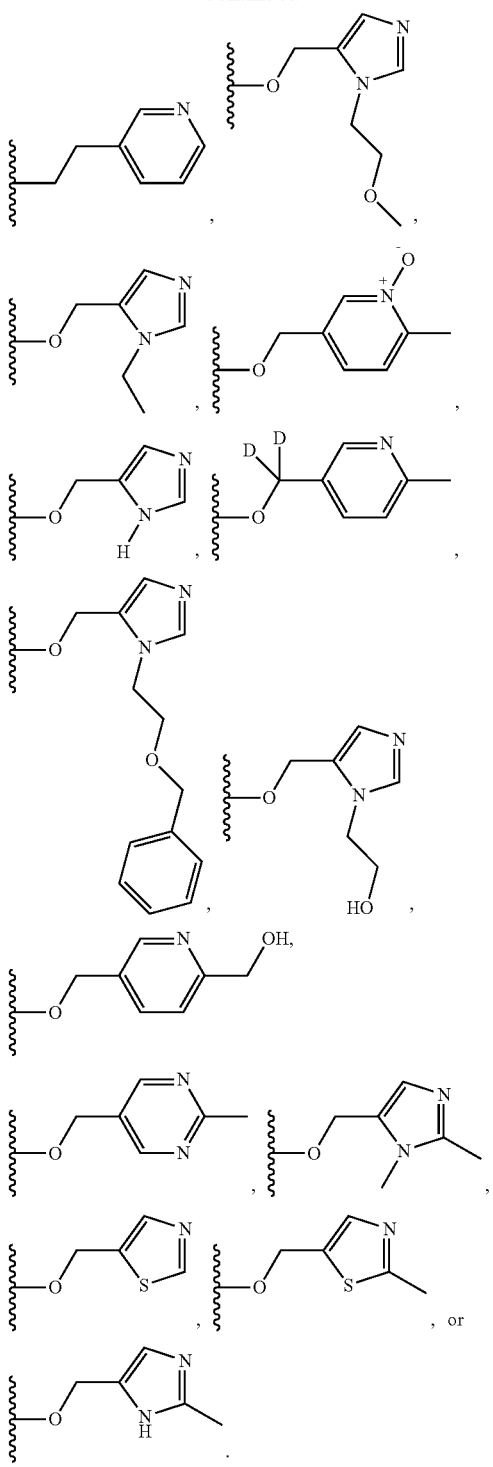

Preferred embodiment includes compounds of Formula 1 where $R^1$ is selected from the group consisting of:

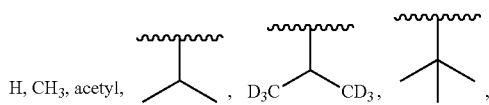

Preferred embodiment includes compounds of Formula 1 where Y is selected from the group consisting of:

Preferred embodiment includes compounds of Formula 1 where Z is selected from the group consisting of:

More preferred embodiment includes compounds of Formula 1 where W is selected from the group consisting of:

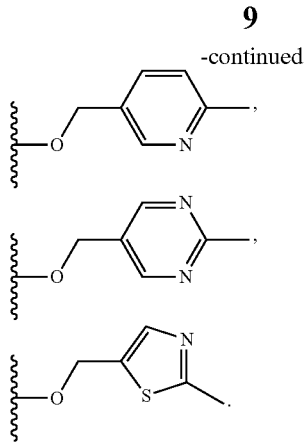

More preferred embodiment includes compounds of Formula 1 where $R^1$ is selected from the group consisting of:

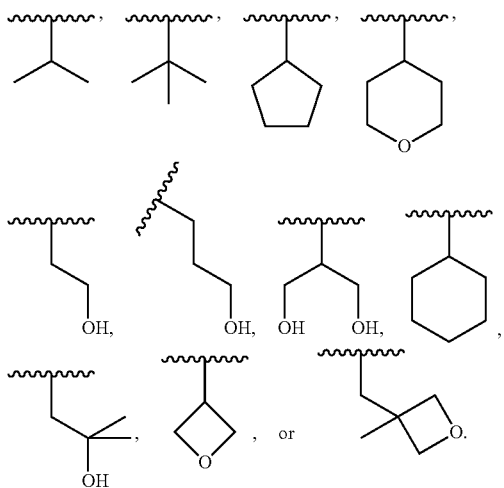

More preferred embodiment includes compounds of Formula 1 where Z is selected from the group consisting of:

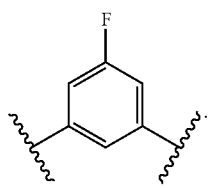

More preferred embodiment includes compounds of Formula 1 where Y—Z—W is selected from the group consisting of:

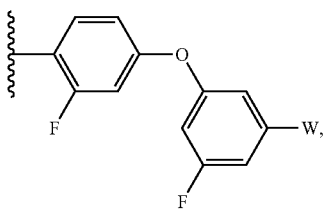

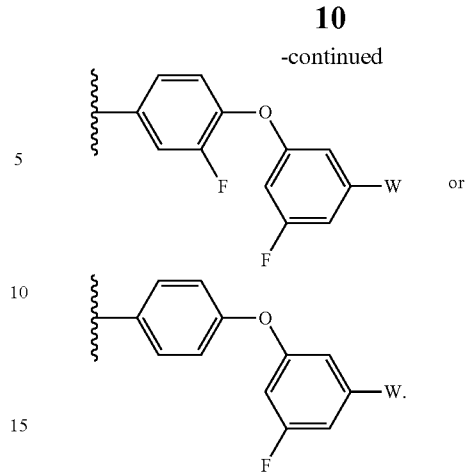

Another aspect of the present invention provides a pharmaceutical composition comprising an effective amount of a compound of Formula 1 and a pharmaceutically acceptable carrier, diluent or excipient.

In another aspect of the present invention, there is provided a use of the compound of Formula 1 as an inhibitor of protein kinase, more particularly, as an inhibitor of Btk.

Another aspect of the present invention provides a method of modulating kinase function, the method comprising contacting a cell with a compound of the present invention in an amount sufficient to modulate the enzymatic activity of a given kinase or kinases, such as Btk, thereby modulating the kinase function.

Another aspect of the present invention provides a method of modulating the target kinase function, the method comprising a) contacting a cell with a compound of the present invention in an amount sufficient to modulate the target kinase function, thereby b) modulating the target kinase activity and signaling.

Another aspect of the present invention provides a probe, the probe comprising a compound of Formula 1 labeled with a detectable label or an affinity tag. In other words, the probe comprises a residue of a compound of Formula 1 covalently conjugated to a detectable label. Such detectable labels include, but are not limited to, a fluorescent moiety, a chemiluminescent moiety, a paramagnetic contrast agent, a metal chelate, a radioactive isotope-containing moiety, or biotin.

DETAILED DESCRIPTION OF PREFERRED EMBODIMENTS

The present invention relates to novel kinase inhibitors. These compounds are found to have activity as inhibitors of protein kinases: including members of the tyrosine kinases Aurora, SRC (more specifically Lck) and Tec (more specifically Btk) kinase families.

Compounds of the present invention may be formulated into a pharmaceutical composition which comprises an effective amount of a compound of Formula 1 with a pharmaceutically acceptable diluent or carrier. For example, the pharmaceutical compositions may be in a conventional pharmaceutical form suitable for oral administration (e.g., tablets, capsules, granules, powders and syrups), parenteral administration (e.g., injections (intravenous, intramuscular, or subcutaneous)), drop infusion preparations, inhalation, eye lotion, topical administration (e.g., ointment), or suppositories. Regardless of the route of administration selected the compounds may be formulated into pharmaceutically acceptable dosage forms by conventional methods known to those skilled in the art.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be acceptable in the sense of being compatible with the other ingredients of the formulation, including the active ingredient, and not injurious or harmful to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salt" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like (See, for example, Berge et al. (1977) "Pharmaceutical Salts", J. Pharm. Sci. 66: 1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

As used herein, the term "affinity tag" means a ligand or group, linked either to a compound of the present invention or to a protein kinase domain, that allows the conjugate to be extracted from a solution.

The term "alkyl" refers to substituted or unsubstituted saturated hydrocarbon groups, including straight-chain alkyl and branched-chain alkyl groups, including haloalkyl groups such as trifluoromethyl and 2,2,2-trifluoroethyl, etc. Representative alkyl groups include methyl, ethyl, n-propyl, isopropyl, n-butyl, t-butyl, isobutyl, sec-butyl, (cyclohexyl)methyl, cyclopropylmethyl, n-pentyl, n-hexyl, n-heptyl, n-octyl, and the like. The terms "alkenyl" and "alkynyl" refer to substituted or unsubstituted unsaturated aliphatic groups analogous in length and possible substitution to the alkyls described above, but that contain at least one double or triple bond respectively. Representative alkenyl groups include vinyl, propen-2-yl, crotyl, isopenten-2-yl, 1,3-butadien-2-yl), 2,4-pentadienyl, and 1,4-pentadien-3-yl. Representative alkynyl groups include ethynyl, 1- and 3-propynyl, and 3-butynyl. In certain preferred embodiments, alkyl substituents are lower alkyl groups, e.g., having from 1 to 6 carbon atoms. Similarly, alkenyl and alkynyl preferably refer to lower alkenyl and alkynyl groups, e.g., having from 2 to 6 carbon atoms. As used herein, "alkylene" refers to an alkyl group with two open valencies (rather than a single valency), such as $-(CH_2)_{1-10}-$ and substituted variants thereof.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "alkoxyalkyl" refers to an alkyl group substituted with an alkoxy group, thereby forming an ether.

The terms "amide" and "amido" are art-recognized as an amino-substituted carbonyl and includes a moiety that can be represented by the general formula:

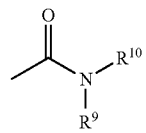

wherein $R^9$, $R^{10}$ are as defined above. Preferred embodiments of the amide will not include imides, which may be unstable.

The terms "amine" and "amino" are art-recognized and refer to both unsubstituted and substituted amines and salts thereof, e.g., a moiety that can be represented by the general formulae:

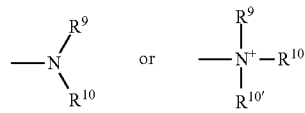

wherein $R^9$, $R^{10}$ and $R^{10'}$ each independently represent a hydrogen, an alkyl, an alkenyl, $-(CH_2)_m-R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The term "aralkyl", as used herein, refers to an alkyl group substituted with an aryl group, for example —$(CH_2)_n$—Ar.

The term "heteroaralkyl", as used herein, refers to an alkyl group substituted with a heteroaryl group, for example —$(CH_2)_n$-Het.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, anthracene, and phenanthrene.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Representative carbocyclic groups include cyclopentyl, cyclohexyl, 1-cyclohexenyl, and 3-cyclohexen-1-yl, cycloheptyl.

The term "carbonyl" is art-recognized and includes such moieties as can be represented by the general formula:

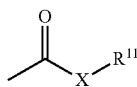

wherein X is a bond or represents an oxygen or a sulfur, and $R^{11}$ represents a hydrogen, an alkyl, an alkenyl, —$(CH_2)_m$—$R^8$ or a pharmaceutically acceptable salt. Where X is an oxygen and $R^{11}$ is not hydrogen, the formula represents an "ester". Where X is an oxygen, and $R^{11}$ is a hydrogen, the formula represents a "carboxylic acid".

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, tetrahydropyran, piperidine, piperazine, pyrrolidine, morpholine, lactones, and lactams.

The term "hydrocarbon", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

As used herein, the term "probe" means a compound of the invention which is labeled with either a detectable label or an affinity tag, and which is capable of binding, either covalently or non-covalently, to a protein kinase domain. When, for example, the probe is non-covalently bound, it may be displaced by a test compound. When, for example, the probe is bound covalently, it may be used to form cross-linked adducts, which may be quantified and inhibited by a test compound.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Compounds of the invention also include all isotopes of atoms present in the intermediates and/or final compounds. Isotopes include those atoms having the same atomic number but different mass numbers. For example, isotopes of hydrogen include deuterium and tritium.

General Synthetic Methods

General Synthetic Method A:

Ulmann condensation of phenol 1-i with ester 1-ii provided intermediate 1-iii. Saponification of intermediate 1-iii yielded intermediate 1-iv. Conversion of intermediate 1-iv to its acid chloride, using for example oxalyl chloride and DMF, provided intermediate 1-v. Condensation of intermediate 1-v with malononitrile yielded intermediate 1-vi. Methylation of intermediate 1-vi with TMS-diazomethane provided intermediate 1-vii. Condensation of 1-vii with hydrazine yielded intermediate 1-viii. Condensation of intermediate 1-viii with formamidine yielded intermediate 1-ix. Intermediate 1-ix was treated with alcohol $R^1OH$, under Mitsunobu conditions, to provide the desired compounds or intermediates of general formula 1-x.

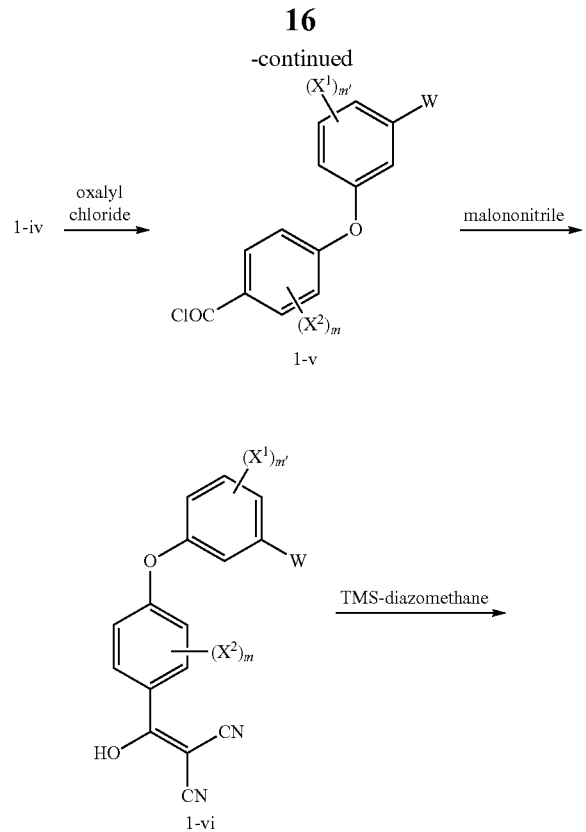

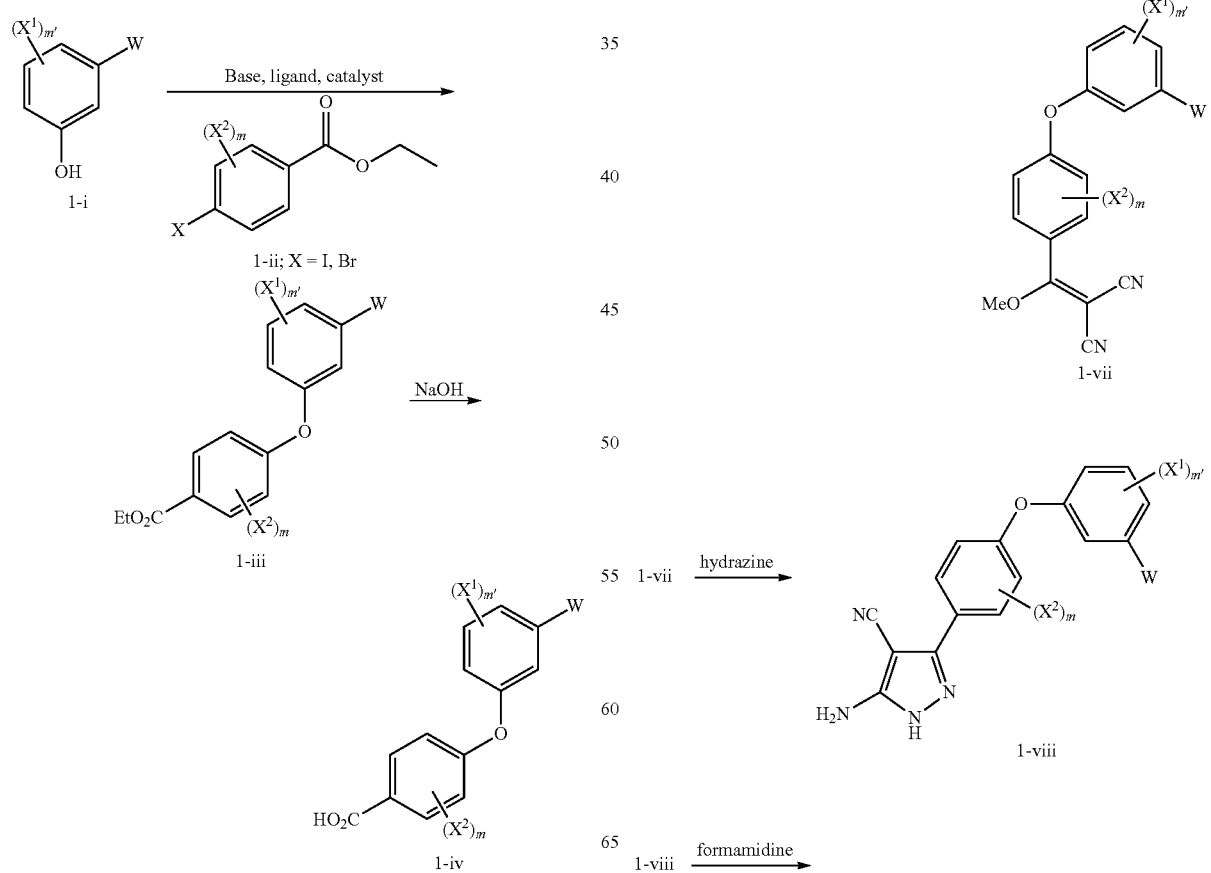

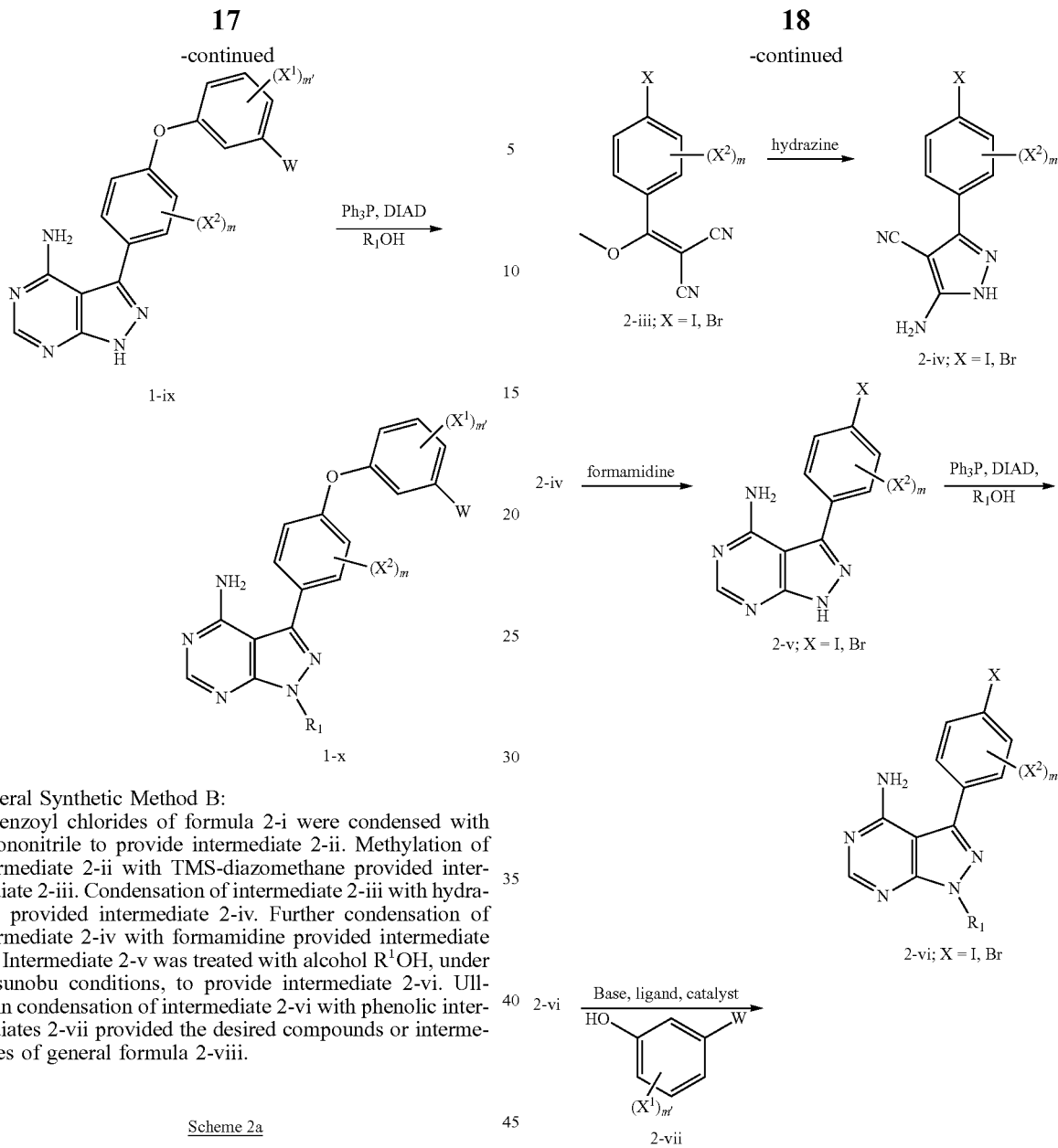

General Synthetic Method B:

Benzoyl chlorides of formula 2-i were condensed with malononitrile to provide intermediate 2-ii. Methylation of intermediate 2-ii with TMS-diazomethane provided intermediate 2-iii. Condensation of intermediate 2-iii with hydrazine provided intermediate 2-iv. Further condensation of intermediate 2-iv with formamidine provided intermediate 2-v. Intermediate 2-v was treated with alcohol $R^1OH$, under Mitsunobu conditions, to provide intermediate 2-vi. Ullmann condensation of intermediate 2-vi with phenolic intermediates 2-vii provided the desired compounds or intermediates of general formula 2-viii.

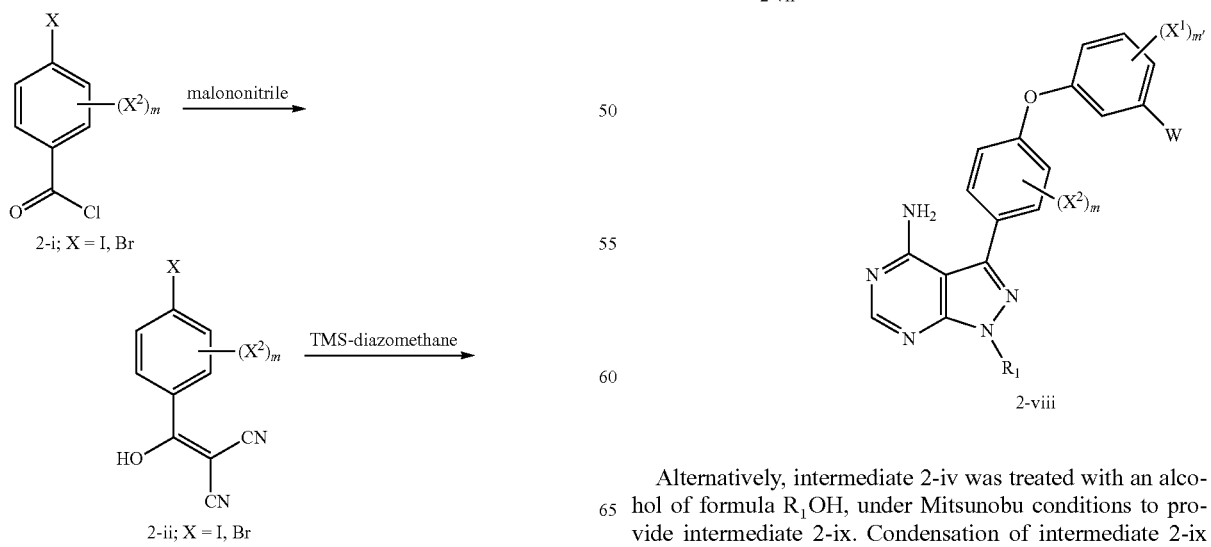

Alternatively, intermediate 2-iv was treated with an alcohol of formula $R_1OH$, under Mitsunobu conditions to provide intermediate 2-ix. Condensation of intermediate 2-ix with formamidine provided intermediate 2-vi.

Scheme 2b

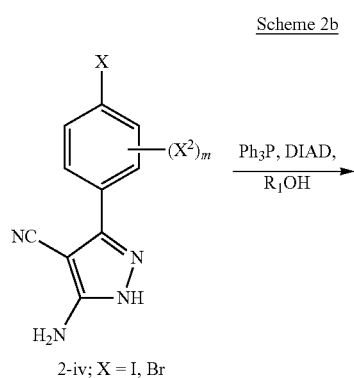

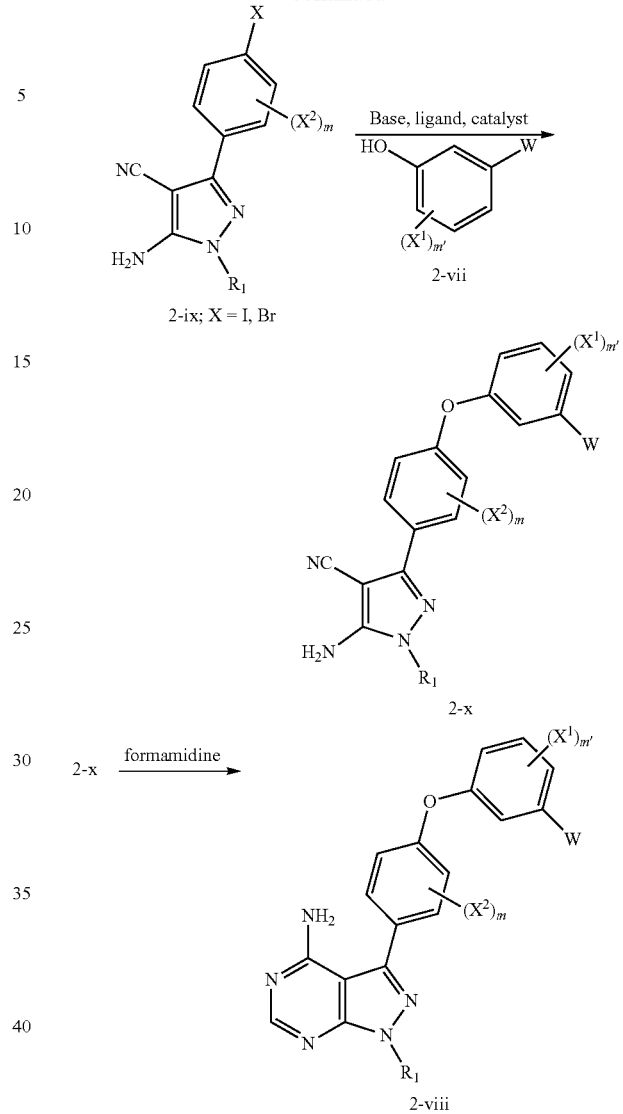

In a similar manner, condensation of intermediate 2-iii with a hydrazine of formula R₁NHNH₂ provided intermediate 2-ix. Ullmann condensation of intermediate 2-ix with phenolic intermediates 2-vii provided intermediates 2-x. Condensation of intermediate 2-x with formamidine provided the desired compounds or intermediates of general formula 2-viii.

Alternatively, trimethyl orthoformate and ammonia can be used in place of formamidine, for example, in the conversion of intermediate 2-x to compounds of formula 2-viii.

EXEMPLIFICATION

The following synthetic methods are intended to be representative of the chemistry used to prepare compounds of Formula 1 and are not intended to be limiting.

Synthesis of Compound 1

Scheme 2c

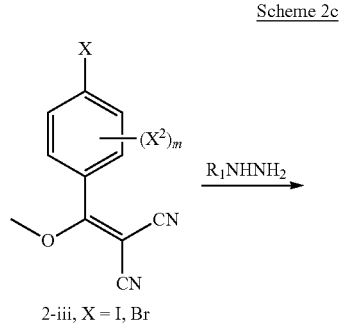

Scheme 3

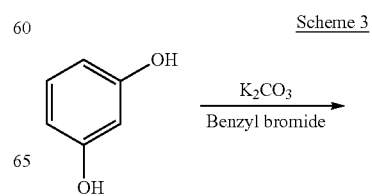

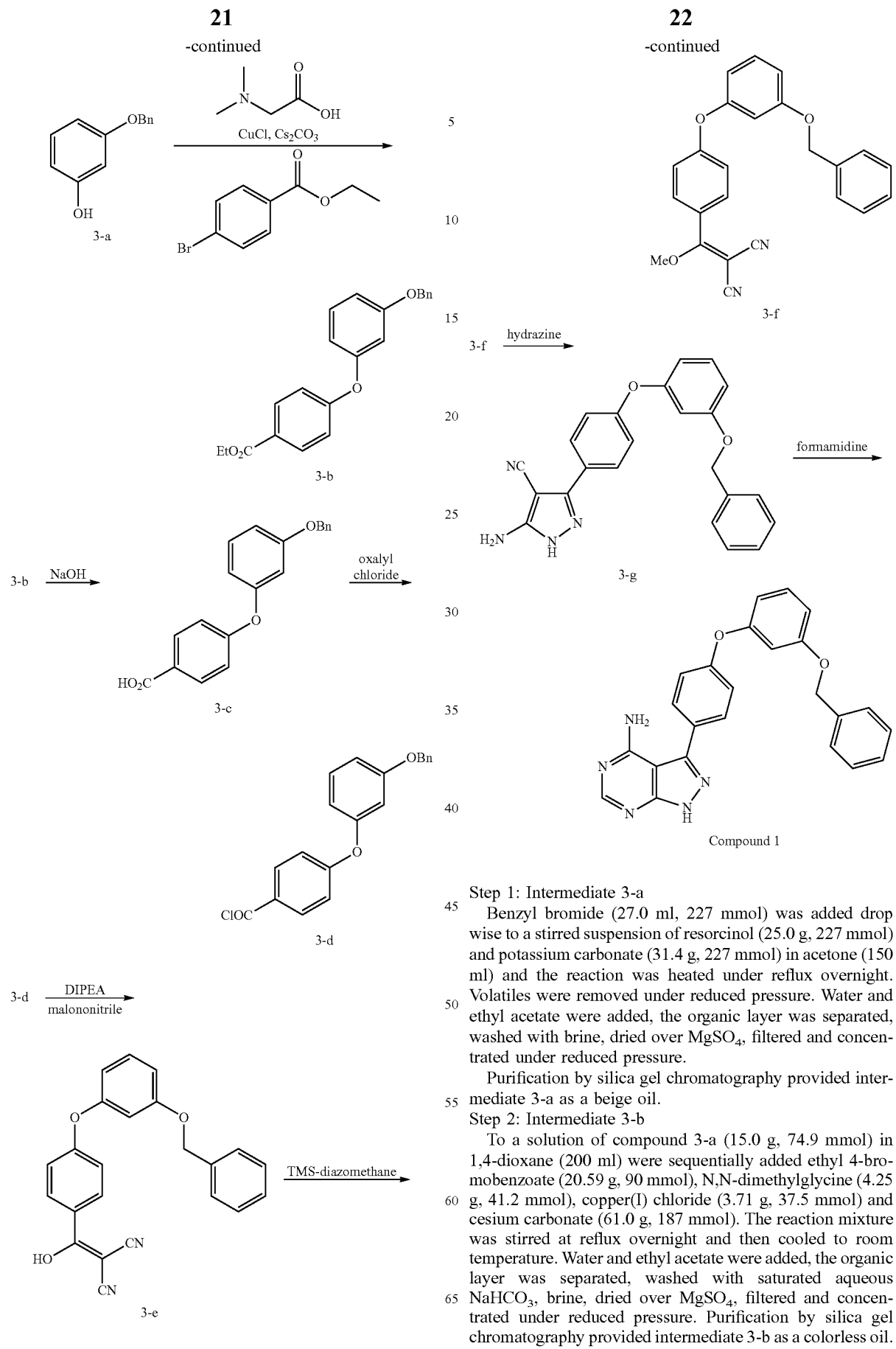

Step 1: Intermediate 3-a

Benzyl bromide (27.0 ml, 227 mmol) was added drop wise to a stirred suspension of resorcinol (25.0 g, 227 mmol) and potassium carbonate (31.4 g, 227 mmol) in acetone (150 ml) and the reaction was heated under reflux overnight. Volatiles were removed under reduced pressure. Water and ethyl acetate were added, the organic layer was separated, washed with brine, dried over MgSO$_4$, filtered and concentrated under reduced pressure.

Purification by silica gel chromatography provided intermediate 3-a as a beige oil.

Step 2: Intermediate 3-b

To a solution of compound 3-a (15.0 g, 74.9 mmol) in 1,4-dioxane (200 ml) were sequentially added ethyl 4-bromobenzoate (20.59 g, 90 mmol), N,N-dimethylglycine (4.25 g, 41.2 mmol), copper(I) chloride (3.71 g, 37.5 mmol) and cesium carbonate (61.0 g, 187 mmol). The reaction mixture was stirred at reflux overnight and then cooled to room temperature. Water and ethyl acetate were added, the organic layer was separated, washed with saturated aqueous NaHCO$_3$, brine, dried over MgSO$_4$, filtered and concentrated under reduced pressure. Purification by silica gel chromatography provided intermediate 3-b as a colorless oil.

Step 3: Intermediate 3-c

To a solution of intermediate 3-b (17.5 g, 50.2 mmol) in THF (200 ml) and MeOH (100 ml) was added 2N sodium hydroxide (100 ml, 200 mmol) and the reaction was stirred at room temperature overnight. Volatiles were removed under reduced pressure. 10% aqueous HCl and ethyl acetate were added to the residue, the organic layer was separated, washed with brine, dried over $MgSO_4$, filtered and concentrated under reduced pressure to provide intermediate 3-c as beige solid.

Step 4: Intermediate 3-d

To a suspension of intermediate 3-c (16.1 g, 50.3 mmol) in dichloromethane (100 ml) were added DMF (0.1 ml, 1.29 mmol) and oxalyl chloride (4.4 ml, 50.3 mmol). The solution was stirred at room temperature for 2 hours. Volatiles were removed under reduced pressure to provide intermediate 3-d as beige solid.

Step 5: Intermediate 3-e

To a solution of intermediate 3-d (16.5 g, 48.9 mmol) in toluene (50 ml) and THF (7 ml), cooled to −10° C., were added malononitrile (3.19 ml, 50.2 mmol) and DIPEA (17.5 ml, 100 mmol) in toluene (50 mL), drop wise, over a period of 30 minutes. After the addition was completed, the reaction was stirred for 1 hour at 0° C. and room temperature overnight. Volatiles were removed under reduced pressure. 1M aqueous HCl and ethyl acetate were added, the organic layer was separated, washed with 1M HCl and brine, dried over $MgSO_4$, filtered and concentrated under reduced pressure to provide intermediate 3-e as beige solid.

Step 6: Intermediate 3-f

To a solution of intermediate 3-e (18.1 g, 49.1 mmol) in acetonitrile (177 ml) and methanol (19.0 ml), cooled to 0° C., were added DIPEA (10.3 ml, 59.0 mmol) and a 2M solution of (diazomethyl)trimethylsilane in hexanes (27.0 ml, 54.0 mmol). After the addition was completed, the reaction was stirred at room temperature overnight. Acetic acid (0.56 ml, 9.83 mmol) was added, the reaction was then stirred for 30 minutes and volatiles were removed under reduced pressure. A saturated aqueous solution of $NaHCO_3$ and ethyl acetate were added, the organic layer was separated, washed with brine, dried over $MgSO_4$, filtered and concentrated under reduced pressure. Purification by silica gel chromatography provided intermediate 3-f as yellow solid.

Step 7: Intermediate 3-g

To a suspension of intermediate 3-f (8.05 g, 21.1 mmol) in ethanol (10.5 ml) was added a solution of hydrazine monohydrate (2.76 ml, 56.8 mmol). The reaction was stirred at 100° C. for 1 hour and then cooled to room temperature. Water was added; a precipitate formed and was collected by filtration, washed with diethyl ether and dried in vacuo to provide intermediate 3-g as an off-white solid.

Step 8: Compound 1

Intermediate 3-g (8.0 g, 20.92 mmol) was added to a solution of formamidine (58.4 ml, 1464 mmol) and the reaction was stirred at 180° C. for 2 hours and then cooled to room temperature. Water and ethyl acetate were added; the organic layer was separated, washed with brine, dried over $MgSO_4$, filtered and concentrated under reduced pressure to provide compound 1 as beige solid. MS (m/z) M+H=410.2

Synthesis of Compound 2

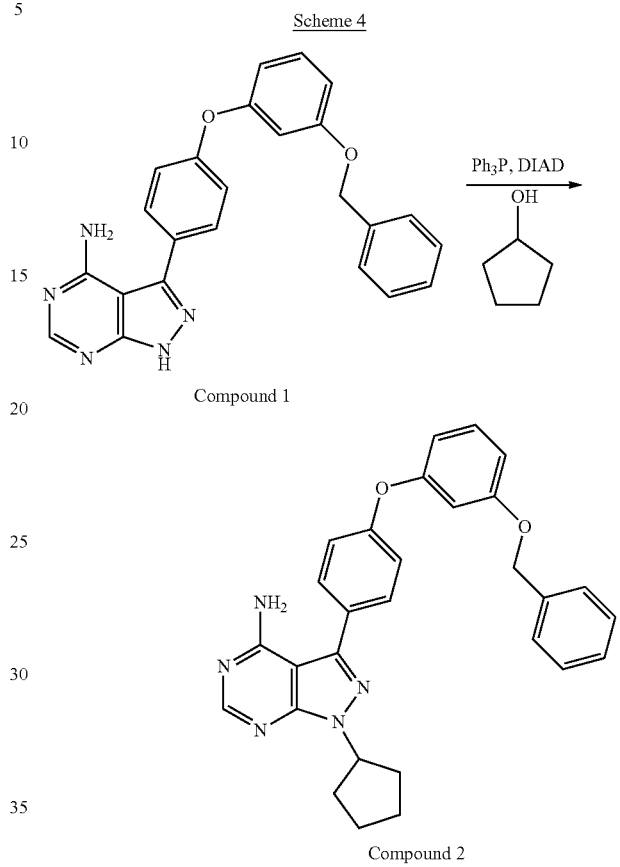

To a solution of cyclopentanol (316 mg, 3.66 mmol) in THF was added triphenylphosphine (961 mg, 3.66 mmol) and DIAD (712 μl, 3.66 mmol). The yellow solution was stirred for 5 minutes, compound 1 (1.0 g, 2.44 mmol) was added and the reaction was then stirred at room temperature overnight. Volatiles were removed under reduced pressure. Purification by silica gel chromatography provided compound 2 as an off-white solid. MS (m/z) M+H=478.2

Synthesis of Compound 3

Scheme 5

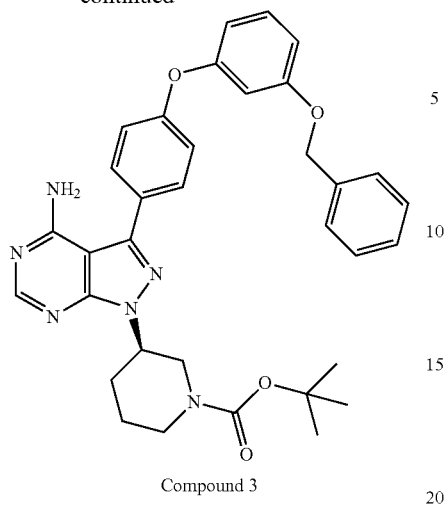

Compound 3

To a solution of (S)-tert-butyl 3-hydroxypiperidine-1-carboxylate (5.65 g, 28.1 mmol) in THF was added triphenylphosphine (7.37 g, 28.1 mmol) and DIAD (5.46 ml, 28.1 mmol). The yellow solution was stirred for 5 minutes, compound 1 (10.0 g, 24.42 mmol) was added and the reaction was then stirred at room temperature overnight. Volatiles were removed under reduced pressure. Purification by silica gel chromatography provided compound 3 as a white foam. MS (m/z) M+H=593.1

Synthesis of Compound 4

Scheme 6

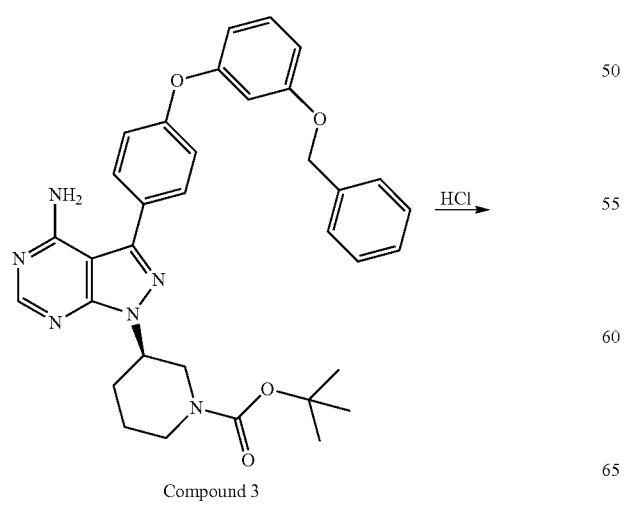

Compound 3

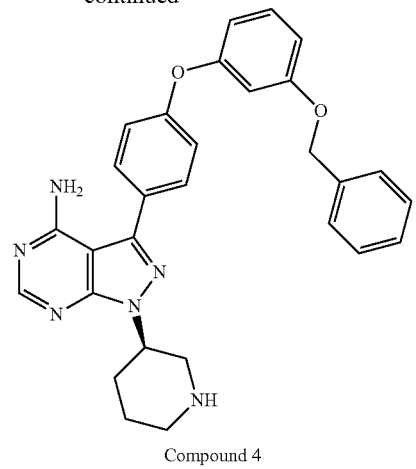

Compound 4

To a solution of compound 3 (1.88 g, 3.17 mmol) in dichloromethane was added 4N HCl in 1,4-dioxane (19.82 ml, 79.0 mmol) and the reaction was stirred at room temperature for 2 hours. Volatiles were removed under reduced pressure. Purification by reverse phase chromatography eluting with a 1% aqueous HCl/methanol gradient provided compound 4.2HCl as a white solid. MS (m/z) M+H=493.1

Synthesis of Compound 5

Scheme 7

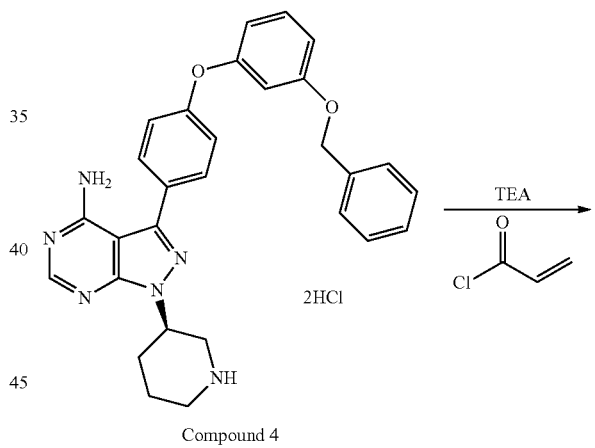

Compound 4

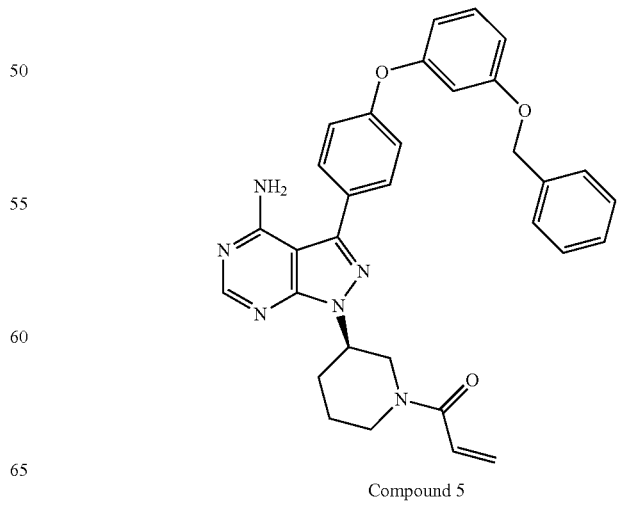

Compound 5

To a solution of compound 4.2HCl (100 mg, 0.17 mmol) in dichloromethane (2 ml) cooled to 0° C. were sequentially added TEA (99 μl, 0.70 mmol) and acryloyl chloride (17.6 mg, 0.19 mmol). The reaction was stirred at 0° C. for 1 hour. A saturated aqueous solution of ammonium chloride was added, the organic layer was separated, washed with brine, dried over MgSO$_4$, filtered and concentrated under reduced pressure. Purification by silica gel chromatography provided compound 5 as a white solid. MS (m/z) M+H=547.1

Synthesis of Compound 6

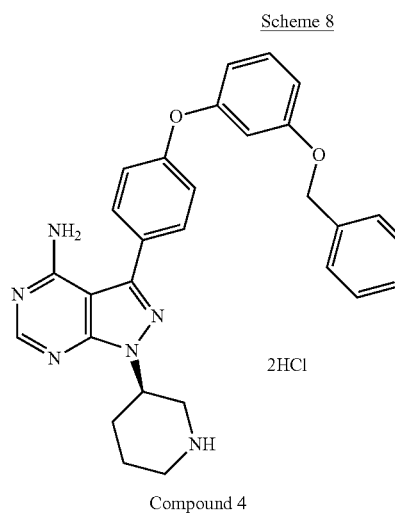

Scheme 8

Compound 4

Compound 6

To a solution of compound 4.2 HCl (1.8 g, 3.18 mmol) in dichloromethane (32 ml) cooled to 0° C. were sequentially added TEA (1.77 ml, 12.73 mmol) and acetyl chloride (249 μl, 3.50 mmol). The reaction was stirred at 0° C. for 1 hour and room temperature overnight. A saturated aqueous solution of ammonium chloride was added, the organic layer was separated, washed with brine, dried over MgSO$_4$, filtered and concentrated under reduced pressure. Purification by reverse phase chromatography eluting with 1% aqueous HCl/methanol gradient provided compound 6.HCl as beige solid. MS (m/z) M+H=535.1

Synthesis of Intermediate 9-d

Scheme 9

9-a 9-b 9-c 9-d

Step 1: Intermediate 9-a

To a solution of 4-bromobenzoyl chloride (25.0 g, 114 mmol) in toluene (200 ml) and THF (30 ml), cooled to −10° C., were sequentially added malononitrile (7.60 ml, 120.0 mmol) and DIPEA (39.8 ml, 228 mmol) in toluene (50 mL) drop wise over a period of 1 hour. After the addition was completed, the reaction was stirred for 1 hour at 0° C. and room temperature overnight. Volatiles were removed under reduced pressure. 1N HCl and ethyl acetate were added to the residue, the organic layer was separated, washed twice with 1N HCl and brine, dried over MgSO$_4$, filtered and concentrated under reduced pressure to provide intermediate 9-a as yellow solid.

Step 2: Intermediate 9-b

To a solution of intermediate 9-a (26.4 g, 106 mmol) in acetonitrile (300 ml) and methanol (35.0 ml), cooled to 0°

C., was added DIPEA (22.2 ml, 127 mmol) and a 2M solution of diazomethyl)trimethylsilane in hexanes (58.3 ml, 117 mmol). After the addition was completed, the reaction was stirred at room temperature overnight. Acetic acid (1.21 ml, 21.2 mmol) was added, the reaction was stirred for 30 minutes and volatiles were removed under reduced pressure. A saturated aqueous solution of NaHCO$_3$ and ethyl acetate were added, the organic layer was separated, washed with brine, dried over MgSO$_4$, filtered and concentrated under reduced pressure. Purification by silica gel chromatography provided intermediate 9-b as a yellow solid.

Step 3: Intermediate 9-c

To a suspension of intermediate 9-b (4.49 g, 17.07 mmol) in ethanol (8.5 ml) was added a solution of hydrazine monohydrate (2.23 ml, 46.1 mmol) and the reaction was stirred at 100° C. for 1 hour and then cooled to room temperature. Volatiles were removed under reduced pressure to provide intermediate 9-c as a yellow solid.

Step 4: Intermediate 9-d

Intermediate 9-c (4.49 g, 17.07 mmol) was added to a solution of formamidine (40.8 ml, 1024 mmol) and the reaction was stirred at 180° C. for 3 hours and then cooled to room temperature. Ethanol was added; a precipitate formed and was collected by filtration, dried in vacuo to provide intermediate 9-d as a beige solid.

Synthesis of Intermediate 10-a

Scheme 10

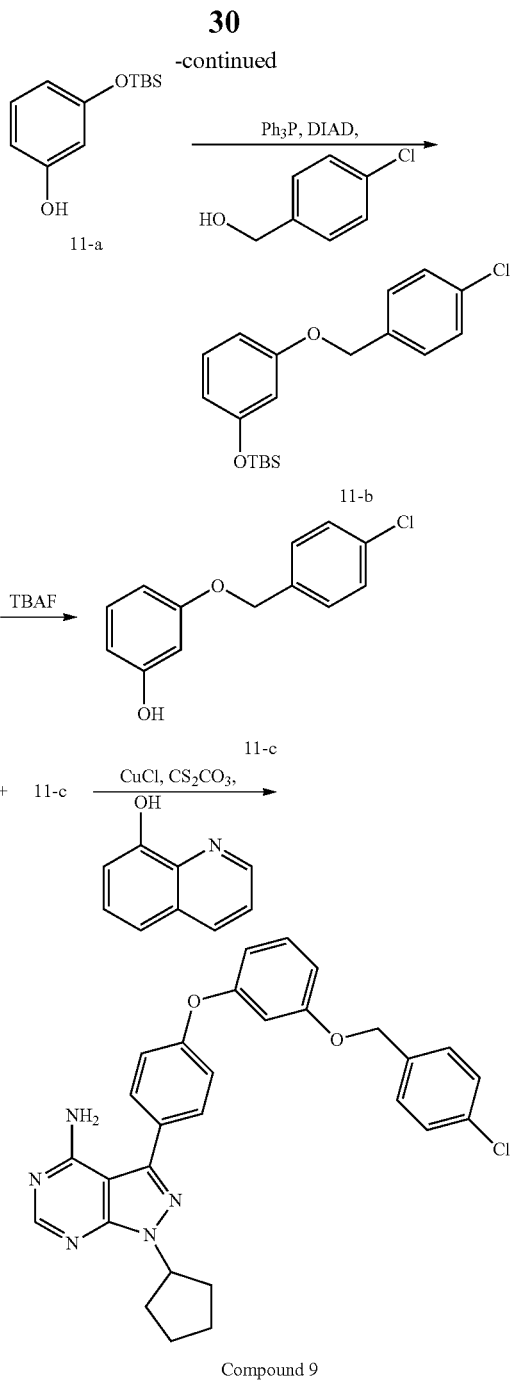

To a solution of intermediate 9-d (1.0 g, 3.45 mmol) in THF was added triphenylphosphine (1.35 g, 5.17 mmol), cyclopentanol (0.47 ml, 5.17 mmol) and DIAD (1.0 ml, 5.17 mmol) and the reaction was then stirred at room temperature overnight. Volatiles were removed under reduced pressure. Purification by silica gel chromatography provided intermediate 10-a as white solid. MS (m/z) M+H=359.6

Synthesis of Compound 9

Scheme 11

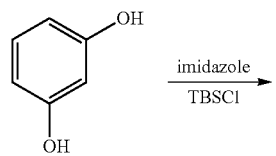

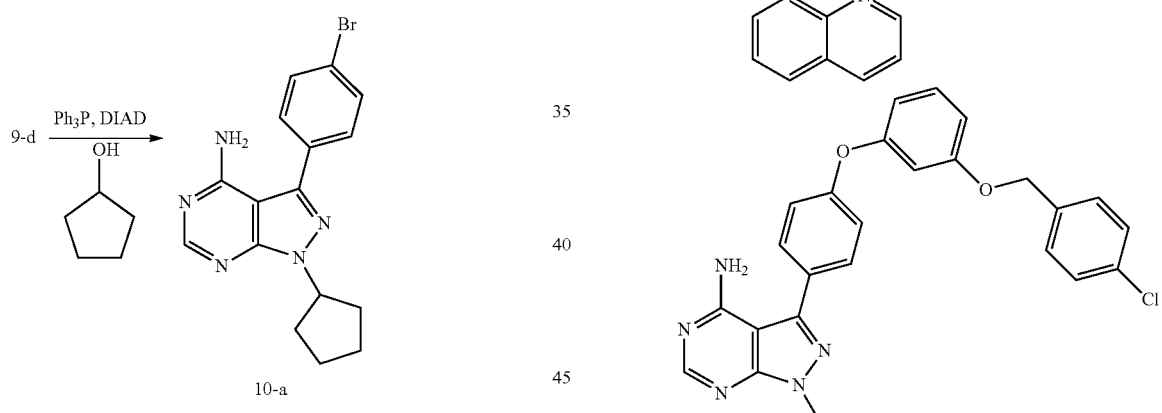

Compound 9

Step 1: Intermediate 11-a

To a solution of resorcinol (15.0 g, 136 mmol) in DMF (100 ml), cooled to 0° C., were added imidazole (19.48 g, 286 mmol) and tert-butylchlorodimethylsilane (21.56 g, 143 mmol). The reaction was then stirred at room temperature overnight. A saturated aqueous solution of ammonium chloride and ethyl acetate were added; the organic layer was separated, washed 3 times with a saturated aqueous solution of ammonium chloride and brine, dried over MgSO$_4$, filtered and concentrated under reduced pressure. Purification by silica gel chromatography provided intermediate 11-a as a colorless oil.

Step 2: Intermediate 11-b

To a solution of (4-chlorophenyl) methanol (1.52 g, 10.70 mmol) in THF (20 mL) were sequentially added intermediate 11-a (2.88 g, 12.84 mmol), triphenylphosphine (3.37 g, 12.84 mmol) and DIAD (2.53 ml, 12.84 mmol) drop wise at room temperature and the reaction was then stirred for 1 hour. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 11-b as a colorless oil.

Step 3: Intermediate 11-c

Tetrabutylammonium fluoride trihydrate (3.93 g, 12.47 mmol) was added to a solution of intermediate 11-b (2.9 g, 8.31 mmol) in THF (15 mL) and the reaction was stirred at room temperature overnight. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 11-c as a colorless oil.

Step 4: Compound 9

A solution of intermediate 10-a (200 mg, 0.56 mmol), intermediate 11-c (229 mg, 0.977 mmol), quinolin-8-ol (16.21 mg, 0.112 mmol), copper (I) chloride (11.05 mg, 0.11 mmol) and cesium carbonate (546 mg, 1.67 mmol), in dimethylacetamide (1 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with a 1% HCl/methanol gradient provided compound 9.HCl as a yellow solid. MS (m/z) M+H=512.2

Synthesis of Intermediate 12-a

Scheme 12

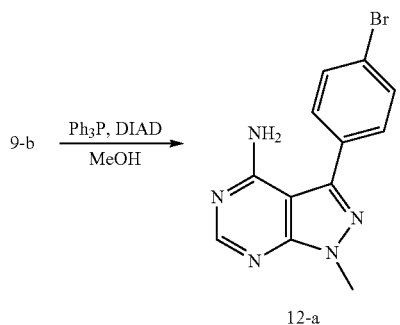

To a solution of intermediate 9-d (500 mg, 1.72 mmol) in THF (8.6 mL), were sequentially added methanol (105 µl, 2.59 mmol), triphenylphosphine (678 mg, 2.59 mmol) and DIAD (503 µl, 2.59 mmol) drop wise at room temperature. The solution was then stirred at room temperature overnight. A precipitate formed and was collected by filtration, dried in vacuo to provide intermediate 12-a as a white solid.

Synthesis of Compound 16

Scheme 13

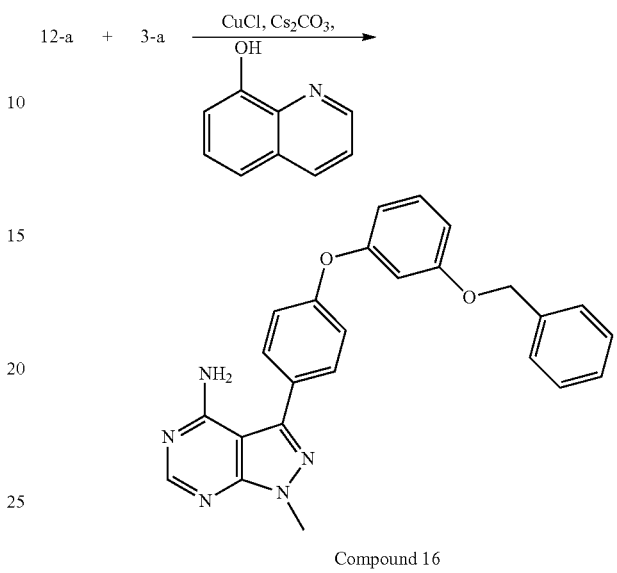

Compound 16

A solution of intermediate 12-a (235 mg, 0.77 mmol), intermediate 3-a (271 mg, 1.35 mmol), quinolin-8-ol (22.4 mg, 0.15 mmol), copper (I) chloride (15.3 mg, 0.15 mmol) and cesium carbonate (755 mg, 2.31 mmol) in dimethylacetamide (1 ml) was degassed with nitrogen for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 1% HCl/methanol gradient provided compound 16.HCl as a beige solid. MS (m/z) M+H=424.2

Synthesis of Compound 17

Scheme 14

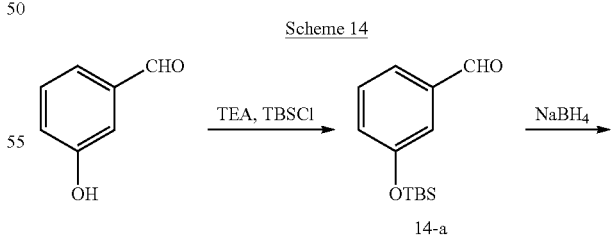

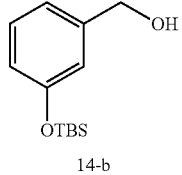

14-b

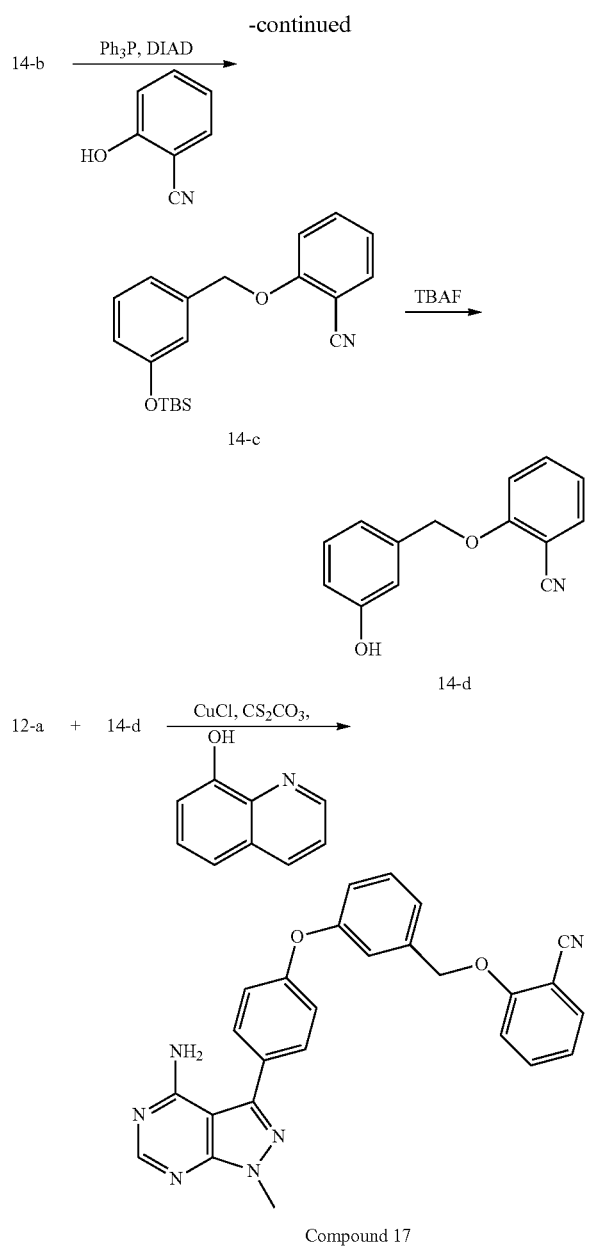

Compound 17

Step 1: Intermediate 14-a

To a solution of 3-hydroxybenzaldehyde (14.73 g, 121 mmol) in dichloromethane (100 mL) were sequentially added triethylamine (25.08 ml, 181 mmol), tert-butylchlorodimethylsilane (20.0 g, 133 mmol) portion wise, and the reaction was stirred at room temperature overnight. 10% aqueous citric acid was added, the organic layer was separated, washed with brine, dried over MgSO₄, filtered and concentrated under reduced pressure. Purification by silica gel chromatography provided intermediate 14-a as a yellow oil.

Step 2: Intermediate 14-b

To a solution of intermediate 14-a (16.0 g, 67.7 mmol) in methanol (100 ml) cooled to 0° C. was added portion wise sodium borohydride (1.28 g, 33.8 mmol). After the addition was completed the reaction was stirred at room temperature for 2 hours. Volatiles were removed under reduced pressure. Water and ethyl acetate were added to the residue, the organic layer was separated, washed with brine, dried over MgSO₄, filtered and concentrated under reduced pressure to provide intermediate 14-b as a yellow oil.

Step 3: Intermediate 14-c

To a solution of intermediate 14-b (1.0 g, 2.09 mmol) in THF (42 mL) were sequentially added 2-hydroxybenzonitrile (600 mg, 5.03 mmol), triphenylphosphine (1.32 g, 5.03 mmol) and DIAD (991 µl, 5.03 mmol) drop wise at room temperature; the reaction was stirred at reflux for 2 hours and then cooled to room temperature. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 14-c as a colorless oil.

Step 2: Intermediate 14-d

To a solution of intermediate 14-c (1.22 g, 3.62 mmol) in THF (36.0 ml) was added tetrabutylammonium fluoride trihydrate (946 mg, 3.62 mmol) and the reaction was stirred at room temperature for 1 hour. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 14-d as a white solid.

Step 2: Compound 17

A solution of intermediate 12-a (200 mg, 0.6 mmol), intermediate 14-d (259 mg, 1.15 mmol), quinolin-8-ol (19.0 mg, 0.13 mmol), copper (I) chloride (13.0 mg, 0.13 mmol) and cesium carbonate (643 mg, 1.97 mmol) in dimethylacetamide (3.0 ml) was degassed with argon for 10 minutes, heated in a sealed tube at 140° C. overnight. After cooling to room temperature, water and ethyl acetate were added, the organic layer was separated, the aqueous layer was extracted twice with ethyl acetate, the combined organic extracts were washed with brine, dried over MgSO₄, filtered and concentrated under reduced pressure. Purification by silica gel chromatography provided compound 17 as a white solid.
MS (m/z) M+H=449.3

Synthesis of Compound 18

Scheme 15

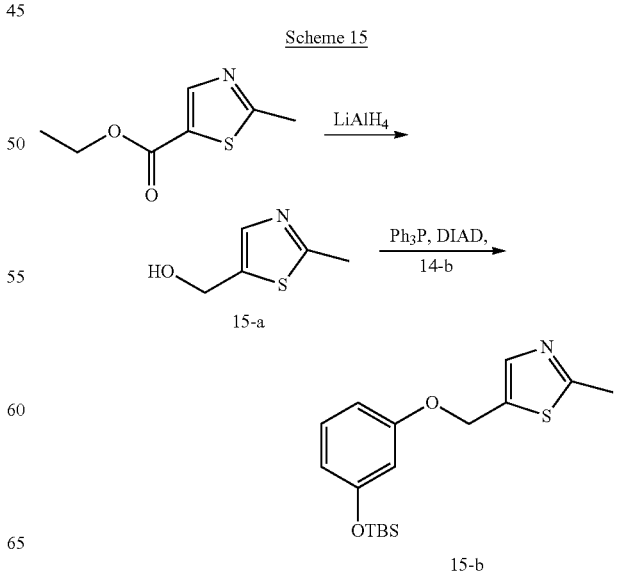

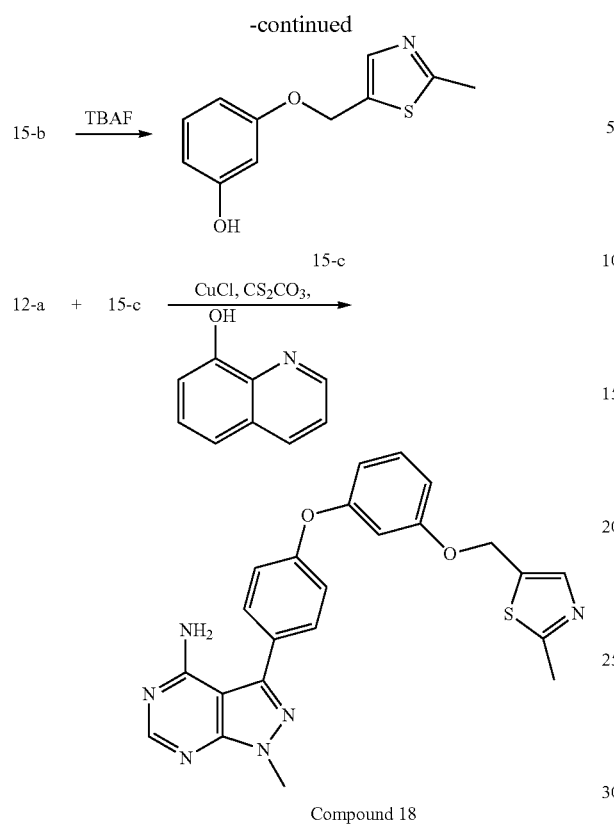

Compound 18

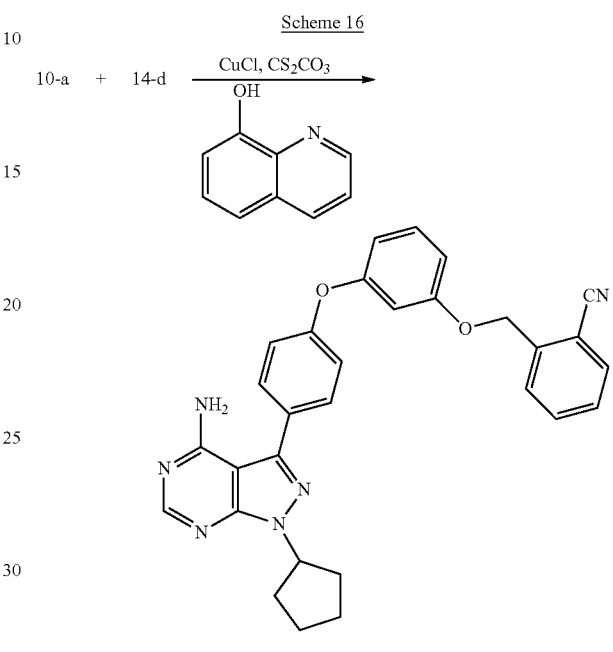

Compound 15

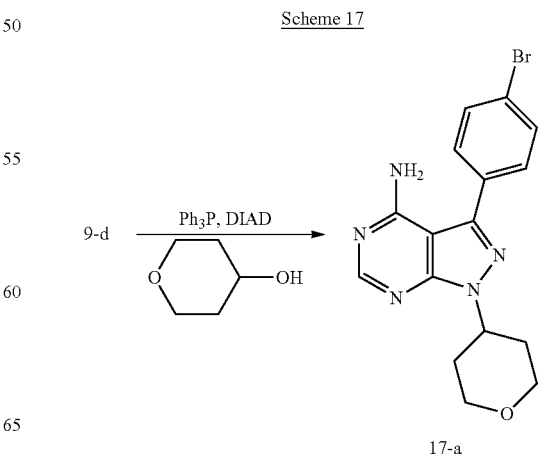

17-a the organic layer was separated, the aqueous layer was extracted twice with ethyl acetate, the combined organic extracts were washed with brine, dried over MgSO₄, filtered and concentrated under reduced pressure. Purification by reverse phase chromatography eluting with 1% HCl/methanol gradient provided compound 18.2HCl as a beige solid. MS (m/z) M+H=445.1

Synthesis of Compound 15

Scheme 16

A solution of intermediate 10-a (200 mg, 0.56 mmol), intermediate 14-d (156 mg, 0.68 mmol), quinolin-8-ol (16.2 mg, 0.11 mmol), copper (I) chloride (11.0 mg, 0.11 mmol) and cesium carbonate (546 mg, 1.67 mmol) in dimethylacetamide (5.5 ml) was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with 1% HCl/methanol gradient provided compound 15.HCl as beige solid. MS (m/z) M+H=503.3

Synthesis of Intermediate 17-a

Scheme 17

Step 1: Intermediate 15-a

To a solution of ethyl 2-methylthiazole-5-carboxylate (5.82 g, 34.0 mmol) in THF (170 ml), cooled to 0° C., was added a 1.0M solution of LiAlH₄ in THF (34.0 ml, 34.0 mmol) and the reaction was slowly warmed to room temperature and stirred overnight. Water (1.3 ml) was slowly added, followed by 15% NaOH (1.3 mL). The solution was stirred for 2 hours at room temperature then filtered over celite. The filtrate was concentrated under reduced pressure to provide intermediate 15-a as a yellow oil.

Step 2: Intermediate 15-b

To a solution of intermediate 15-a (7.75 g, 34.5 mmol) and intermediate 11-a (4.25 g, 32.9 mmol), in THF (33 mL), were sequentially added triphenylphosphine (10.35 g, 39.5 mmol) and DIAD (7.68 ml, 39.5 mmol) drop wise at room temperature. The reaction was then stirred for 18 hours. Volatiles were removed in vacuo. Purification by silica gel chromatography provided intermediate 15-b as a colorless oil.

Step 3: Intermediate 15-c

To a solution of intermediate 15-b (5.5 g, 16.39 mmol), in THF (82.0 ml), was added a 1.0M solution of tetrabutylammonium fluoride in THF (16.4 ml, 16.4 mmol) and the reaction was stirred at room temperature for 30 minutes. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 15-c as beige solid.

Step 4: Compound 18

A solution of intermediate 12-a (200 mg, 0.65 mmol), intermediate 15-c (146 mg, 0.65 mmol), quinolin-8-ol (19.0 mg, 0.13 mmol), copper (I) chloride (13.0 mg, 0.13 mmol) and cesium carbonate (643 mg, 1.97 mmol) in dimethylacetamide (6.5 ml) was degassed with argon for 10 minutes, heated in a sealed tube at 140° C. for 2 hours and then cooled to room temperature. Water and ethyl acetate were added, To a solution of intermediate 9-d (650 mg, 2.24 mmol), in THF (22.0 mL), were sequentially added tetrahydro-2H-pyran-4-ol (320 μl, 3.36 mmol), triphenylphosphine (881 mg, 3.36 mmol) and DIAD (653 μl, 3.36 mmol) drop wise at room temperature. The solution was then stirred at 50° C. overnight. Volatiles were removed in vacuo. Purification by silica gel chromatography provided intermediate 17-a as a white solid.

Synthesis of Compound 22

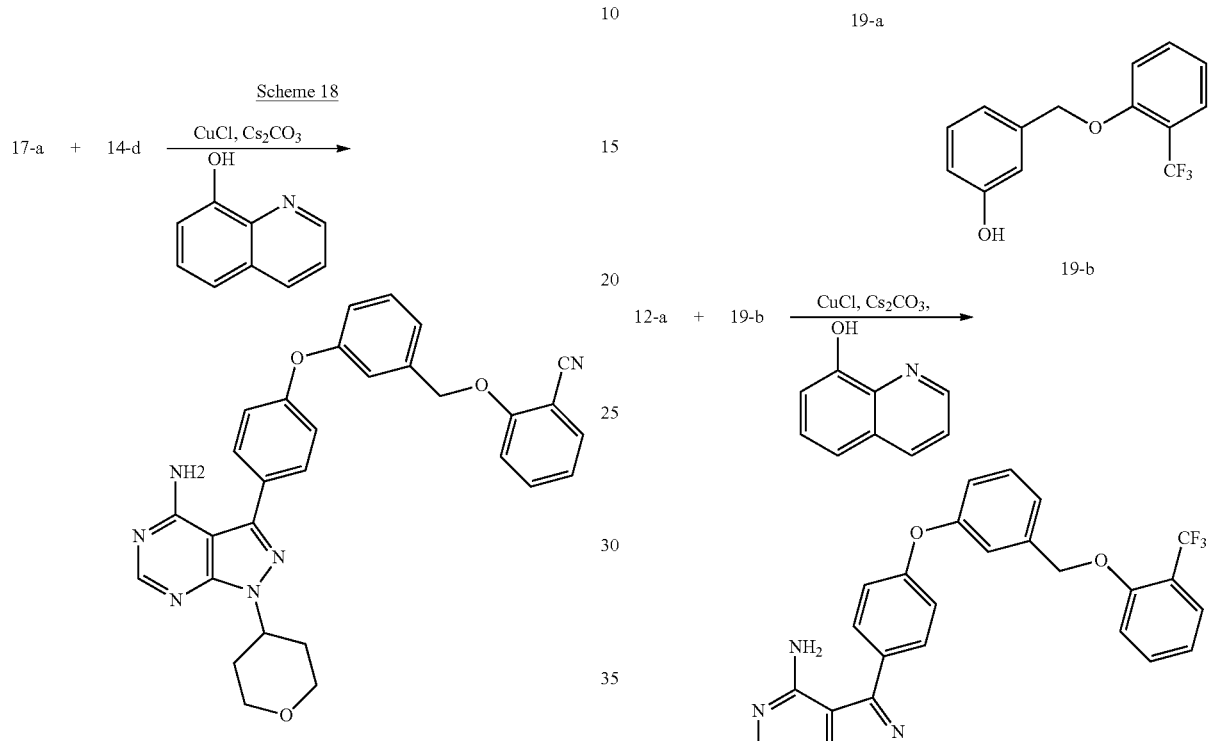

Compound 22

A solution of intermediate 17-a (200 mg, 0.53 mmol), intermediate 14-d (181 mg, 0.80 mmol), quinolin-8-ol (15.5 mg, 0.11 mmol), copper (I) chloride (11.5 mg, 0.11 mmol) and cesium carbonate (348 mg, 1.07 mmol) in dimethylacetamide (5.3 ml) was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with 1% HCl/methanol gradient provided compound 22.HCl as a beige solid. MS (m/z) M+H=519.2

Synthesis of Compound 31

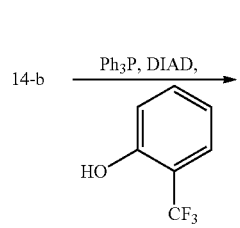

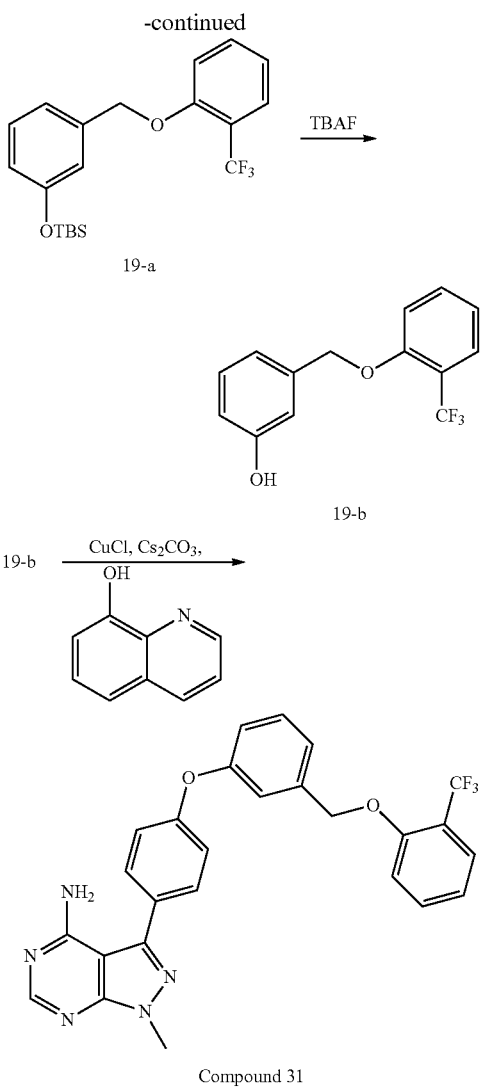

Compound 31

Step 1: Intermediate 19-a

To a solution of intermediate 14-b (10.0 g, 41.9 mmol) in THF (210 mL) were sequentially added 2-(trifluoromethyl)phenol (6.80 g, 41.9 mmol), triphenylphosphine (13.2 g, 50.33 mmol) and DIAD (9.79 ml, 50.3 mmol) drop wise at room temperature. The reaction was then stirred at room temperature overnight. Saturated aqueous ammonium chloride and ethyl acetate were added, the organic layer was separated, washed with brine, dried over MgSO₄, filtered and concentrated under reduced pressure.

Purification by silica gel chromatography provided intermediate 19-a as a colorless oil.

Step 2: Intermediate 19-b

To a solution of intermediate 19-a (13.9 g, 36.3 mmol) in THF (182.0 ml) was added a 1.0M solution of tetrabutylammonium fluoride in THF (36.3 ml, 36.3 mmol) and the reaction was stirred at room temperature for 1 hour. Saturated aqueous ammonium chloride and ethyl acetate were added, the organic layer was separated, washed with brine, dried over MgSO₄, filtered and concentrated under reduced pressure. Purification by silica gel chromatography provided intermediate 19-b as colorless oil.

Step 3: Compound 31

A solution of intermediate 12-a (200 mg, 0.66 mmol), intermediate 19-b (265 mg, 0.98 mmol), quinolin-8-ol (19.0 mg, 0.13 mmol), copper (I) chloride (25.5 mg, 0.13 mmol) and cesium carbonate (429 mg, 1.31 mmol) in dimethylacetamide (6.5 ml) was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with 1% HCl/methanol gradient provided compound 31.HCl as white solid. MS (m/z) M+H=492.1

Synthesis of Compound 32

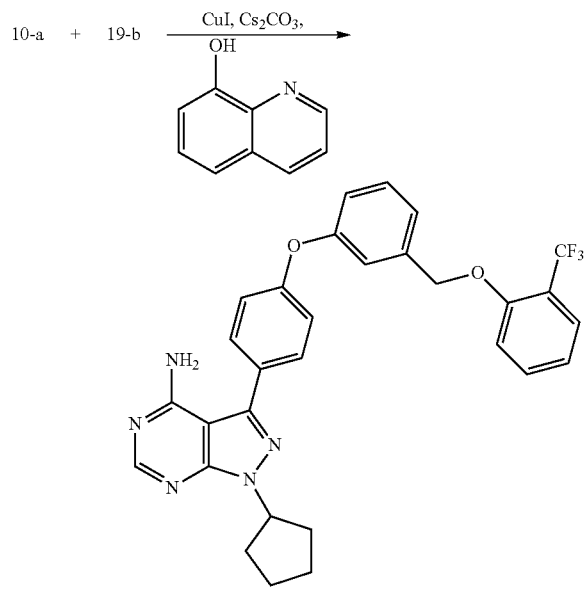

Compound 32

A solution of intermediate 10-a (200 mg, 0.55 mmol), intermediate 19-b (225 mg, 0.83 mmol), quinolin-8-ol (16.2 mg, 0.11 mmol), copper (I) iodide (22.0 mg, 0.11 mmol) and cesium carbonate (364 mg, 1.17 mmol) in dimethylacetamide (5.5 ml) was degassed with argon for 10 minutes, heated in a sealed tube at 140° C. overnight and then cooled to room temperature. Water and ethyl acetate were added, the organic layer was separated, the aqueous layer was extracted twice with ethyl acetate. The combined organic extracts were washed with brine, dried over MgSO$_4$, filtered and concentrated under reduced pressure. Purification by reverse phase chromatography eluting with 1% HCl/methanol gradient provided compound 32.HCl as beige solid. MS (m/z) M+H=546.1

Synthesis of Compound 36

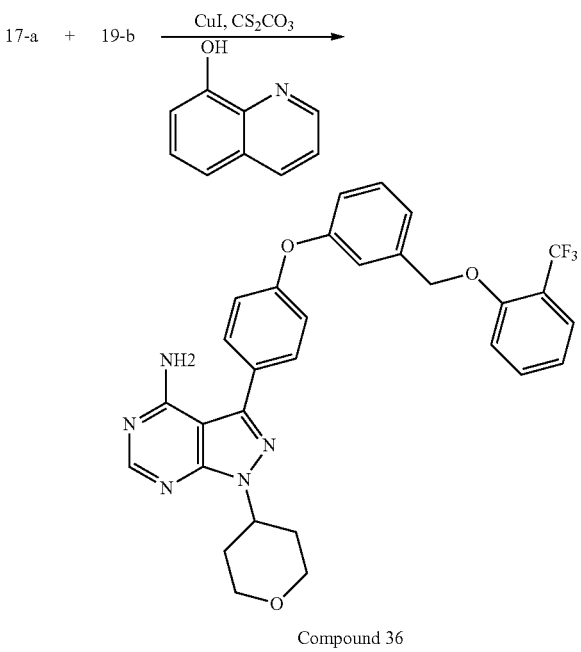

Compound 36

A solution of intermediate 17-a (200 mg, 0.53 mmol), intermediate 19-b (215 mg, 0.80 mmol), quinolin-8-ol (15.5 mg, 0.11 mmol), copper (I) iodide (20.3 mg, 0.11 mmol) and cesium carbonate (348 mg, 1.06 mmol) in dimethylacetamide (5.3 ml) was degassed with argon for 10 minutes, heated in a sealed tube at 140° C. overnight and then cooled to room temperature. Water and ethyl acetate were added, the organic layer was separated, the aqueous layer was extracted twice with ethyl acetate. The combined organic extracts were washed with brine, dried over MgSO$_4$, filtered and concentrated under reduced pressure. Purification by reverse phase chromatography eluting with 1% HCl/methanol gradient provided compound 36.HCl as beige solid. MS (m/z) M+H=562.2

Synthesis of Compound 20

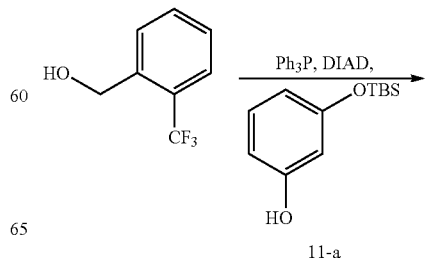

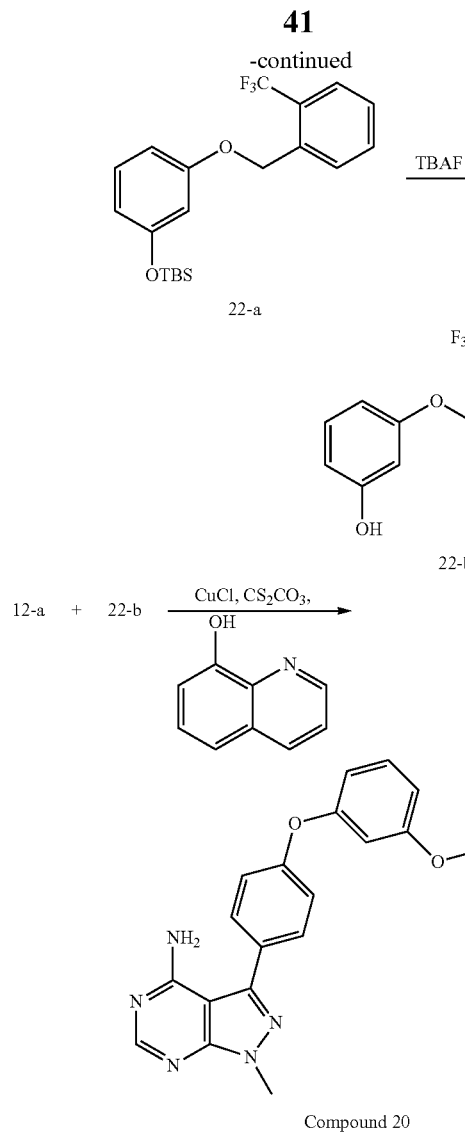

Compound 20

Step 1: Intermediate 22-a

To a solution of 2-(trifluoromethyl)phenylmethanol (1.43 g, 8.10 mmol) in THF (8.10 mL) were sequentially added intermediate 11-a (2.0 g, 8.91 mmol), triphenylphosphine (2.55 g, 9.72 mmol) and DIAD (1.89 ml, 9.72 mmol) drop wise at room temperature. The reaction was then stirred overnight at room temperature. Saturated aqueous ammonium chloride and ethyl acetate were added, the organic layer was separated, washed with brine, dried over MgSO$_4$, filtered and concentrated under reduced pressure. Purification by silica gel chromatography provided intermediate 22-a as a colorless oil.

Step 2: Intermediate 22-b

Tetrabutylammonium fluoride trihydrate (1.81 g, 5.75 mmol) was added to a solution of intermediate 22-a (2.2 g, 5.75 mmol) in THF (23 mL) and the reaction was stirred at room temperature for 1 hour. Saturated aqueous ammonium chloride and ethyl acetate were added, the organic layer was separated, washed with brine, dried over MgSO$_4$, filtered and concentrated under reduced pressure. Purification by silica gel chromatography provided intermediate 22-b as a colorless oil.

Step 3: Compound 20

A solution of intermediate 12-a (200 mg, 0.65 mmol), intermediate 22-b (309 mg, 1.15 mmol), quinolin-8-ol (19.1 mg, 0.13 mmol), copper (I) chloride (13.0 mg, 0.13 mmol) and cesium carbonate (429 mg, 1.31 mmol), in dimethylacetamide (6.5 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with a 1% HCl/methanol gradient provided compound 20.HCl as beige solid. MS (m/z) M+H=492.1

Synthesis of Compound 29

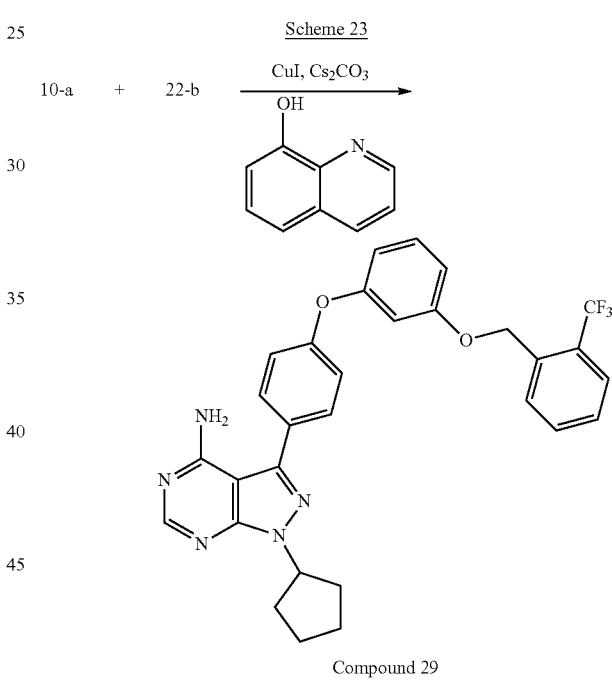

Compound 29

A solution of intermediate 10-a (200 mg, 0.55 mmol), intermediate 22-b (225 mg, 0.83 mmol), quinolin-8-ol (16.2 mg, 0.11 mmol), copper (I) iodide (21.2 mg, 0.11 mmol) and cesium carbonate (364 mg, 1.11 mmol), in dimethylacetamide (5.5 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with a 1% HCl/methanol gradient provided compound 29.HCl as beige solid. MS (m/z) M+H=546.2

Synthesis of Compound 23

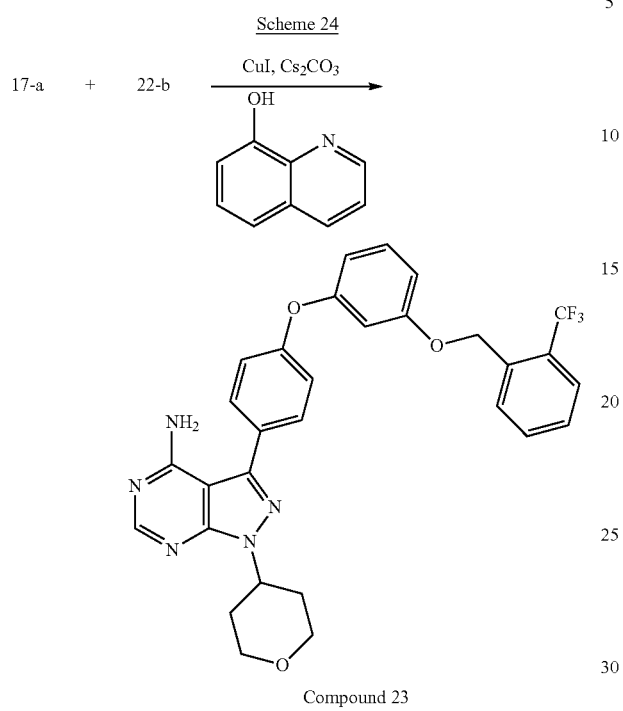

Compound 23

A solution of intermediate 17-a (200 mg, 0.53 mmol), intermediate 22-b (215 mg, 0.80 mmol), quinolin-8-ol (15.5 mg, 0.11 mmol), copper (I) iodide (20.4 mg, 0.11 mmol) and cesium carbonate (348 mg, 1.07 mmol), in dimethylacetamide (5.3 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with a 1% HCl/methanol gradient provided compound 23.HCl as beige solid. MS (m/z) M+H=562.1

Synthesis of Compound 30

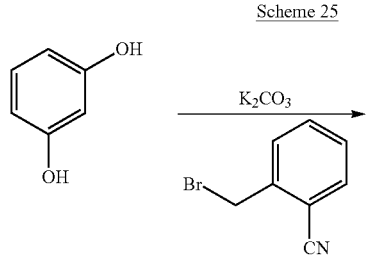

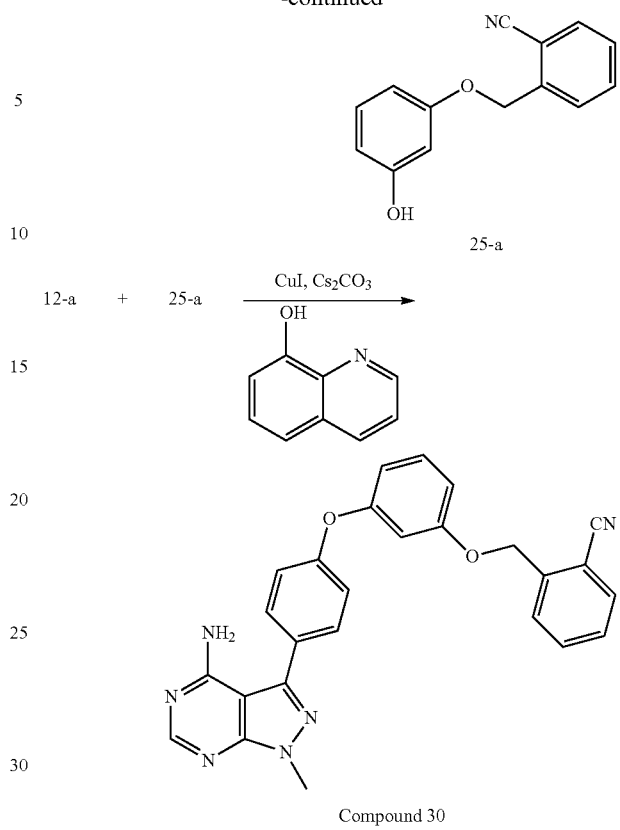

Compound 30

Step 1: Intermediate 25-a

To a solution of 2-(bromomethyl)benzonitrile (1.0 g, 5.10 mmol) and resorcinol (2.81 g, 25.5 mmol) in acetone (51.0 mL) was added cesium carbonate (3.32 g, 10.20 mmol) and the reaction was then stirred at reflux for 2 hours. Volatiles were removed under reduced pressure. Saturated aqueous ammonium chloride and ethyl acetate were added, the organic layer was separated, washed with brine, dried over MgSO₄, filtered and concentrated under reduced pressure. Purification by silica gel chromatography provided intermediate 25-a as white solid.

Step 2: Compound 30

A solution of intermediate 12-a (200 mg, 0.65 mmol), intermediate 25-a (222 mg, 0.98 mmol), quinolin-8-ol (19.1 mg, 0.13 mmol), copper (I) iodide (25.0 mg, 0.13 mmol) and cesium carbonate (429 mg, 1.31 mmol), in dimethylacetamide (6.5 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO₄, filtered and concentrated under reduced pressure. Purification by reverse phase chromatography eluting with a 1% HCl/methanol gradient provided compound 30.HCl as beige solid. MS (m/z) M+H=449.4

Synthesis of Compound 12

Scheme 26

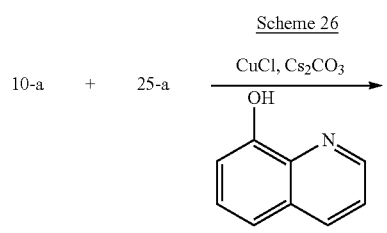

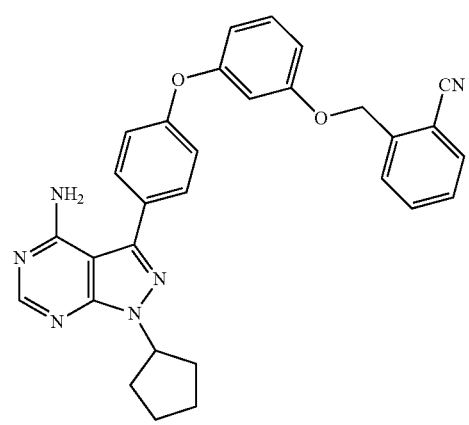

Compound 12

A solution of intermediate 10-a (200 mg, 0.55 mmol), intermediate 25-a (220 mg, 0.98 mmol), quinolin-8-ol (16.2 mg, 0.11 mmol), copper (I) chloride (11.0 mg, 0.11 mmol) and cesium carbonate (546 mg, 1.67 mmol), in dimethylacetamide (5.5 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with a 1% HCl/methanol gradient provided compound 12.HCl as a beige solid. MS (m/z) M+H=503.2

Synthesis of Compound 35

Scheme 27

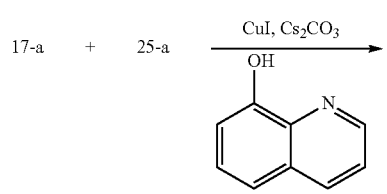

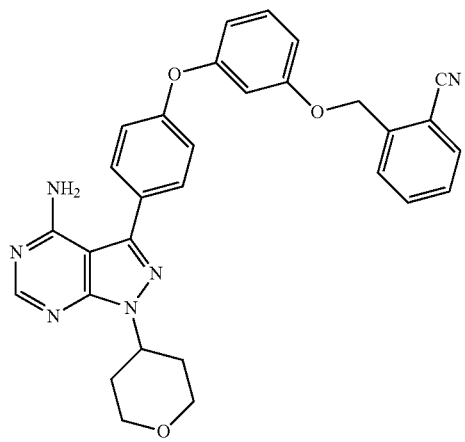

Compound 35

A solution of intermediate 17-a (200 mg, 0.55 mmol), intermediate 25-a (181.0 mg, 0.80 mmol), quinolin-8-ol (15.5 mg, 0.11 mmol), copper (I) iodide (20.3 mg, 0.11 mmol) and cesium carbonate (348 mg, 1.07 mmol), in dimethylacetamide (5.3 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with a 1% HCl/methanol gradient provided compound 35.HCl as beige solid. MS (m/z) M+H=519.2

Synthesis of Compound 10

Scheme 28

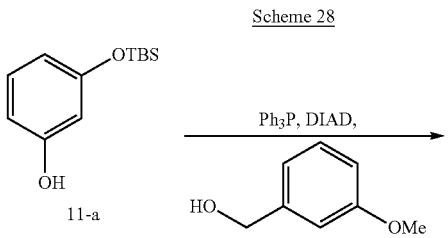

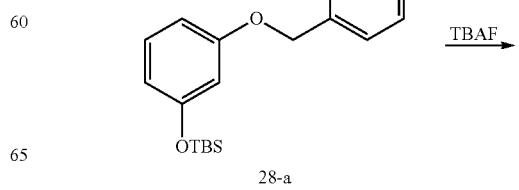

28-a the organic layer was separated, the aqueous layer was extracted twice with ethyl acetate, the combined organic extracts were washed with brine, dried over MgSO₄, filtered and concentrated under reduced pressure. Purification by reverse phase chromatography eluting with a 1% HCl/methanol gradient provided compound 10.HCl as a yellow solid. MS (m/z) M+H=508.1

Synthesis of Intermediate 29-i

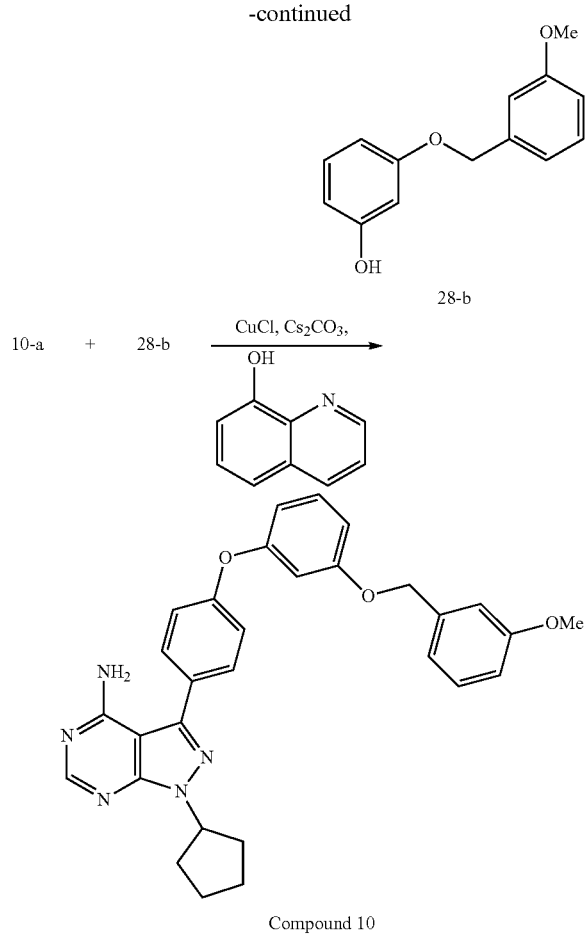

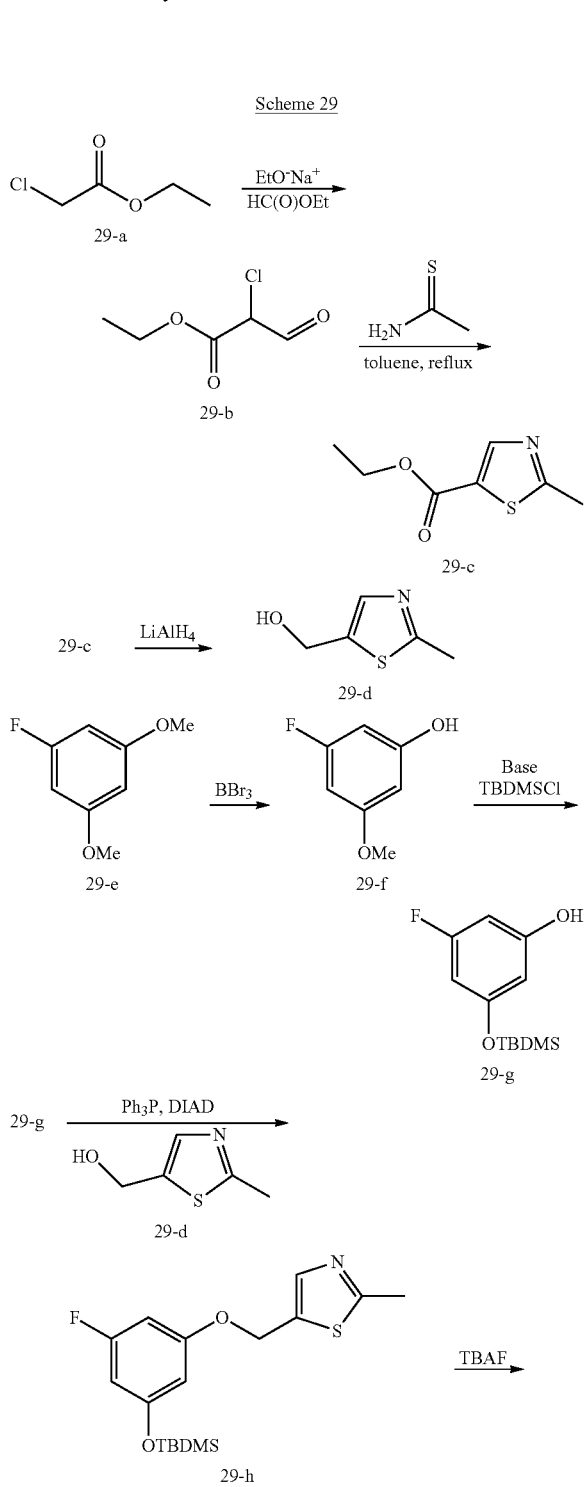

Step 1: Intermediate 28-a

To a solution of (3-methoxyphenyl)methanol (1.38 g, 10.0 mmol) in THF (20.0 mL) were sequentially added intermediate 11-a (2.69 g, 12.0 mmol), triphenylphosphine (3.15 g, 12.0 mmol) and DIAD (2.36 ml, 12.0 mmol) drop wise at room temperature and the reaction was then stirred overnight at room temperature. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 28-a as a colorless oil.

Step 2: Intermediate 28-b

Tetrabutylammonium fluoride trihydrate (2.88 g, 9.14 mmol) was added to a solution of intermediate 28-a (2.1 g, 6.10 mmol) in THF (10 mL) and the reaction was stirred at room temperature overnight. A saturated aqueous solution of ammonium chloride and ethyl acetate were added, the organic layer was separated, washed with brine, dried over MgSO₄, filtered and concentrated under reduced pressure. Purification by silica gel chromatography provided intermediate 28-b as a colorless oil.

Step 3: Compound 10

A solution of intermediate 10-a (200 mg, 0.65 mmol), intermediate 28-b (225 mg, 0.97 mmol), quinolin-8-ol (16.2 mg, 0.11 mmol), copper (I) chloride (11.0 mg, 0.1 mmol) and cesium carbonate (546 mg, 1.67 mmol), in dimethylacetamide (5.5 ml), was degassed with argon for 10 minutes, heated in a sealed tube at 140° C. overnight and then cooled to room temperature. Water and ethyl acetate were added,

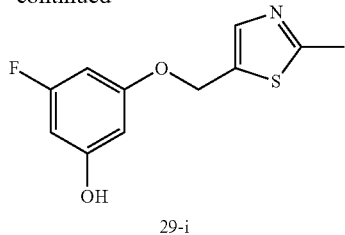

29-i

Step 1: Intermediate 29-b

Ethyl chloroacetate, 29-a (50.0 g, 0.41 mol), and ethyl formate (30.2 g, 0.41 mol) were taken in anhydrous toluene (500 mL) and cooled to 0° C. Sodium ethoxide (35.1 g, 0.49 mol) was added portion wise. The reaction mixture was stirred at 0° C. for 5 hours and then at room temperature overnight. The reaction mixture was quenched with water (250 mL) and washed twice with diethyl ether. The aqueous layer was cooled to 0° C. and acidified to pH 4-5 using 1 N HCl. The aqueous layer was extracted twice with diethyl ether; the combined organic layers were dried over MgSO$_4$ filtered and concentrated under reduced pressure to provide intermediate 29-b as beige oil.

Step 2: Intermediate 29-c

To a solution of ethyl 2-chloro-3-oxopropanoate, 29-b (34.7 g, 230 mmol), in toluene (250 ml) was added thioacetamide (26.0 g, 346.0 mmol), the reaction was stirred at 90° C. overnight and then cooled to room temperature, diluted with water (300 mL) and then neutralized to pH 7 with a saturated aqueous solution of NaHCO$_3$. Ethyl acetate was added, the organic layer was separated, washed with brine, dried over MgSO$_4$, filtered and concentrated under reduced pressure. Purification by silica gel chromatography provided intermediate 29-c as beige oil.

Step 4: Intermediate 29-d

To a solution of intermediate 29-c (22.2 g, 130.0 mmol) in THF (430 ml) cooled to 0° C. was added a 1.0 M solution of LiAlH$_4$ in THF (91.0 ml, 91.0 mmol) and the solution was slowly warmed to room temperature and stirred for 2 hours. Water (3.5 ml) was slowly added, followed by 3.5 ml 15% NaOH (3.5 ml) and water (10.5 ml) and the mixture was stirred for 1 hour. The reaction was filtered over celite and volatiles were removed in vacuo to provide intermediate 29-d as yellow oil.

Step 5: Intermediate 29-f

To a solution of 1-fluoro-3,5-dimethoxybenzene (12.5 g, 80 mmol) in dichloromethane (80 ml), cooled to 0° C., was added 1.0 M solution of boron tribromide in dichloromethane (200 ml, 200 mmol), drop wise over a period of 30 minutes. The reaction was stirred for 1 hour at 0° C. and then slowly warmed to room temperature and stirred for 18 hours. The reaction was cooled to 0° C. and quenched by the slow addition of MeOH and water. After stirring at room temperature for 1 hour the mixture was filtered and volatiles were removed in vacuo. Ethyl acetate was added to the residue; a precipitate formed and was collected by filtration to provide intermediate 29-f as an orange solid.

Step 6: Intermediate 29-g

To a solution of intermediate 29-f (10.25 g, 80.0 mmol) in DMF (50 ml), cooled to 0° C., was added imidazole (5.99 g, 88.0 mmol) and tert-butylchlorodimethylsilane (13.27 g, 88.0 mmol). The reaction was then stirred at room temperature overnight. A saturated aqueous solution of ammonium chloride and ethyl acetate were added, the organic layer was separated, washed 3 times with a saturated aqueous solution of ammonium chloride and brine, dried over MgSO$_4$, filtered and concentrated under reduced pressure. Purification by silica gel chromatography provided intermediate 29-g as a yellow oil.

Step 7: Intermediate 29-h

To a solution of intermediate 29-g (8.0 g, 33.1 mmol) and intermediate 29-d (4.70 g, 36.4 mmol) in THF (20 ml) were sequentially added triphenylphosphine (12.15 g, 46.3 mmol) and DIAD (9.0 ml, 46.3 mmol) at room temperature and the reaction was then stirred at room temperature overnight. Volatiles were removed under reduced pressure. Purification by silica gel chromatography provided intermediate 29-h as a yellow oil.

Step 8: Intermediate 29-i

To a solution of intermediate 29-h (6.0 g, 16.97 mmol) in THF (85 ml) was added a 1.0 M solution of TBAF in THF (16.97 ml, 16.97 mmol) and the reaction was stirred at room temperature for 1 hour. A saturated aqueous solution of ammonium chloride and ethyl acetate were added, the organic layer was separated, washed with brine, dried over MgSO$_4$, filtered and concentrated under reduced pressure. Diethyl ether was added to the residue; a precipitate formed and was collected by filtration to provide intermediate 29-i as white solid.

Synthesis of Intermediate 30-b

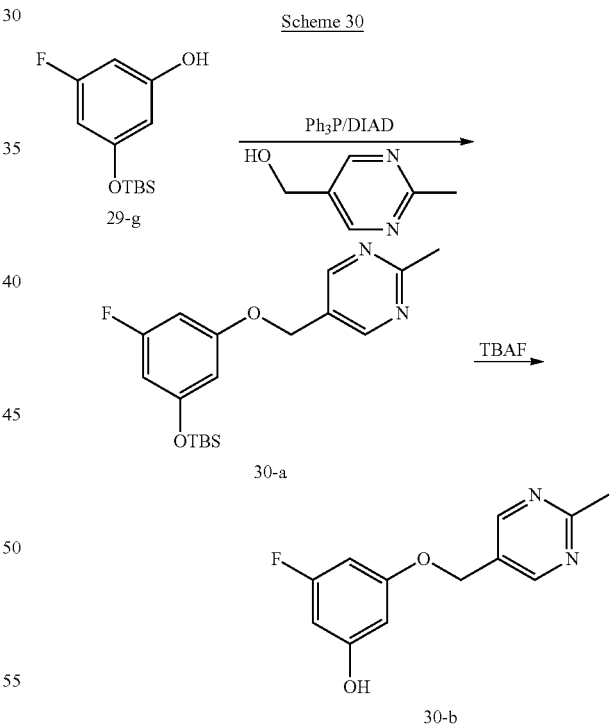

Step 1: Intermediate 30-a

To a solution of intermediate 29-g (9.0 g, 37.1 mmol) and 2-(methylpyrimidin-5-yl)methanol (4.61 g, 37.1 mmol) in THF (37 ml) were sequentially added triphenylphosphine (11.69 g, 44.6 mmol) and DIAD (9.39 ml, 48.3 mmol) at room temperature and the reaction was then stirred at room temperature for 4 days. Volatiles were removed under reduced pressure. Purification by silica gel chromatography provided intermediate 30-a as a yellow solid.

Step 2: Intermediate 30-b

To a solution of intermediate 30-a (12.5 g, 35.9 mmol) in THF (72 ml) was added a 1.0 M solution of TBAF in THF (35.9 ml, 35.9 mmol) and the reaction was stirred at room temperature for 1 hour. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediate 30-b as a white solid.

Synthesis of Intermediate 31-d

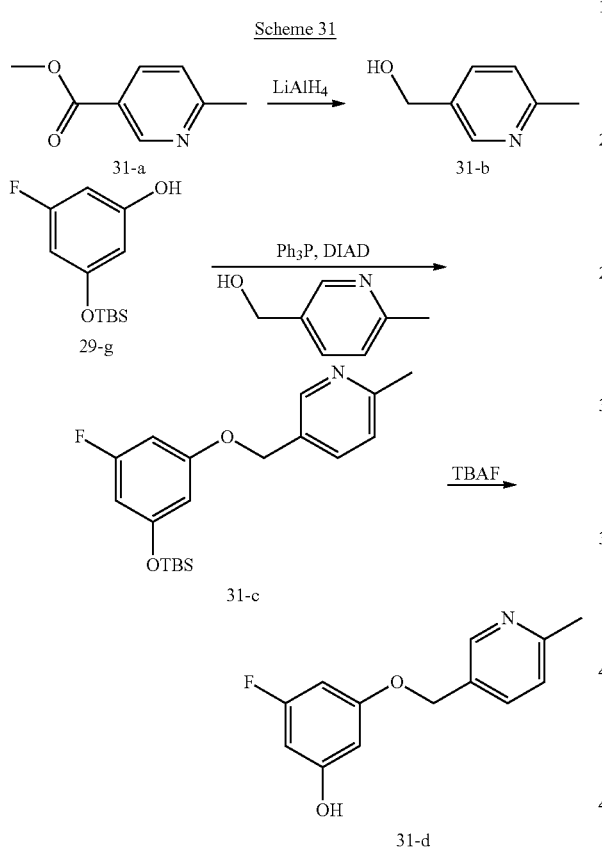

Step 1: Intermediate 31-b

To a solution of methyl 6-methylnicotinate 31-a (20.10 g, 133 mmol) in THF (90 ml) cooled to 0° C. was added drop wise a 1.0 M solution of $LiAlH_4$ in THF (100 ml, 100 mmol) and the reaction was then stirred at 0° C. for 1 hour. Water (3.8 ml) was slowly added, followed by 15% NaOH (3.5 ml) and water (11.4 ml) and the mixture was stirred at room temperature for 1 hour. The reaction was filtered over celite and volatiles were removed in vacuo to provide intermediate 31-b as a yellow oil.

Step 2: Intermediate 31-c

To a solution of intermediate 29-g (13.2 g, 54.5 mmol) and intermediate 31-b (7.38 g, 59.9 mmol) in THF (50 ml) were sequentially added triphenylphosphine (21.43 g, 82.0 mmol) and DIAD (17.10 ml, 87.0 mmol) at room temperature and the reaction was then stirred at room temperature for 1 hour. Volatiles were removed under reduced pressure. Purification by silica gel chromatography provided intermediate 31-c as a colorless oil.

Step 3: Intermediate 31-d

To a solution of intermediate 31-c (7.6 g, 21.87 mmol) in THF (44 ml) was added tetrabutylammonium fluoride trihydrate (5.72 g, 21.87 mmol) and the reaction was stirred at room temperature for 1 hour. Saturated aqueous ammonium chloride and ethyl acetate were added, the organic layer was separated, washed with brine, dried over $MgSO_4$, filtered and concentrated under reduced pressure. Purification by silica gel chromatography provided intermediate 31-d as white solid.

Synthesis of Intermediate 32-f

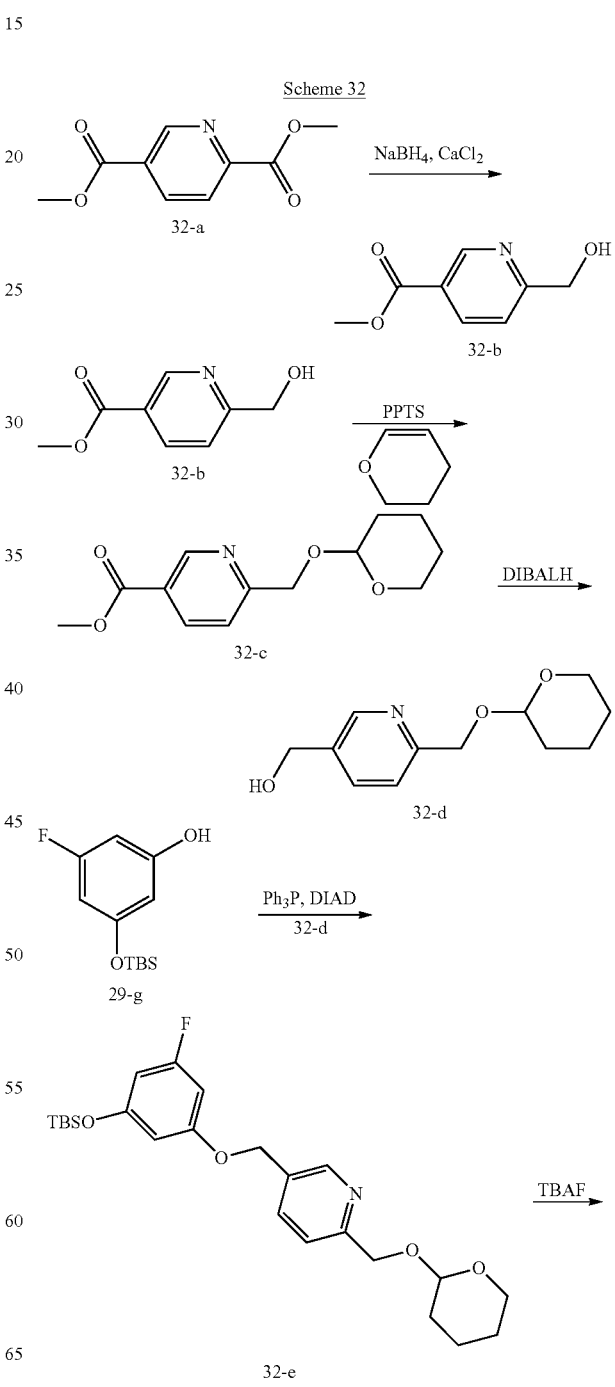

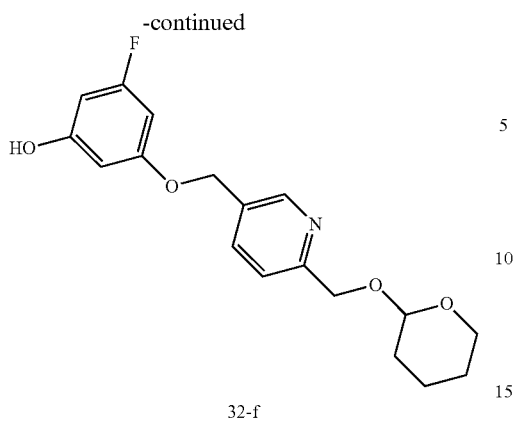

32-f

Step 1: Intermediate 32-b

To a solution of dimethyl pyridine-2,5-dicarboxylate (13.0 g, 66.6 mmol) in a mixture of THF (110 mL) and ethanol (110 mL) was added calcium chloride (29.6 g, 266 mmol). After stirring at room temperature for 30 minutes the reaction was cooled to 0° C. and sodium borohydride (3.78 g, 100 mmol) was added portion wise. After the addition was completed the reaction was stirred at room temperature overnight. A saturated aqueous solution of ammonium chloride and dichloromethane were added, the organic layer was separated and the aqueous phase was extracted twice with dichloromethane. The combined organic extracts were washed with brine, dried over MgSO$_4$, filtered and concentrated under reduced pressure to provide intermediate 32-b as a yellow solid.

Step 2: Intermediate 32-c

To a solution of intermediate 32-b (1.70 g, 10.17 mmol) in dichloromethane (203 mL) was added 3,4-dihydro-2H-pyran (4.28 g, 50.8 mmol) and PPTS (2.56 g, 10.17 mmol) and the reaction was stirred at room temperature overnight. Water was added and the organic layer was separated, washed with brine, dried over MgSO$_4$, filtered and concentrated under reduced pressure to provide intermediate 32-c as a white solid.

Step 3: Intermediate 32-d

To a solution of intermediate 32-c (2.56 g, 10.17 mmol) in THF (51 ml) cooled to 0° C. was added drop wise a 1.0 M solution of DIBALH in hexane (23.39 ml, 23.39 mmol) and the reaction was then stirred at 0° C. for 1.5 hour and room temperature overnight. Water (1.0 ml) was slowly added, followed 15% NaOH (3.5 ml) and water (2.3 ml) and the mixture was stirred at room temperature for 30 minutes. The reaction was filtered over celite and volatiles were removed under reduced pressure. Purification by silica gel chromatography provided intermediate 32-d as a yellow oil.

Step 4: Intermediate 32-e

To a solution of intermediate 29-g (1.57 g, 6.51 mmol) and intermediate 32-d (2.56 g, 7.17 mmol) in THF (7 ml) were sequentially added triphenylphosphine (2.56 g, 9.77 mmol) and DIAD (2.04 ml, 10.42 mmol) at room temperature and the reaction was then stirred at room temperature overnight. Volatiles were removed under reduced pressure. Purification by silica gel chromatography provided intermediate 32-e as a yellow solid.

Step 5: Intermediate 32-f

To a solution of intermediate 32-e (2.2 g, 4.91 mmol) in THF (9.8 ml) was added a 1.0 M solution of TBAF in THF (4.91 ml, 4.91 mmol) and the reaction was stirred at room temperature for 1 hour. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 32-f as a white solid.

Synthesis of Intermediate 33-a

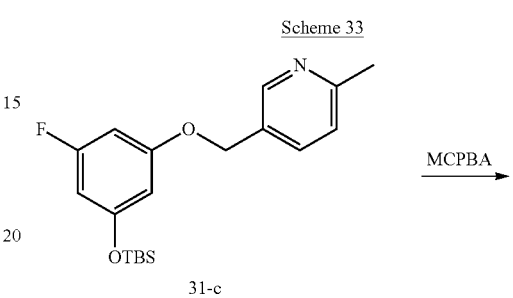

To a solution of intermediate 31-c (424 mg, 1.82 mmol) in dichloromethane (9.0 ml) was added m-CPBA (538 mg, 2.18 mmol) and the reaction was stirred at room temperature for 4 hours. A saturated aqueous solution of NaHCO$_3$ and dichloromethane were added, the organic layer was separated, washed with brine, dried over MgSO$_4$, filtered and concentrated under reduced pressure. Purification by silica gel chromatography provided intermediate 33-a as a white solid.

Synthesis of Intermediate 34-d

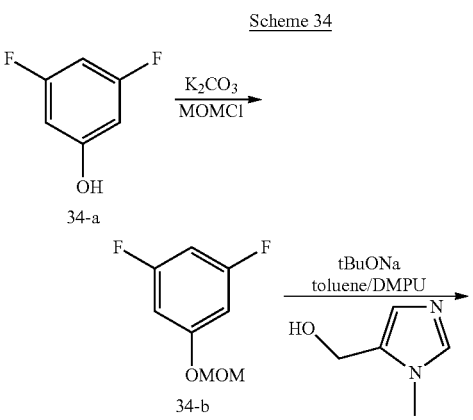

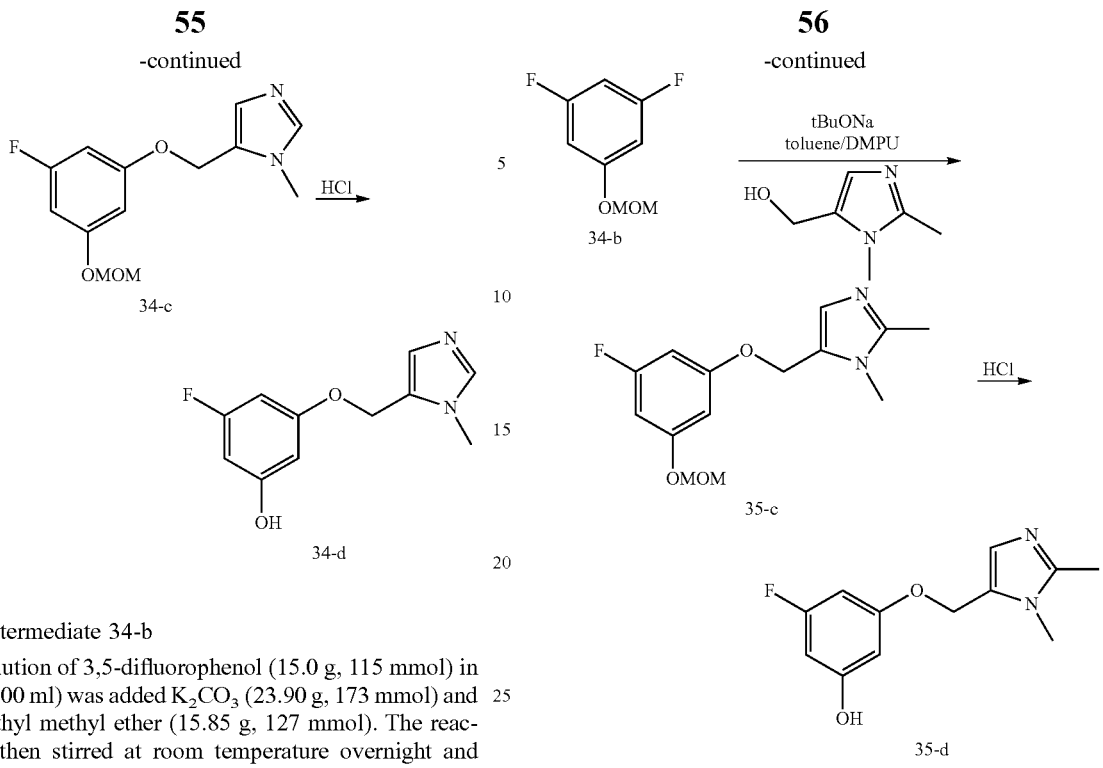

Step 1: Intermediate 34-b

To a solution of 3,5-difluorophenol (15.0 g, 115 mmol) in acetone (200 ml) was added K$_2$CO$_3$ (23.90 g, 173 mmol) and bromomethyl methyl ether (15.85 g, 127 mmol). The reaction was then stirred at room temperature overnight and filtered. The filtrate was concentrated under reduced pressure to provide intermediate 34-b as a colorless oil.

Step 2: Intermediate 34-c

To a solution of (1-methyl-1H-imidazol-5-yl) methanol (3.1 g, 27.6 mmol) and intermediate 34-b (4.01 g, 23.04 mmol) in toluene (25.0 ml) and DMPU (25.0 ml) was added sodium 2-methylpropan-2-olate (4.43 g, 46.1 mmol). The reaction was stirred overnight at 80° C. and then cooled to room temperature. A saturated aqueous solution of ammonium chloride and ethyl acetate were added, the organic layer was separated, washed twice with a saturated aqueous solution of ammonium chloride and brine, dried over MgSO$_4$, filtered and concentrated in vacuo. Purification by silica gel chromatography provided intermediate 34-c as beige oil.

Step 3: Intermediate 34-d

To a solution of intermediate 34-c (3.2 g, 12.02 mmol) in MeOH (25.0 ml) was added 4N HCl in dioxane (10.95 ml, 361.0 mmol) and the reaction was stirred overnight at room temperature. Volatiles were removed in vacuo. Diethyl ether was added to the residue; a precipitate formed and was collected by filtration to provide intermediate 34-d.HCl as a white solid.

Synthesis of Intermediate 35-d

Scheme 35

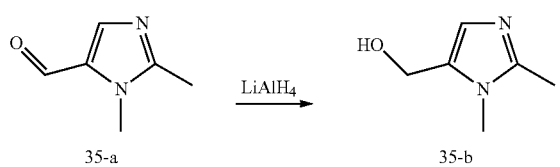

Step 1: Intermediate 35-b

To a solution of 1,2-dimethyl-1H-imidazole-5-carbaldehyde (1.0 g, 8.06 mmol) in THF (40.3 mL) cooled to 0° C. was added drop wise a 1.0 M solution of LiAlH$_4$ in THF (6.04 ml, 6.04 mmol) and the reaction was then stirred at room temperature for 1 hour. Water (250 uL) was slowly added, followed by 15% NaOH (250 uL) and water (750 uL) and the mixture was stirred at room temperature for 1 hour. The reaction was filtered over celite and volatiles were removed in vacuo to provide intermediate 35-b as a white solid.

Step 2: Intermediate 35-c

To a solution of intermediate 35-b (1.50 g, 11.89 mmol) and intermediate 34-b (2.07 g, 11.89 mmol) in DMPU (11.89 mL) and toluene (11.89 mL) was added sodium 2-methylpropan-2-olate (3.43 g, 35.7 mmol) at room temperature. The reaction was stirred overnight at 80° C. and then cooled to room temperature. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 35-c as a yellow oil.

Step 3: Intermediate 35-d

To a solution of intermediate 35-c (3.30 g, 11.77 mmol) in MeOH (36.2 mL) was added 4N HCl in dioxane (10.7 mL, 353 mmol) and the reaction was stirred at room temperature overnight. Volatiles were removed under reduced pressure. Diethyl ether was added to the residue; a precipitate formed and was collected by filtration to provide intermediate 35-d.HCl as a white solid.

Synthesis of Intermediate 36-f

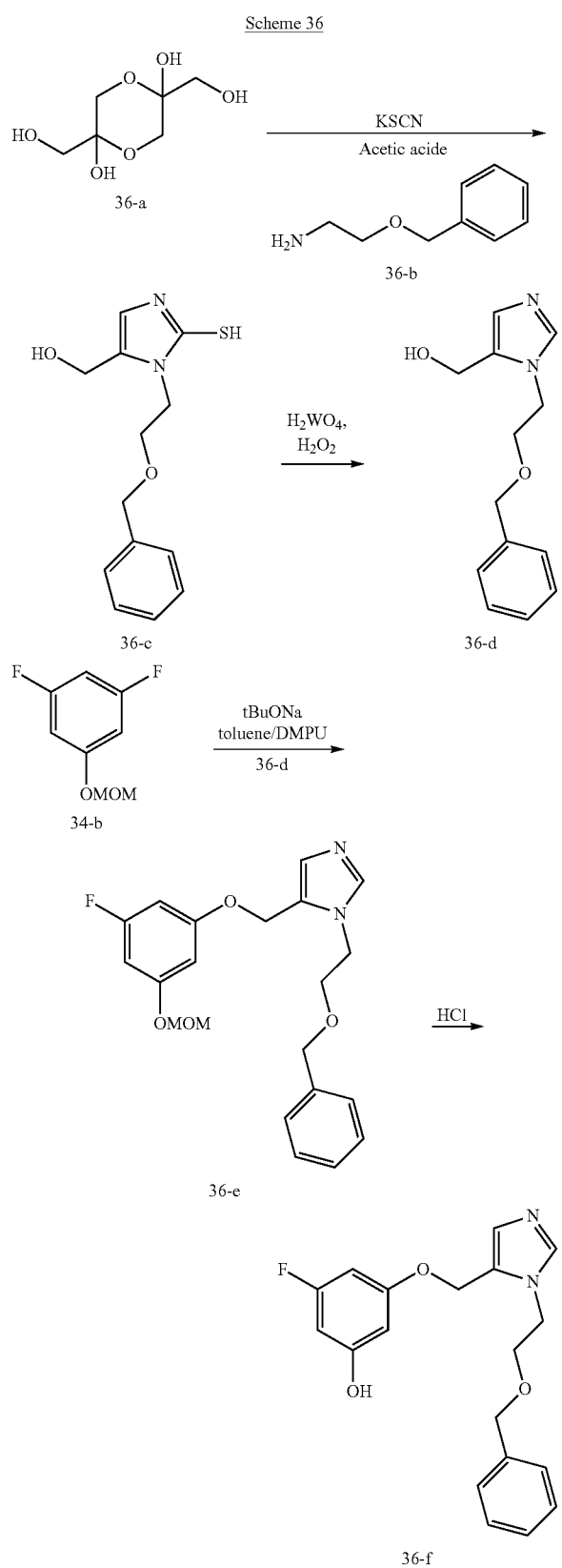

Step 1: Intermediate 36-c

To a suspension of 2-(benzyloxy)ethanamine HCl, 36-b (2.08 g, 11.10 mmol), and 2,5-bis(hydroxymethyl)-1,4-dioxane-2,5-diol 36-a (2.00 g, 11.10 mmol) in iPrOH (8 mL), were sequentially added potassium thiocyanate (1.62 g, 16.7 mmol) and acetic acid (2.03 mL, 35.5 mmol) drop wise. The mixture was stirred at room temperature overnight. Water was added; a precipitate formed and was collected by filtration to provide intermediate 36-c as a white solid.

Step 2: Intermediate 36-d

To a solution of intermediate 36-c (1.5 g, 5.67 mmol) and $H_2WO_4$ (14 mg, 0.057 mmol) in MeOH (22.7 mL) at 40° C. was added $H_2O_2$ (1.85 mL, 18.16 mmol) drop wise. The mixture was stirred at reflux overnight and then cooled to room temperature. Volatiles were removed under reduced pressure. Purification by silica gel chromatography provided intermediate 36-d as a colorless oil.

Step 3: Intermediate 36-e

To a solution of intermediate 36-d (1.46 g, 6.32 mmol) and intermediate 34-b (1.0 g, 5.74 mmol) in DMPU (11.48 ml) and toluene (11.48 ml) was added sodium 2-methylpropan-2-olate (1.10 g, 11.48 mmol) at room temperature. The reaction was stirred overnight at 80° C. and then cooled to room temperature. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediate 36-e as a colorless oil.

Step 4: Intermediate 36-f

To a solution of intermediate 36-e (400 mg, 1.03 mmol) in MeOH (10.4 mL) was added 4N HCl in dioxane (2.50 mL, 10.0 mmol) the reaction was stirred at room temperature overnight. Volatiles were removed under reduced pressure to provide intermediate 36-f.HCl as a white solid.

Synthesis of Intermediates 37-f and 37-f'

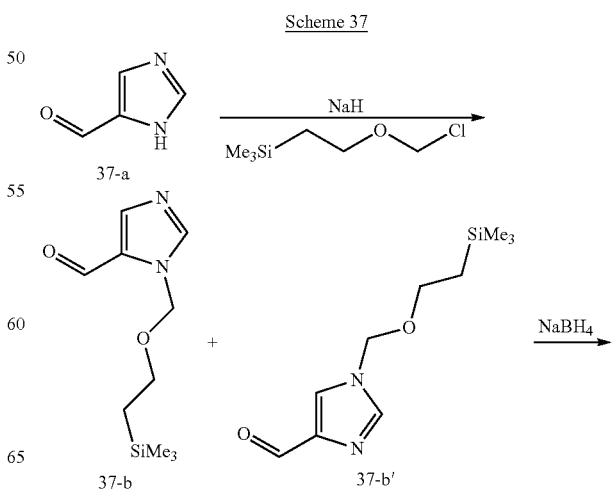

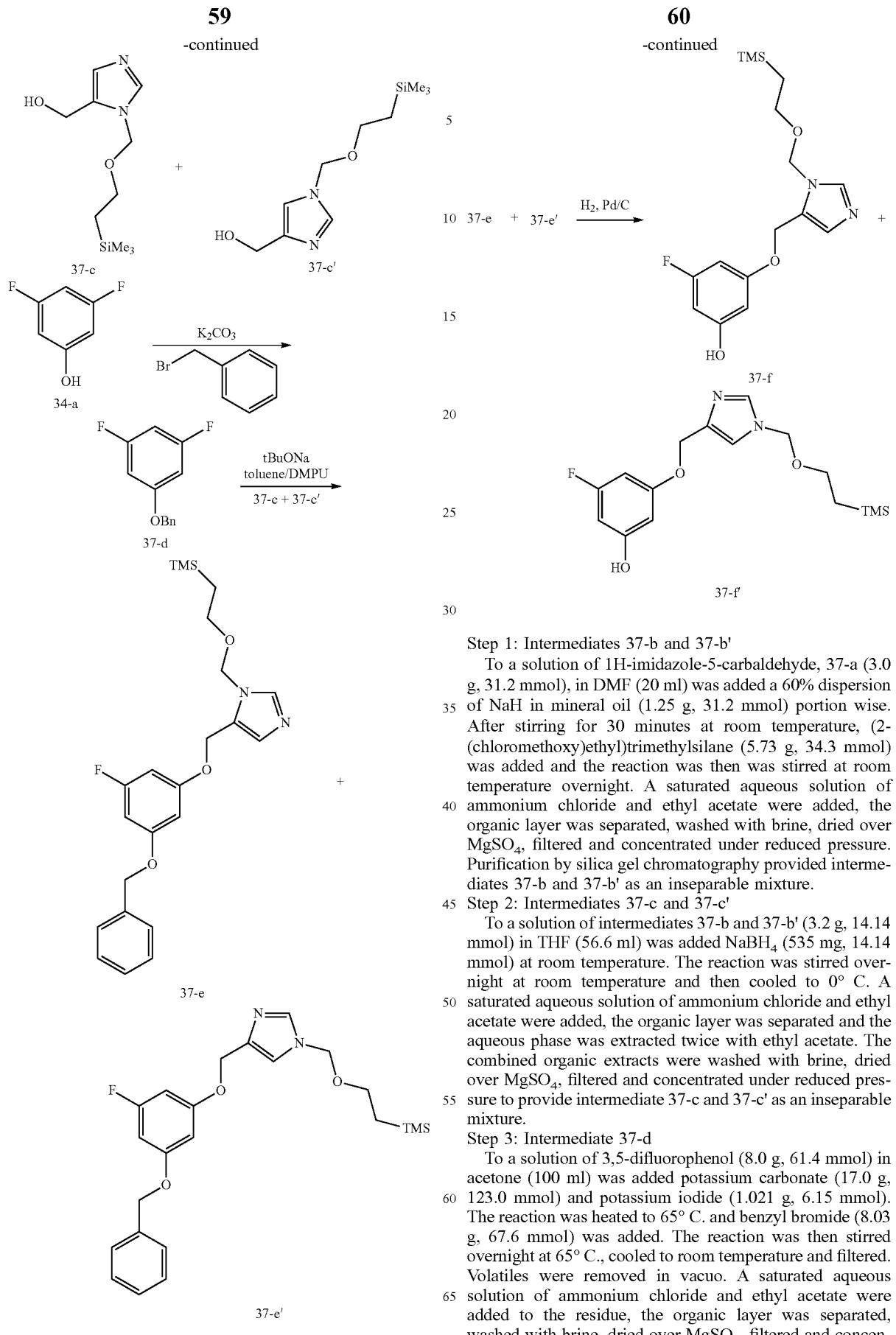

Step 1: Intermediates 37-b and 37-b'

To a solution of 1H-imidazole-5-carbaldehyde, 37-a (3.0 g, 31.2 mmol), in DMF (20 ml) was added a 60% dispersion of NaH in mineral oil (1.25 g, 31.2 mmol) portion wise. After stirring for 30 minutes at room temperature, (2-(chloromethoxy)ethyl)trimethylsilane (5.73 g, 34.3 mmol) was added and the reaction was then was stirred at room temperature overnight. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediates 37-b and 37-b' as an inseparable mixture.

Step 2: Intermediates 37-c and 37-c'

To a solution of intermediates 37-b and 37-b' (3.2 g, 14.14 mmol) in THF (56.6 ml) was added NaBH$_4$ (535 mg, 14.14 mmol) at room temperature. The reaction was stirred overnight at room temperature and then cooled to 0° C. A saturated aqueous solution of ammonium chloride and ethyl acetate were added, the organic layer was separated and the aqueous phase was extracted twice with ethyl acetate. The combined organic extracts were washed with brine, dried over MgSO$_4$, filtered and concentrated under reduced pressure to provide intermediate 37-c and 37-c' as an inseparable mixture.

Step 3: Intermediate 37-d

To a solution of 3,5-difluorophenol (8.0 g, 61.4 mmol) in acetone (100 ml) was added potassium carbonate (17.0 g, 123.0 mmol) and potassium iodide (1.021 g, 6.15 mmol). The reaction was heated to 65° C. and benzyl bromide (8.03 g, 67.6 mmol) was added. The reaction was then stirred overnight at 65° C., cooled to room temperature and filtered. Volatiles were removed in vacuo. A saturated aqueous solution of ammonium chloride and ethyl acetate were added to the residue, the organic layer was separated, washed with brine, dried over MgSO$_4$, filtered and concentrated in vacuo. Purification by silica gel chromatography provided intermediate 37-d as a colorless oil.

Step 4: Intermediate 37-e and 37-e'

To a solution of intermediates 37-c and 37-c' (1.0 g, 4.38 mmol) and intermediate 37-d (877 mg, 3.98 mmol) in DMPU (7.96 ml) and toluene (7.96 ml) was added sodium 2-methylpropan-2-olate (765 mg, 3.98 mmol) at room temperature. The reaction was stirred overnight at 80° C. and then cooled to room temperature. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediates 37-e and 37-e' as an inseparable mixture.

Step 5: Intermediates 37-f and 37-f'

A methanol solution of intermediate 37-e and 37-e' (140 mg, 0.32 mmol) was treated with 10% palladium on carbon (70 mg, 0.045 mmol) and purged with $H_2$. The solution was stirred under $H_2$ (1 atm) for 2 hours before being filtered through celite. The filtrate was concentrated in vacuo to provide intermediate 37-f and 37-f' as an inseparable mixture.

Synthesis of Intermediates 38-e and 38-e'

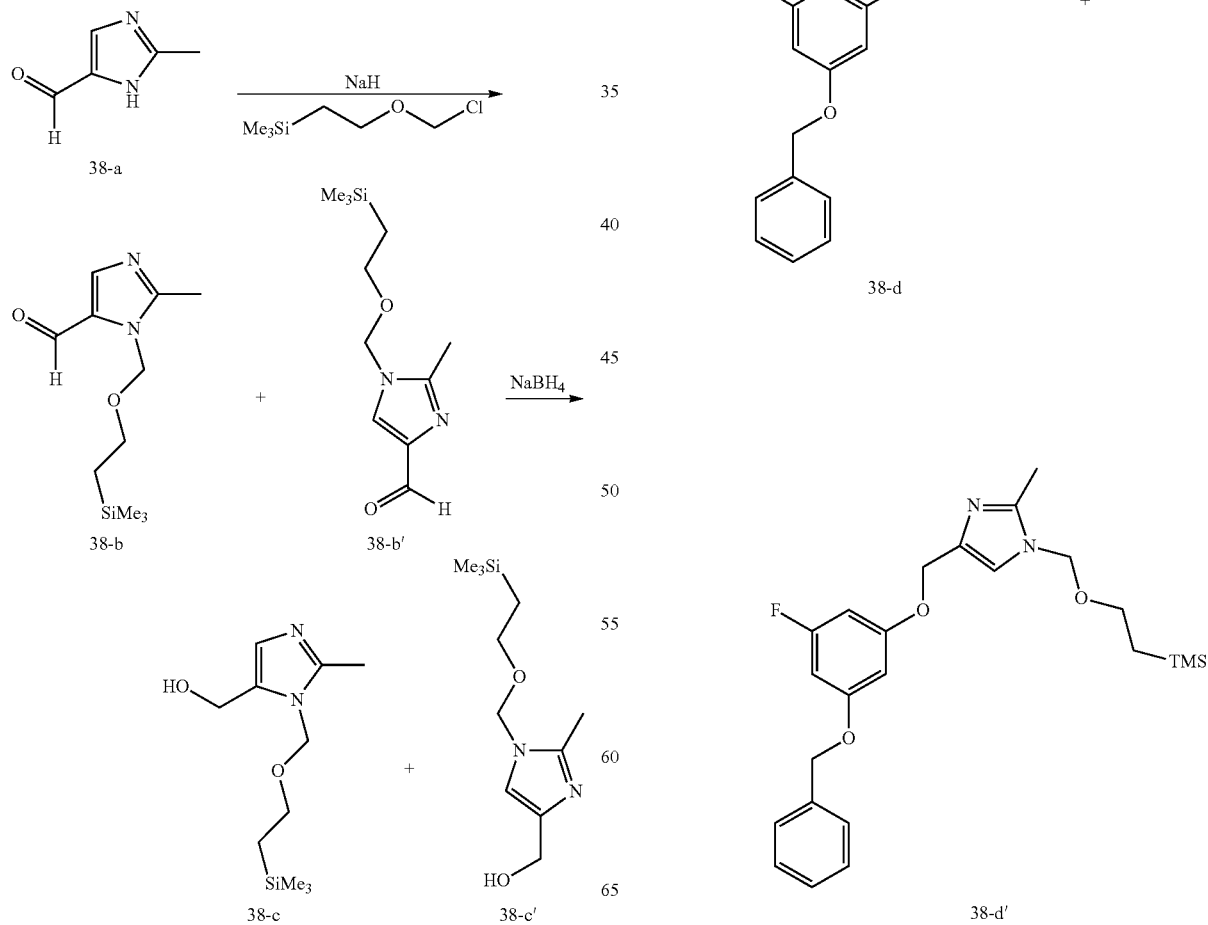

63

-continued

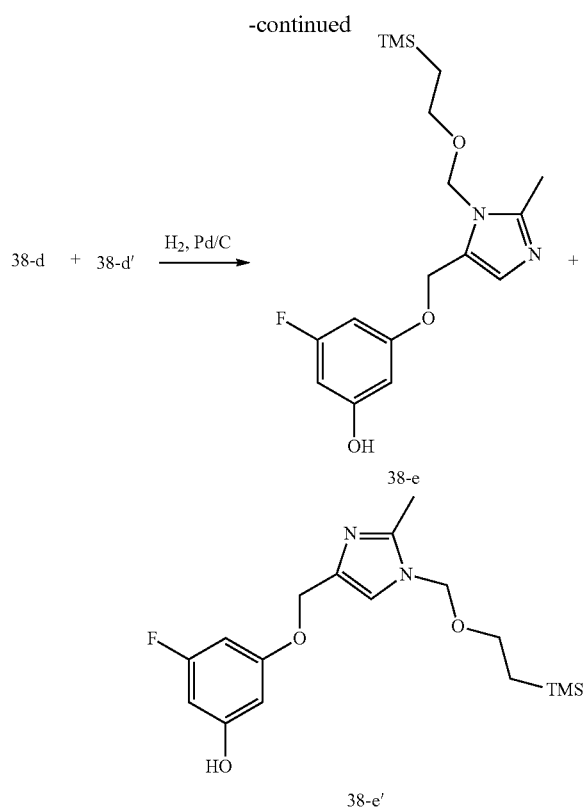

Step 1: Intermediates 38-b and 38-b'

To a solution of 1H-imidazole-5-carbaldehyde (5.0 g, 45.4 mmol) in DMF (20 mL) was added a 60% dispersion of NaH mineral oil (1.81 g, 45.4 mmol) portion wise. After stirring for 30 minutes at room temperature, (2-(chloromethoxy)ethyl)trimethylsilane (9.08 g, 54.5 mmol) was added and the reaction was then stirred at room temperature overnight. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediates 38-b and 38-b' as an inseparable mixture.

Step 2: Intermediates 38-c and 38-c'

To a solution of intermediate 38-b and 38-b' (7.0 g, 29.1 mmol) in THF (116.0 ml) was added $NaBH_4$ (1.10 g, 29.1 mmol) at room temperature. The reaction was stirred overnight at room temperature and then cooled to 0° C. A saturated aqueous solution of ammonium chloride and ethyl acetate were added, the organic layer was separated and the aqueous phase was extracted twice with ethyl acetate. The combined organic extracts were washed with brine, dried over $MgSO_4$, filtered and concentrated under reduced pressure to provide intermediates 38-c and 38-c' as an inseparable mixture.

Step 3: Intermediate 38-d and 38-d'

To a solution of intermediate 38-c and 38-c' (1.0 g, 4.13 mmol) and intermediate 37-d (826 mg, 3.75 mmol) in DMPU (7.50 ml) and toluene (7.50 ml) was added sodium 2-methylpropan-2-olate (721 mg, 7.50 mmol) at room temperature. The reaction was stirred overnight at 80° C. and then cooled to room temperature. A saturated aqueous solution of ammonium chloride and ethyl acetate were added, the organic layer was separated, washed with brine, dried over $MgSO_4$, filtered and concentrated under reduced pres-

64 sure. Purification by silica gel chromatography provided intermediates 38-d and 38-d' as an inseparable mixture.

Step 4: Intermediates 38-e and 38-e'

A methanol solution of intermediates 38-d and 38-d' (200 mg, 0.45 mmol) was treated with 10% palladium on carbon (96 mg, 0.045 mmol) and purged with $H_2$. The solution was stirred under $H_2$ (1 atm) for 2 hours before being filtered through celite. The filtrate was concentrated in vacuo to provide intermediate 38-e and 38-e' as an inseparable mixture.

Synthesis of Intermediate 39-b

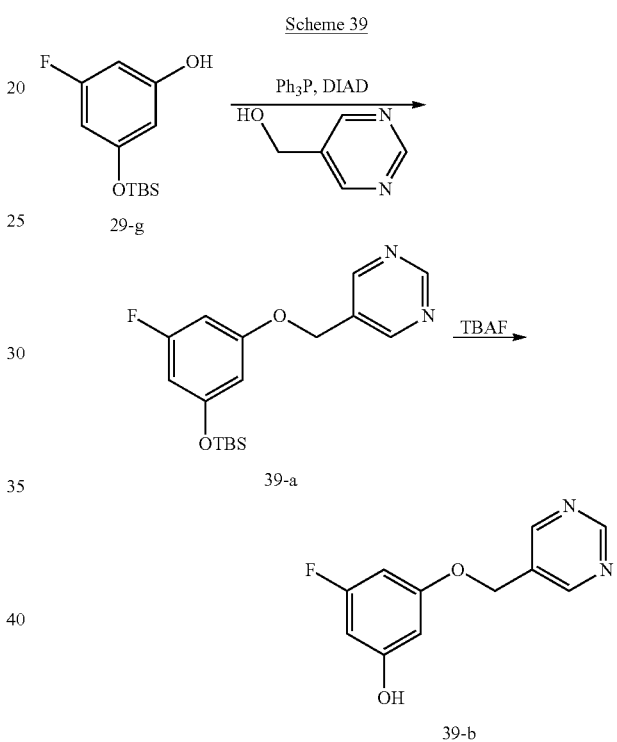

Step 1: Intermediate 39-a

To a solution of intermediate 29-g (4.20 g, 17.3 mmol) and pyrimidin-5-ylmethanol (1.90 g, 17.3 mmol) in THF (35 mL) were sequentially added triphenylphosphine (5.91 g, 22.5 mmol) and DIAD (4.38 mL, 22.5 mmol) at room temperature and the reaction was then stirred at room temperature for 3 hours. Volatiles were removed under reduced pressure. Purification by silica gel chromatography provided intermediate 39-a as a white solid.

Step 2: Intermediate 39-b

To a solution of intermediate 39-a (5.80 g, 17.3 mmol) in THF (35 mL) was added a 1.0 M solution of TBAF in THF (17.3 ml, 17.3 mmol) and the reaction was stirred at room temperature for 1 hour. A saturated aqueous solution of ammonium chloride and ethyl acetate were added, the organic layer was separated, washed with brine, dried over $MgSO_4$, filtered and concentrated under reduced pressure. Purification by silica gel chromatography provided intermediate 39-b as a white solid.

Synthesis of Intermediate 40-b

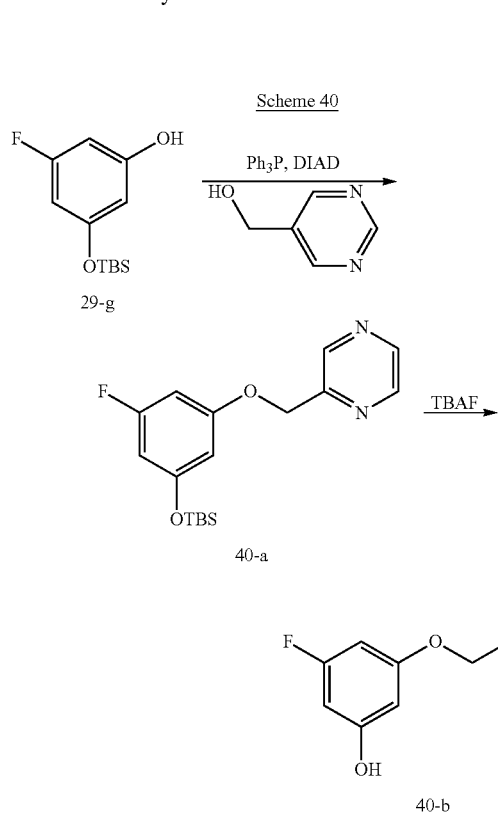

Step 1: Intermediate 40-a

To a solution of intermediate 29-g (4.62 g, 19.1 mmol) and pyrazin-2-ylmethanol (2.10 g, 19.1 mmol) in THF (38 mL) were sequentially added triphenylphosphine (7.50 g, 28.6 mmol) and DIAD (5.19 ml, 26.7 mmol) at room temperature and the reaction was then stirred at room temperature overnight. Volatiles were removed under reduced pressure. Purification by silica gel chromatography provided intermediate 40-a as a colorless oil.

Step 2: Intermediate 40-b

To a solution of intermediate 40-a (3.40 g, 10.2 mmol) in THF (20 mL) was added a 1.0 M solution of TBAF in THF (10.2 ml, 10.2 mmol) and the reaction was stirred at room temperature for 1 hour. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 40-b as a white solid.

Synthesis of Intermediate 41-b

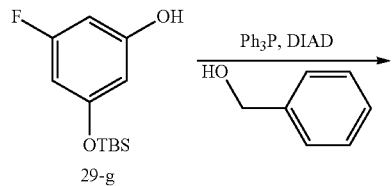

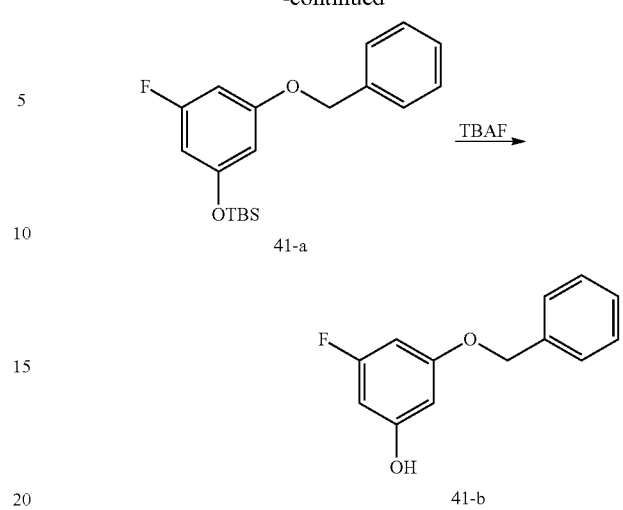

Step 1: Intermediate 41-a

To a solution of intermediate 29-g (2.60 g, 10.7 mmol) and benzyl alcohol (1.39 g, 12.9 mmol) in THF (20 mL) were sequentially added triphenylphosphine (3.94 g, 15.02 mmol) and DIAD (2.92 mL, 15.0 mmol) at room temperature and the reaction was then stirred at room temperature overnight. Volatiles were removed under reduced pressure. Purification by silica gel chromatography provided intermediate 41-a as colorless oil.

Step 2: Intermediate 41-b

To a solution of intermediate 41-a (1.40 g, 4.21 mmol) in THF (10 ml) was added a 1.0 M solution of TBAF in THF (4.63 ml, 4.63 mmol) and the reaction was stirred at room temperature overnight. A saturated aqueous solution of ammonium chloride and ethyl acetate were added, the organic layer was separated, washed with brine, dried over MgSO$_4$, filtered and concentrated under reduced pressure. Purification by silica gel chromatography provided intermediate 41-b as a colorless oil.

Synthesis of Intermediate 42-d

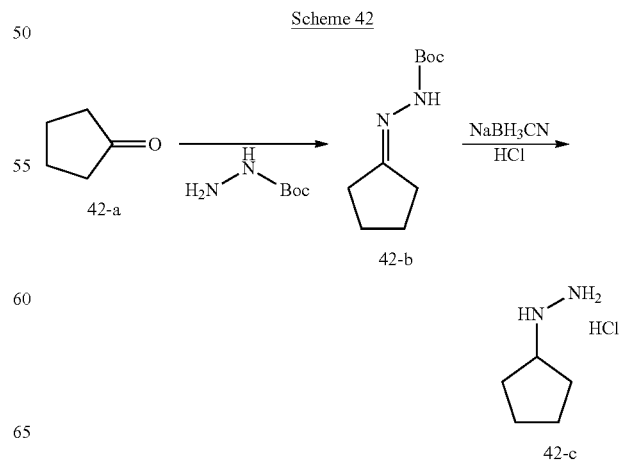

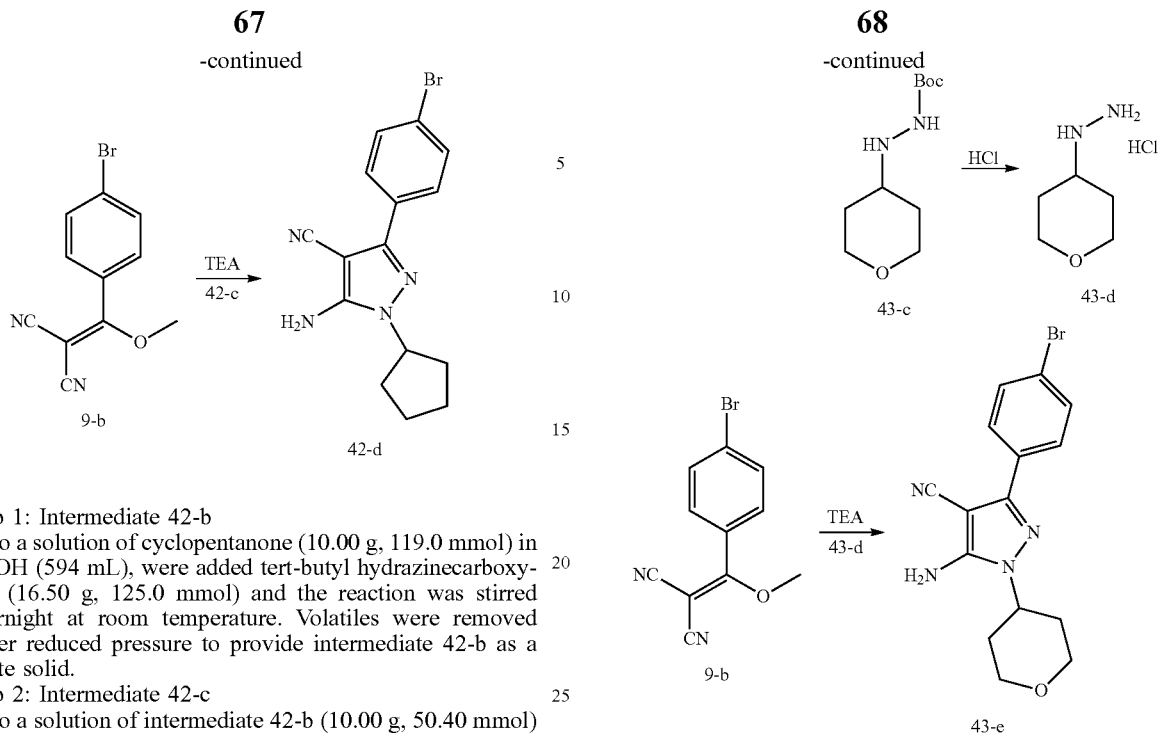

Step 1: Intermediate 42-b

To a solution of cyclopentanone (10.00 g, 119.0 mmol) in MeOH (594 mL), were added tert-butyl hydrazinecarboxylate (16.50 g, 125.0 mmol) and the reaction was stirred overnight at room temperature. Volatiles were removed under reduced pressure to provide intermediate 42-b as a white solid.

Step 2: Intermediate 42-c

To a solution of intermediate 42-b (10.00 g, 50.40 mmol) in THF (50.4 mL) and MeOH (50.4 mL) was added sodium cyanoborohydride (3.80 g, 60.5 mmol) portion wise. The reaction was refluxed under argon for 10 minutes, and then cooled to room temperature. 6N HCl (25 mL) was added, the mixture was refluxed for 3 hours, cooled to room temperature and stirred overnight. The reaction was filtered to remove inorganic insoluble material and the filtrate was concentrated under reduced pressure and azeotroped three times with toluene. The residue was dissolved in hot isopropanol, cooled to room temperature, diluted with ether and then cooled to 0° C. A precipitate formed and was collected by filtration to provide intermediate 42-c.HCl as a white solid.

Step 3: Intermediate 42-d

To a solution of intermediate 9-b (3.00 g, 11.4 mmol) and TEA (3.50 mL, 25.1 mmol) in EtOH (11.4 mL) was added intermediate 42-c.HCl (1.86 g, 13.7 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure. Purification by silica gel chromatography provided intermediate 42-d as a white solid.

Synthesis of Intermediate 43-e

Scheme 43

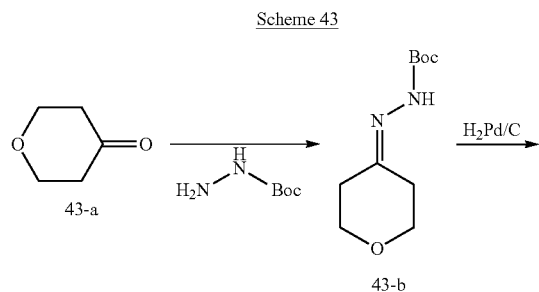

Step 1: Intermediate 43-b

To a solution of dihydro-2H-pyran-4-(3H)-one (15.0 g, 150.0 mmol) in MeOH (749 mL), were added tert-butyl hydrazinecarboxylate (20.79 g, 157.0 mmol) and the reaction was stirred overnight at room temperature. Volatiles were removed under reduced pressure to provide intermediate 43-b as a white solid.

Step 2: Intermediate 43-c

A methanol solution of intermediate 43-b (32.1 g, 150.0 mmol) was treated with 10% palladium on carbon (6.39 g, 3.00 mmol), acetic acid (100 µL) and purged with H$_2$. The solution was stirred under H$_2$ (1 atm) overnight before being filtered through celite. The filtrate was concentrated in vacuo to provide intermediate 43-c as a white solid.

Step 3: Intermediate 43-d

To a solution of intermediate 43-c (32.4 g, 150 mmol) in MeOH (300 mL) was added 4N HCl in 1,4-dioxane (300 ml, 1200 mmol) and the reaction was stirred at room temperature for 5 hours. Diethyl ether was added and a precipitate formed which was collected by filtration to provide intermediate 43-d.HCl as a white solid.

Step 4: Intermediate 43-e

To a solution of intermediate 9-b (5.00 g, 19.0 mmol) and TEA (5.30 mL, 38.0 mmol) in EtOH (19.0 mL) was added intermediate 43-c.HCl (3.48 g, 22.81 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure to provide intermediate 43-e as a yellow solid.

Synthesis of Intermediate 44-d

Scheme 44

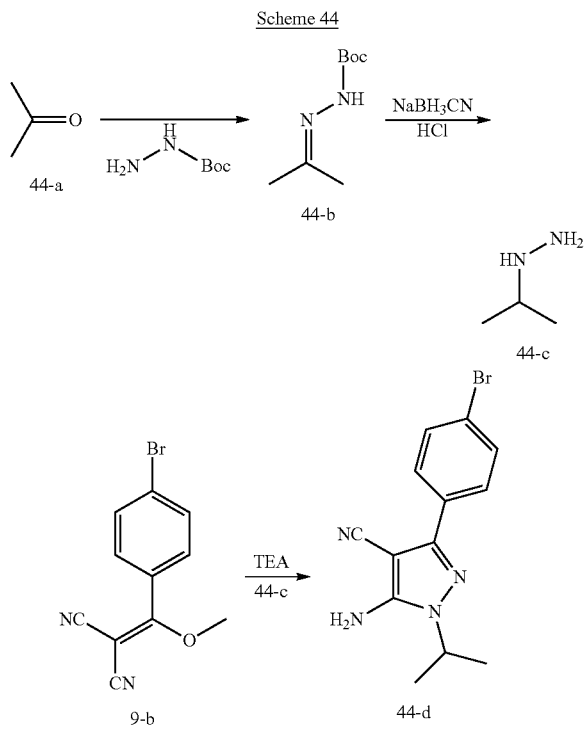

Step 1: Intermediate 44-b tert-Butyl hydrazinecarboxylate (7.60 g, 57.5 mmol) was added to acetone (50 mL) and the reaction was stirred overnight at room temperature. Volatiles were removed under reduced pressure to provide intermediate 44-b as a white solid.

Step 2: Intermediate 44-c

To a solution of intermediate 44-b (9.90 g, 57.5 mmol) in THF (57.5 mL) and MeOH (57.5 mL) was added sodium cyanoborohydride (4.34 g, 69.0 mmol) portion wise. The reaction was refluxed under nitrogen for 10 minutes, and then cooled to room temperature. 6N HCl (30 mL) was added, the mixture was refluxed for 3 hours, cooled to room temperature and stirred overnight. The reaction was filtered to remove inorganic insoluble material and the filtrate was concentrated under reduced pressure and azeotroped three times with toluene for complete water removal. The residue was dissolved in hot isopropanol, cooled to room temperature, diluted with ether and then cooled to 0° C. A precipitate formed and was collected by filtration to provide intermediate 44-c.HCl as a white solid.

Step 3: Intermediate 44-d

To a solution of intermediate 9-b (12.61 g, 47.9 mmol) and TEA (14.70 mL, 105.0 mmol) in EtOH (96.0 ml) was added intermediate 44-c.HCl (6.36 g, 57.5 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over $MgSO_4$, filtered and concentrated under reduced pressure. Purification by silica gel chromatography provided intermediate 44-d as a white solid.

Synthesis of Intermediate 45-a

Scheme 45

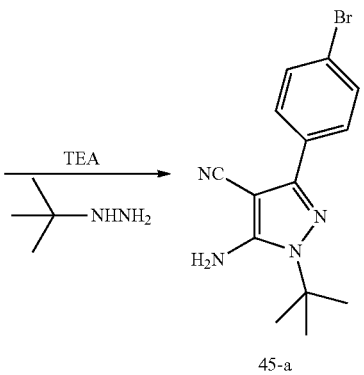

To a solution of intermediate 9-b (2.0 g, 7.60 mmol) and TEA (2.12 ml, 15.2 mmol) in EtOH (7.60 mL) was added tert-butylhydrazine hydrochloride (1.13 g, 9.12 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over $MgSO_4$, filtered and concentrated under reduced pressure to provide intermediate 45-a as a yellow solid.

Synthesis of Intermediate 46-a

Scheme 46

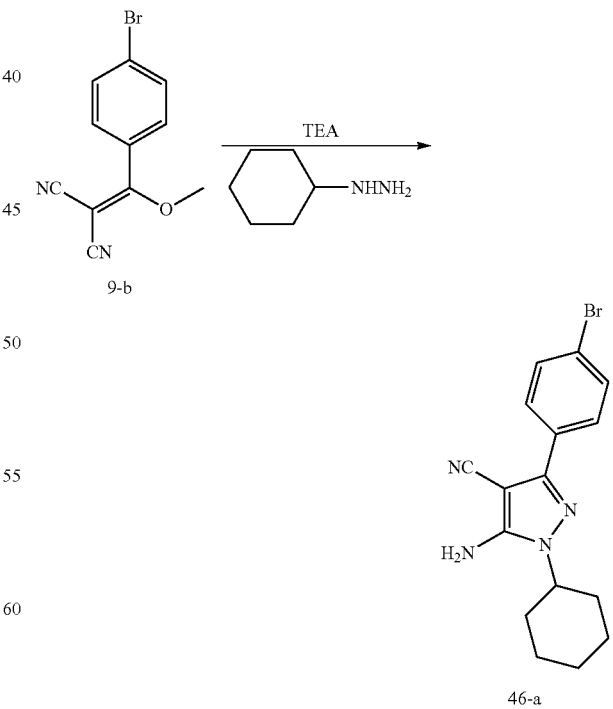

To a solution of intermediate 9-b (1.45 g, 5.53 mmol) and TEA (1.54 mL, 11.1 mmol) in EtOH (15.0 mL) was added cyclohexylhydrazine hydrochloride (1.00 g, 6.64 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure to provide intermediate 46-a as a yellow solid.

Synthesis of Intermediate 47-a

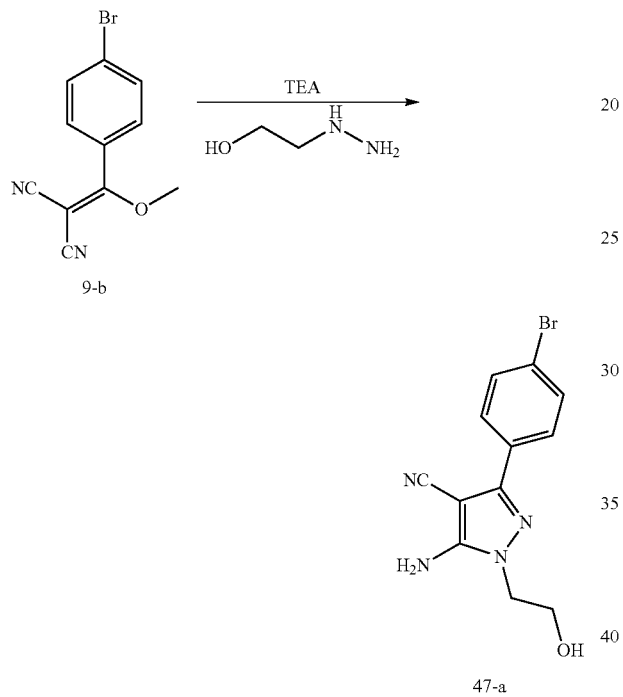

To a solution of intermediate 9-b (2.00 g, 7.60 mmol) and TEA (1.27 mL, 9.12 mmol) in EtOH (7.60 mL) was added 2-hydroxyethylhydrazine (618 μL, 9.12 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure to provide intermediate 47-a as a white solid.

Synthesis of Intermediate 48-c

Scheme 48

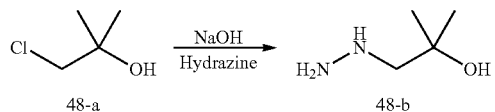

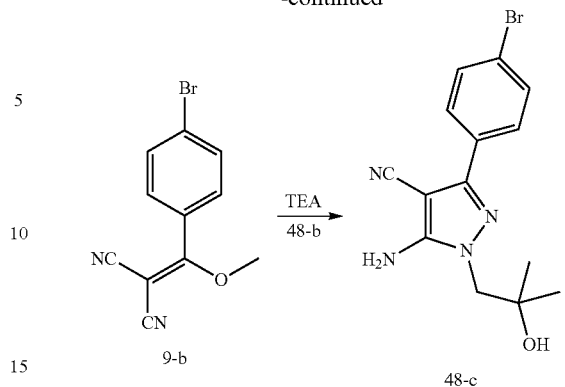

Step 1: Intermediate 48-b
To a mixture of sodium hydroxide (7.37 g, 184.0 mmol) and hydrazine monohydrate (46.10 g, 921.0 mmol) heated to 95° C., was added 1-chloro-2-methylpropan-2-ol (20.00 g, 184.0 mmol). The reaction was stirred overnight at 95° C. and then cooled to room temperature. Volatiles were removed under reduced pressure. THF (40 mL) and diethyl ether (40 mL) were added to the residue; a precipitate formed which was removed by filtration. The filtrate was concentrated under reduced pressure to provide intermediate 48-b as a colorless oil.

Step 2: Intermediate 48-c
To a solution of intermediate 9-b (4.45 g, 16.9 mmol) and TEA (4.71 mL, 33.8 mmol) in EtOH (15.0 mL) was added intermediate 48-b (1.76 g, 16.9 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure to provide intermediate 48-c as a white solid.

Synthesis of Intermediate 49-c

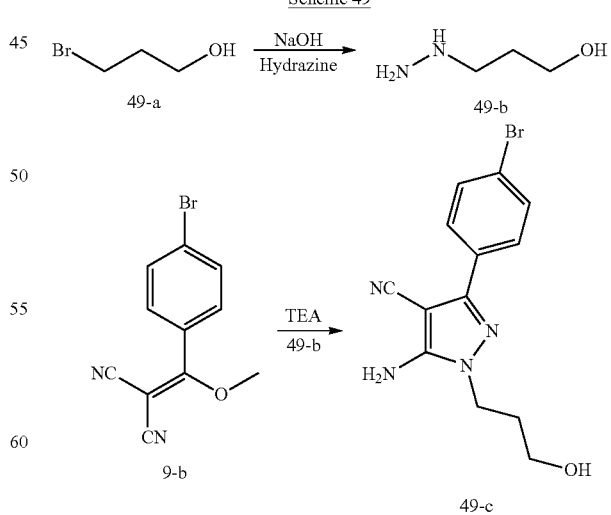

Step 1: Intermediate 49-b
To a mixture of sodium hydroxide (1.15 g, 28.8 mmol) and hydrazine monohydrate (7.20 g, 144.0 mmol) heated to 95° C., was added 3-bromo-1-propanol (4.00 g, 28.8 mmol) and the reaction was stirred overnight at 95° C. and then cooled to room temperature. Volatiles were removed under reduced pressure. Ethanol was added to the residue; a precipitate formed and was removed by filtration. The filtrate was concentrated under reduced pressure and 1M HCl in diethyl was added to the residue. After stirring for 15 minutes a precipitate formed and was collected by filtration to provide intermediate 49-b.HCl as a white solid.

Step 2: Intermediate 49-c

To a solution of intermediate 9-b (1.12 g, 4.28 mmol) and TEA (1.19 mL, 8.56 mmol) in EtOH (10.0 mL) was added intermediate 49-b.HCl (650 mg, 5.13 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure to provide intermediate 49-c as a white solid.

Synthesis of Intermediate 50-c

Step 2: Intermediate 50-b

To a solution of intermediate 50-a (10.0 g, 49.0 mmol) in THF (49.0 mL) and MeOH (49.0 mL) was added sodium cyanoborohydride (3.69 g, 58.8 mmol) portion wise. The reaction was refluxed under nitrogen for 10 minutes, and then cooled to room temperature. 6N HCl (40 mL) was added, the mixture was refluxed for 3 hours, cooled to room temperature and stirred overnight. The reaction was filtered to remove inorganic insoluble material and the filtrate was concentrated under reduced pressure and azeotroped three times with toluene to provide intermediate 50-b.HCl as a white solid.

Step 3: Intermediate 50-c

To a solution of intermediate 9-b (10.70 g, 40.9 mmol) and TEA (12.5 mL, 90.0 mmol) in EtOH (40.9 mL) was added intermediate 50-b.HCl (7.00 g, 49.1 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure. Purification by silica gel chromatography provided intermediate 50-c as a beige solid.

Synthesis of Intermediate 51-a

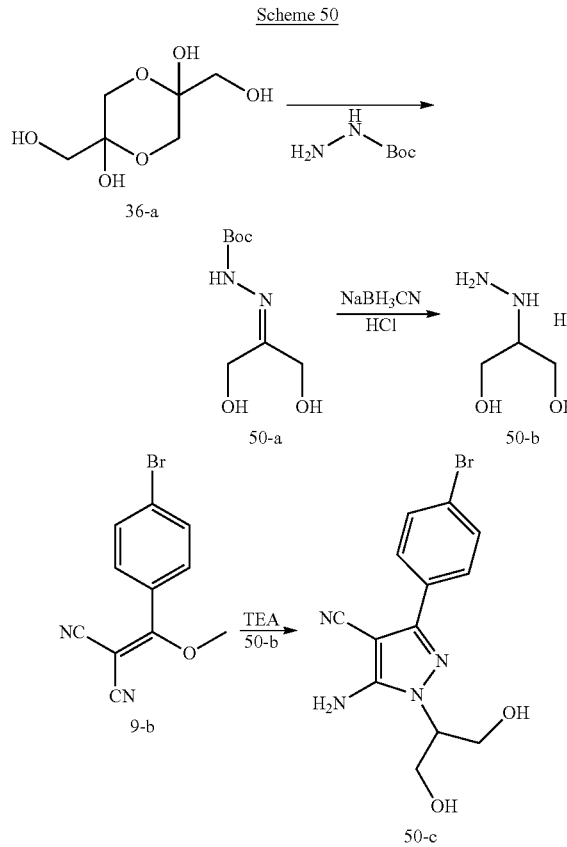

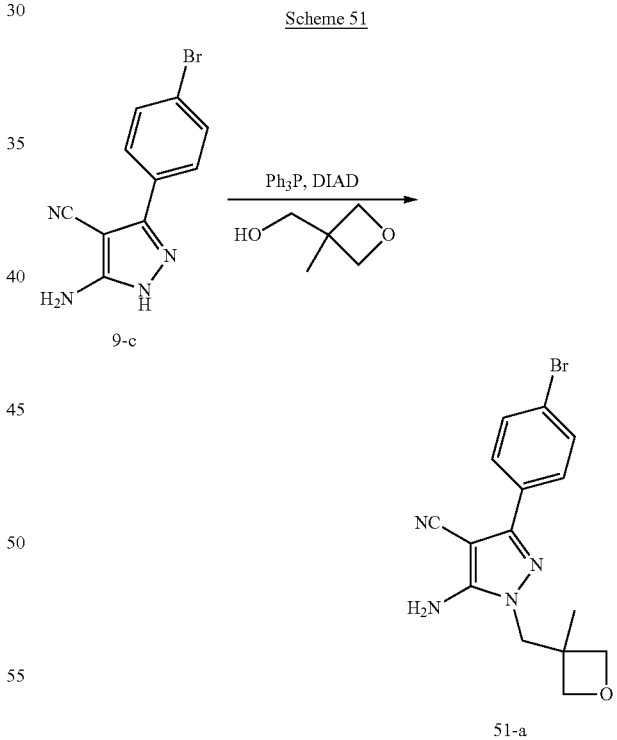

Step 1: Intermediate 50-a

Dihydroxyacetone dimer (15.0 g) and tert-butyl hydrazinecarboxylate (22.01 g) were dissolved in ethanol (500 mL) and this solution was stirred at room temperature for 2 days. After the reaction mixture was concentrated under reduced pressure, the resulting residue was recrystallized from ethyl acetate to provide intermediate 50-a as a white solid.

To a solution of intermediate 9-c (1.40 g, 5.32 mmol) and 3-methyloxetan-3-yl)methanol (1.08 g, 10.64 mmol) in THF (5.3 mL) were sequentially added triphenylphosphine (1.67 g, 6.39 mmol) and DIAD (1.13 mL, 5.85 mmol) at room temperature and the reaction was then stirred at room temperature for 4 days. Volatiles were removed under reduced pressure. Purification by silica gel chromatography provided intermediate 51-a as a white solid.

Synthesis of Intermediate 52-a

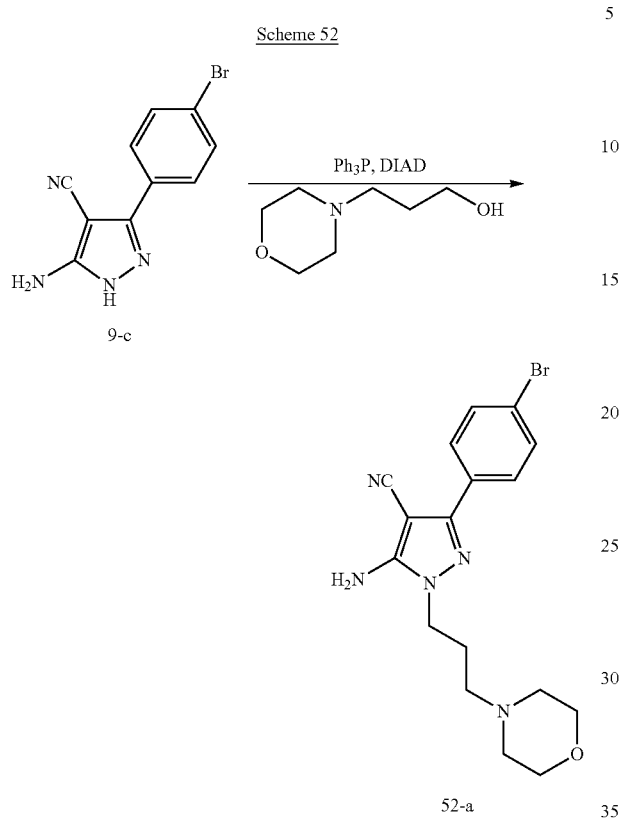

To a solution of intermediate 9-c (500 mg, 1.90 mmol) and 3-morpholinopropan-1-ol (263 µl, 1.90 mmol) in THF (19.0 ml) cooled to 0° C. were sequentially added triphenylphosphine (498 mg, 1.90 mmol) and DIAD (370 µl, 1.90 mmol). The reaction was stirred at 0° C. for 1 hour and room temperature overnight. Volatiles were removed under reduced pressure. Purification by silica gel chromatography provided intermediate 52-a as a white foam.

Synthesis of Intermediate 53-a

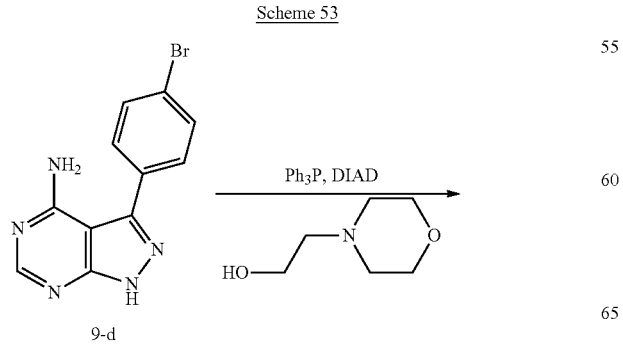

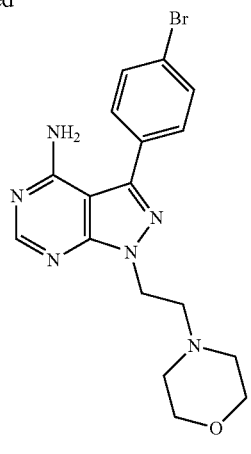

To a solution of intermediate 9-d (3.00 g, 10.3 mmol) and N-(2-hydroxyethyl)morpholine (1.88 ml, 15.1 mmol) in THF (103 ml) cooled to 0° C. were sequentially added triphenylphosphine (4.07 mg, 15.1 mmol) and DIAD (3.02 ml, 15.5 mmol). The reaction was stirred at 50° C. overnight. Volatiles were removed under reduced pressure. Purification by silica gel chromatography provided intermediate 53-a as a white solid.

Synthesis of Intermediate 54-a

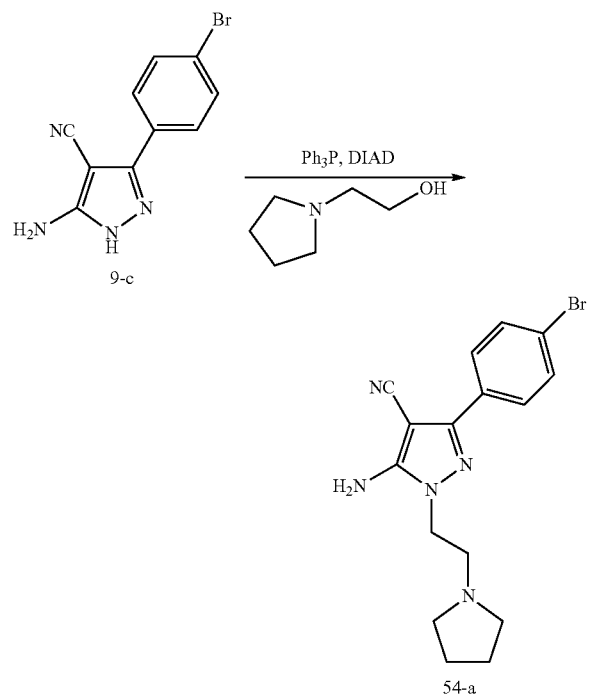

To a solution of intermediate 9-c (500 mg, 1.90 mmol) and 2-(pyrrolidin-1-yl)ethanol (219 mg, 1.90 mmol) in THF (9.5 ml) cooled to 0° C. were sequentially added triphenylphosphine (498 mg, 1.90 mmol) and DIAD (370 µl, 1.90 mmol). The reaction was stirred at 0° C. for 1 hour and room temperature for 30 minutes. Volatiles were removed under reduced pressure. Purification by silica gel chromatography provided intermediate 54-a as yellow solid.

Synthesis of Compound 65

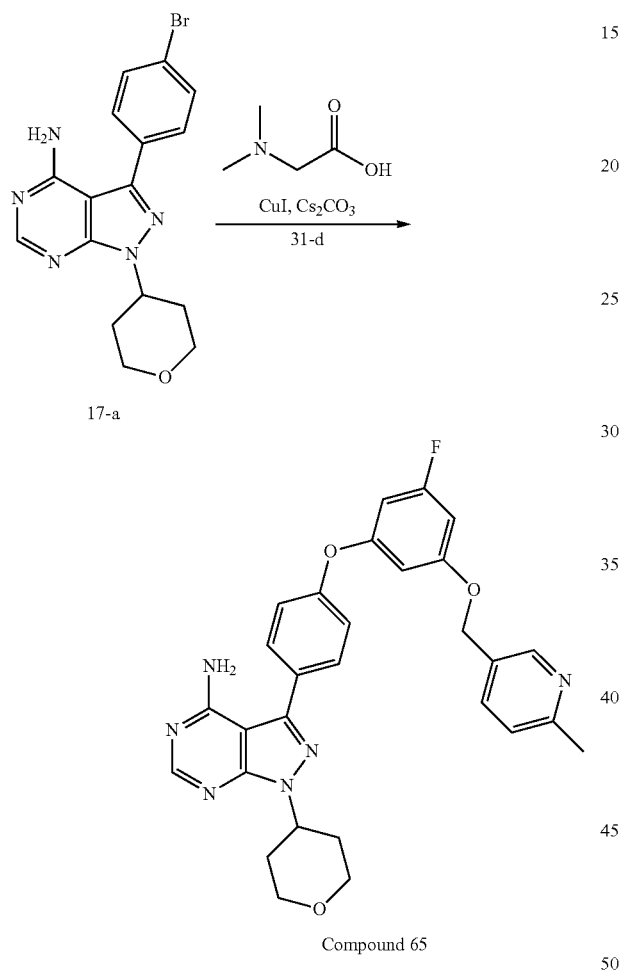

To a solution of intermediate 17-a (321 mg, 0.85 mmol) and intermediate 31-d (200 mg, 0.85 mmol) in 1,4-dioxane (4.30 ml) were sequentially added N,N-dimethylglycine (265 mg, 2.57 mmol), copper(I) iodide (163 mg, 0.85 mmol) and cesium carbonate (1.12 g, 3.43 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over $MgSO_4$, filtered and concentrated under reduced pressure. Purification by reverse phase chromatography eluting with a 1% aqueous HCl/methanol gradient provided compound 65.2HCl as a white solid.

Synthesis of Compound 85

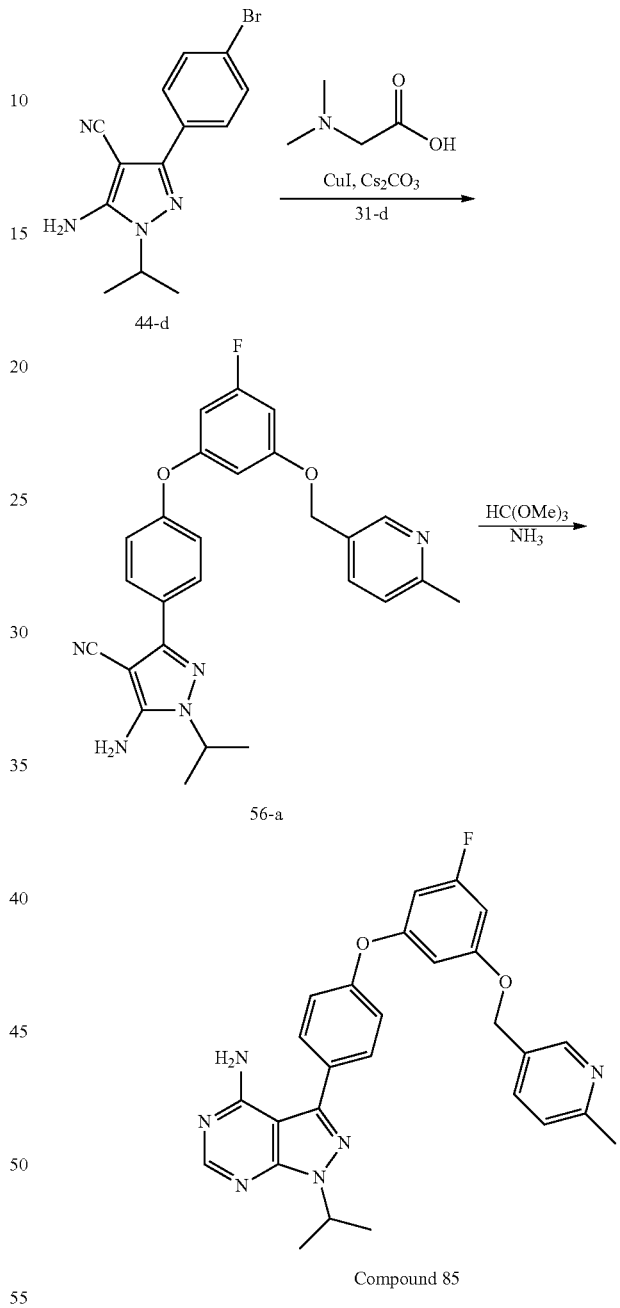

Step 1: Intermediate 56-a

To a solution of intermediate 44-d (5.00 g, 16.4 mmol) and intermediate 31-d (4.20 g, 18.0 mmol) in 1,4-dioxane (54.6 ml) were sequentially added N,N-dimethylglycine (3.80 g, 36.9 mmol), copper(I) iodide (2.34 g, 12.29 mmol) and cesium carbonate (21.35 g, 65.5 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 56-a.HCl as a white solid.

Step 2: Compound 85

Intermediate 56-a.HCl (3.13 g, 6.84 mmol) and trimethyl orthoformate (48.7 ml, 445.0 mmol) were heated at 110° C. for 3 hours. Excess trimethyl orthoformate was removed in vacuo and the residue was treated with ammonia (7.0 N in MeOH) (48.9 ml, 342.0 mmol). The mixture was stirred at room temperature for 3 days and volatiles were removed under reduced pressure. Purification by reverse phase chromatography eluting with a 1% aqueous HCl/methanol gradient provided compound 85.2HCl as a white solid. MS (m/z) M+H=485.2

Synthesis of Compound 91

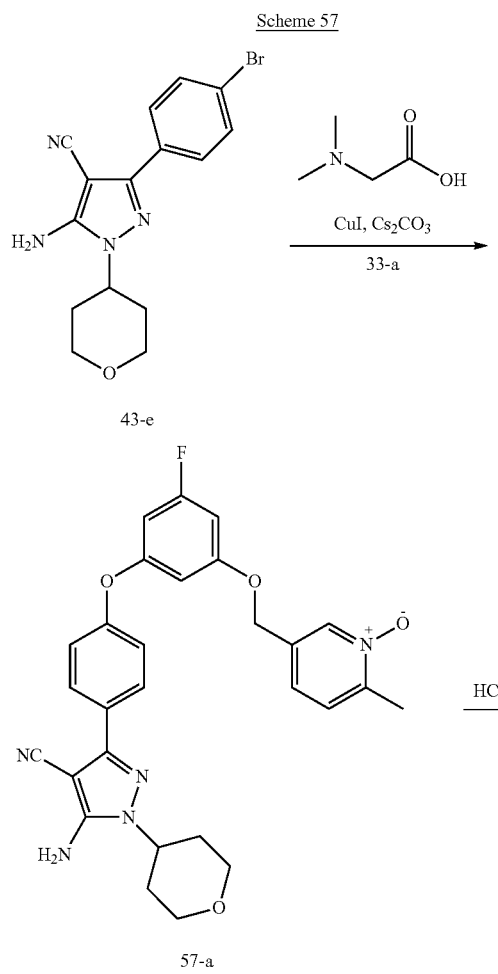

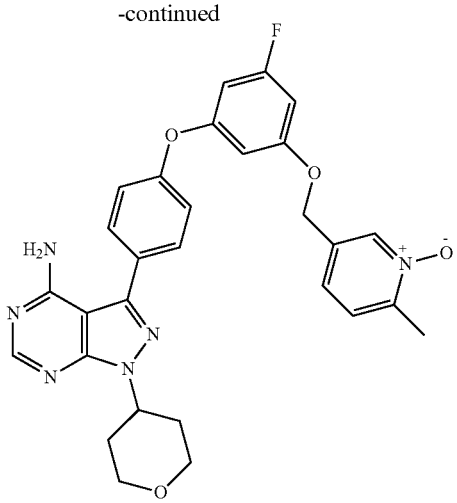

Compound 91

Step 1: Intermediate 57-a

To a solution of intermediate 43-e (192 mg, 0.55 mmol) and intermediate 33-a (190 mg, 0.66 mmol) in 1,4-dioxane (2.8 ml) were sequentially added N,N-dimethylglycine (129 mg, 1.24 mmol), copper(I) iodide (79 mg, 0.42 mmol) and cesium carbonate (722 mg, 2.21 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 57-a as a yellow foam.

Step 2: Compound 91

Intermediate 57-a (286 mg, 0.55 mmol) and trimethyl orthoformate (3.94 ml, 36.0 mmol) were heated at 110° C. for 1 hour. Excess trimethyl orthoformate was removed in vacuo and the residue was treated with 7.0 N ammonia in MeOH (3.96 ml, 27.7 mmol). The mixture was stirred at room temperature for 3 days and volatiles were removed under reduced pressure. Purification by reverse phase chromatography eluting with a 1% aqueous HCl/methanol gradient provided compound 91.HCl as white solid. MS (m/z) M+H=543.1

Synthesis of Compound 101

Scheme 58

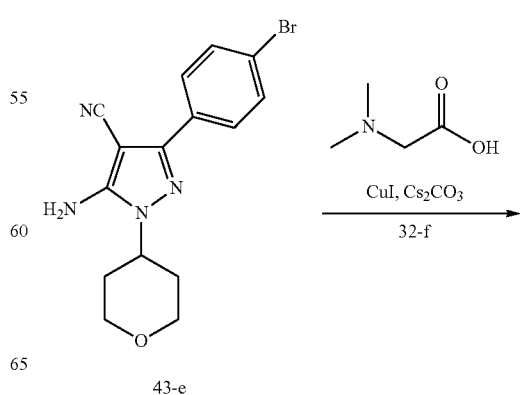

81

-continued

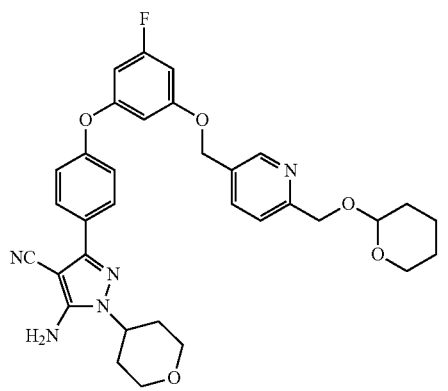

58-a

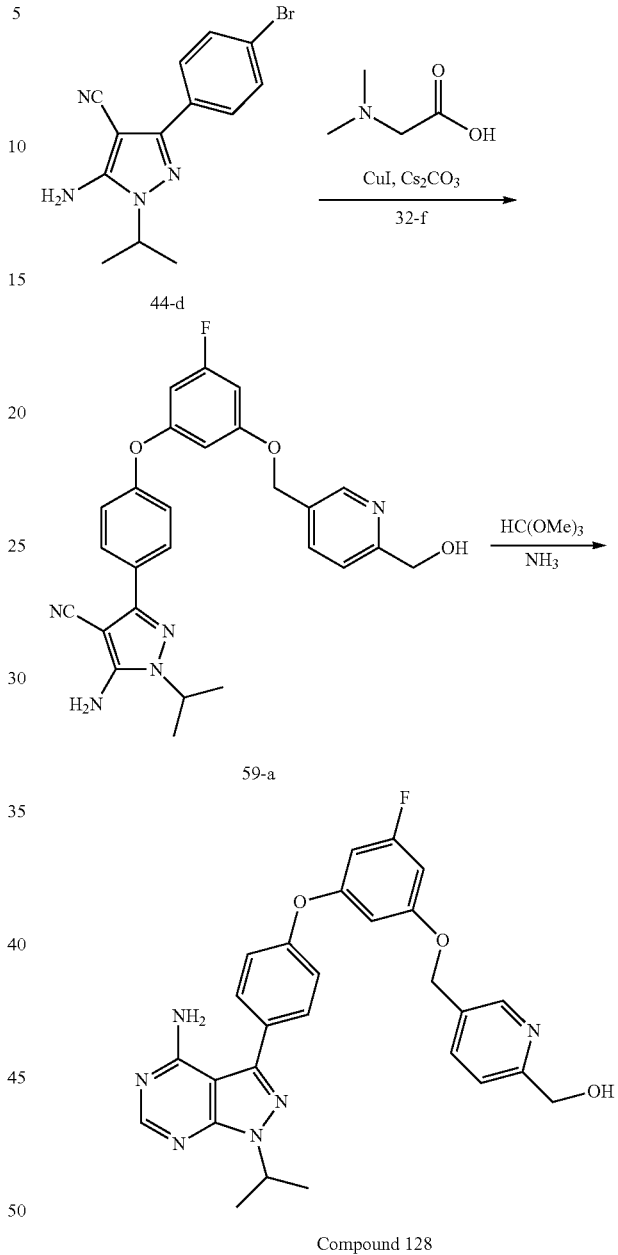

Compound 101

Step 1: Intermediate 58-a

To a solution of intermediate 43-e (400 mg, 1.15 mmol) and intermediate 32-f (384 mg, 1.15 mmol) in 1,4-dioxane (2.8 ml) were sequentially added N,N-dimethylglycine (267 mg, 2.59 mmol), copper(I) iodide (165 mg, 0.86 mmol) and cesium carbonate (1.50 g, 4.61 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over $MgSO_4$, filtered and concentrated under reduced pressure to provide intermediate 58-a as a beige foam.

Step 2: Compound 101

Intermediate 58-a (690 mg, 1.15 mmol) and trimethyl orthoformate (8.18 ml, 74.8 mmol) were heated at 110° C. for 4 days. Excess trimethyl orthoformate was removed in vacuo and the residue was treated with 7.0 N ammonia in MeOH (8.21 ml, 57.5 mmol). The mixture was stirred at room temperature overnight and volatiles were removed under reduced pressure. Purification by reverse phase chromatography eluting with a 1% aqueous HCl/methanol gradient provided compound 101.2HCl as a white solid. MS (m/z) M+H=543.1

82

Synthesis of Compound 128

Scheme 59

Step 1: Intermediate 59-a

To a solution of intermediate 44-d (261 mg, 0.85 mmol) and intermediate 32-f (285 mg, 0.85 mmol) in 1,4-dioxane (2.8 ml) were sequentially added N,N-dimethylglycine (198 mg, 1.92 mmol), copper(I) iodide (122 mg, 0.64 mmol) and cesium carbonate (1.11 g, 3.42 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over $MgSO_4$, filtered and concentrated under reduced pressure to provide Purification by reverse phase chromatography eluting with a 1% aqueous HCl/methanol gradient provided intermediate 59-a.HCl as a beige foam.

Step 2: Compound 128

Intermediate 59-a (405 mg, 0.85 mmol) and trimethyl orthoformate (6.08 ml, 55.6 mmol) were heated at 110° C. for 1 hour. Excess trimethyl orthoformate was removed in vacuo and the residue was treated with 7.0 N ammonia in MeOH (6.11 ml, 42.8 mmol). The mixture was stirred at room temperature for 3 days and volatiles were removed under reduced pressure. Purification by reverse phase chromatography eluting with a 1% aqueous HCl/methanol gradient provided compound 128.2HCl as a white solid. MS (m/z) M+H=501.1

Synthesis of Compound 78

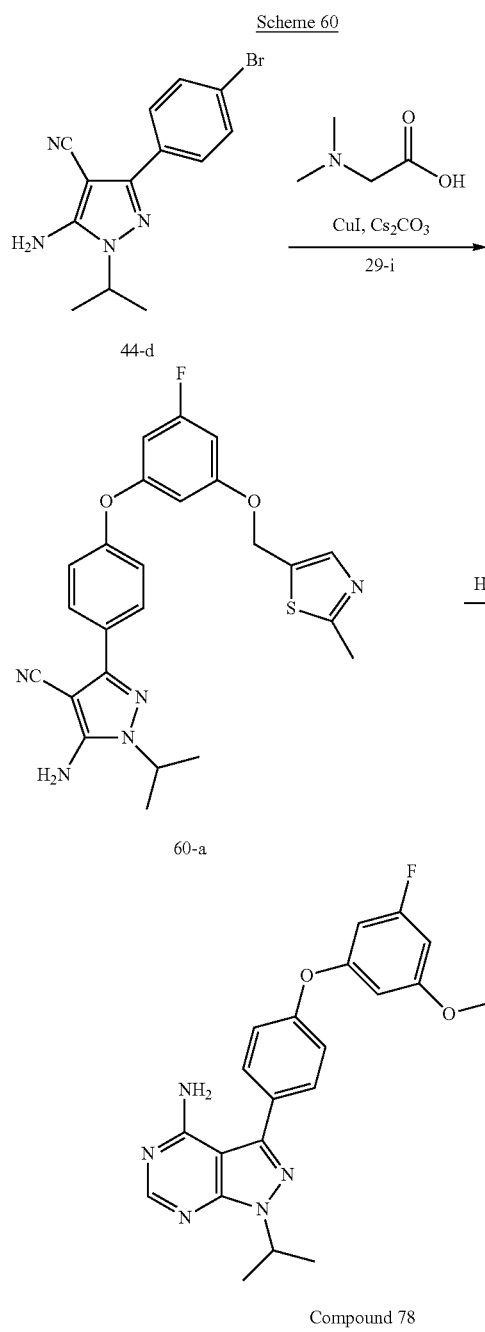

Compound 78

Step 1: Intermediate 60-a

To a solution of intermediate 44-d (300 mg, 0.98 mmol) and intermediate 29-i (259 mg, 1.08 mmol) in 1,4-dioxane (3.9 ml) were sequentially added N,N-dimethylglycine (304 mg, 2.95 mmol), copper(I) iodide (187 mg, 0.98 mmol) and cesium carbonate (961 mg, 2.95 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 60-a.HCl as a beige foam.

Step 2: Compound 78

Intermediate 60-a.HCl (265 mg, 0.57 mmol) and trimethyl orthoformate (1.87 ml, 17.16 mmol) were heated at 110° C. for 1 hour. Excess trimethyl orthoformate was removed in vacuo and the residue was treated with 7.0 N ammonia in MeOH (5.7 ml, 11.44 mmol). The mixture was stirred at room temperature overnight and volatiles were removed under reduced pressure. Purification by reverse phase chromatography eluting with a 1% aqueous HCl/methanol gradient provided compound 78.2HCl as beige solid. MS (m/z) M+H=491.2

Synthesis of Compound 58

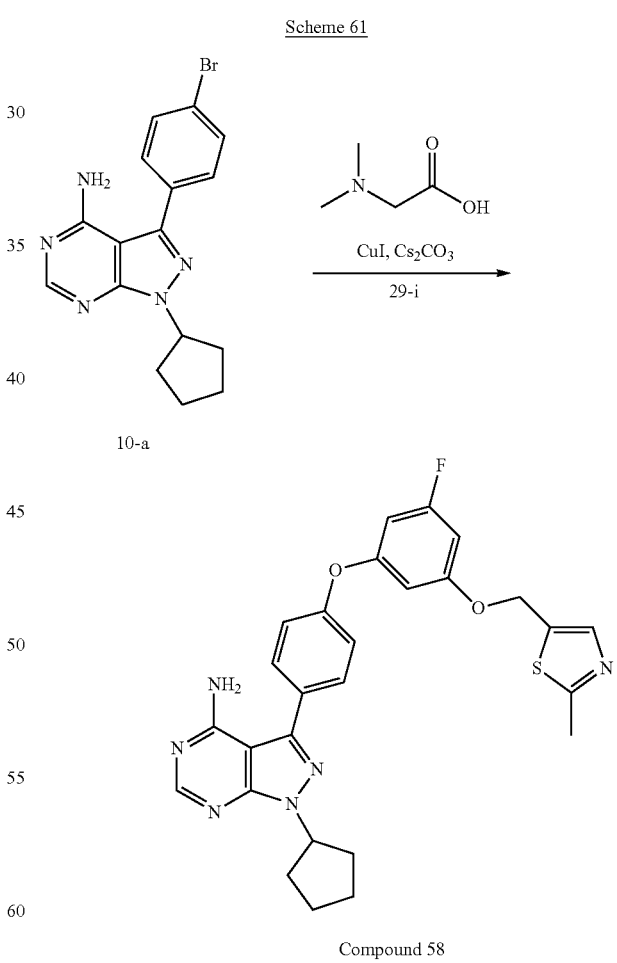

Compound 58

To a solution of intermediate 10-a (3.96 g, 11.1 mmol) and intermediate 29-i (2.91 g, 12.2 mmol) in 1,4-dioxane (55.3 ml) were sequentially added N,N-dimethylglycine (3.42 g, 33.2 mmol), copper(I) iodide (2.10 g, 11.07 mmol) and cesium carbonate (10.82 g, 33.2 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided compound 58.2HCl as a beige solid. MS (m/z) M+H=517.2

Synthesis of Compound 117

Step 1: Intermediate 62-a

To a solution of intermediate 48-c (200 mg, 0.59 mmol) and intermediate 29-i (157 mg, 0.65 mmol) in 1,4-dioxane (1.50 ml) were sequentially added N,N-dimethylglycine (92 mg, 0.89 mmol), copper(I) iodide (57 mg, 0.29 mmol) and cesium carbonate (583 mg, 1.79 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 62-a.HCl as a beige solid.

Step 2: Compound 117

Intermediate 62-a.HCl (322 mg, 0.65 mmol) and trimethyl orthoformate (3.0 ml, 19.57 mmol) were heated at 110° C. for 1 hour. Excess trimethyl orthoformate was removed in vacuo and the residue was treated with ammonia (7.0 N in MeOH) (1.85 ml, 13.0 mmol). The mixture was stirred at room temperature overnight and volatiles were removed under reduced pressure. Purification by reverse phase chromatography eluting with a 1% aqueous HCl/methanol gradient provided compound 117.2HCl as a white solid. MS (m/z) M+H=521.1

Synthesis of Compound 100

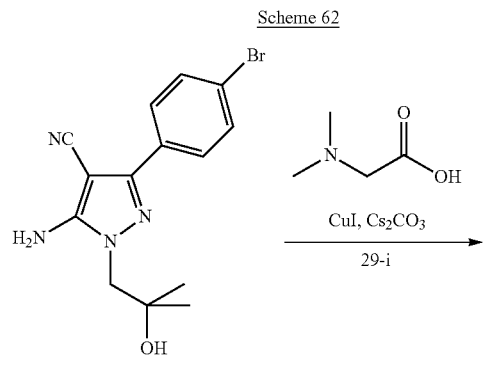

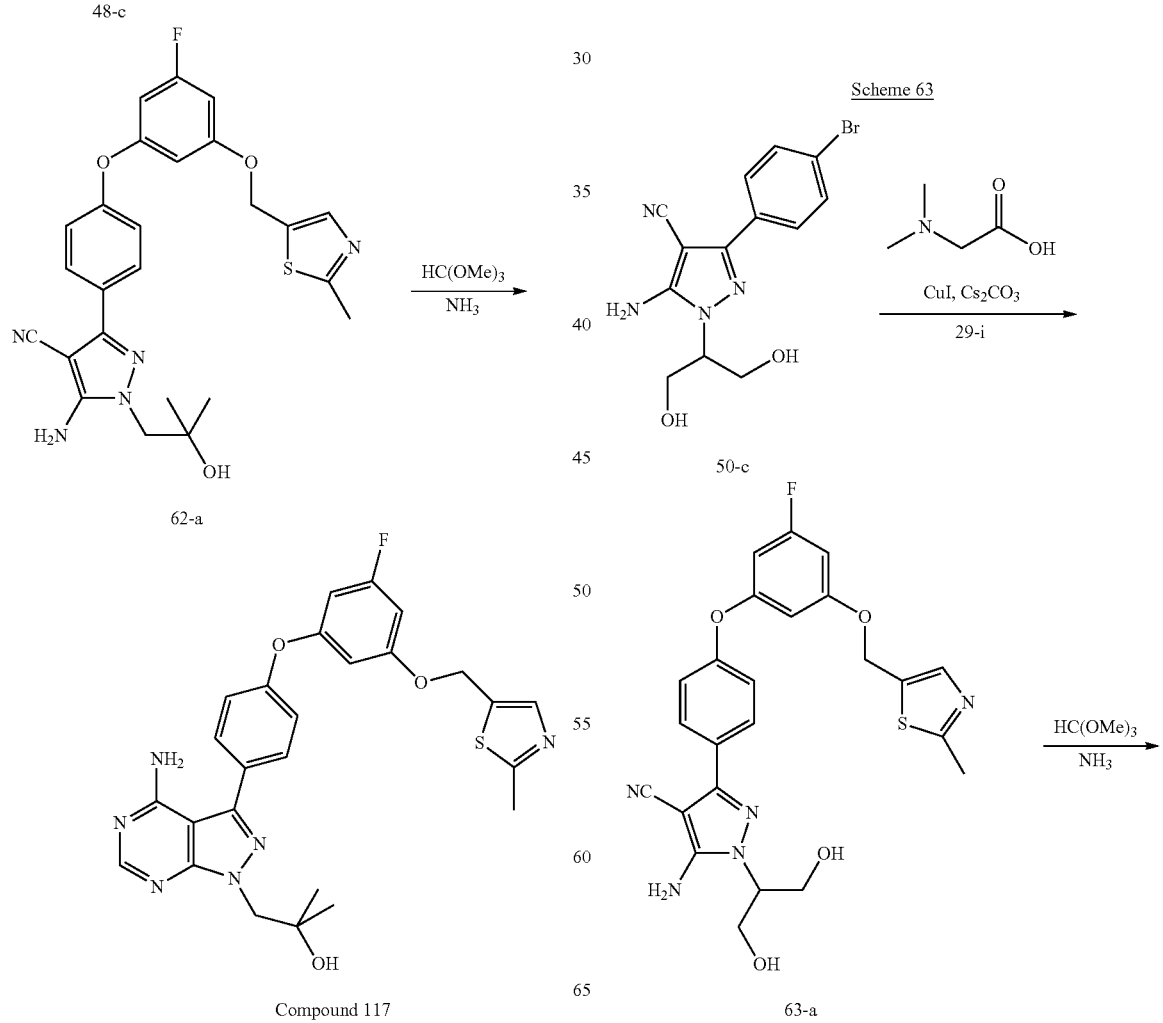

87

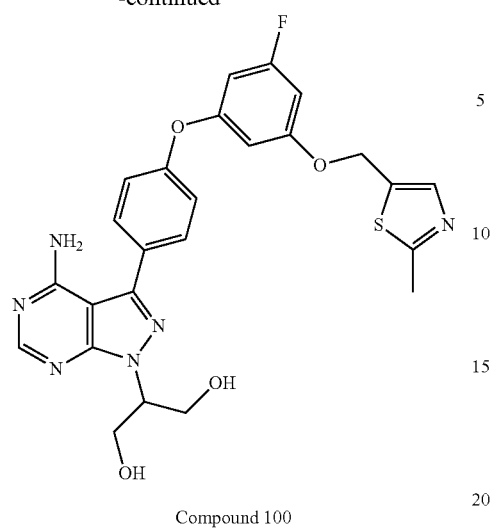

Compound 100

Step 1: Intermediate 63-a

To a solution of intermediate 50-c (1.42 g, 4.21 mmol) and intermediate 29-i (1.10 g, 4.63 mmol) in 1,4-dioxane (16.8 ml) were sequentially added N,N-dimethylglycine (1.30 g, 12.6 mmol), copper(I) iodide (802 mg, 4.21 mmol) and cesium carbonate (4.12 g, 12.63 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 63-a.HCl as a white solid.

Step 2: Compound 100

Intermediate 63-a.HCl (577 mg, 1.16 mmol) and trimethyl orthoformate (3.82 ml, 35.0 mmol) were heated at 110° C. for 3 hours. Excess trimethyl orthoformate was removed in vacuo and the residue was treated with 7.0 N ammonia in MeOH (3.30 ml, 23.32 mmol). The mixture was stirred at room temperature overnight and volatiles were removed under reduced pressure. Purification by reverse phase chromatography eluting with a 1% aqueous HCl/methanol gradient provided compound 100.2HCl as white solid. MS (m/z) M+H=523.2

88

Synthesis of Compound 113

Scheme 64

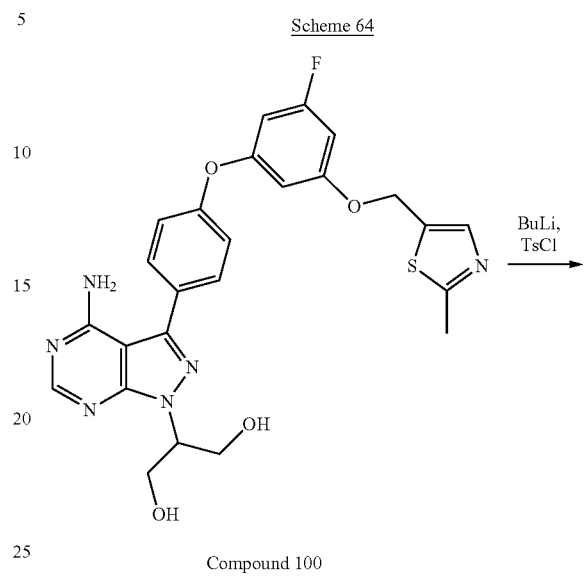

Compound 100

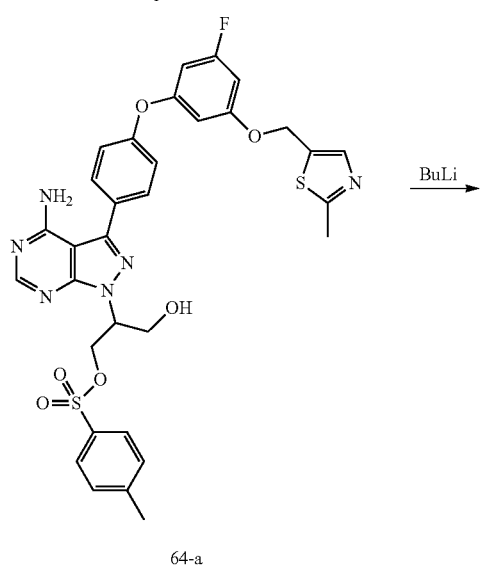

64-a

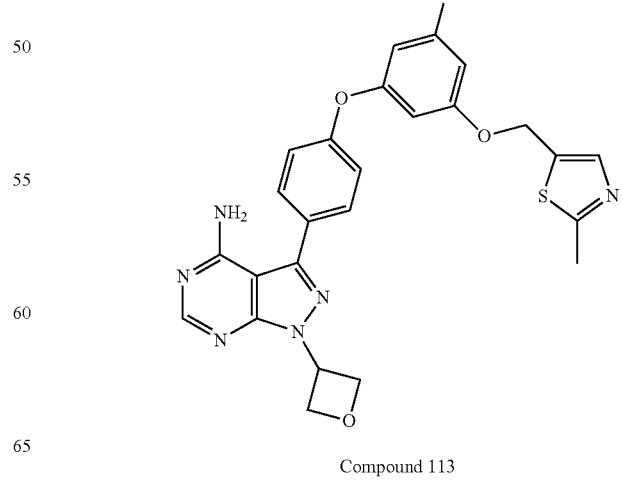

Compound 113

Step 1: Intermediate 64-a

To a solution of compound 100 (198.0 mg, 0.38 mmol) in THF cooled to −10° C. was slowly added a 2.5 M solution of n-butyllithium in THF (304 μl, 0.76 mmol). After stirring for 30 minutes, para-toluenesulfonyl chloride (72.0 mg, 0.38 mmol) in THF (2 ml) was added. The reaction was stirred at 60° C. overnight and then cooled to room temperature. Water and ethyl acetate were added, the organic layer was separated, washed with brine, dried over MgSO$_4$, filtered and concentrated under reduced pressure. Purification by silica gel chromatography provided intermediate 64-a as beige foam.

Step 2: Compound 113

To a solution of intermediate 64-a (85.0 mg, 0.12 mmol) in THF cooled to −10° C. was slowly added a 2.5 M solution of n-butyllithium in THF (110.0 μl, 0.27 mmol). The reaction was stirred at 60° C. overnight and then cooled to room temperature. Water and ethyl acetate were added, the organic layer was separated, washed with brine, dried over MgSO$_4$, filtered and concentrated under reduced pressure. Purification by silica gel chromatography provided compound 113 as pale yellow foam. MS (m/z) M+H=505.2

Synthesis of Compound 125

Scheme 65

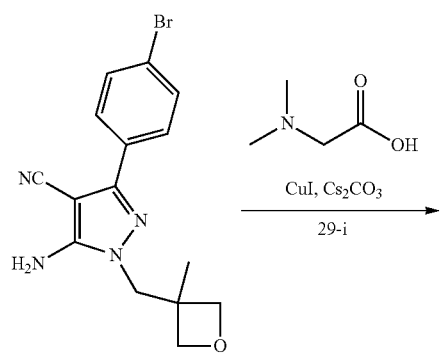

51-a

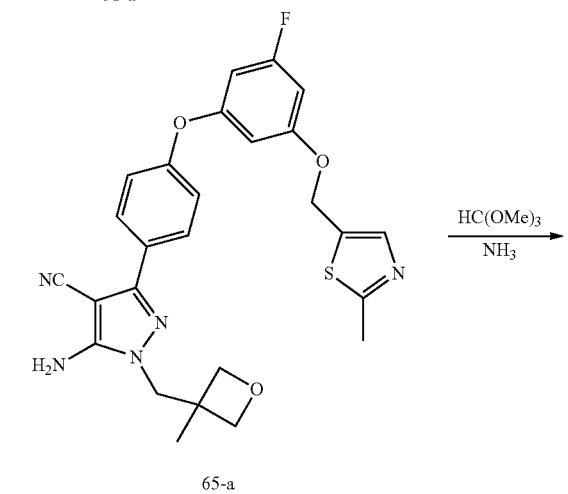

65-a

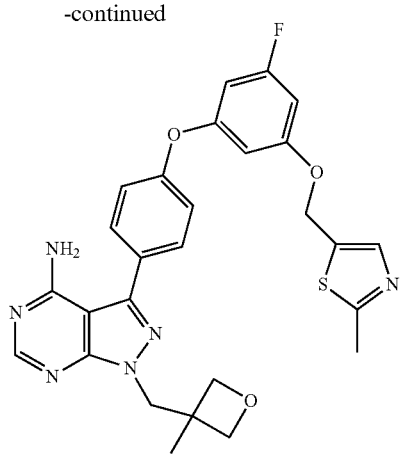

Compound 125

Step 1: Intermediate 65-a

To a solution of intermediate 51-a (300 mg, 0.86 mmol) and intermediate 29-i (262 mg, 0.95 mmol) in 1,4-dioxane (1.50 ml) were sequentially added N,N-dimethylglycine (267 mg, 2.59 mmol), copper(I) iodide (165 mg, 0.86 mmol) and cesium carbonate (845 mg, 2.59 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by silica gel chromatography provided intermediate 65-a as a beige foam.

Step 2: Compound 125

Intermediate 65-a (120 mg, 0.23 mmol), trimethyl orthoformate (260 μl, 2.3 mmol) and PTSA (catalytic) were stirred at room temperature for 1 hour. Excess trimethyl orthoformate was removed in vacuo and the residue was treated with 7.0 N ammonia in MeOH (652 μl, 4.6 mmol). The mixture was stirred at room temperature for 3 days and volatiles were removed under reduced pressure. Purification by silica gel chromatography provided compound 125 as a white solid. MS (m/z) M+H=533.2

Synthesis of Compound 54

Scheme 66

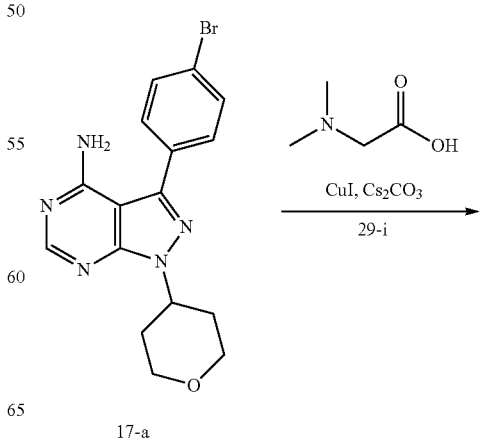

17-a

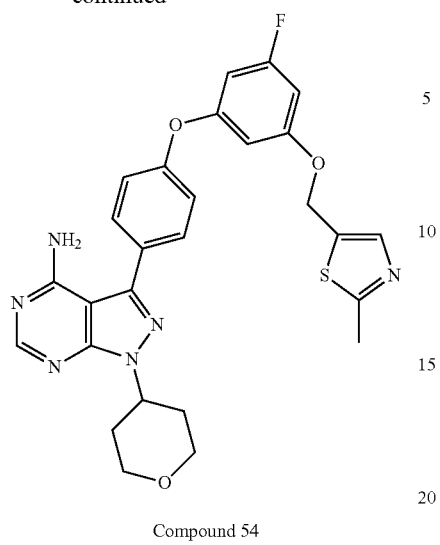

Compound 54

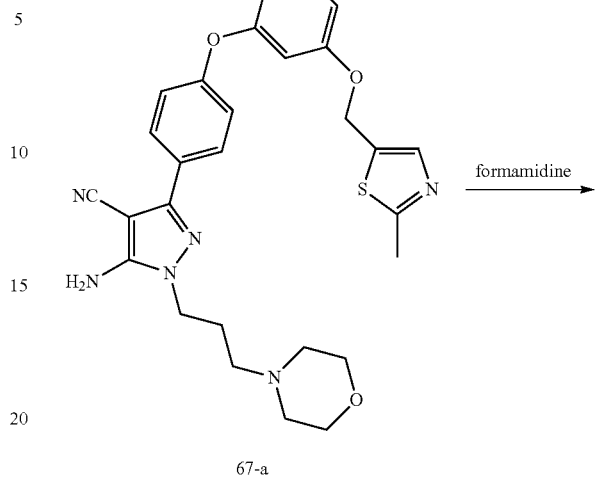

67-a

To a solution of intermediate 17-a (1.20 g, 3.21 mmol) and intermediate 29-i (844 mg, 3.53 mmol) in DMF (16.0 ml) were sequentially added N,N-dimethylglycine (992 mg, 9.62 mmol), copper(I) iodide (611 mg, 3.21 mmol) and cesium carbonate (4.18 g, 12.83 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided compound 54.2HCl as a yellow solid. MS (m/z) M+H=533.1

Synthesis of Compound 55

Scheme 67

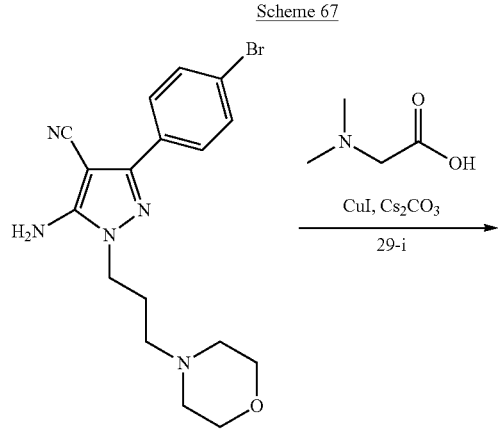

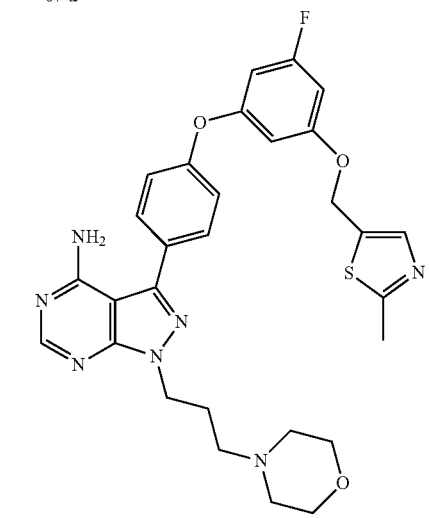

Compound 55

Step 1: Intermediate 67-a

To a solution of intermediate 52-a (397.0 mg, 1.00 mmol) and intermediate 29-i (268 mg, 1.12 mmol) in 1,4-dioxane (5.0 ml) were sequentially added N,N-dimethylglycine (157 mg, 1.53 mmol), copper(I) iodide (97.0 mg, 050 mmol) and cesium carbonate (995 mg, 3.05 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure to provide intermediate 67-a as beige foam.

Step 2: Compound 55

Formamide (2.84 ml, 71.3 mmol) was added to intermediate 67-a (559 mg, 1.0 mmol) and the reaction was stirred at 180° C. for 2 hours. Water and ethyl acetate were added, the organic layer was separated, washed with brine, dried over MgSO$_4$, filtered and concentrated under reduced pressure. Purification by reverse phase chromatography eluting with a 1% aqueous HCl/methanol gradient provided compound 55.3HCl as beige solid. MS (m/z) M+H=576.2

Synthesis of Compound 52

Scheme 68

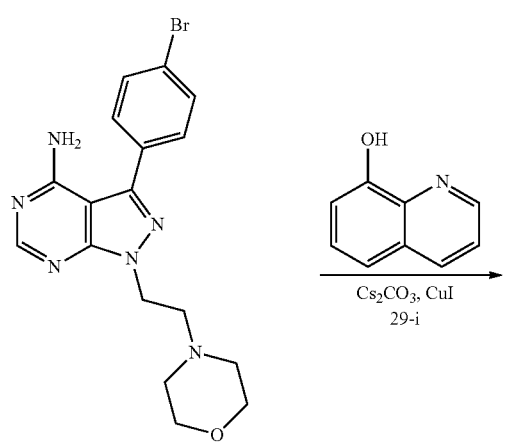

53-a

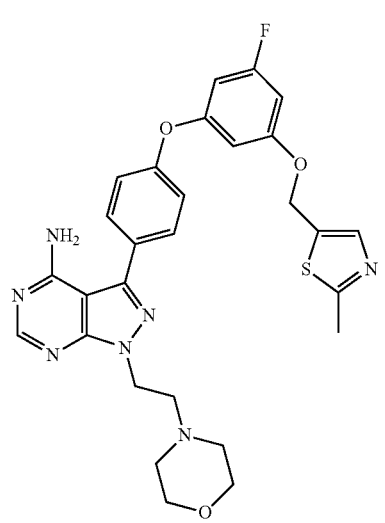

Compound 52

To a solution of intermediate 53-a (1.0 g, 2.48 mmol) and intermediate 29-i (771 mg, 3.22 mmol) in DMAC (12.4 ml) were sequentially added quinolin-8-(36.0 mg, 0.24 mmol), copper(I) iodide (47.0 mg, 0.24 mmol) and cesium carbonate (808 mg, 2.48 mmol) and the reaction was heated at 140° C. for 2 hours. A saturated aqueous solution of ammonium chloride and ethyl acetate were added, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided compound 52.3HCl as white solid. MS (m/z) M+H=562.1

Synthesis of Compound 57

Scheme 69

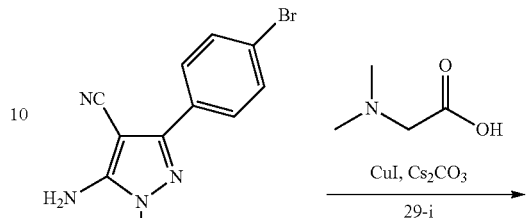

54-a

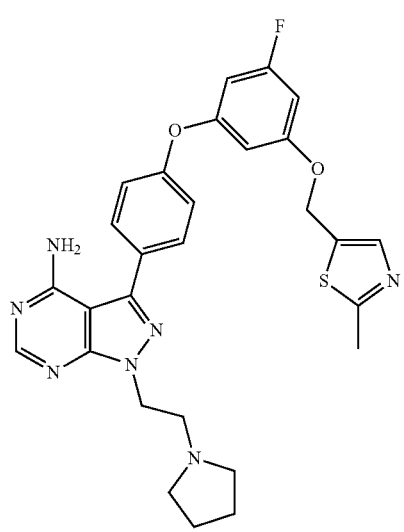

69-a

Compound 57

Step 1: Intermediate 69-a

To a solution of intermediate 54-a (425.0 mg, 1.18 mmol) and intermediate 29-i (282 mg, 1.18 mmol) in 1,4-dioxane (5.9 ml) were sequentially added N,N-dimethylglycine (182 mg, 1.77 mmol), copper(I) iodide (112 mg, 0.59 mmol) and cesium carbonate (1.15 g, 3.54 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over $MgSO_4$, filtered and concentrated under reduced pressure to provide intermediate 69-a as a beige foam.

Step 2: Compound 57

Formamide (5.53 ml, 139.0 mmol) was added to intermediate 69-a (600 mg, 1.15 mmol) and the reaction was stirred at 180° C. for 4 hours. Water and ethyl acetate were added, the organic layer was separated, washed with brine, dried over $MgSO_4$, filtered and concentrated under reduced pressure. Purification by reverse phase chromatography eluting with a 1% aqueous HCl/methanol gradient provided compound 57.3HCl as beige solid. MS (m/z) M+H=546.2

Synthesis of Compound 102

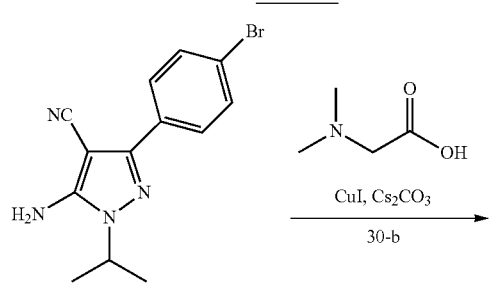

Scheme 70

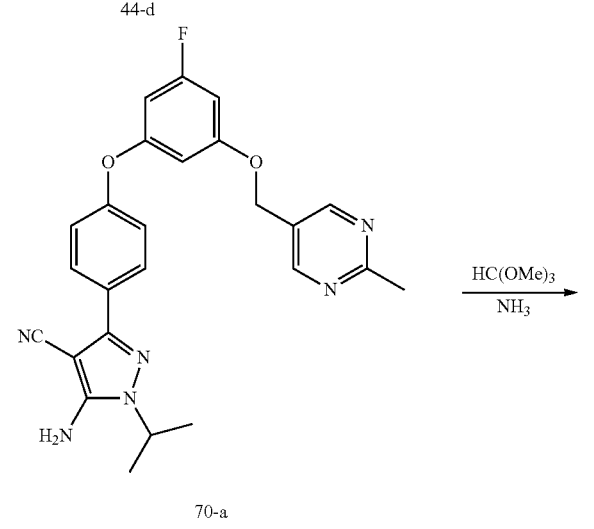

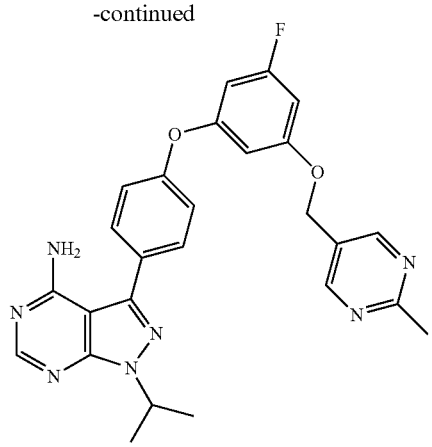

Compound 102

Step 1: Intermediate 70-a

To a solution of intermediate 44-d (4.00 g, 13.1 mmol) and intermediate 30-b (3.38 g, 14.4 mmol) in 1,4-dioxane (43.7 ml) were sequentially added N,N-dimethylglycine (3.04 g, 29.5 mmol), copper(I) iodide (1.87 g, 9.83 mmol) and cesium carbonate (17.08 g, 52.4 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over $MgSO_4$, filtered and concentrated under reduced pressure. Purification by reverse phase chromatography eluting with a 1% aqueous HCl/methanol gradient provided intermediate 70-a.HCl as beige foam.

Step 2: Compound 102

Intermediate 70-a.HCl (3.80 g, 7.68 mmol) and trimethyl orthoformate (54.6 ml, 499.0 mmol) were heated at 110° C. for 1 hour. Excess trimethyl orthoformate was removed in vacuo and the residue was treated with 7.0 N ammonia in MeOH (54.8 ml, 384.0 mmol). The mixture was stirred at room temperature for 2 days and volatiles were removed under reduced pressure. Purification by reverse phase chromatography eluting with a 1% aqueous HCl/methanol gradient provided compound 102.2HCl as white solid. MS (m/z) M+H=486.2

Synthesis of Compound 129

Scheme 71

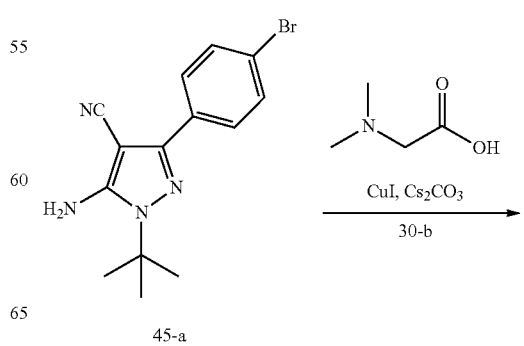

Synthesis of Compound 106

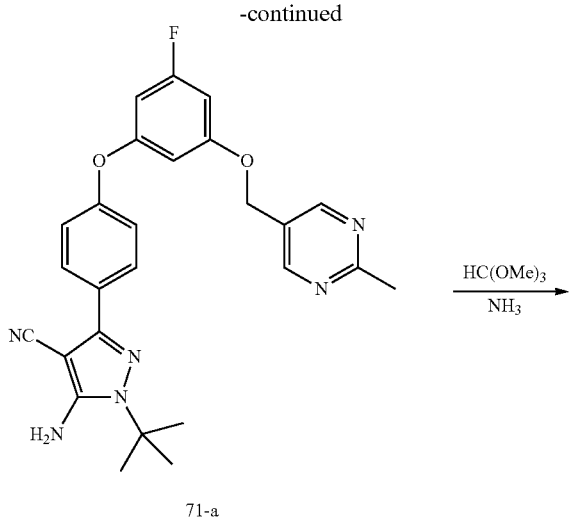

71-a

Compound 129

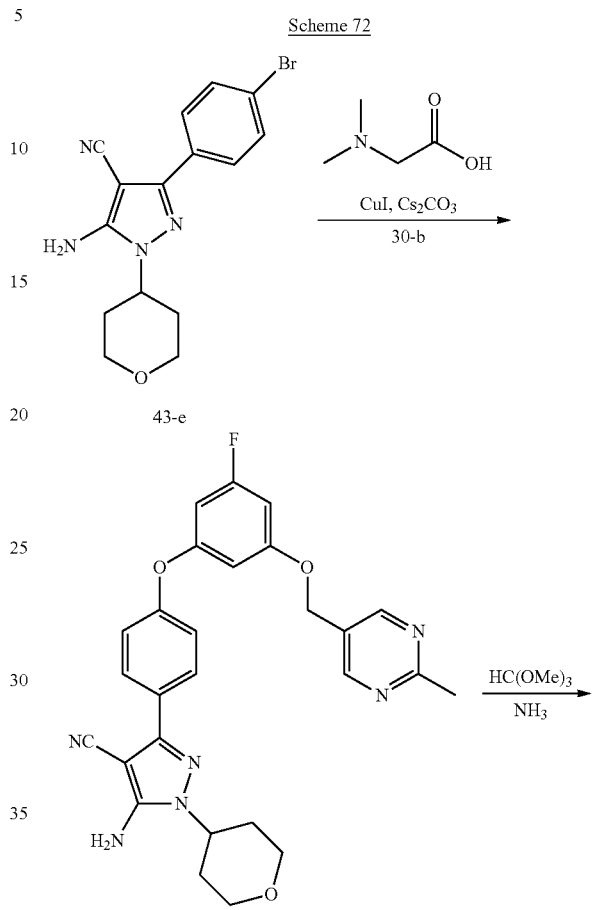

Scheme 72

43-e 72-a

Compound 106

Step 1: Intermediate 71-a

To a solution of intermediate 45-a (350 mg, 1.10 mmol) and intermediate 30-b (283 mg, 1.20 mmol) in 1,4-dioxane (4.3 ml) were sequentially added N,N-dimethylglycine (1.07 g, 3.29 mmol), copper(I) iodide (209 mg, 1.10 mmol) and cesium carbonate (985 mg, 3.02 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 71-a.HCl as a beige solid.

Step 2: Compound 129

Intermediate 71-a.HCl (403.0 mg, 0.85 mmol) and trimethyl orthoformate (6.07 ml, 55.5 mmol) were heated at 110° C. for 3 hours. Excess trimethyl orthoformate was removed in vacuo and the residue was treated with 7.0 N ammonia in MeOH (6.07 ml, 42.7 mmol). The mixture was stirred at room temperature overnight and volatiles were removed under reduced pressure. Purification by reverse phase chromatography eluting with a 1% aqueous HCl/methanol gradient provided compound 129.2HCl as beige solid. MS (m/z) M+H=500.1

Step 1: Intermediate 72-a

To a solution of intermediate 43-e (350 mg, 1.00 mmol) and intermediate 30-b (260 mg, 1.10 mmol) in 1,4-dioxane (4.0 ml) were sequentially added N,N-dimethylglycine (312 mg, 3.02 mmol), copper(I) iodide (192 mg, 1.00 mmol) and cesium carbonate (985 mg, 3.02 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO₄, filtered and concentrated under reduced pressure. Purification by reverse phase chromatography eluting with a 1% aqueous HCl/methanol gradient provided intermediate 72-a.HCl as a beige solid.

Step 2: Compound 106

Intermediate 72-a.HCl (263 mg, 0.52 mmol) and trimethyl orthoformate (1.72 ml, 15.8 mmol) were heated at 110° C. for 2 hours. Excess trimethyl orthoformate was removed in vacuo and the residue was treated with 7.0 N ammonia in MeOH (46.2 ml, 324 mmol). The mixture was stirred at room temperature overnight and volatiles were removed under reduced pressure. Purification by reverse phase chromatography eluting with a 1% aqueous HCl/methanol gradient provided compound 106.2HCl as a beige solid. MS (m/z) M+H=528.1

Synthesis of Compound 114

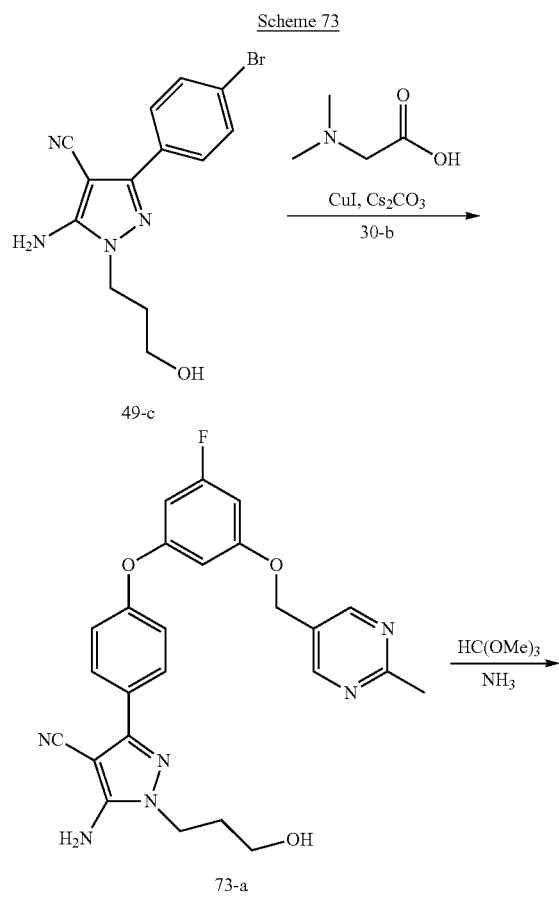

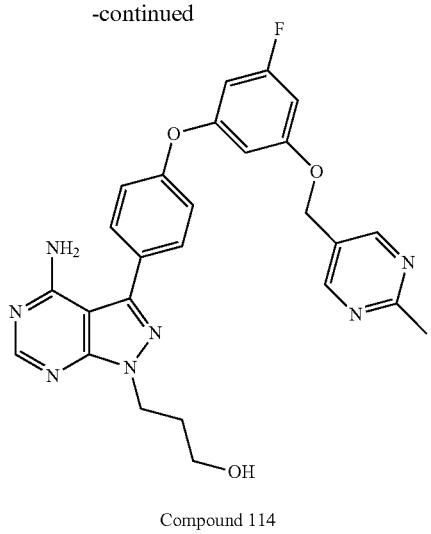

Compound 114

Step 1: Intermediate 73-a

To a solution of intermediate 49-c (250 mg, 0.78 mmol) and intermediate 30-b (201 mg, 0.85 mmol) in 1,4-dioxane (3.1 ml) were sequentially added N,N-dimethylglycine (241 mg, 2.33 mmol), copper(I) iodide (148 mg, 0.78 mmol) and cesium carbonate (761 mg, 2.33 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO₄, filtered and concentrated under reduced pressure. Purification by reverse phase chromatography eluting with a 1% aqueous HCl/methanol gradient provided intermediate 73-a.HCl as a beige solid.

Step 2: Compound 114

Intermediate 73-a.HCl (106 mg, 0.22 mmol) and trimethyl orthoformate (737 μl, 6.74 mmol) were heated at 110° C. for 3 hours. Excess trimethyl orthoformate was removed in vacuo and the residue was treated with 7.0 N ammonia in MeOH (2.24 ml, 4.49 mmol). The mixture was stirred at room temperature overnight and volatiles were removed under reduced pressure. Purification by reverse phase chromatography eluting with a 1% aqueous HCl/methanol gradient provided compound 114.2HCl as a beige solid. MS (m/z) M+H=502.2

Synthesis of Compound 130

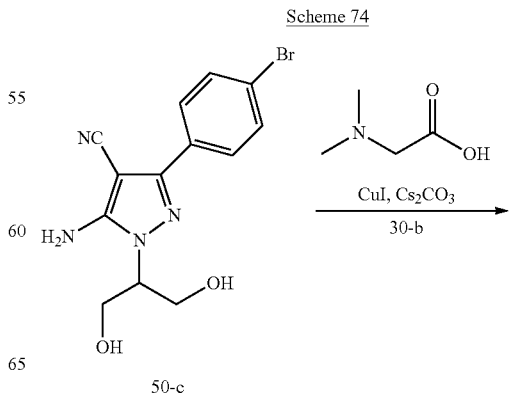

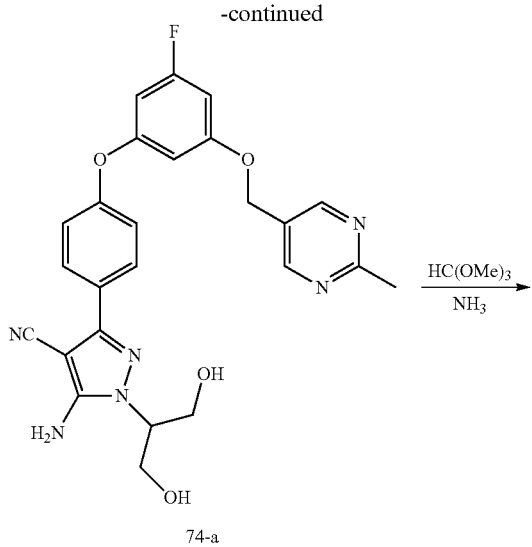

74-a

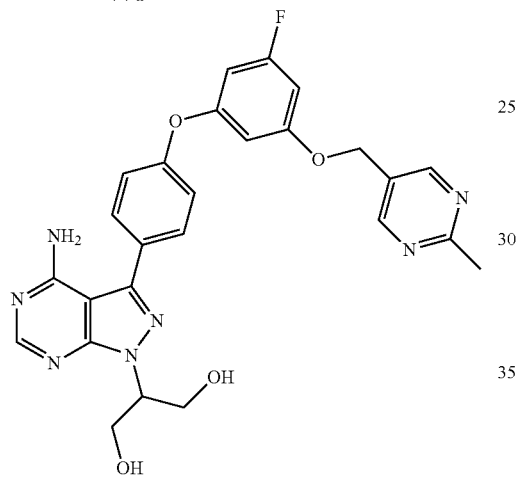

Compound 130

Step 1: Intermediate 74-a

To a solution of intermediate 50-c (300 mg, 0.89 mmol) and intermediate 30-b (229 mg, 0.97 mmol) in 1,4-dioxane (890 μl) were sequentially added N,N-dimethylglycine (275 mg, 2.67 mmol), copper(I) iodide (169 mg, 0.89 mmol) and cesium carbonate (870 mg, 2.67 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 74-a.HCl as beige solid.

Step 2: Compound 130

A solution of intermediate 74-a (125 mg, 0.25 mmol), trimethyl orthoformate (836 μl, 7.65 mmol) and PTSA (catalytic) was stirred at room temperature for 3 hours. Excess trimethyl orthoformate was removed in vacuo and the residue was treated with ammonia (7.0 N in MeOH) (2.55 ml, 5.10 mmol). The mixture was stirred at room temperature for 2 days and volatiles were removed under reduced pressure. Purification by reverse phase chromatography eluting with a 1% aqueous HCl/methanol gradient provided compound 130.2HCl as a white solid. MS (m/z) M+H=518.1

Synthesis of Compound 97

Scheme 75

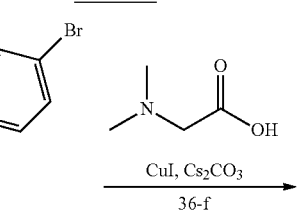

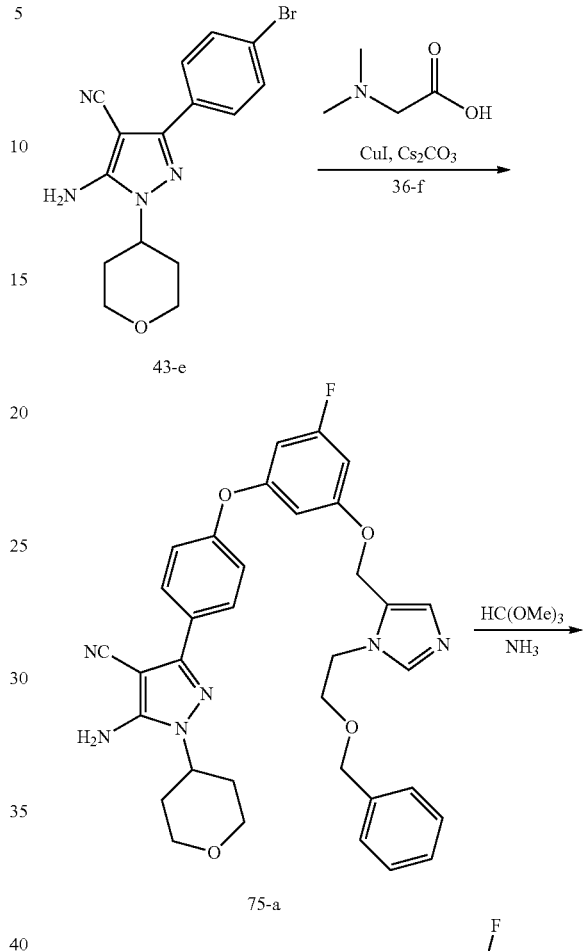

Compound 97

Step 1: Intermediate 75-a

To a solution of intermediate 43-e (101 mg, 0.29 mmol) and intermediate 36-f (110 mg, 0.32 mmol) in 1,4-dioxane (1.4 ml) were sequentially added N,N-dimethylglycine (90 mg, 0.87 mmol), copper(I) iodide (56 mg, 0.29 mmol) and cesium carbonate (381 mg, 1.17 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO₄, filtered and concentrated under reduced pressure. Purification by silica gel chromatography provided intermediate 75-a as a beige solid.

Step 2: Compound 97

Intermediate 75-a (160 mg, 0.26 mmol), trimethyl orthoformate (1.86 ml, 17.09 mmol) and TFA (catalytic) were heated at 110° C. for 1 hour. Excess trimethyl orthoformate was removed in vacuo and the residue was treated with 7.0 N ammonia in MeOH (1.87 ml, 13.14 mmol). The mixture was stirred at 50° C. overnight and volatiles were removed under reduced pressure. Purification by reverse phase chromatography eluting with a 1% aqueous HCl/methanol gradient provided compound 97.2HCl as a beige solid. MS (m/z) M+H=636.1

Synthesis of Compound 99

Scheme 76

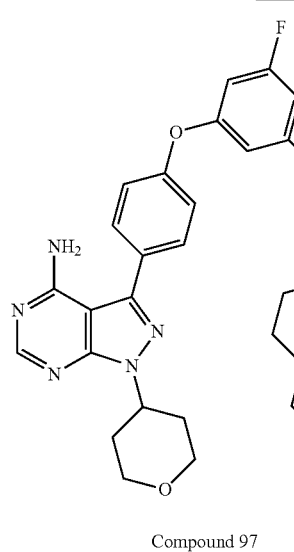

Compound 97

Compound 99

A solution of compound 97.2HCl (100 mg, 0.15 mmol) in ethyl acetate was treated with 10% palladium on carbon (32 mg, 0.015 mmol) and purged with H₂. The solution was stirred under H₂ (1 atm) for 1 hour before being filtered through celite. The filtrate was concentrated in vacuo. Purification by reverse phase chromatography eluting with a 1% aqueous HCl/methanol gradient provided compound 99.2HCl as white solid. MS (m/z) M+H=546.2

Synthesis of Compound 93

Scheme 77

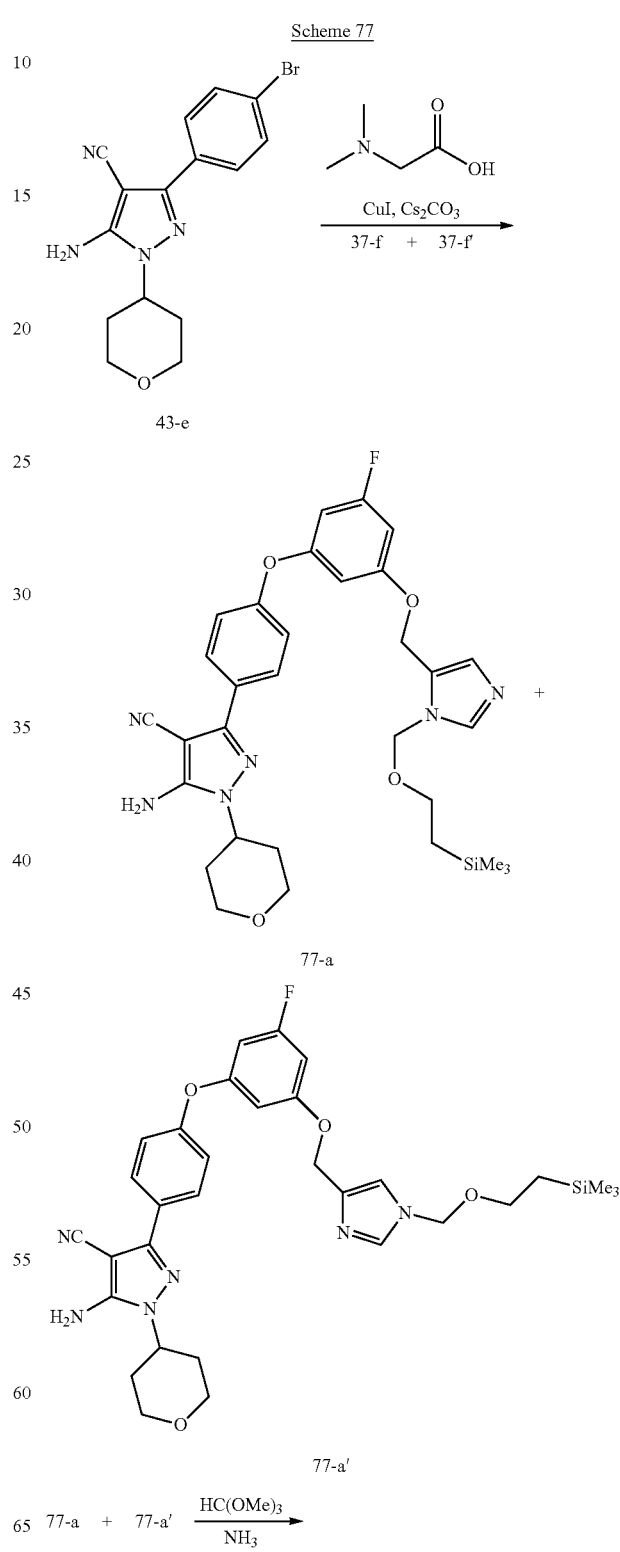

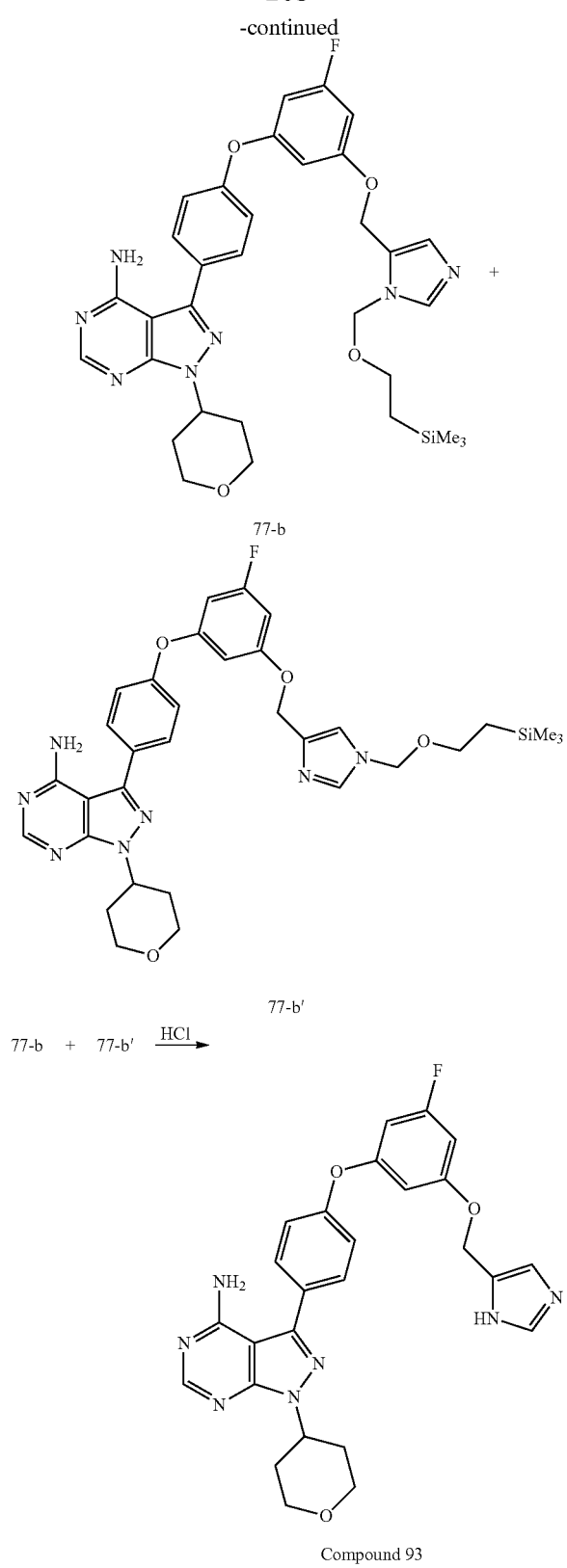

77-b 77-b'

77-b + 77-b' →(HCl)

Compound 93

Step 1: Intermediates 77-a and 77-a'
To a solution of intermediate 43-e (115 mg, 0.33 mmol) and intermediates 37-f and 37-f' (123 mg, 0.36 mmol) in 1,4-dioxane (1.6 ml) were sequentially added N,N-dimethylglycine (102 mg, 0.99 mmol), copper(I) iodide (63 mg, 0.33 mmol) and cesium carbonate (431 mg, 1.32 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by silica gel chromatography provided intermediate 77-a and 77-a' as an inseparable mixture.

Step 2: Intermediates 77-b and 77-b'
A solution of intermediates 77-a and 77-a' (100 mg, 0.16 mmol), trimethyl orthoformate (2.0 ml, 18.28 mmol) and PTSA (catalytic) was stirred at room temperature for 1 hour. Excess trimethyl orthoformate was removed in vacuo and the residue was treated with 7.0 N ammonia in MeOH (2.0 ml, 14.1 mmol). The mixture was stirred at room temperature for 3 days and volatiles were removed under reduced pressure. Purification by silica gel chromatography provided intermediates 77-b and 77-b' as an inseparable mixture.

Step 3: Compound 93
4N HCl in 1,4-dioxane (2 mL) was added to intermediates 77-b and 77-b' (60 mg, 0.09 mmol) band the mixture was stirred for 1 hour at room temperature. Volatiles were removed under reduced pressure. Purification by reverse phase chromatography eluting with a 1% aqueous HCl/methanol gradient provided compound 93.2HCl as a white solid. MS (m/z) M+H=502.2

Synthesis of Compound 118

Scheme 78

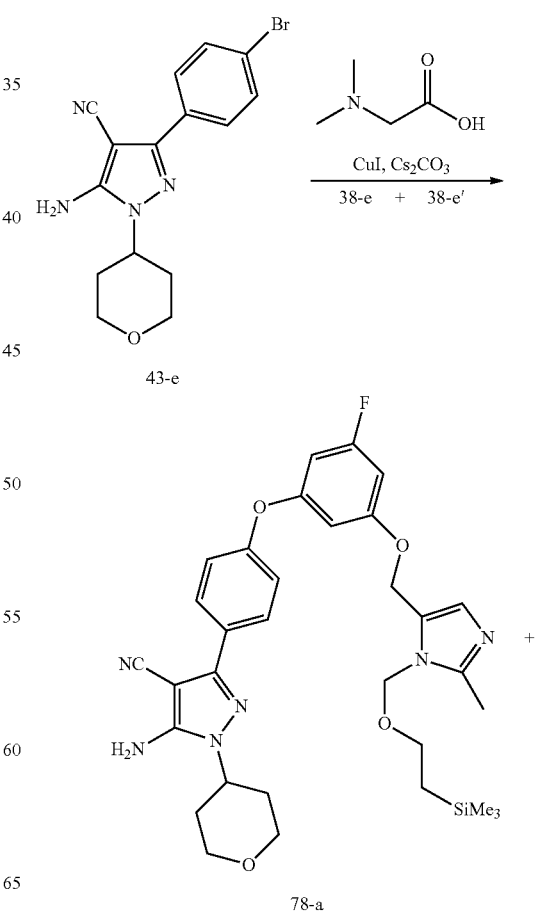

43-e

CuI, Cs$_2$CO$_3$ → 38-e + 38-e'

78-a

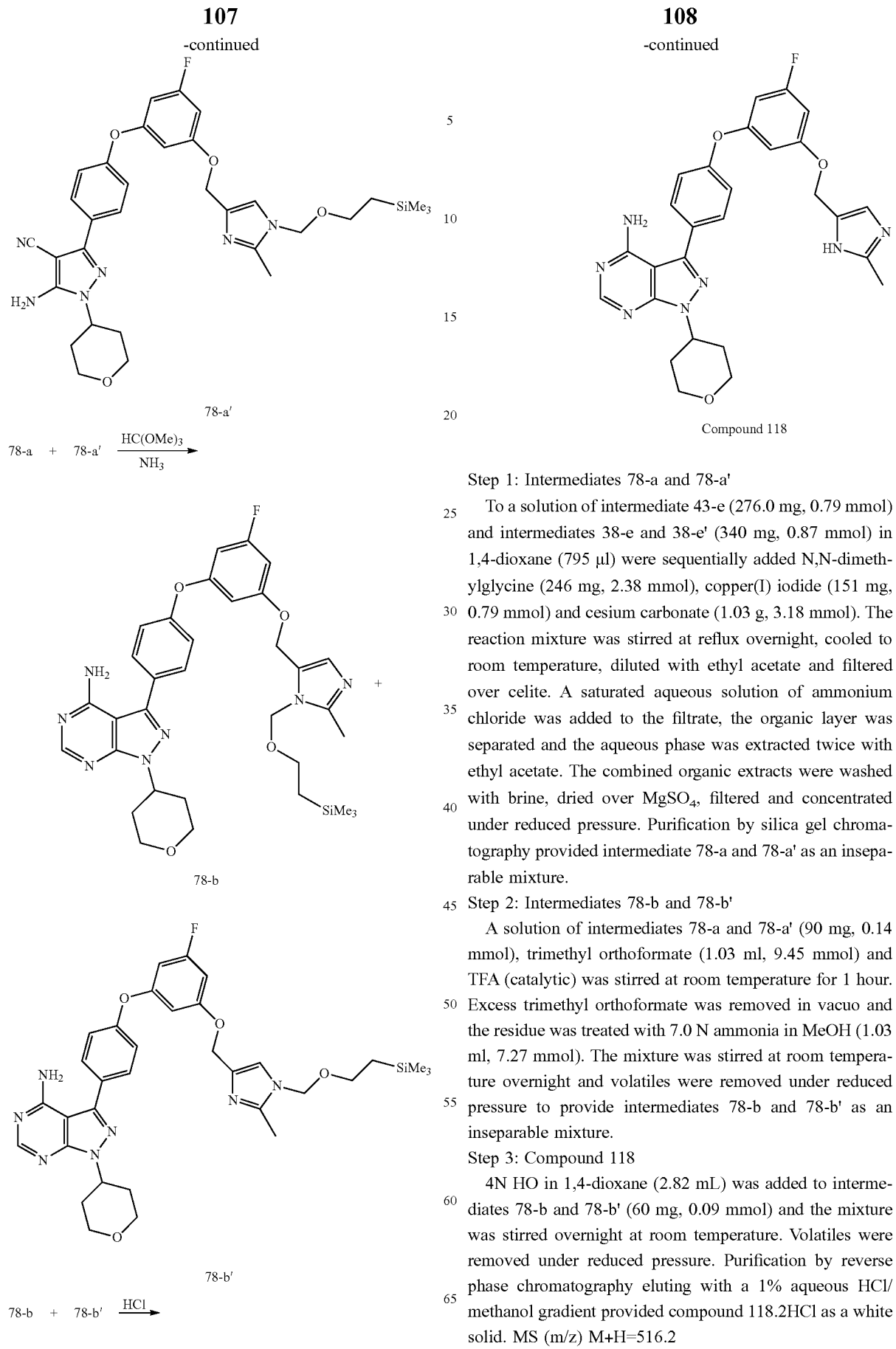

Step 1: Intermediates 78-a and 78-a'

To a solution of intermediate 43-e (276.0 mg, 0.79 mmol) and intermediates 38-e and 38-e' (340 mg, 0.87 mmol) in 1,4-dioxane (795 μl) were sequentially added N,N-dimethylglycine (246 mg, 2.38 mmol), copper(I) iodide (151 mg, 0.79 mmol) and cesium carbonate (1.03 g, 3.18 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over $MgSO_4$, filtered and concentrated under reduced pressure. Purification by silica gel chromatography provided intermediate 78-a and 78-a' as an inseparable mixture.

Step 2: Intermediates 78-b and 78-b'

A solution of intermediates 78-a and 78-a' (90 mg, 0.14 mmol), trimethyl orthoformate (1.03 ml, 9.45 mmol) and TFA (catalytic) was stirred at room temperature for 1 hour. Excess trimethyl orthoformate was removed in vacuo and the residue was treated with 7.0 N ammonia in MeOH (1.03 ml, 7.27 mmol). The mixture was stirred at room temperature overnight and volatiles were removed under reduced pressure to provide intermediates 78-b and 78-b' as an inseparable mixture.

Step 3: Compound 118

4N HO in 1,4-dioxane (2.82 mL) was added to intermediates 78-b and 78-b' (60 mg, 0.09 mmol) and the mixture was stirred overnight at room temperature. Volatiles were removed under reduced pressure. Purification by reverse phase chromatography eluting with a 1% aqueous HCl/methanol gradient provided compound 118.2HCl as a white solid. MS (m/z) M+H=516.2

109
Synthesis of Compound 90
Scheme 79

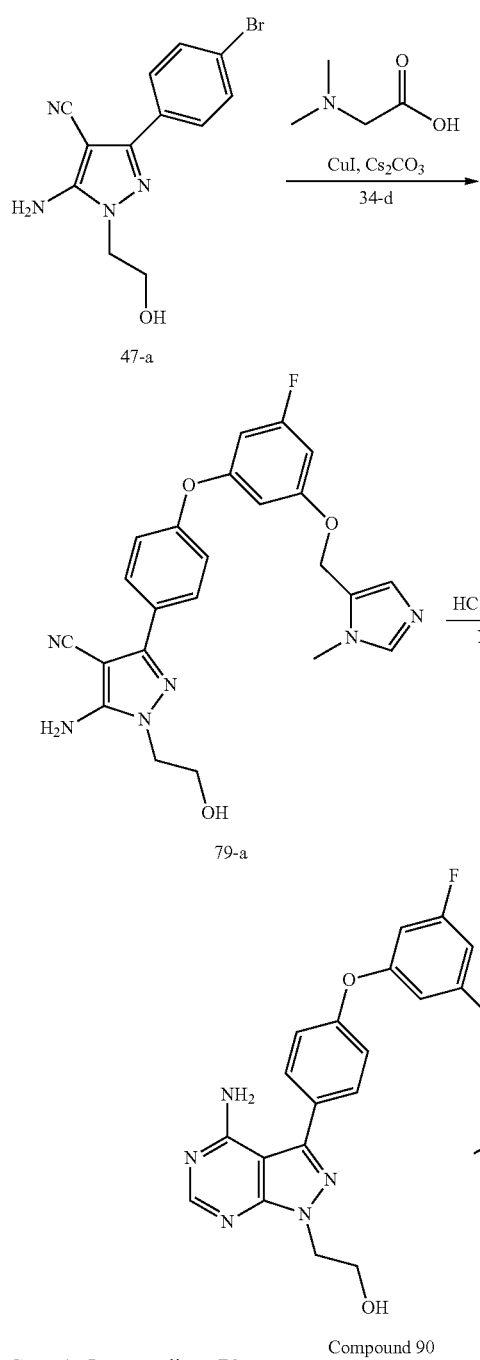

Compound 90

Step 1: Intermediate 79-a

To a solution of intermediate 79-a (310 mg, 1.0 mmol) and intermediate 34-d (313 mg, 1.21 mmol) in 1,4-dioxane (2.5 ml) were sequentially added N,N-dimethylglycine (156 mg, 1.51 mmol), copper(I) iodide (96.0 mg, 0.50 mmol) and cesium carbonate (1.31 g, 4.04 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over $MgSO_4$, filtered and concentrated under reduced pressure. Purification by reverse phase chromatography eluting with a 1% aqueous HCl/methanol gradient provided intermediate 79-a as a beige solid.

Step 2: Compound 90

Intermediate 79-a (280 mg, 0.62 mmol) and trimethyl orthoformate (2.05 ml, 18.7 mmol) were heated at 110° C. for 3 hours. Excess trimethyl orthoformate was removed in vacuo and the residue was treated with 7.0 N ammonia in MeOH (1.78 ml, 12.5 mmol). The mixture was stirred at room temperature overnight and volatiles were removed under reduced pressure. Purification by reverse phase chromatography eluting with a 1% aqueous HCl/methanol gradient provided compound 90.2HCl as a beige solid. MS (m/z) M+H=476.2

Synthesis of Compound 103
Scheme 80

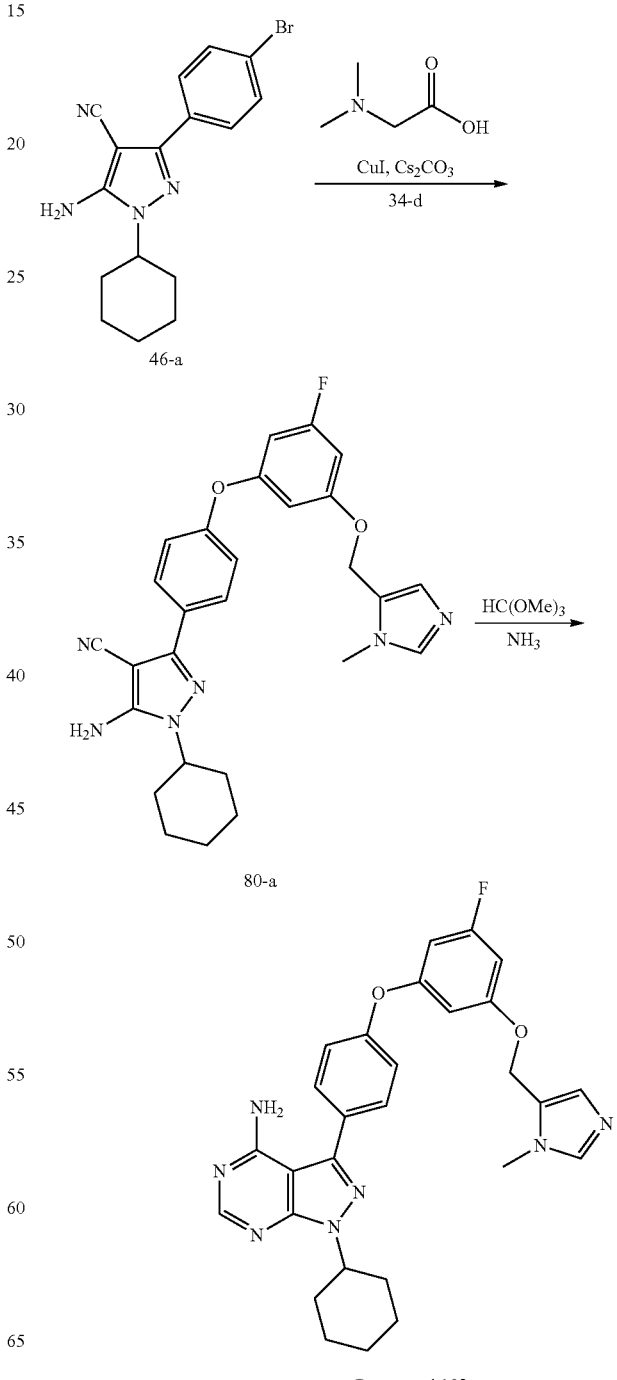

Compound 103

Step 1: Intermediate 80-a

To a solution of intermediate 46-a (300 mg, 0.87 mmol) and intermediate 34-d (247 mg, 0.95 mmol) in 1,4-dioxane (2.1 ml) were sequentially added N,N-dimethylglycine (134 mg, 1.30 mmol), copper(I) iodide (83 mg, 0.43 mmol) and cesium carbonate (1.13 g, 3.48 mmol). The reaction mixture was stirred at reflux overnight, cooled to room temperature, diluted with ethyl acetate and filtered over celite. A saturated aqueous solution of ammonium chloride was added to the filtrate, the organic layer was separated and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 80-a.HCl as a beige solid.

Step 2: Compound 103

Intermediate 80-a.HCl (65.0 mg, 0.13 mmol) and trimethyl orthoformate (3.0 ml, 4.01 mmol) were heated at 110° C. for 3 hours. Excess trimethyl orthoformate was removed in vacuo and the residue was treated with 7.0 N ammonia in MeOH (378 µl, 2.65 mmol). The mixture was stirred at room temperature overnight and volatiles were removed under reduced pressure. Purification by reverse phase chromatography eluting with a 1% aqueous HCl/methanol gradient provided compound 103.2HCl as a white solid. MS (m/z) M+H=514.2

Synthesis of Compound 120

Scheme 81

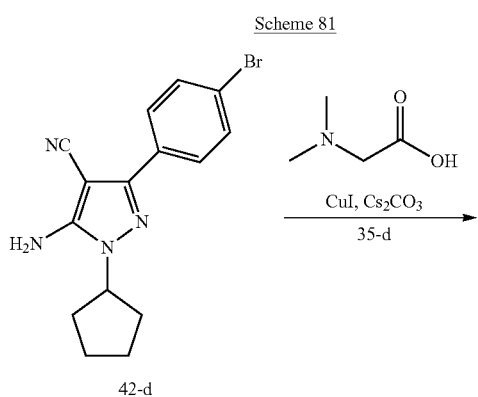

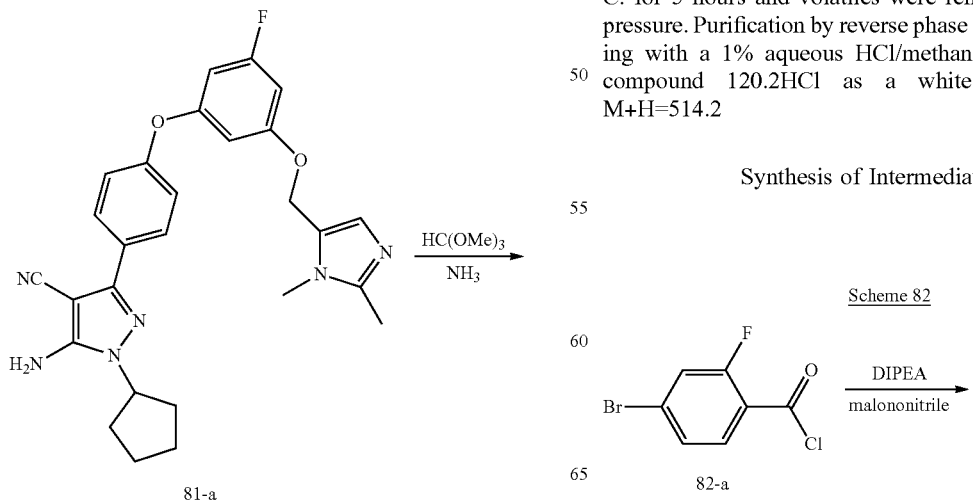

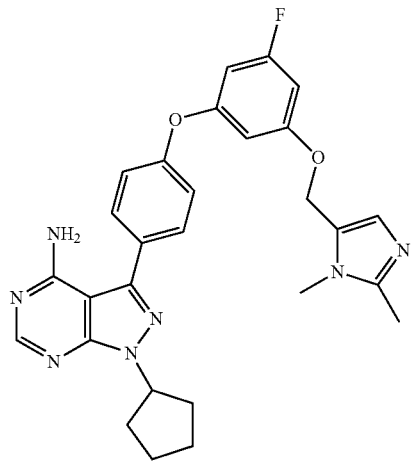

Compound 120

Step 1: Intermediate 81-a

To a solution of intermediate 42-d (176 mg, 0.53 mmol) and intermediate 35-d (145 mg, 0.53 mmol) in 1,4-dioxane (3.5 ml) were sequentially added N,N-dimethylglycine (123 mg, 1.19 mmol), copper(I) iodide (76 mg, 0.40 mmol) and cesium carbonate (693 mg, 2.13 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 81-a.HCl as a yellow foam.

Step 2: Compound 120

Intermediate 81-a.HCl (259 mg, 0.53 mmol) and trimethyl orthoformate (3.78 ml, 34.6 mmol) were heated at 110° C. for 1 hour. Excess trimethyl orthoformate was removed in vacuo and the residue was treated with 7.0 N ammonia in MeOH (3.80 ml, 26.6 mmol). The mixture was heated at 60° C. for 5 hours and volatiles were removed under reduced pressure. Purification by reverse phase chromatography eluting with a 1% aqueous HCl/methanol gradient provided compound 120.2HCl as a white solid. MS (m/z) M+H=514.2

Synthesis of Intermediate 82-c

Scheme 82

-continued

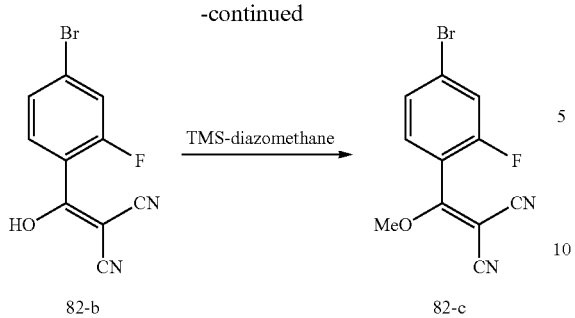

82-b            82-c

Step 1: Intermediate 82-b

To a solution of 4-bromo-2-fluorobenzoyl chloride (16.27 g, 68.5 mmol) in toluene (85 ml) and THF (8.5 ml), cooled to −10° C., were sequentially added malononitrile (4.75 g, 71.9 mmol) and DIPEA (23.93 ml, 137.0 mmol) in toluene (25 mL) drop wise over a period of 1 hour. After the addition was completed, the reaction was stirred for 2 hours at 0° C. and room temperature for an additional 2 hours. Volatiles were removed under reduced pressure. 1N HCl and ethyl acetate were added to the residue; the organic layer was separated, washed twice with 1N HCl and brine, dried over MgSO₄, filtered and concentrated under reduced pressure to provide intermediate 82-b as a yellow solid.

Step 2: Intermediate 82-c

To a solution of intermediate 82-b (18.29 g, 68.5 mmol) in acetonitrile (247 ml) and methanol (27.4 ml), cooled to 0° C., was added DIPEA (14.36 ml, 82.0 mmol) and a 2M solution of diazomethyl)trimethylsilane in hexanes (37.7 ml, 75.0 mmol). After the addition was completed, the reaction was stirred at room temperature overnight. Acetic acid (1.17 ml, 20.5 mmol) was added, the reaction was stirred for 30 minutes and volatiles were removed under reduced pressure. A saturated aqueous solution of NaHCO₃ and ethyl acetate were added, the organic layer was separated, washed with brine, dried over MgSO₄, filtered and concentrated under reduced pressure. Purification by silica gel chromatography provided intermediate 82-c as a yellow solid.

Synthesis of Intermediate 83-a

Scheme 83

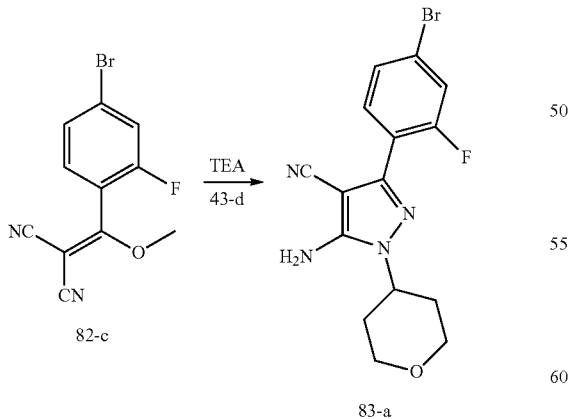

To a solution of intermediate 82-c (2.0 g, 7.12 mmol) and TEA (1.98 ml, 14.23 mmol) in EtOH (3.50 ml) was added intermediate 43-d.HCl (1.30 g, 8.54 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO₄, filtered and concentrated under reduced pressure to provide intermediate 83-a as a yellow solid.

Synthesis of Compound 60

Scheme 84

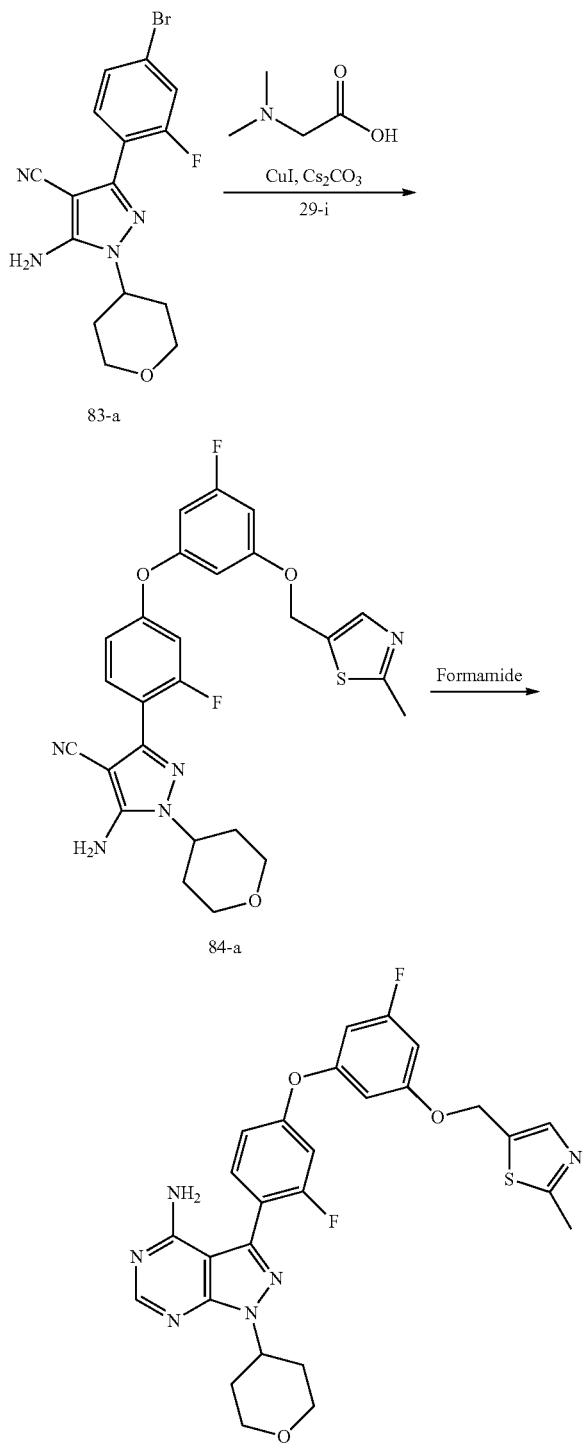

Compound 60

Step 1: Intermediate 84-a

To a solution of intermediate 83-a (2.60 g, 7.12 mmol) and intermediate 29-i (1.00 g, 4.18 mmol) in 1,4-dioxane (20.9 ml) were sequentially added N,N-dimethylglycine (646 mg, 6.27 mmol), copper(I) iodide (398 mg, 2.09 mmol) and cesium carbonate (4.09 g, 12.5 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided intermediate 84-a as a beige solid.

Step 2: Compound 60

Formamide (11.7 ml, 293 mmol) was added to intermediate 84-a (2.18 g, 4.18 mmol) and the reaction was stirred at 180° C. overnight. Water and ethyl acetate were added, the organic layer was separated, washed with brine, dried over MgSO$_4$, filtered and concentrated under reduced pressure. Purification by reverse phase chromatography eluting with a 1% aqueous HCl/methanol gradient provided compound 60.2HCl as white solid. MS (m/z) M+H=551.2

Synthesis of Compound 73

Scheme 85

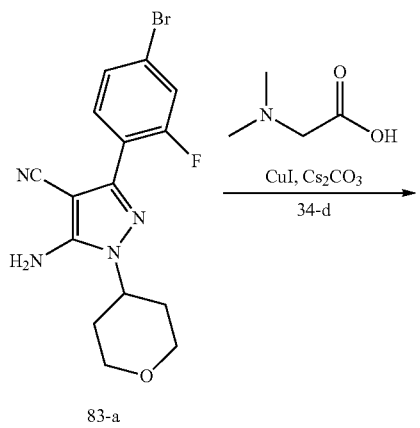

83-a

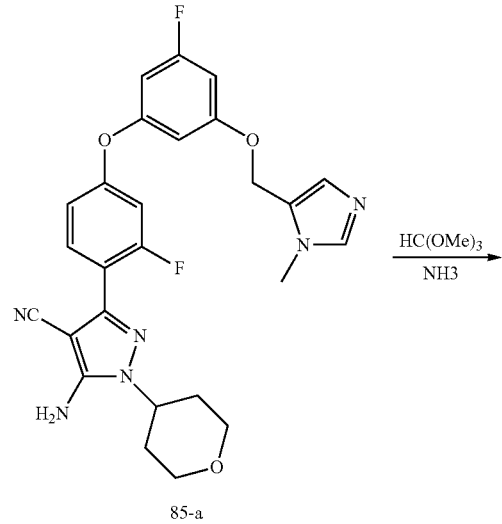

85-a

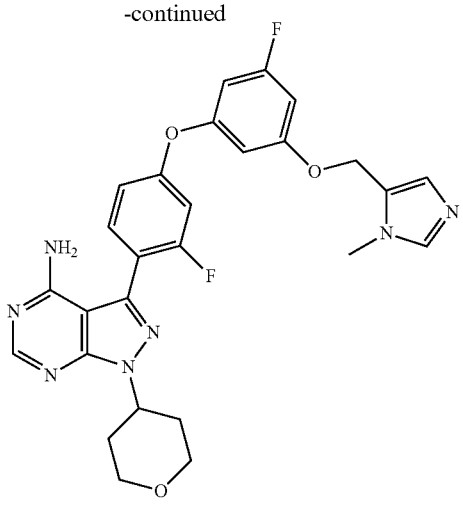

Compound 73

Step 1: Intermediate 85-a

To a solution of intermediate 83-a (2.60 g, 7.12 mmol) and intermediate 34-d (1.0 g, 4.18 mmol) in 1,4-dioxane (20.9 ml) were sequentially added N,N-dimethylglycine (646 mg, 6.27 mmol), copper(I) iodide (398 mg, 2.09 mmol) and cesium carbonate (4.09 g, 12.5 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by silica gel chromatography provided intermediate 85-a as a beige solid.

Step 2: Compound 73

Intermediate 85-a (195.0 mg, 0.38 mmol) and trimethyl orthoformate (1.26 ml, 11.59 mmol) were heated at 110° C. for 3 hours. Excess trimethyl orthoformate was removed in vacuo and the residue was treated with 7.0 N ammonia in MeOH (3.86 ml, 7.72 mmol). The mixture was stirred at room temperature overnight and volatiles were removed under reduced pressure. Purification by reverse phase chromatography eluting with a 1% aqueous HCl/methanol gradient provided compound 73.HCl as white solid. MS (m/z) M+H=534.1

Synthesis of Compound 95

Scheme 86

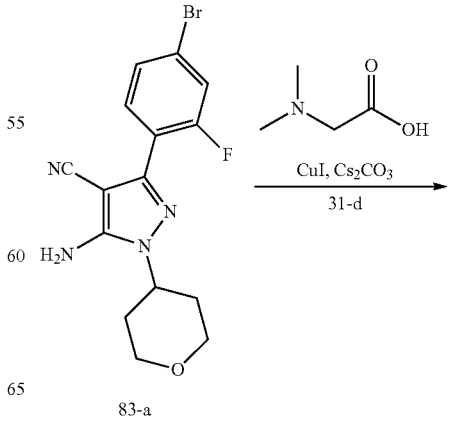

83-a

-continued

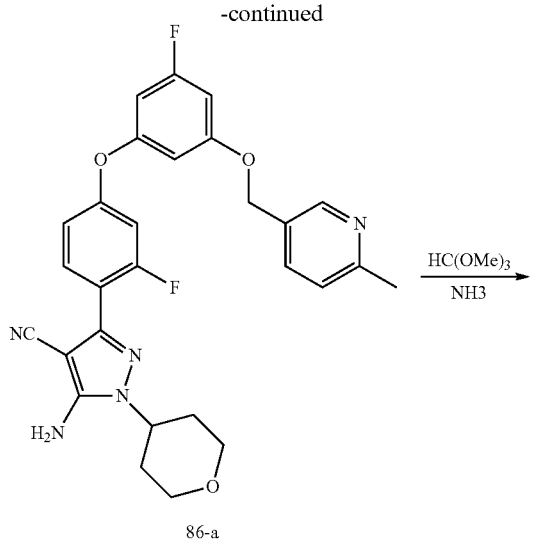

86-a

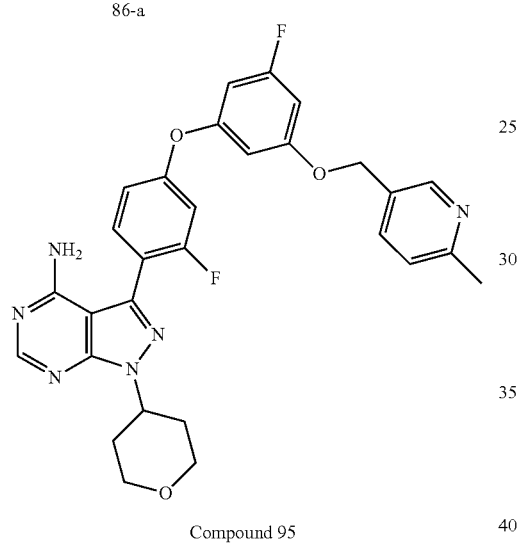

Compound 95

Step 1: Intermediate 86-a

To a solution of intermediate 83-a (200 mg, 0.54 mmol) and intermediate 31-d (177 mg, 0.65 mmol) in 1,4-dioxane (3.65 ml) were sequentially added N,N-dimethylglycine (127 mg, 1.23 mmol), copper(I) iodide (7.8 mg, 0.41 mmol) and cesium carbonate (714 mg, 2.19 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 86-a.HCl as a beige solid.

Step 2: Compound 95

Intermediate 86-a.HCl (284 mg, 0.54 mmol) and trimethyl orthoformate (3.90 ml, 35.6 mmol) were heated at 110° C. for 1 hour. Excess trimethyl orthoformate was removed in vacuo and the residue was treated with 7.0 N ammonia in MeOH (3.91 ml, 27.4 mmol). The mixture was stirred at room temperature overnight and volatiles were removed under reduced pressure. Purification by reverse phase chromatography eluting with a 1% aqueous HCl/methanol gradient provided compound 95.2HCl as white solid. MS (m/z) M+H=545.2

Synthesis of Intermediate 87-a

Scheme 87

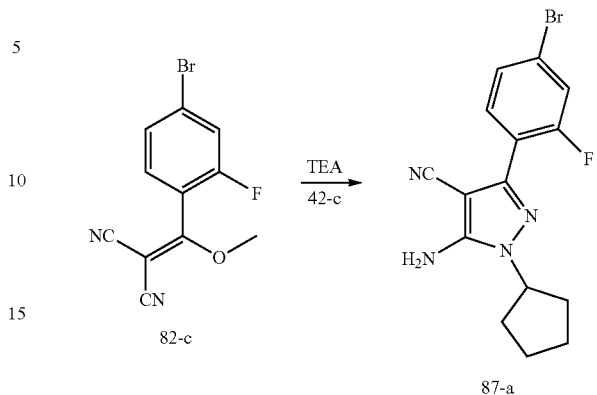

To a solution of intermediate 82-c (1.00 g, 3.56 mmol) and TEA (1.09 ml, 7.83 mmol) in EtOH (3.50 ml) was added intermediate 42-c (583 mg, 4.27 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure. Purification by silica gel chromatography provided intermediate 87-a as beige solid.

Synthesis of Compound 92

Scheme 88

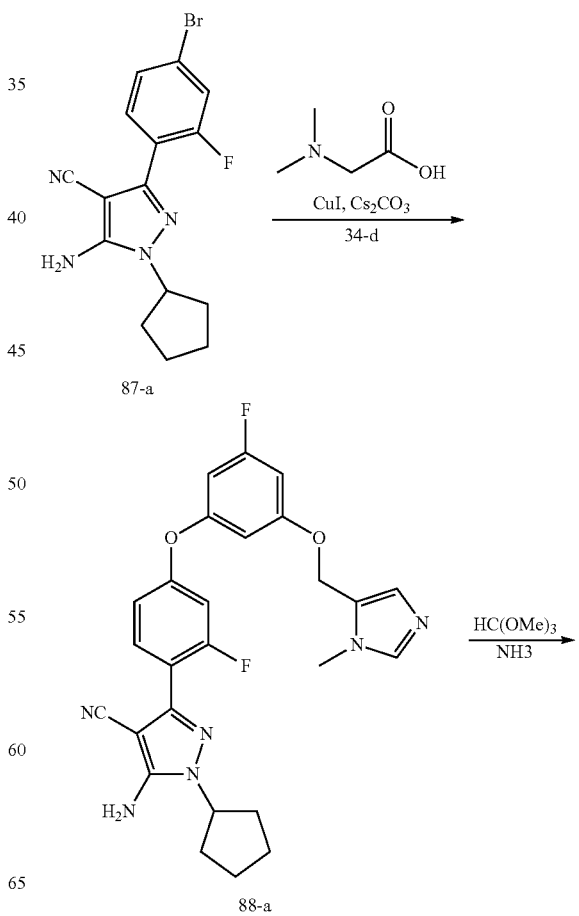

-continued

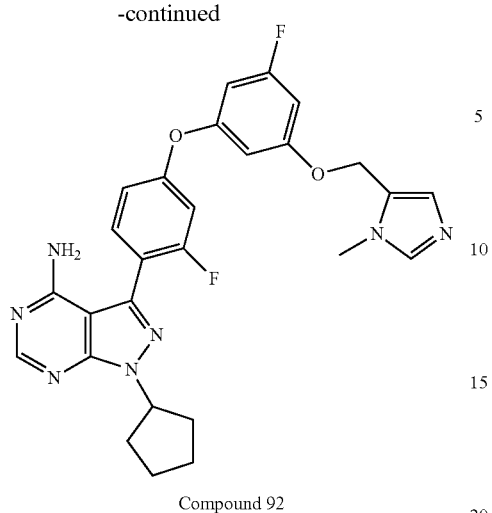

Compound 92

Step 1: Intermediate 88-a

To a solution of intermediate 87-a (452 mg, 1.29 mmol) and intermediate 34-d (368 mg, 1.42 mmol) in 1,4-dioxane (5.20 ml) were sequentially added N,N-dimethylglycine (400 mg, 3.88 mmol), copper(I) iodide (247 mg, 1.29 mmol) and cesium carbonate (1.26 g, 3.88 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 88-a.HCl as a beige solid.

Step 2: Compound 92

Intermediate 88-a.HCl (124.0 mg, 0.25 mmol) and trimethyl orthoformate (935 µl, 7.63 mmol) were heated at 110° C. for 3 hours. Excess trimethyl orthoformate was removed in vacuo and the residue was treated with 7.0 N ammonia in MeOH (2.54 ml, 5.09 mmol). The mixture was stirred at room temperature overnight and volatiles were removed under reduced pressure. Purification by reverse phase chromatography eluting with a 1% aqueous HCl/methanol gradient provided compound 92.2HCl as a beige solid. MS (m/z) M+H=518.2

Synthesis of Intermediate 89-a

Scheme 89

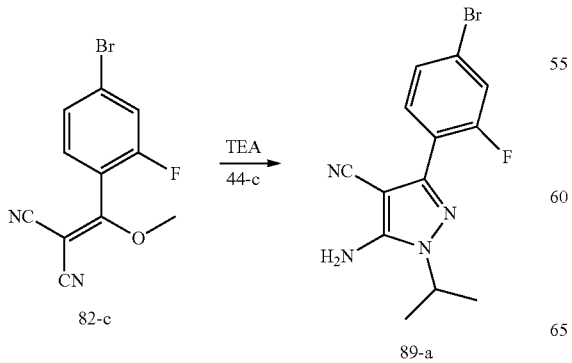

To a solution of intermediate 82-c (2.0 g, 7.12 mmol) and TEA (2.18 ml, 15.65 mmol) in EtOH (7.12 ml) was added intermediate isopropylhydrazine hydrochloride (944 mg, 8.54 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over MgSO$_4$, filtered and concentrated under reduced pressure. Purification by silica gel chromatography provided intermediate 89-a as a beige solid.

Synthesis of Compound 98

Scheme 90

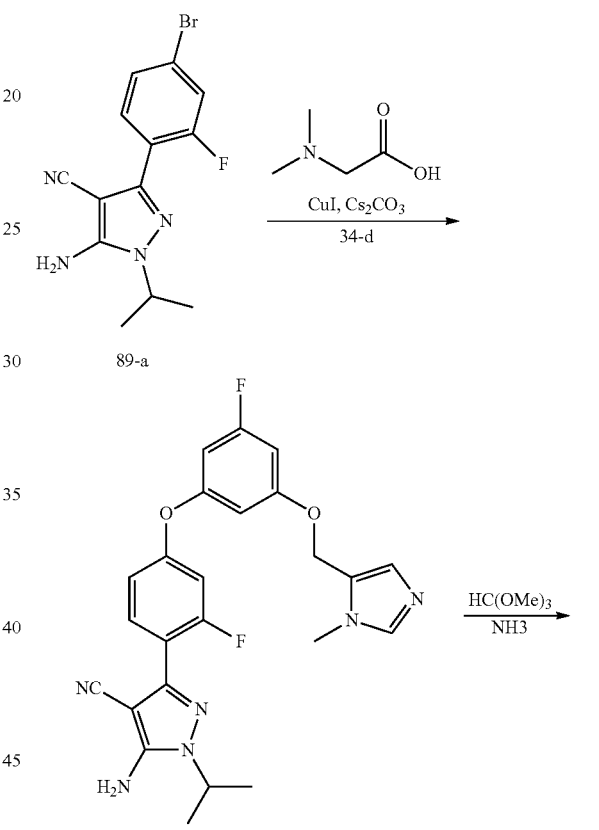

Step 1: Intermediate 90-a

To a solution of intermediate 89-a (400 mg, 1.24 mmol) and intermediate 34-d (352 mg, 1.36 mmol) in 1,4-dioxane (4.9 ml) were sequentially added N,N-dimethylglycine (383 mg, 3.71 mmol), copper(I) iodide (236 mg, 1.24 mmol) and cesium carbonate (1.21 g, 3.71 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over $MgSO_4$, filtered and concentrated under reduced pressure. Purification by reverse phase chromatography eluting with a 1% aqueous HCl/methanol gradient provided intermediate 90-a.HCl as beige solid.

Step 2: Compound 98

Intermediate 90-a.HCl (208 mg, 0.45 mmol) and trimethyl orthoformate (1.47 ml, 13.4 mmol) were heated at 110° C. for 3 hours. Excess trimethyl orthoformate was removed in vacuo and the residue was treated with 7.0 N ammonia in MeOH (4.48 ml, 8.96 mmol). The mixture was stirred at room temperature for 3 days and volatiles were removed under reduced pressure. Purification by reverse phase chromatography eluting with a 1% aqueous HCl/methanol gradient provided compound 98.2HCl as a beige solid. MS (m/z) M+H=492.2

Synthesis of Intermediate 91-d

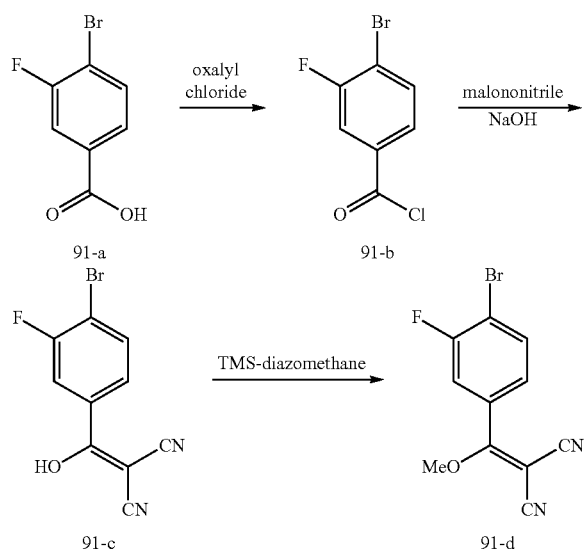

Step 1: Intermediate 91-b

To a suspension of 4-bromo-3-fluorobenzoic acid (15.0 g, 68.5 mmol) in dichloromethane (342.0 ml) was added DMF (106.0 µl, 1.37 mmol) and oxalylyl chloride (8.99 ml, 103.0 mmol). The solution was then stirred at room temperature for 3 hours. Volatiles were removed under reduced pressure to provide intermediate 91-b as a yellow solid.

Step 2: Intermediate 91-c

To a solution of intermediate 91-b (16.27 g, 68.5 mmol) in toluene (85.0 ml) and THF (8.5 ml) cooled to −10° C. were sequentially added malononitrile (4.75 g, 71.9 mmol) and DIPEA (23.93 ml, 137 mmol) drop wise over a period of 15 minutes. The reaction was stirred at 0° C. for 2 hours and room temperature for an additional 2 hours. Volatiles were removed under reduced pressure. Ethyl acetate and 1N HCl were added, the organic layer was separated, washed with brine, dried over $MgSO_4$, filtered and concentrated in vacuo to provide intermediate 91-c as a yellow solid.

Step 3: Intermediate 91-d

To a solution of intermediate 91-c (18.29 g, 68.5 mmol) in acetonitrile (247.0 ml) and MeOH (27.4 ml) cooled to 0° C. were sequentially added DIPEA (14.36 ml, 82.0 mmol) and a 2M solution of TMS-Diazomethane in hexanes (37.7 ml, 75.0 mmol). The reaction was then stirred for 5 hours at room temperature. Acetic acid (1.17 ml, 20.55 mmol) was then added and the reaction was stirred for an additional 30 minutes. Volatiles were removed under reduced pressure. A saturated aqueous solution of $NaHCO_3$ and ethyl acetate was added, the organic layer was separated, washed with brine, dried over $MgSO_4$, filtered and concentrated in vacuo. Purification by silica gel chromatography provided intermediate 91-d as a beige solid.

Synthesis of Intermediate 92-a

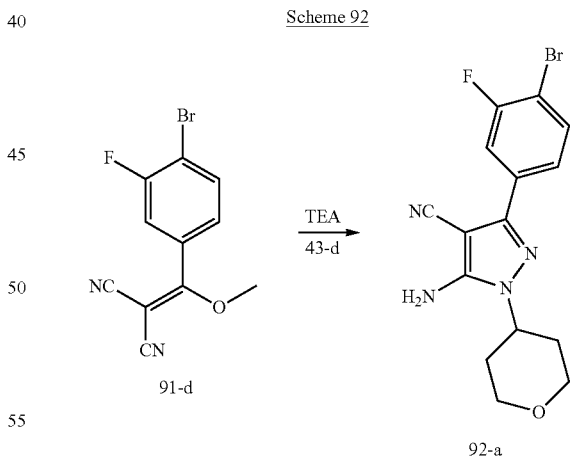

To a solution of intermediate 91-d (2.0 g, 7.12 mmol) and TEA (1.98 ml, 14.23 mmol) in EtOH (3.50 ml) was added intermediate 43-d.HCl (1.30 g, 8.54 mmol) and the reaction was then stirred for 2 hours at 100° C. Volatiles were removed under reduced pressure. A saturated aqueous solution of ammonium chloride and ethyl acetate were added to the residue, the organic layer was separated, washed with brine, dried over $MgSO_4$, filtered and concentrated under reduced pressure. Purification by silica gel chromatography provided intermediate 92-a as a beige solid.

Synthesis of Compound 59

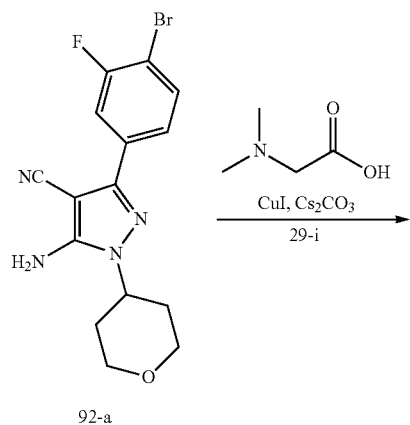

Step 1: Intermediate 93-a

To a solution of intermediate 92-a (2.60 g, 7.12 mmol) and intermediate 29-i (1.0 g, 4.18 mmol) in 1,4-dioxane (20.90 ml) were sequentially added N,N-dimethylglycine (646 mg, 6.27 mmol), copper(I) iodide (398 mg, 2.09 mmol) and cesium carbonate (4.09 g, 12.54 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO₄, filtered and concentrated under reduced pressure. Purification by silica gel chromatography provided intermediate 93-a as a beige solid.

Step 2: Compound 59

Formamide (11.67 ml, 293.0 mmol) was added to intermediate 93-a (2.18 g, 4.18 mmol) and the reaction was stirred at 180° C. overnight then cooled to room temperature. Water and ethyl acetate were added, the organic layer was separated, washed with brine, dried over MgSO₄, filtered and concentrated under reduced pressure. Purification by reverse phase chromatography eluting with a 1% aqueous HCl/methanol gradient provided compound 59.2HCl as a yellow solid. MS (m/z) M+H=551.1

Synthesis of Compound 72

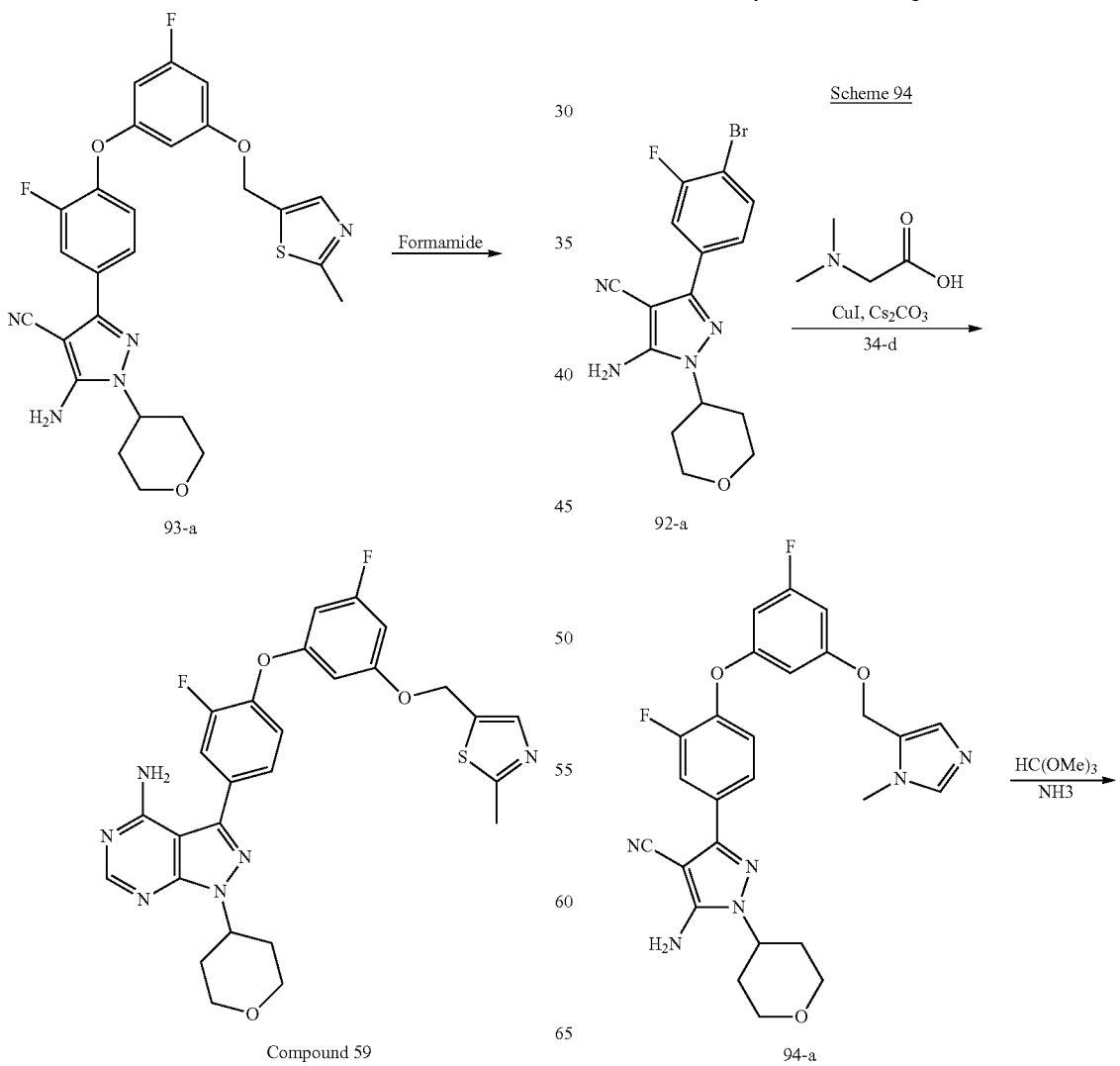

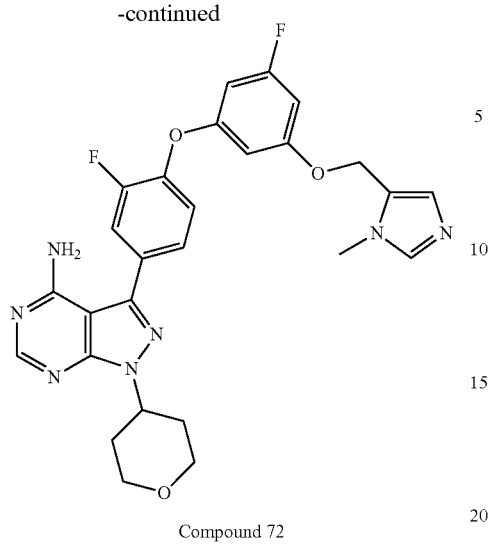

Compound 72

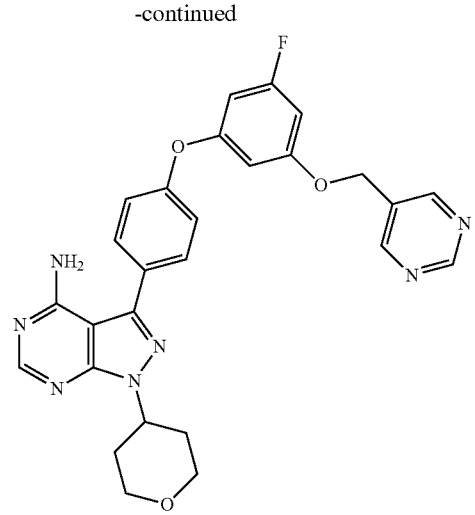

Compound 68

Step 1: Intermediate 94-a

To a solution of intermediate 92-a (291.0 mg, 0.79 mmol) and intermediate 34-d (227.0 mg, 0.87 mmol) in 1,4-dioxane (3.2 ml) were sequentially added N,N-dimethylglycine (247.0 mg, 2.39 mmol), copper(I) iodide (152.0 mg, 0.79 mmol) and cesium carbonate (780 mg, 2.39 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided intermediate 94-a.HCl as a beige solid.

Step 2: Compound 72:

Intermediate 94-a.HCl (56.0 mg, 0.11 mmol) and trimethyl orthoformate (363 µl, 3.32 mmol) were heated at 110° C. for 3 hours. Excess trimethyl orthoformate was removed in vacuo and the residue was treated with 7.0 N ammonia in MeOH (1.10 ml, 2.21 mmol). The mixture was stirred at room temperature overnight and volatiles were removed under reduced pressure. Purification by reverse phase chromatography eluting with a 1% aqueous HCl/methanol gradient provided compound 72.2HCl as a white solid. MS (m/z) M+H=534.2

To a solution of intermediate 17-a (300.0 mg, 0.80 mmol) and intermediate 39-b (177.0 mg, 0.80 mmol) in 1,4-dioxane (3.6 ml) were sequentially added N,N-dimethylglycine (372.0 mg, 3.61 mmol), copper(I) iodide (229.0 mg, 1.20 mmol) and cesium carbonate (1.04 g, 3.21 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided compound 68.2HCl as a beige solid. MS (m/z) M+H=514.2

Synthesis of Compound 69

Synthesis of Compound 68

Scheme 95

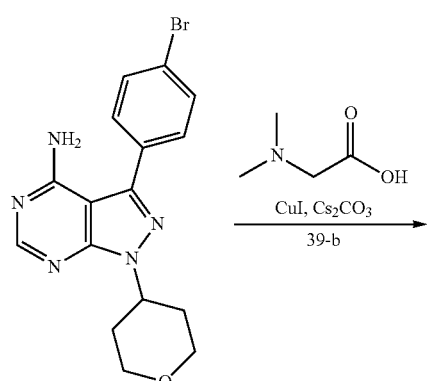

17-a

Scheme 96

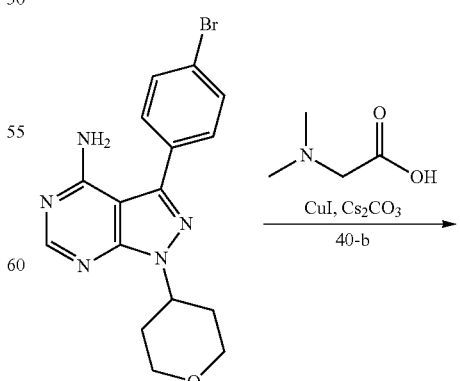

17-a

127
-continued

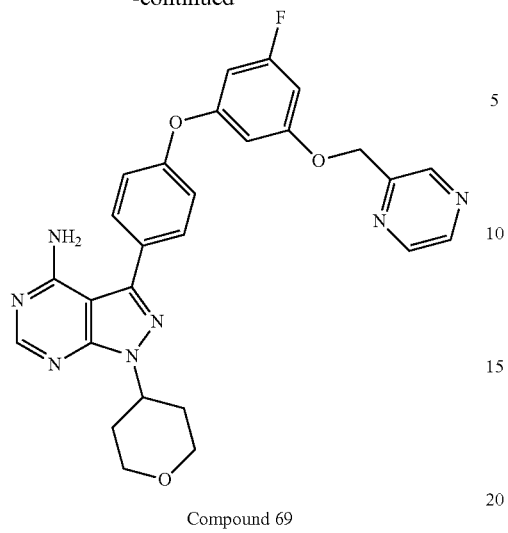

Compound 69

128
-continued

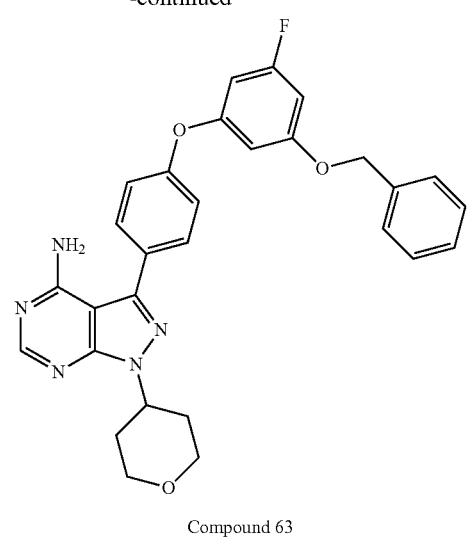

Compound 63

To a solution of intermediate 17-a (300.0 mg, 0.80 mmol) and intermediate 40-b (177.0 mg, 0.80 mmol) in 1,4-dioxane (3.6 ml) were sequentially added N,N-dimethylglycine (372.0 mg, 3.61 mmol), copper(I) iodide (229.0 mg, 1.20 mmol) and cesium carbonate (1.04 g, 3.21 mmol). The reaction mixture was stirred at reflux overnight, cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over MgSO$_4$, filtered and concentrated under reduced pressure. Purification by reverse phase chromatography eluting with a 1% aqueous HCl/methanol gradient provided compound 69.2HCl as a beige solid. MS (m/z) M+H=514.2

A solution of intermediate 17-a (437 mg, 1.17 mmol), intermediate 11-c (255 mg, 1.17 mmol), quinolin-8-ol (34 mg, 0.23 mmol), copper (I) iodide (44.0 mg, 0.23 mmol) and cesium carbonate (761 mg, 2.33 mmol), in dimethylacetamide (1.2 ml), was degassed with argon for 10 minutes, heated in a sealed tube at 140° C. overnight and then cooled to room temperature. Water and ethyl acetate were added, the organic layer was separated, the aqueous layer was extracted twice with ethyl acetate, the combined organic extracts were washed with brine, dried over MgSO$_4$, filtered and concentrated under reduced pressure. Purification by reverse phase chromatography eluting with a 1% HCl/methanol gradient provided compound 63.HCl as a yellow solid. MS (m/z) M+H=512.2

Synthesis of Compound 63

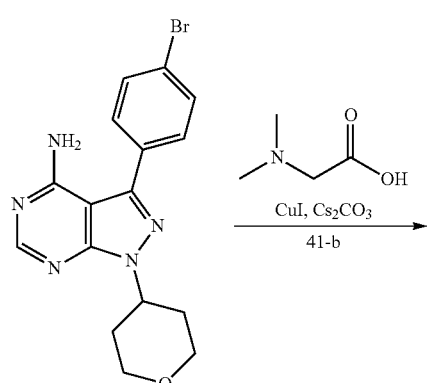

Synthesis of Compound 67

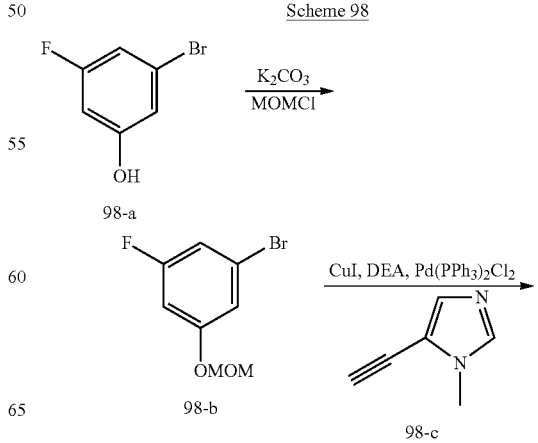

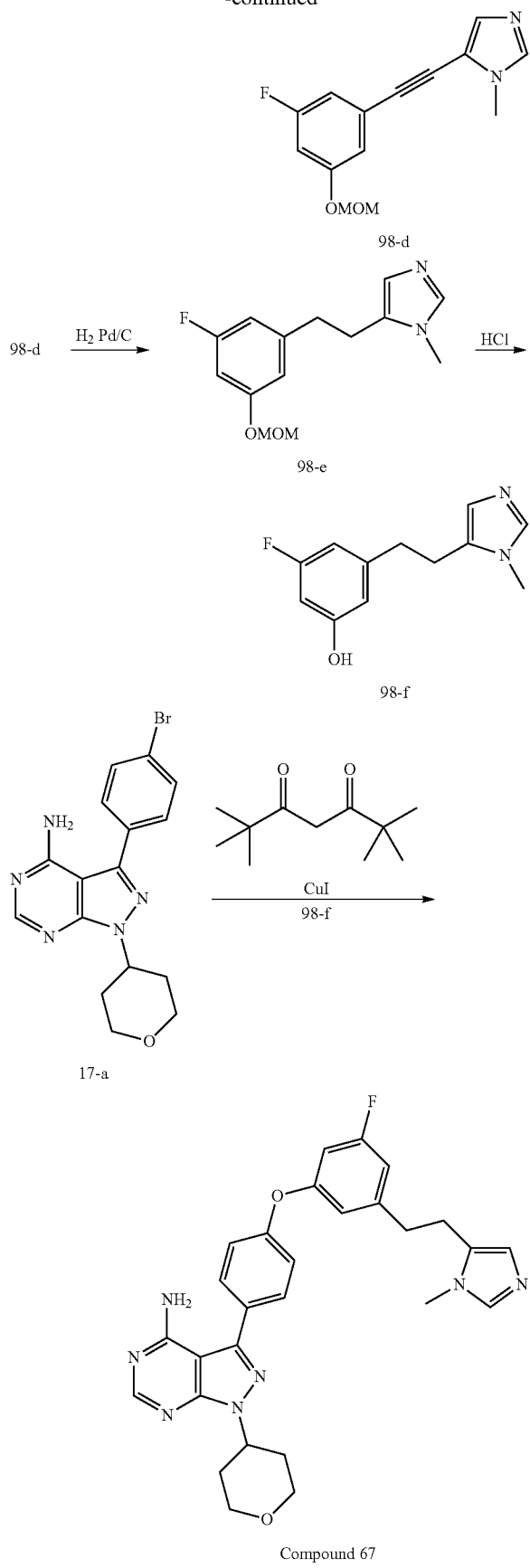

Step 1: Intermediate 98-b

To a solution of 3-bromo-5-fluorophenol, 98-a (25.00 g, 131.0 mmol), in acetone (654 ml) were sequentially added $K_2CO_3$ (27.10 g, 196.0 mmol) and chloro(methoxy)methane (11.59 g, 144.0 mmol). The reaction was stirred at room temperature for 2 hours and then filtered. The filtrate was concentrated under reduced pressure to provide intermediate 98-b as a yellow oil.

Step 2: Intermediate 98-d

To a solution of intermediate 98-b (2.00 g, 8.51 mmol) in DMF (17.02 ml), were sequentially added diethylamine (975 μl, 9.36 mmol), copper(I)iodide (65 mg, 0.34 mmol) and 5-ethynyl-1-methyl-1H-imidazole 98-c (948 mg, 8.93 mmol). After copper(I)iodide has completely dissolved, Dichlorobis(triphenylphosphine)palladium(II) (119 mg, 0.17 mmol) was added and the reaction was then stirred at 100° C. overnight and then cooled to room temperature. Water and ethyl acetate were added, the organic layer was separated, the aqueous layer was extracted twice with ethyl acetate, the combined organic extracts were washed with brine, dried over $MgSO_4$, filtered and concentrated under reduced pressure. Purification by silica gel chromatography provided intermediate 98-d as a beige solid Step 3: Intermediate 98-e A solution of intermediate 98-d (600.0 mg, 2.3 mmol) in methanol was treated with 10% palladium on carbon (245.0 mg, 0.01 mmol) and purged with $H_2$. The solution was stirred under $H_2$ (1 atm) overnight before being filtered through celite. The filtrate was concentrated in vacuo to provide intermediate 98-e as a yellow oil.

Step 4: Intermediate 98-f

To a solution of intermediate 98-e (2.4 g, 9.08 mmol) in MeOH (17 ml) was added 4N HCl in dioxane (2.76 ml, 91 mmol). The reaction mixture was stirred at room temperature for 2 hours. Volatiles were removed under reduced pressure, diethyl ether was added to the residue; a precipitate formed and was collected by filtration to provide intermediate 98-f.HCl as a white solid.

Step 5: Compound 67

A solution of intermediate 17-a (292 mg, 0.78 mmol), intermediate 98-f.HCl (200 mg, 0.78 mmol), tetramethylheptane-3,5-dione (287 mg, 1.56 mmol), copper (I) iodide (148 mg, 0.78 mmol) and cesium carbonate (762 mg, 2.33 mmol), in NMP (3.9 ml), was degassed with argon for 10 minutes, heated in a sealed tube at 120° C. overnight and then cooled to room temperature, diluted with ethyl acetate and filtered over celite. A saturated aqueous solution of ammonium chloride was added to the filtrate, the organic layer was separated, and the aqueous phase was extracted twice with ethyl acetate. The combined organic extracts were washed with brine, dried over $MgSO_4$, filtered and concentrated under reduced pressure. Purification by reverse phase chromatography eluting with a 1% HCl/methanol gradient provided compound 67.2HCl as a yellow solid. MS (m/z) M+H=514.3

Compounds 7, 8, 11, 13, 14, 19, 21, 24 to 28, 33, 34, 37 to 51, 53, 56, 61, 62, 64, 66, 70, 71, 74-77, 79 to 84, 86 to 89, 94, 96, 104, 105, 107 to 112, 115, 116, 119, 121, 122, 123, 124, 126, 127, 131, 132, and 133 were prepared using similar methods to those described above.

Table 1 summarizes representative compound of Formula 1.

TABLE 1
| Example Compounds of Formula 1 |||
| Compound | Structure | MS (m/z) |
| --- | --- | --- |
| 1 | 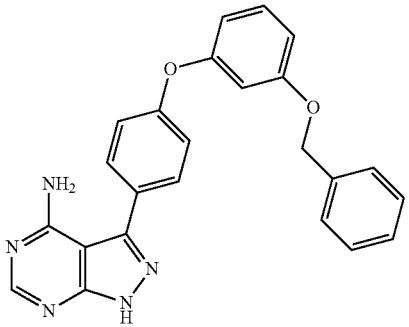 [SMILES: Nc1ncnc2[nH]nc(-c3ccc(Oc4cccc(OCc5ccccc5)c4)cc3)c12] | [M + H]⁺ = 410.2 |
| 2 | 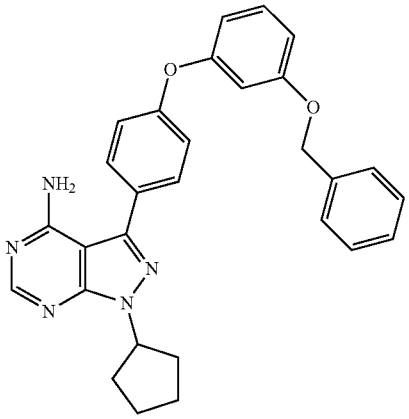 [SMILES: Nc1ncnc2c1c(-c1ccc(Oc3cccc(OCc4ccccc4)c3)cc1)nn2C1CCCC1] | [M + H]⁺ = 478.2 |
| 3 | 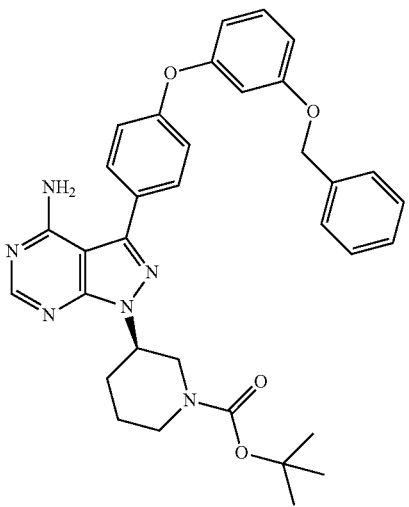 [SMILES: CC(C)(C)OC(=O)N1CCC[C@@H](n2nc(-c3ccc(Oc4cccc(OCc5ccccc5)c4)cc3)c3c(N)ncnc32)C1] | [M + H]⁺ = 593.1 |

TABLE 1-continued
Example Compounds of Formula 1
| Compound | Structure | MS (m/z) |
|---|---|---|
| 4 | 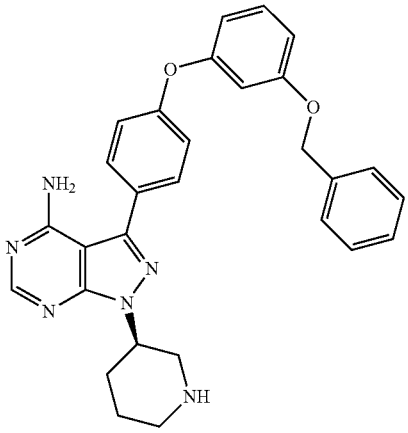 [SMILES: Nc1ncnc2c1c(-c1ccc(Oc3cccc(OCc4ccccc4)c3)cc1)nn2[C@@H]1CCCNC1] | [M + H]⁺ = 493.1 |
| 5 | 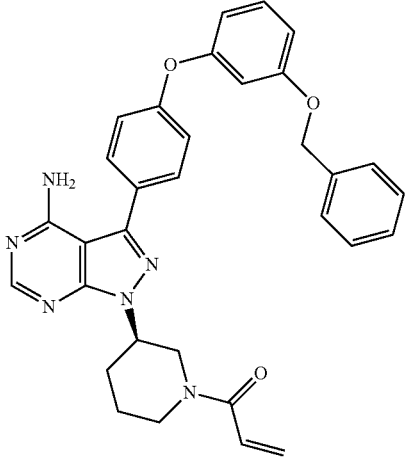 [SMILES: C=CC(=O)N1CCC[C@@H](n2nc(-c3ccc(Oc4cccc(OCc5ccccc5)c4)cc3)c3c(N)ncnc32)C1] | [M + H]⁺ = 547.1 |
| 6 | 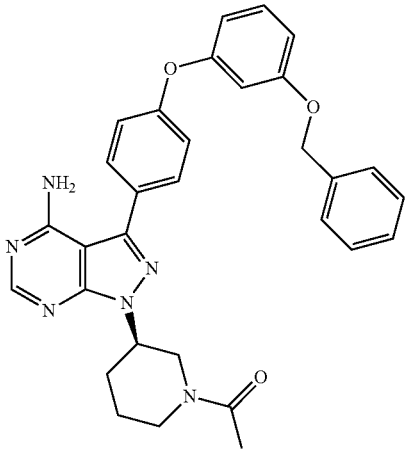 [SMILES: CC(=O)N1CCC[C@@H](n2nc(-c3ccc(Oc4cccc(OCc5ccccc5)c4)cc3)c3c(N)ncnc32)C1] | [M + H]⁺ = 535.1 |

TABLE 1-continued
Example Compounds of Formula 1
| Compound | Structure | MS (m/z) |
|---|---|---|
| 7 | 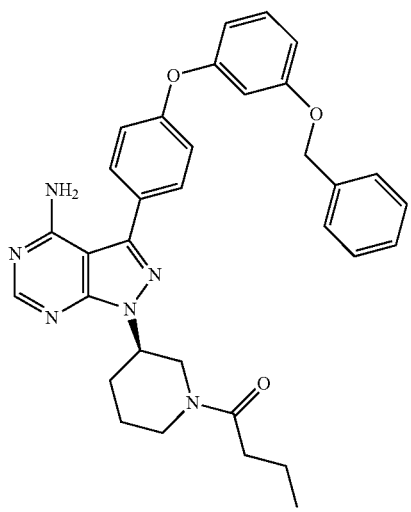 [SMILES: CCCC(=O)N1CCC[C@@H](n2nc(-c3ccc(Oc4cccc(OCc5ccccc5)c4)cc3)c3c(N)ncnc32)C1] | [M + H]⁺ = 563.1 |
| 8 | 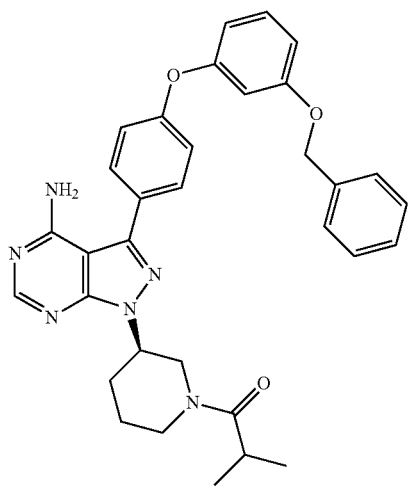 [SMILES: CC(C)C(=O)N1CCC[C@@H](n2nc(-c3ccc(Oc4cccc(OCc5ccccc5)c4)cc3)c3c(N)ncnc32)C1] | [M + H]⁺ = 563.1 |
| 9 | 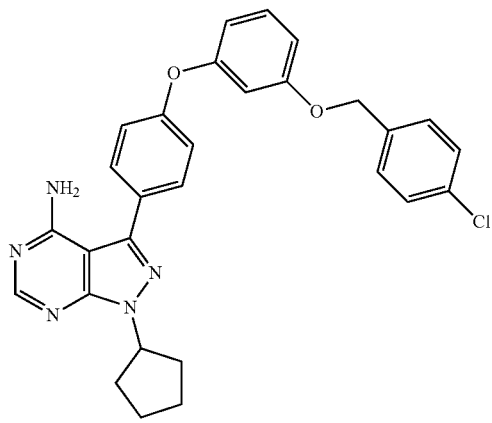 [SMILES: Nc1ncnc2c1c(-c1ccc(Oc3cccc(OCc4ccc(Cl)cc4)c3)cc1)nn2C1CCCC1] | [M + H]⁺ = 512.2 |

TABLE 1-continued

Example Compounds of Formula 1

| Compound | Structure | MS (m/z) |
|---|---|---|
| 10 | 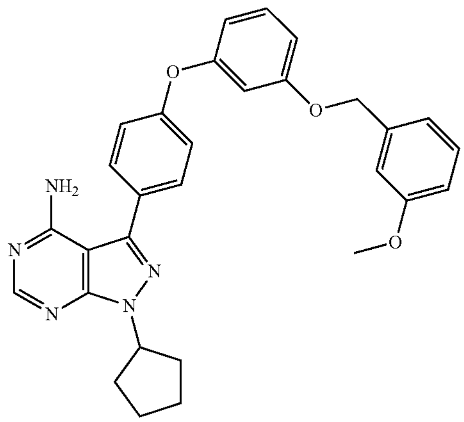 [SMILES: COc1cccc(COc2cccc(Oc3ccc(-c4nn(C5CCCC5)c5ncnc(N)c45)cc3)c2)c1] | [M + H]+ = 508.1 |
| 11 | 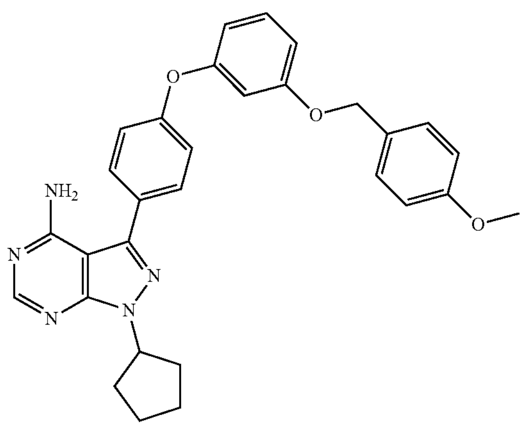 [SMILES: COc1ccc(COc2cccc(Oc3ccc(-c4nn(C5CCCC5)c5ncnc(N)c45)cc3)c2)cc1] | [M + H]+ = 508.2 |
| 12 | 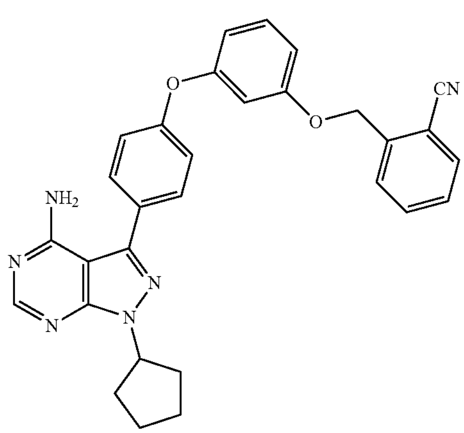 [SMILES: N#Cc1ccccc1COc1cccc(Oc2ccc(-c3nn(C4CCCC4)c4ncnc(N)c34)cc2)c1] | [M + H]+ = 503.2 |

TABLE 1-continued

Example Compounds of Formula 1

| Compound | Structure | MS (m/z) |
|---|---|---|
| 13 | 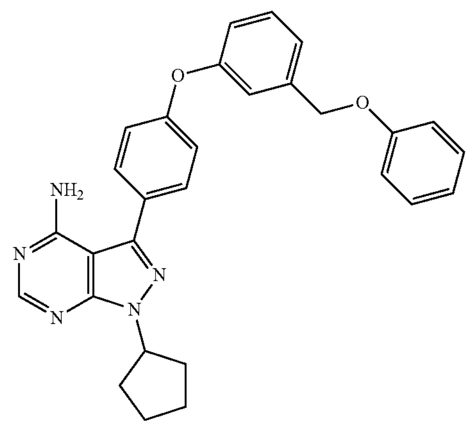 [SMILES: Nc1ncnc2c1c(-c1ccc(Oc3cccc(COc4ccccc4)c3)cc1)nn2C1CCCC1] | [M + H]⁺ = 478.2 |
| 14 | 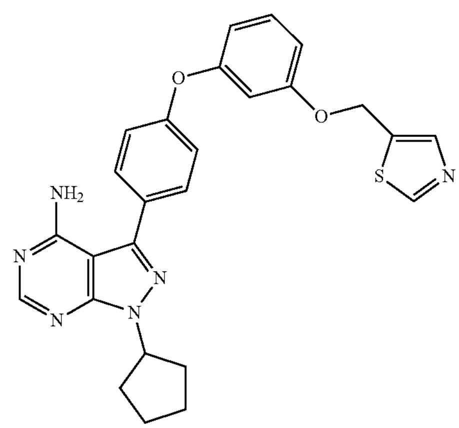 [SMILES: Nc1ncnc2c1c(-c1ccc(Oc3cccc(OCc4cncs4)c3)cc1)nn2C1CCCC1] | [M + H]⁺ = 485.2 |
| 15 | 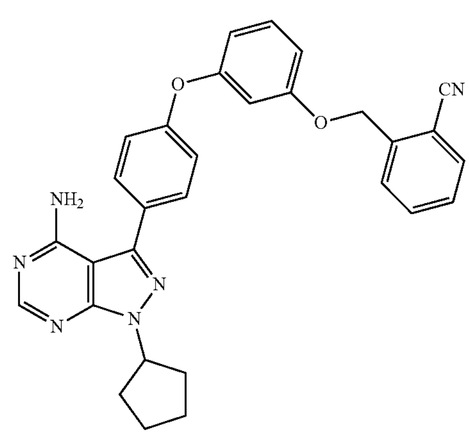 [SMILES: N#Cc1ccccc1COc1cccc(Oc2ccc(-c3nn(C4CCCC4)c4ncnc(N)c34)cc2)c1] | [M + H]⁺ = 503.3 |

TABLE 1-continued

| Compound | Structure | MS (m/z) |
|---|---|---|
| 16 | 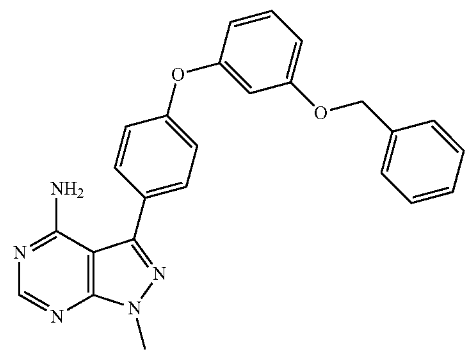 [SMILES: Cn1nc(-c2ccc(Oc3cccc(OCc4ccccc4)c3)cc2)c2c(N)ncnc21] | [M + H]⁺ = 424.2 |
| 17 | 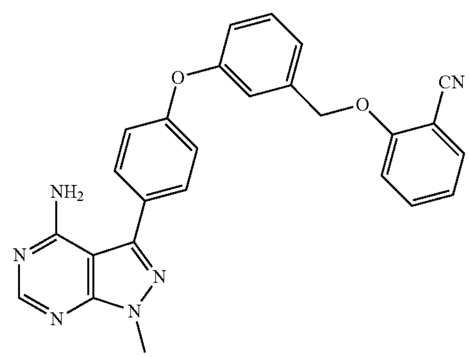 [SMILES: Cn1nc(-c2ccc(Oc3cccc(COc4ccccc4C#N)c3)cc2)c2c(N)ncnc21] | [M + H]⁺ = 449.3 |
| 18 | 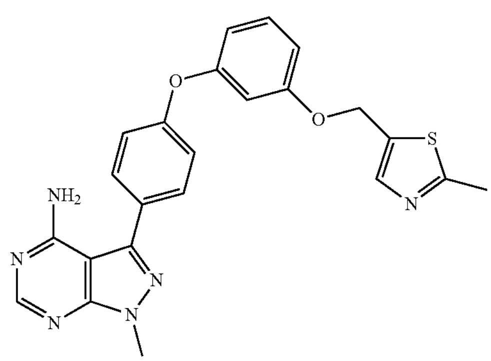 [SMILES: Cc1ncc(COc2cccc(Oc3ccc(-c4nn(C)c5ncnc(N)c45)cc3)c2)s1] | [M + H]⁺ = 445.1 |
| 19 | 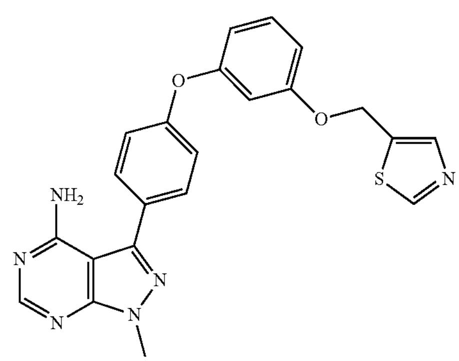 [SMILES: Cn1nc(-c2ccc(Oc3cccc(OCc4cncs4)c3)cc2)c2c(N)ncnc21] | [M + H]⁺ = 431.4 |

TABLE 1-continued
Example Compounds of Formula 1
| Compound | Structure | MS (m/z) |
|---|---|---|
| 20 | 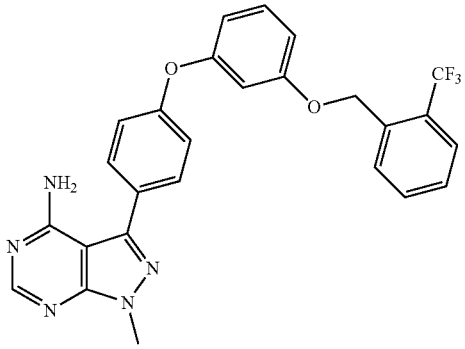 [SMILES: Cn1nc(-c2ccc(Oc3cccc(OCc4ccccc4C(F)(F)F)c3)cc2)c2c(N)ncnc21] | [M + H]⁺ = 492.1 |
| 21 | 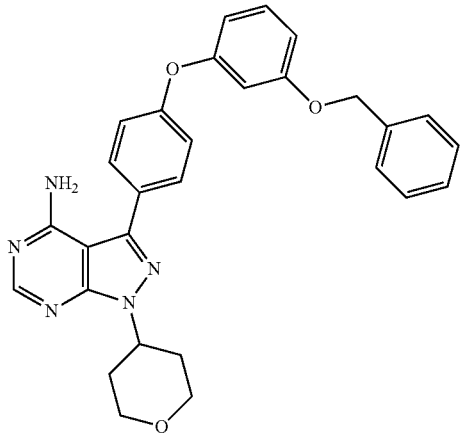 [SMILES: Nc1ncnc2c1c(-c1ccc(Oc3cccc(OCc4ccccc4)c3)cc1)nn2C1CCOCC1] | [M + H]⁺ = 494.2 |
| 22 | 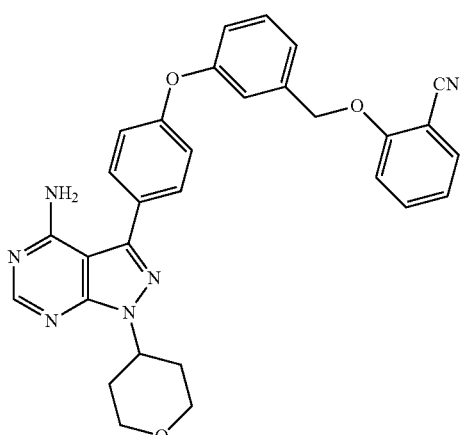 | [M + H]⁺ = 519.2 |

TABLE 1-continued

Example Compounds of Formula 1

| Compound | Structure | MS (m/z) |
|---|---|---|
| 23 | 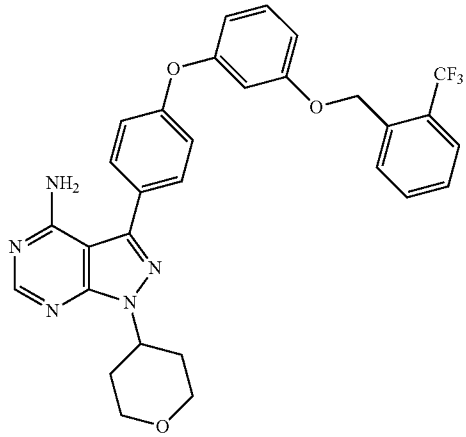 [SMILES: Nc1ncnc2c1c(-c1ccc(Oc3cccc(OCc4ccccc4C(F)(F)F)c3)cc1)nn2C1CCOCC1] | [M + H]⁺ = 562.1 |
| 24 | 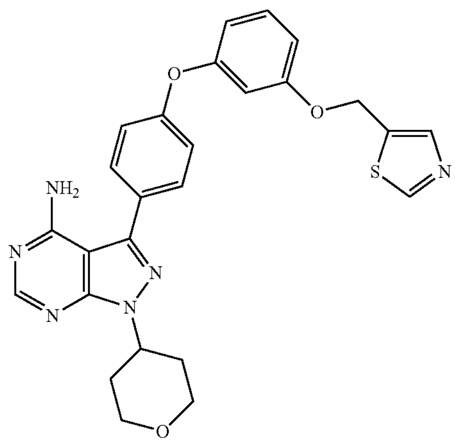 [SMILES: Nc1ncnc2c1c(-c1ccc(Oc3cccc(OCc4cncs4)c3)cc1)nn2C1CCOCC1] | [M + H]⁺ = 501.2 |
| 25 | 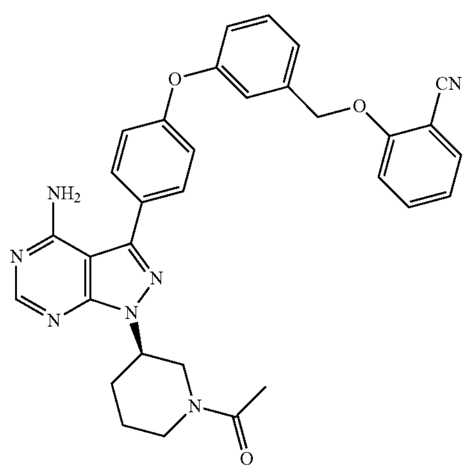 [SMILES: CC(=O)N1CCC[C@@H](n2nc(-c3ccc(Oc4cccc(COc5ccccc5C#N)c4)cc3)c3c(N)ncnc32)C1] | [M + H]⁺ = 560.2 |

TABLE 1-continued

Example Compounds of Formula 1

| Compound | Structure | MS (m/z) |
|---|---|---|
| 26 | 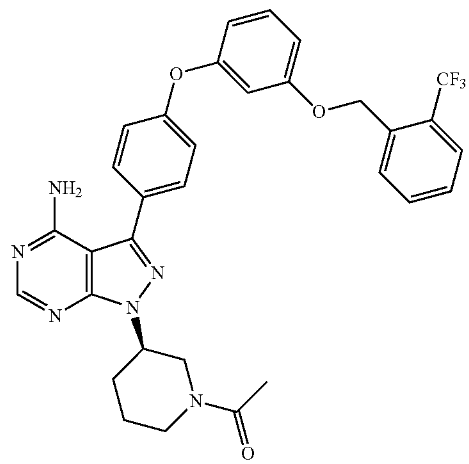 [SMILES: CC(=O)N1CCC[C@@H](n2nc(-c3ccc(Oc4cccc(OCc5ccccc5C(F)(F)F)c4)cc3)c3c(N)ncnc32)C1] | [M + H]⁺ = 603.1 |
| 27 | 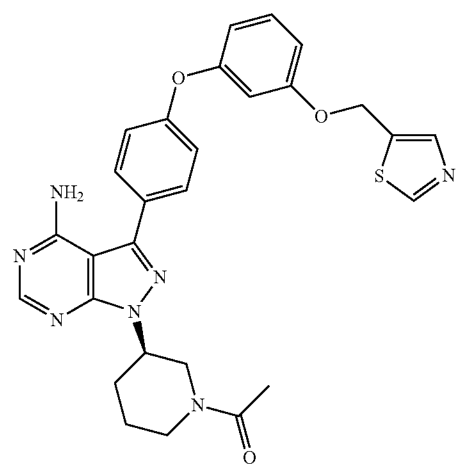 [SMILES: CC(=O)N1CCC[C@@H](n2nc(-c3ccc(Oc4cccc(OCc5cncs5)c4)cc3)c3c(N)ncnc32)C1] | [M + H]⁺ = 542.2 |
| 28 | 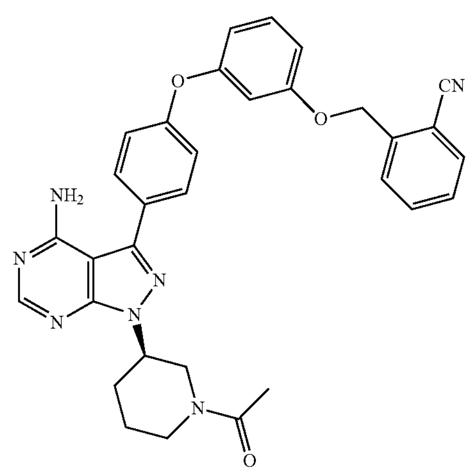 [SMILES: CC(=O)N1CCC[C@@H](n2nc(-c3ccc(Oc4cccc(OCc5ccccc5C#N)c4)cc3)c3c(N)ncnc32)C1] | [M + H]⁺ = 560.2 |

TABLE 1-continued

Example Compounds of Formula 1

| Compound | Structure | MS (m/z) |
|---|---|---|
| 29 | 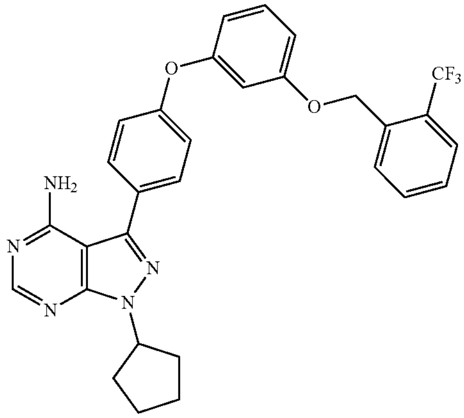 [SMILES: Nc1ncnc2c1c(-c1ccc(Oc3cccc(OCc4ccccc4C(F)(F)F)c3)cc1)nn2C1CCCC1] | [M + H]+ = 546.2 |
| 30 | 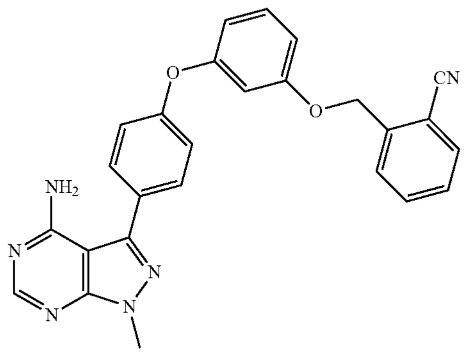 [SMILES: Cn1nc(-c2ccc(Oc3cccc(OCc4ccccc4C#N)c3)cc2)c2c(N)ncnc21] | [M + H]+ = 449.4 |
| 31 | 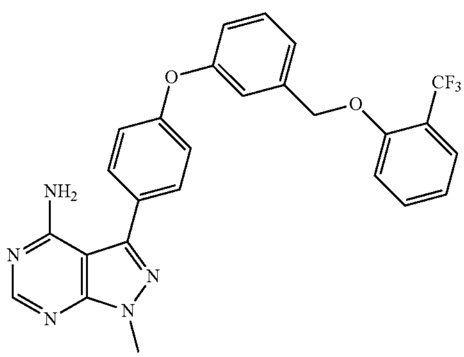 [SMILES: Cn1nc(-c2ccc(Oc3cccc(COc4ccccc4C(F)(F)F)c3)cc2)c2c(N)ncnc21] | [M + H]+ = 492.1 |
| 32 | 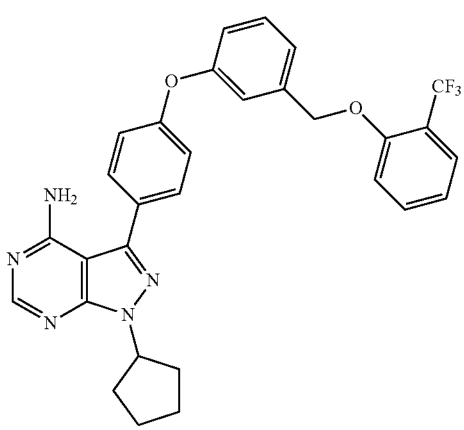 [SMILES: Nc1ncnc2c1c(-c1ccc(Oc3cccc(COc4ccccc4C(F)(F)F)c3)cc1)nn2C1CCCC1] | [M + H]+ = 546.1 |

TABLE 1-continued

Example Compounds of Formula 1

| Compound | Structure | MS (m/z) |
|---|---|---|
| 33 | 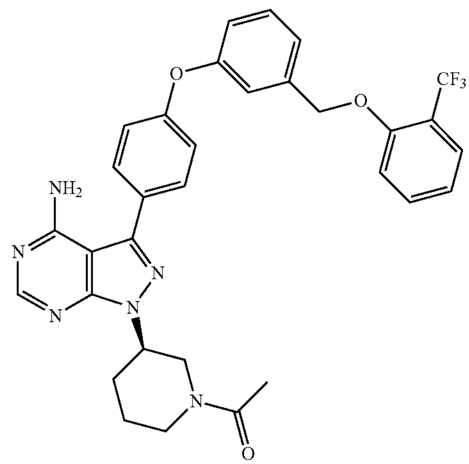 | [M + H]⁺ = 603.1 |
| 34 | 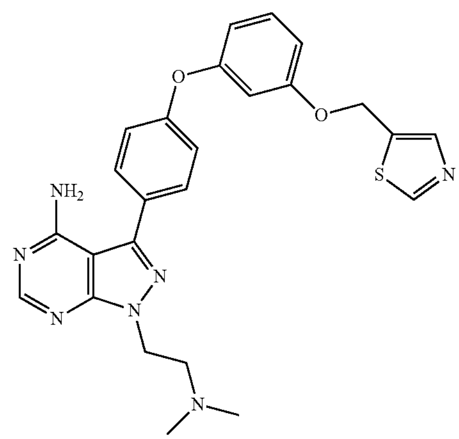 [SMILES: CN(C)CCn1nc(-c2ccc(Oc3cccc(OCc4cncs4)c3)cc2)c2c(N)ncnc21] | [M + H]⁺ = 488.3 |
| 35 | 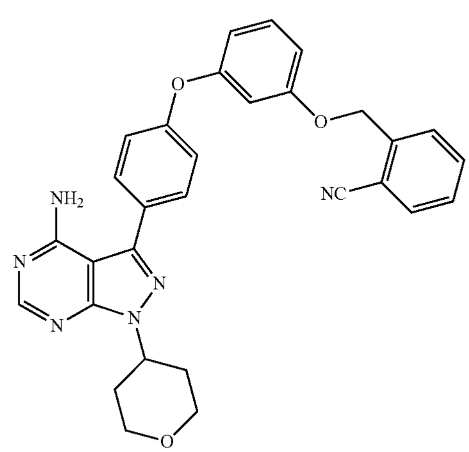 [SMILES: N#Cc1ccccc1COc1cccc(Oc2ccc(-c3nn(C4CCOCC4)c4ncnc(N)c34)cc2)c1] | [M + H]⁺ = 519.2 |

TABLE 1-continued

Example Compounds of Formula 1

| Compound | Structure | MS (m/z) |
|---|---|---|
| 36 | 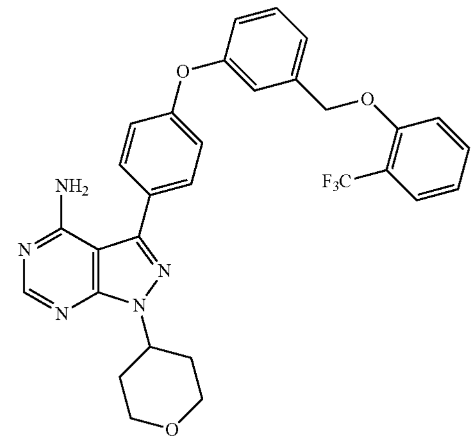 [SMILES: Nc1ncnc2c1c(-c1ccc(Oc3cccc(COc4ccccc4C(F)(F)F)c3)cc1)nn2C1CCOCC1] | [M + H]⁺ = 562.2 |
| 37 | 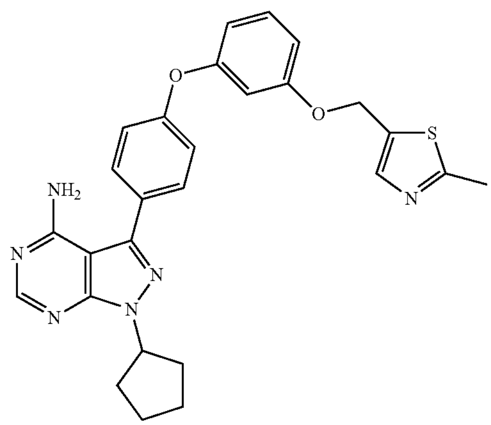 [SMILES: Cc1ncc(COc2cccc(Oc3ccc(-c4nn(C5CCCC5)c5ncnc(N)c45)cc3)c2)s1] | [M + H]⁺ = 499.1 |
| 38 | 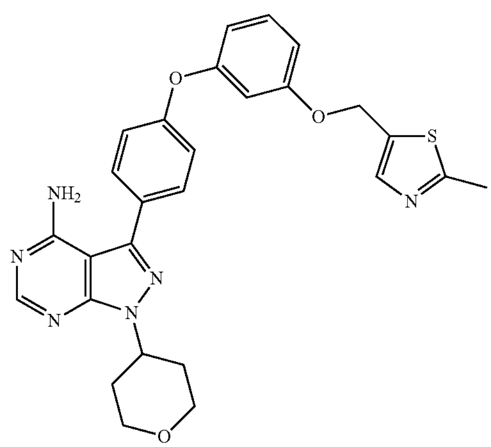 [SMILES: Cc1ncc(COc2cccc(Oc3ccc(-c4nn(C5CCOCC5)c5ncnc(N)c45)cc3)c2)s1] | [M + H]⁺ = 515.1 |

TABLE 1-continued

Example Compounds of Formula 1

| Compound | Structure | MS (m/z) |
|---|---|---|
| 39 | 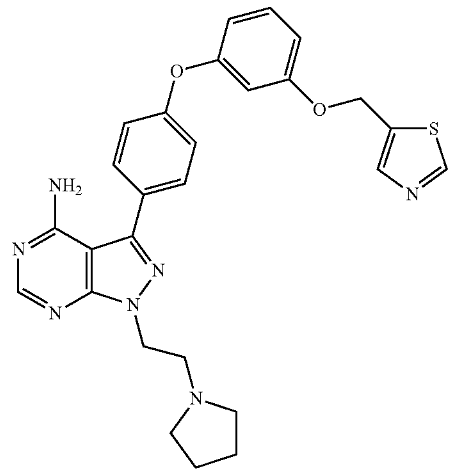 [SMILES: Nc1ncnc2c1c(-c1ccc(Oc3cccc(OCc4cncs4)c3)cc1)nn2CCN1CCCC1] | [M + H]⁺ = 514.2 |
| 40 | 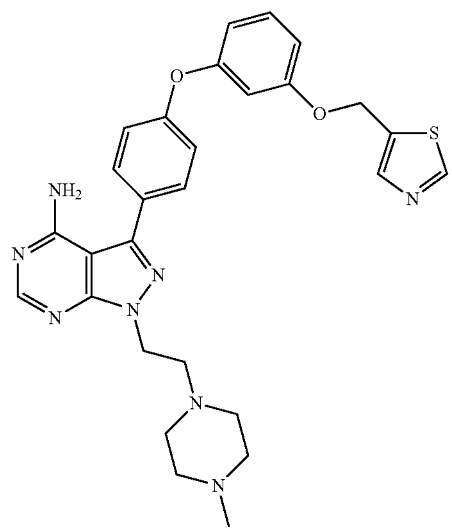 [SMILES: CN1CCN(CCn2nc(-c3ccc(Oc4cccc(OCc5cncs5)c4)cc3)c3c(N)ncnc32)CC1] | [M + H]⁺ = 543.1 |
| 41 | 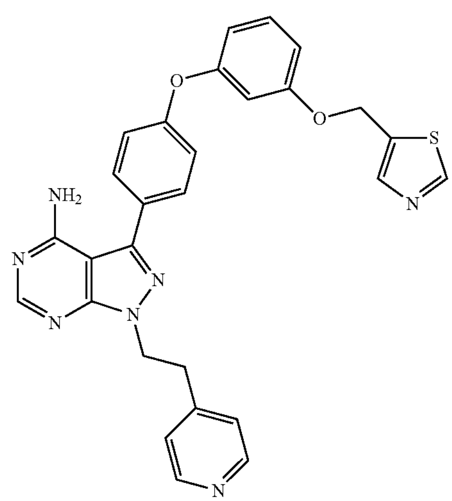 [SMILES: Nc1ncnc2c1c(-c1ccc(Oc3cccc(OCc4cncs4)c3)cc1)nn2CCc1ccncc1] | [M + H]⁺ = 522.1 |

TABLE 1-continued

Example Compounds of Formula 1

| Compound | Structure | MS (m/z) |
|---|---|---|
| 42 | 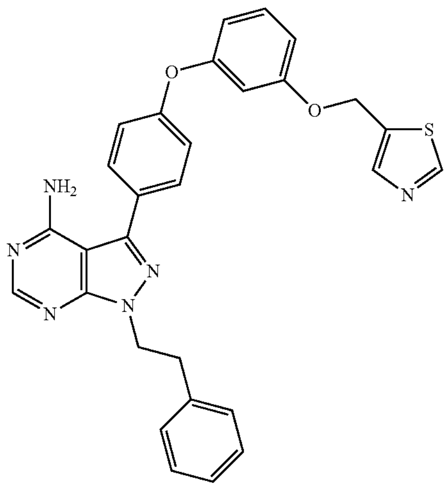 [SMILES: Nc1ncnc2c1c(-c1ccc(Oc3cccc(OCc4cncs4)c3)cc1)nn2CCc1ccccc1] | [M + H]⁺ = 521.2 |
| 43 | 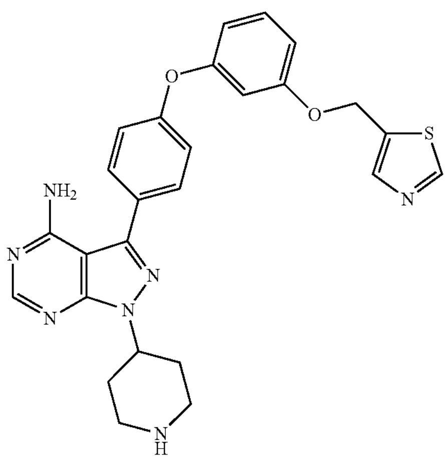 [SMILES: Nc1ncnc2c1c(-c1ccc(Oc3cccc(OCc4cncs4)c3)cc1)nn2C1CCNCC1] | [M + H]⁺ = 500.2 |
| 44 | 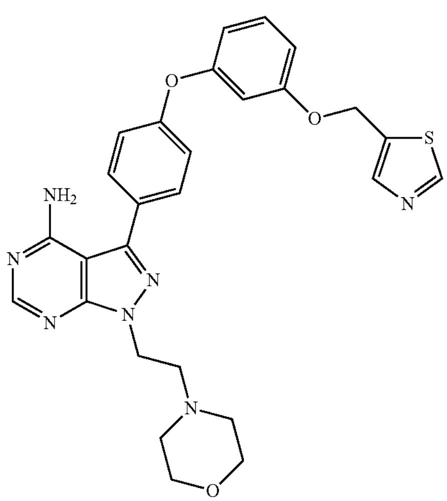 [SMILES: Nc1ncnc2c1c(-c1ccc(Oc3cccc(OCc4cncs4)c3)cc1)nn2CCN1CCOCC1] | [M + H]⁺ = 530.1 |

TABLE 1-continued

| Example Compounds of Formula 1 | | |
|---|---|---|
| Compound | Structure | MS (m/z) |
| 45 | | [M + H]+ = 452.1 |
| 46 | | [M + H]+ = 519.1 |
| 47 | | [M + H]+ = 542.1 |

TABLE 1-continued

Example Compounds of Formula 1

| Compound | Structure | MS (m/z) |
|---|---|---|
| 48 | 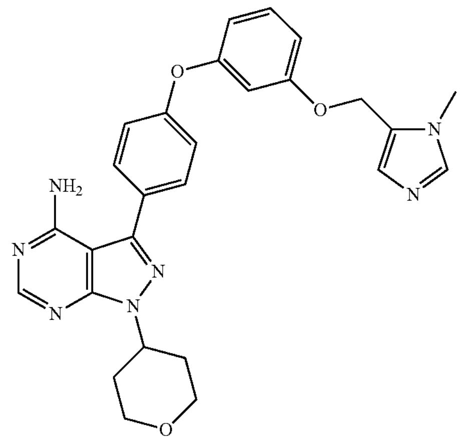 [SMILES: Cn1cncc1COc1cccc(Oc2ccc(-c3nn(C4CCOCC4)c4ncnc(N)c34)cc2)c1] | [M + H]⁺ = 498.2 |
| 49 | 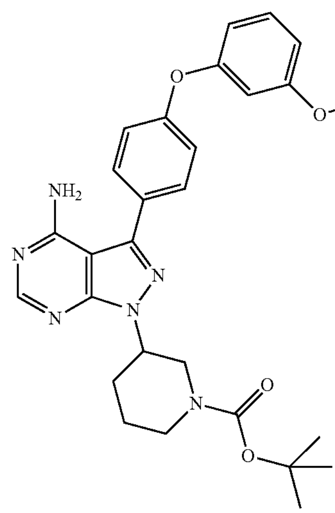 | [M + H]⁺ = 600.1 |
| 50 | 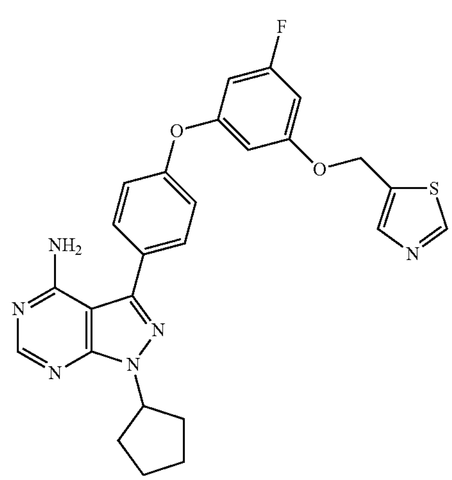 [SMILES: Nc1ncnc2c1c(-c1ccc(Oc3cc(F)cc(OCc4cncs4)c3)cc1)nn2C1CCCC1] | [M + H]⁺ = 503.2 |

TABLE 1-continued

| Compound | Structure | MS (m/z) |
|---|---|---|
| 51 | 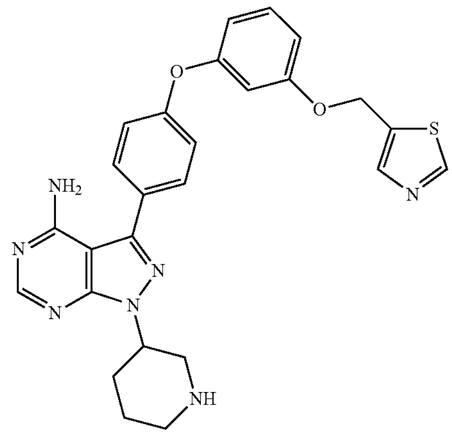 [SMILES: Nc1ncnc2c1c(-c1ccc(Oc3cccc(OCc4cncs4)c3)cc1)nn2C1CCCNC1] | [M + H]⁺ = 500.2 |
| 52 | 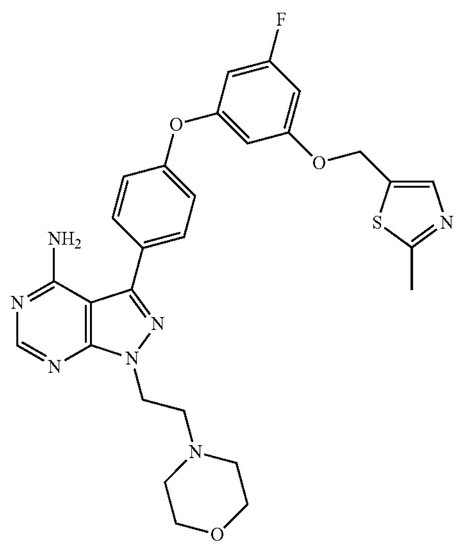 [SMILES: Cc1ncc(COc2cc(F)cc(Oc3ccc(-c4nn(CCN5CCOCC5)c5ncnc(N)c45)cc3)c2)s1] | [M + H]⁺ = 562.1 |
| 53 | 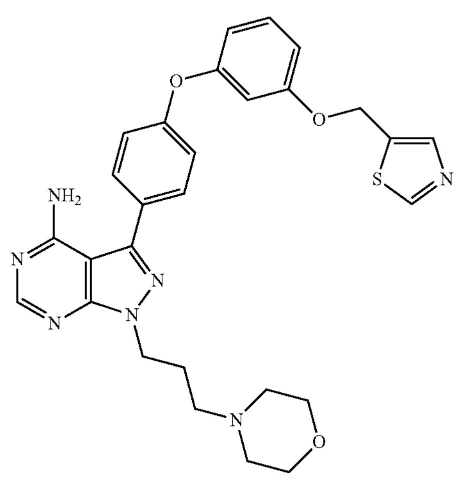 [SMILES: Nc1ncnc2c1c(-c1ccc(Oc3cccc(OCc4cncs4)c3)cc1)nn2CCCN1CCOCC1] | [M + H]⁺ = 544.2 |

TABLE 1-continued

Example Compounds of Formula 1

| Compound | Structure | MS (m/z) |
|---|---|---|
| 54 | 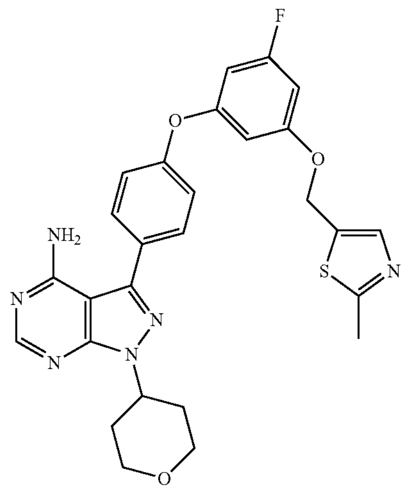 [SMILES: Cc1ncc(COc2cc(F)cc(Oc3ccc(-c4nn(C5CCOCC5)c5ncnc(N)c45)cc3)c2)s1] | [M + H]⁺ = 533.1 |
| 55 | 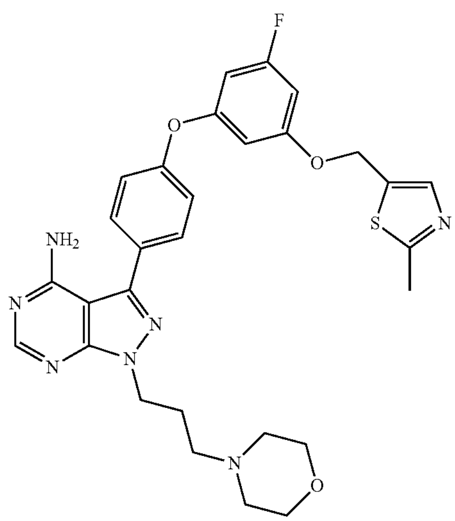 [SMILES: Cc1ncc(COc2cc(F)cc(Oc3ccc(-c4nn(CCCN5CCOCC5)c5ncnc(N)c45)cc3)c2)s1] | [M + H]⁺ = 576.2 |
| 56 | 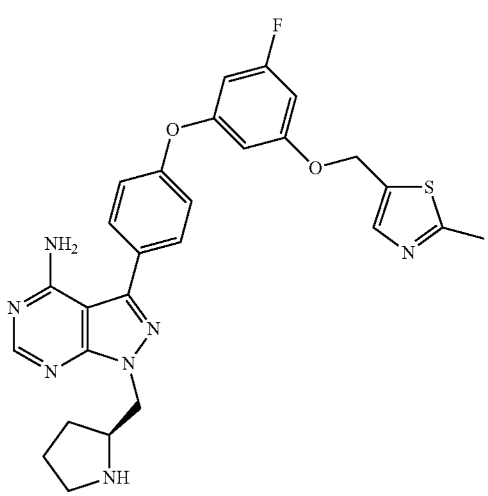 [SMILES: Cc1ncc(COc2cc(F)cc(Oc3ccc(-c4nn(C[C@@H]5CCCN5)c5ncnc(N)c45)cc3)c2)s1] | [M + H]⁺ = 532.2 |

TABLE 1-continued
| Compound | Structure | MS (m/z) |
|---|---|---|
| 57 | 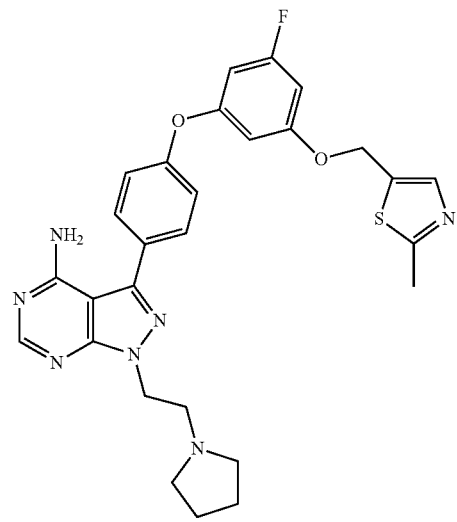 [SMILES: Cc1ncc(COc2cc(F)cc(Oc3ccc(-c4nn(CCN5CCCC5)c5ncnc(N)c45)cc3)c2)s1] | [M + H]⁺ = 546.2 |
| 58 | 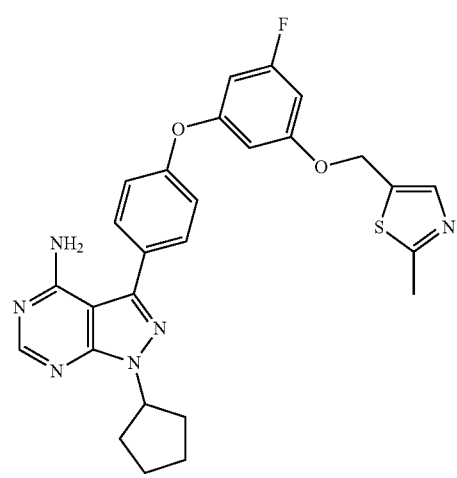 [SMILES: Cc1ncc(COc2cc(F)cc(Oc3ccc(-c4nn(C5CCCC5)c5ncnc(N)c45)cc3)c2)s1] | [M + H]⁺ = 517.2 |
| 59 | 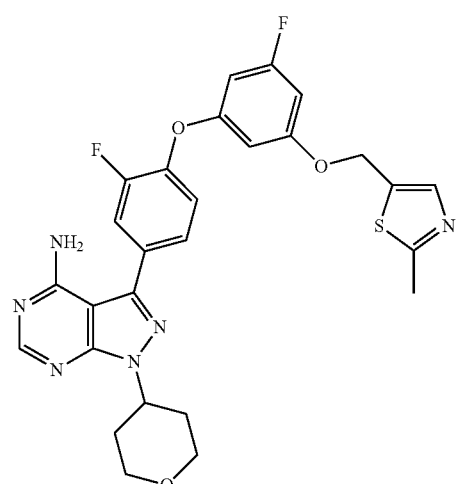 | [M + H]⁺ = 551.1 |

TABLE 1-continued

Example Compounds of Formula 1

| Compound | Structure | MS (m/z) |
|---|---|---|
| 60 | 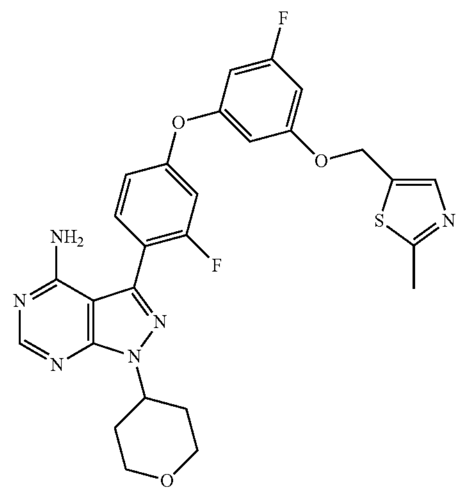 [SMILES: Cc1ncc(COc2cc(F)cc(Oc3ccc(-c4nn(C5CCOCC5)c5ncnc(N)c45)c(F)c3)c2)s1] | [M + H]+ = 551.2 |
| 61 | 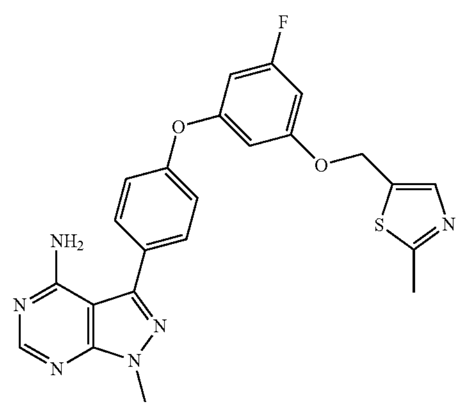 [SMILES: Cc1ncc(COc2cc(F)cc(Oc3ccc(-c4nn(C)c5ncnc(N)c45)cc3)c2)s1] | [M + H]+ = 463.2 |
| 62 | 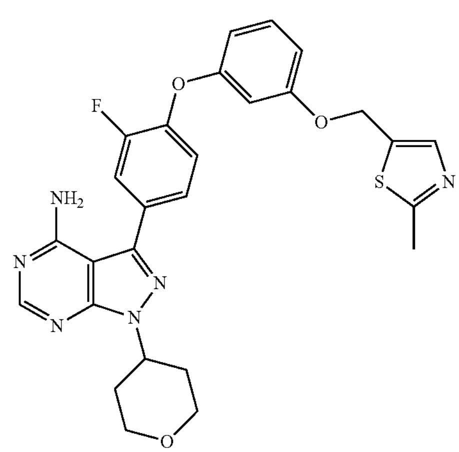 [SMILES: Cc1ncc(COc2cccc(Oc3ccc(-c4nn(C5CCOCC5)c5ncnc(N)c45)cc3F)c2)s1] | [M + H]+ = 533.2 |

TABLE 1-continued

Example Compounds of Formula 1

| Compound | Structure | MS (m/z) |
|---|---|---|
| 63 | 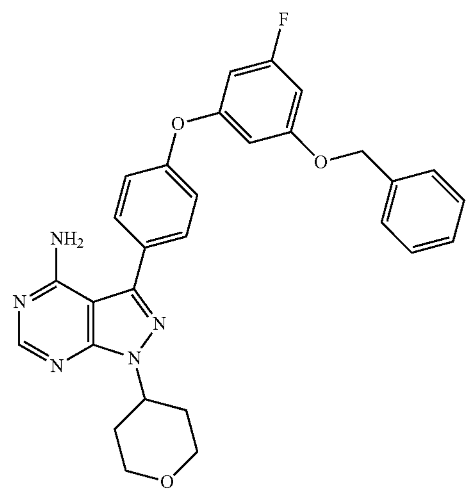 [SMILES: Nc1ncnc2c1c(-c1ccc(Oc3cc(F)cc(OCc4ccccc4)c3)cc1)nn2C1CCOCC1] | [M + H]⁺ = 512.2 |
| 64 | 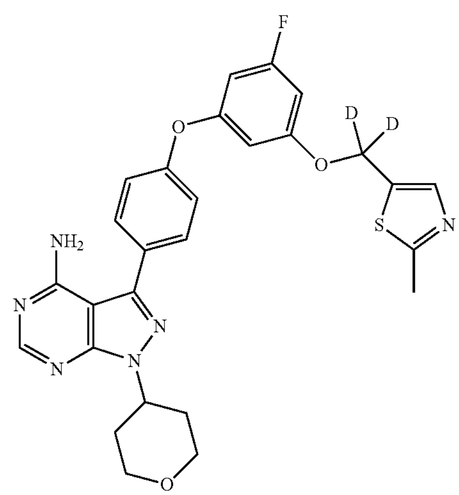 [SMILES: [2H]C([2H])(Oc1cc(F)cc(Oc2ccc(-c3nn(C4CCOCC4)c4ncnc(N)c34)cc2)c1)c1cnc(C)s1] | [M + H]⁺ = 535.2 |
| 65 | 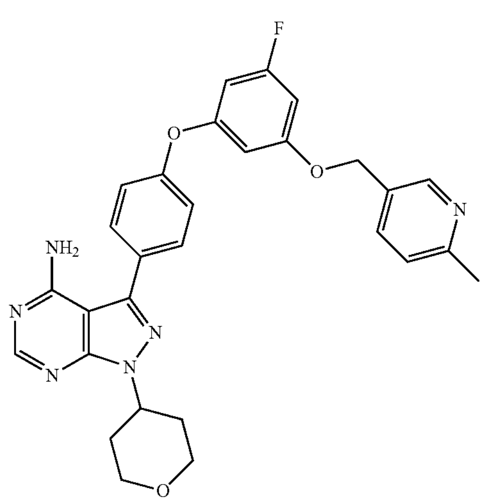 | [M + H]⁺ = 527.2 |

TABLE 1-continued

Example Compounds of Formula 1

| Compound | Structure | MS (m/z) |
|---|---|---|
| 66 | 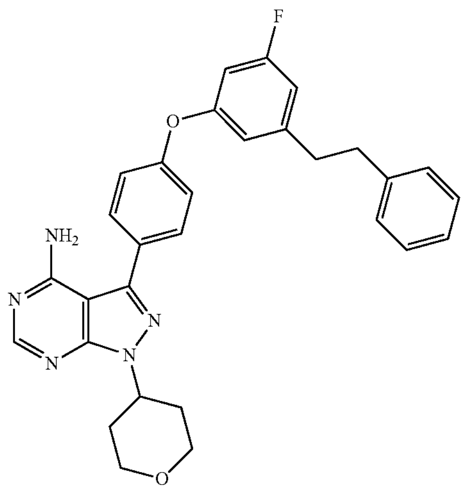 [SMILES: Nc1ncnc2c1c(-c1ccc(Oc3cc(F)cc(CCc4ccccc4)c3)cc1)nn2C1CCOCC1] | [M + H]⁺ = 510.2 |
| 67 | 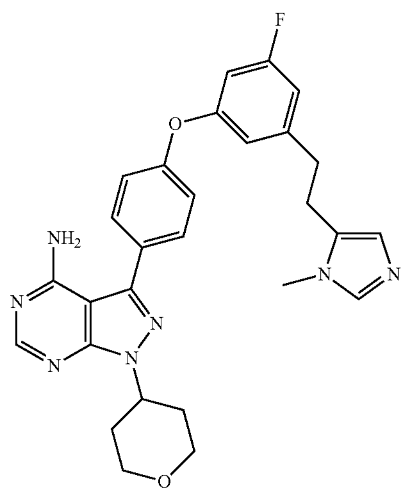 [SMILES: Cn1cncc1CCc1cc(F)cc(Oc2ccc(-c3nn(C4CCOCC4)c4ncnc(N)c34)cc2)c1] | [M + H]⁺ = 514.3 |
| 68 | 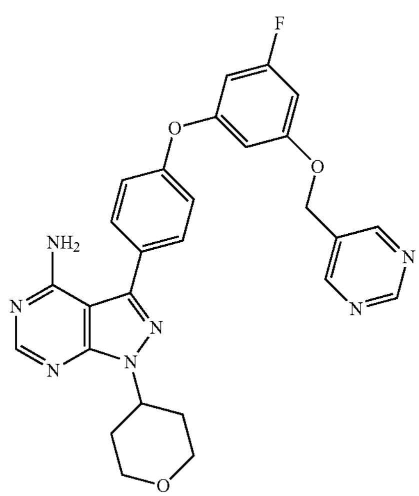 [SMILES: Nc1ncnc2c1c(-c1ccc(Oc3cc(F)cc(OCc4cncnc4)c3)cc1)nn2C1CCOCC1] | [M + H]⁺ = 514.2 |

TABLE 1-continued

| Example Compounds of Formula 1 | | |
|---|---|---|
| Compound | Structure | MS (m/z) |
| 69 | | [M + H]⁺ = 514.2 |
| 70 | | [M + H]⁺ = 533.2 |
| 71 | | [M + H]⁺ = 516.1 |

TABLE 1-continued
Example Compounds of Formula 1
| Compound | Structure | MS (m/z) |
|---|---|---|
| 72 | 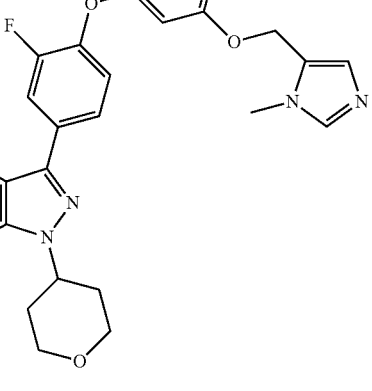 | [M + H]⁺ = 534.2 |
| 73 | 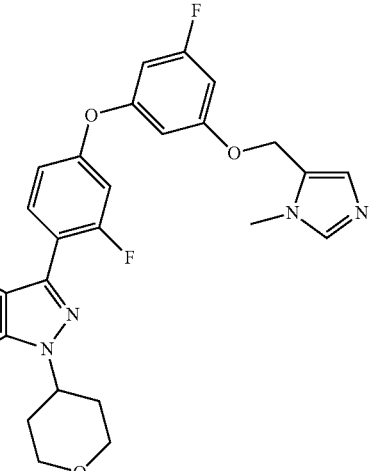 | [M + H]⁺ = 534.1 |
| 74 | 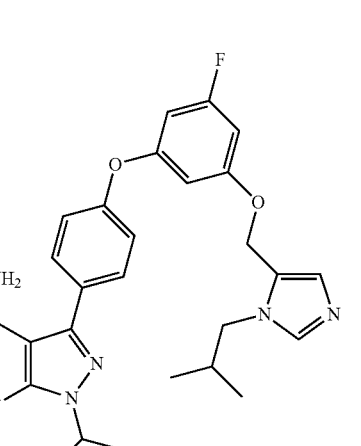 | [M + H]⁺ = 558.2 |

TABLE 1-continued
Example Compounds of Formula 1
| Compound | Structure | MS (m/z) |
|---|---|---|
| 75 | 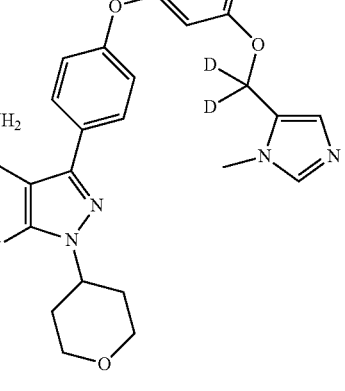 | [M + H]+ = 518.1 |
| 76 | 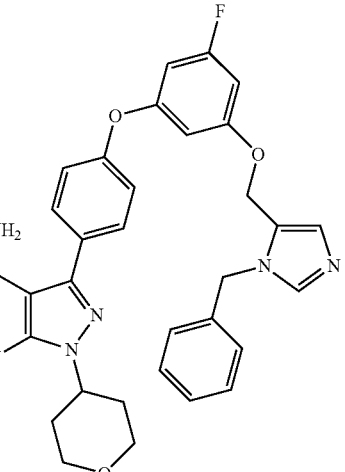 | [M + H]+ = 592.1 |
| 77 | 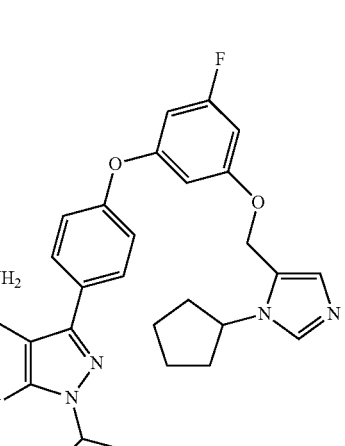 | [M + H]+ = 570.2 |

TABLE 1-continued

Example Compounds of Formula 1

| Compound | Structure | MS (m/z) |
|---|---|---|
| 78 | 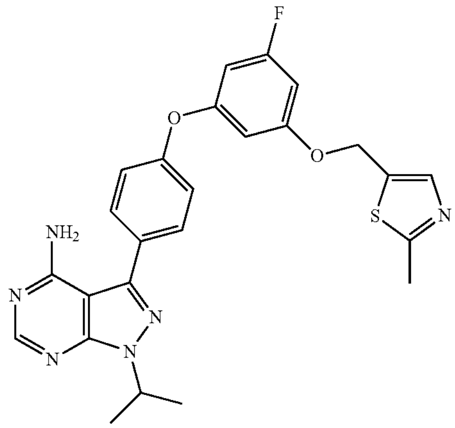 [SMILES: Cc1ncc(COc2cc(F)cc(Oc3ccc(-c4nn(C(C)C)c5ncnc(N)c45)cc3)c2)s1] | [M + H]⁺ = 491.2 |
| 79 | 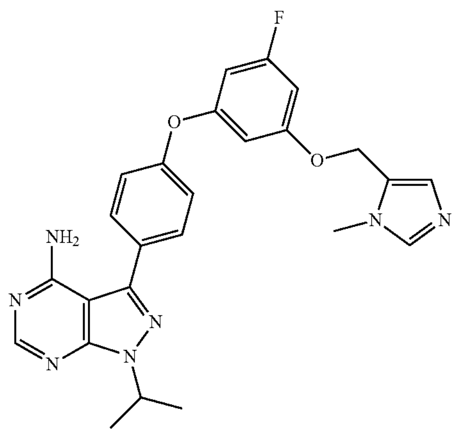 [SMILES: CC(C)n1nc(-c2ccc(Oc3cc(F)cc(OCc4cncn4C)c3)cc2)c2c(N)ncnc21] | [M + H]⁺ = 474.2 |
| 80 | 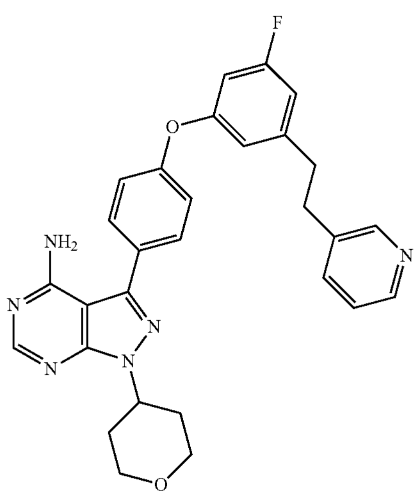 [SMILES: Nc1ncnc2c1c(-c1ccc(Oc3cc(F)cc(CCc4cccnc4)c3)cc1)nn2C1CCOCC1] | [M + H]⁺ = 511.2 |

TABLE 1-continued

Example Compounds of Formula 1

| Compound | Structure | MS (m/z) |
|---|---|---|
| 81 | 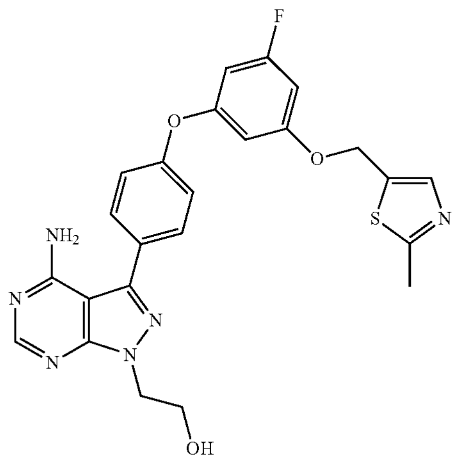 [SMILES: Cc1ncc(COc2cc(F)cc(Oc3ccc(-c4nn(CCO)c5ncnc(N)c45)cc3)c2)s1] | [M + H]⁺ = 493.2 |
| 82 | 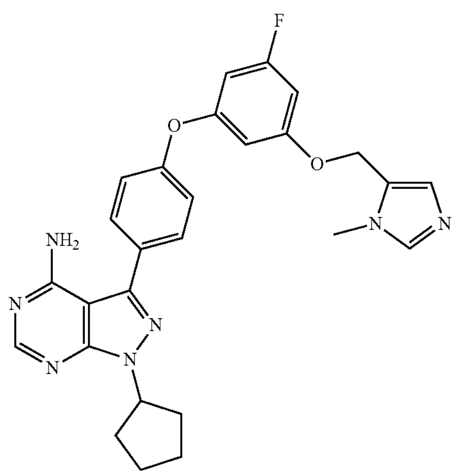 [SMILES: Cn1cncc1COc1cc(F)cc(Oc2ccc(-c3nn(C4CCCC4)c4ncnc(N)c34)cc2)c1] | [M + H]⁺ = 500.2 |
| 83 | 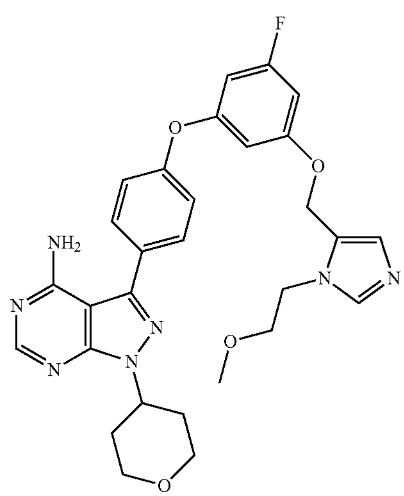 [SMILES: COCCn1cncc1COc1cc(F)cc(Oc2ccc(-c3nn(C4CCOCC4)c4ncnc(N)c34)cc2)c1] | [M + H]⁺ = 560.2 |

TABLE 1-continued

Example Compounds of Formula 1

| Compound | Structure | MS (m/z) |
|---|---|---|
| 84 | 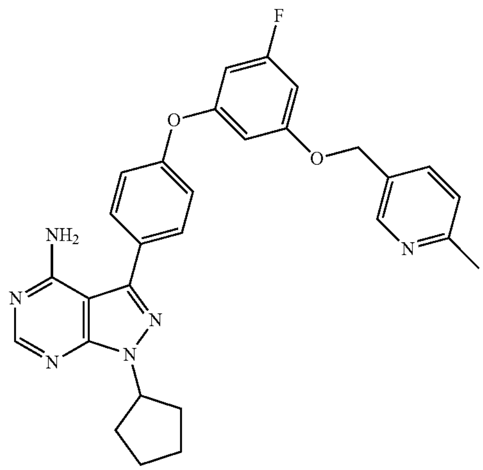 [SMILES: Cc1ccc(COc2cc(F)cc(Oc3ccc(-c4nn(C5CCCC5)c5ncnc(N)c45)cc3)c2)cn1] | [M + H]⁺ = 511.2 |
| 85 | 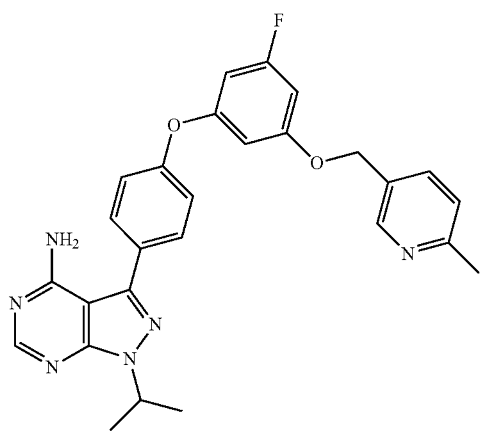 [SMILES: Cc1ccc(COc2cc(F)cc(Oc3ccc(-c4nn(C(C)C)c5ncnc(N)c45)cc3)c2)cn1] | [M + H]⁺ = 485.2 |
| 86 | 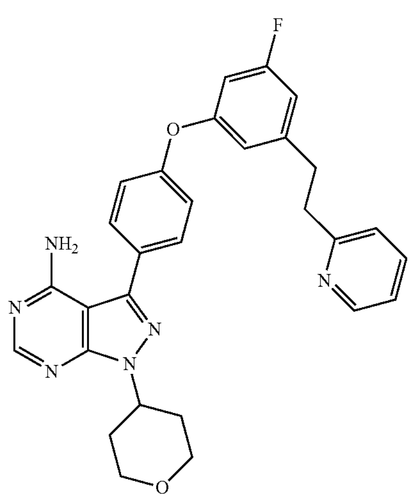 [SMILES: Nc1ncnc2c1c(-c1ccc(Oc3cc(F)cc(CCc4ccccn4)c3)cc1)nn2C1CCOCC1] | [M + H]⁺ = 511.2 |

TABLE 1-continued

Example Compounds of Formula 1

| Compound | Structure | MS (m/z) |
|---|---|---|
| 87 | 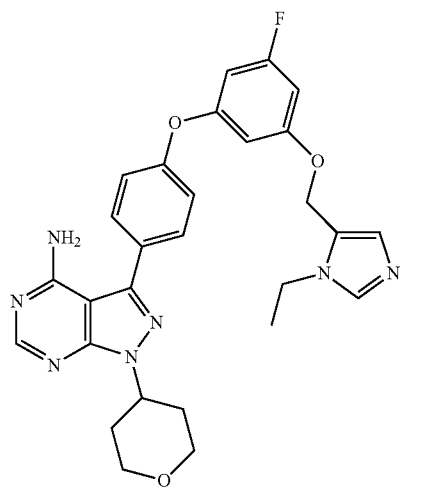 [SMILES: CCn1cncc1COc1cc(F)cc(Oc2ccc(-c3nn(C4CCOCC4)c4ncnc(N)c34)cc2)c1] | [M + H]⁺ = 530.2 |
| 88 | 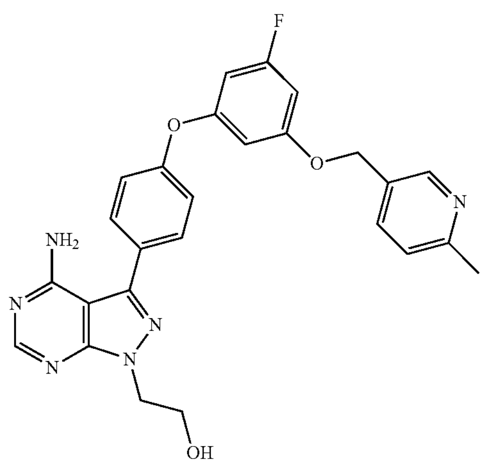 [SMILES: Cc1ccc(COc2cc(F)cc(Oc3ccc(-c4nn(CCO)c5ncnc(N)c45)cc3)c2)cn1] | [M + H]⁺ = 487.2 |
| 89 | 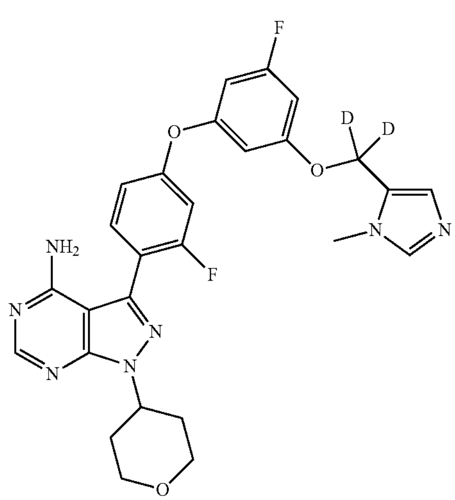 [SMILES: [2H]C([2H])(Oc1cc(F)cc(Oc2ccc(-c3nn(C4CCOCC4)c4ncnc(N)c34)c(F)c2)c1)c1cncn1C] | [M + H]⁺ = 536.1 |

TABLE 1-continued

Example Compounds of Formula 1

| Compound | Structure | MS (m/z) |
|---|---|---|
| 90 | 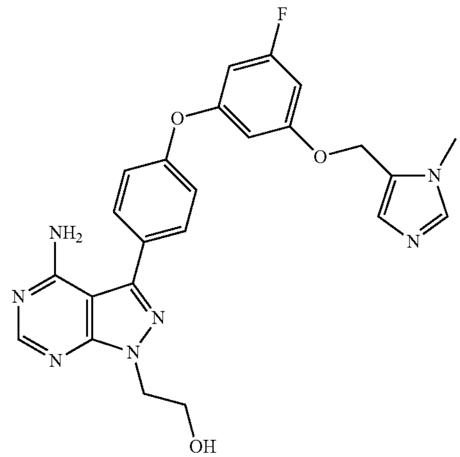 [SMILES: Cn1cncc1COc1cc(F)cc(Oc2ccc(-c3nn(CCO)c4ncnc(N)c34)cc2)c1] | [M + H]+ = 476.2 |
| 91 | 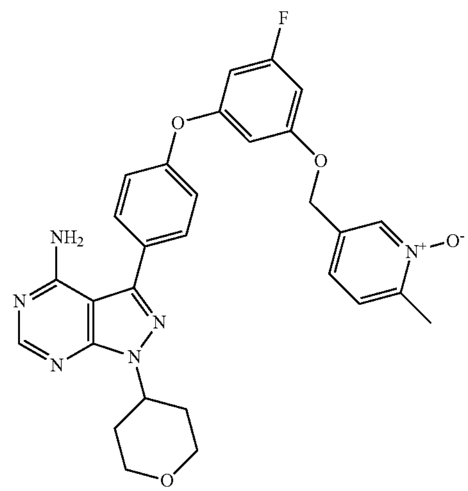 [SMILES: Cc1ccc(COc2cc(F)cc(Oc3ccc(-c4nn(C5CCOCC5)c5ncnc(N)c45)cc3)c2)c[n+]1[O-]] | [M + H]+ = 543.1 |
| 92 | 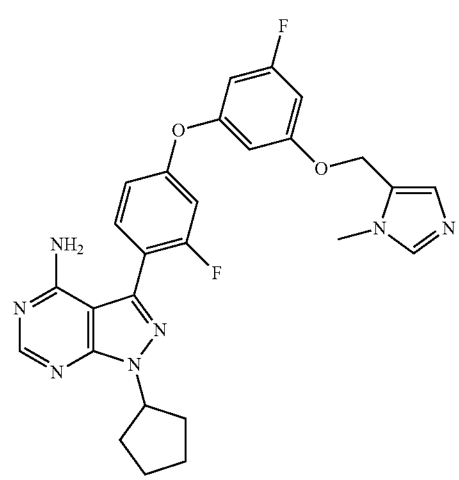 [SMILES: Cn1cncc1COc1cc(F)cc(Oc2ccc(-c3nn(C4CCCC4)c4ncnc(N)c34)c(F)c2)c1] | [M + H]+ = 518.2 |

TABLE 1-continued

Example Compounds of Formula 1

| Compound | Structure | MS (m/z) |
|---|---|---|
| 93 | 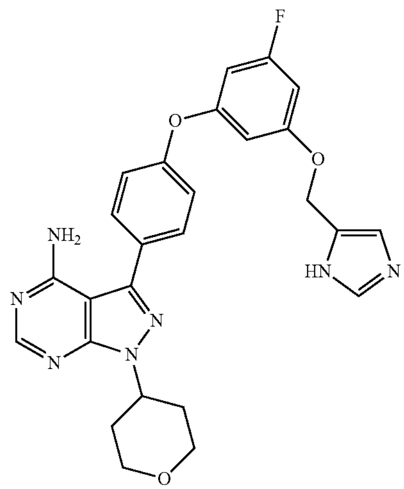 [SMILES: Nc1ncnc2c1c(-c1ccc(Oc3cc(F)cc(OCc4cnc[nH]4)c3)cc1)nn2C1CCOCC1] | [M + H]+ = 502.2 |
| 94 | 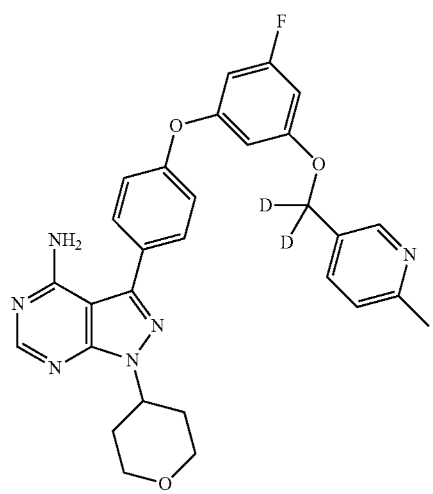 [SMILES: [2H]C([2H])(Oc1cc(F)cc(Oc2ccc(-c3nn(C4CCOCC4)c4ncnc(N)c34)cc2)c1)c1ccc(C)nc1] | [M + H]+ = 529.2 |
| 95 | 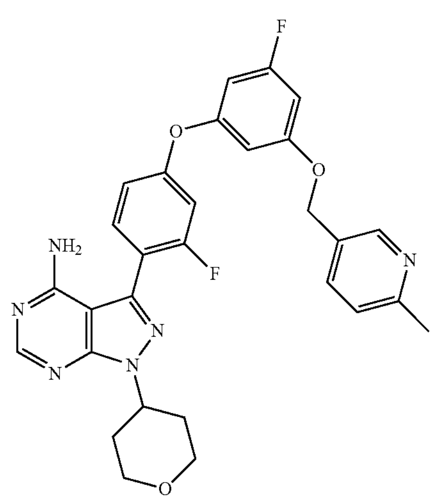 [SMILES: Cc1ccc(COc2cc(F)cc(Oc3ccc(-c4nn(C5CCOCC5)c5ncnc(N)c45)c(F)c3)c2)cn1] | [M + H]+ = 545.2 |

TABLE 1-continued

Example Compounds of Formula 1

| Compound | Structure | MS (m/z) |
|---|---|---|
| 96 | 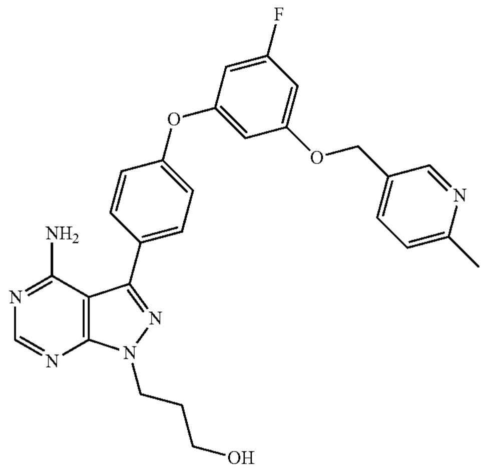 [SMILES: Cc1ccc(COc2cc(F)cc(Oc3ccc(-c4nn(CCCO)c5ncnc(N)c45)cc3)c2)cn1] | [M + H]⁺ = 501.2 |
| 97 | 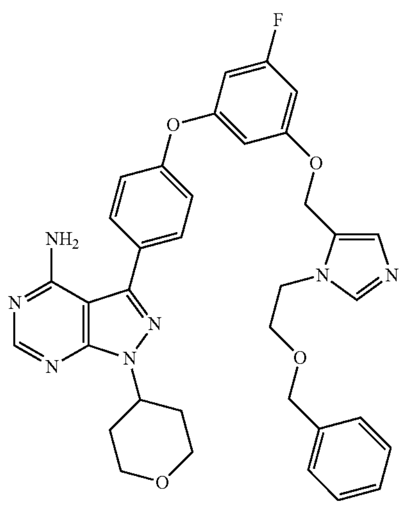 [SMILES: Nc1ncnc2c1c(-c1ccc(Oc3cc(F)cc(OCc4cncn4CCOCc4ccccc4)c3)cc1)nn2C1CCOCC1] | [M + H]⁺ = 636.1 |
| 98 | 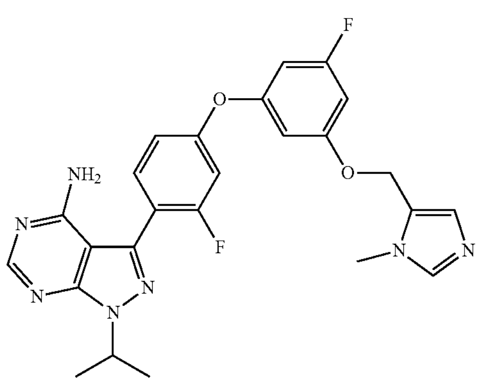 [SMILES: CC(C)n1nc(-c2ccc(Oc3cc(F)cc(OCc4cncn4C)c3)cc2F)c2c(N)ncnc21] | [M + H]⁺ = 492.2 |

TABLE 1-continued

Example Compounds of Formula 1

| Compound | Structure | MS (m/z) |
|---|---|---|
| 99 | 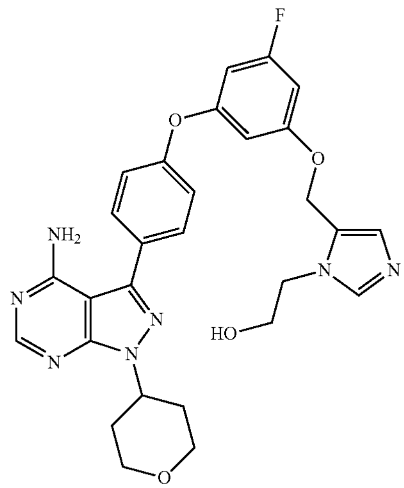 [SMILES: Nc1ncnc2c1c(-c1ccc(Oc3cc(F)cc(OCc4cncn4CCO)c3)cc1)nn2C1CCOCC1] | [M + H]⁺ = 546.2 |
| 100 | 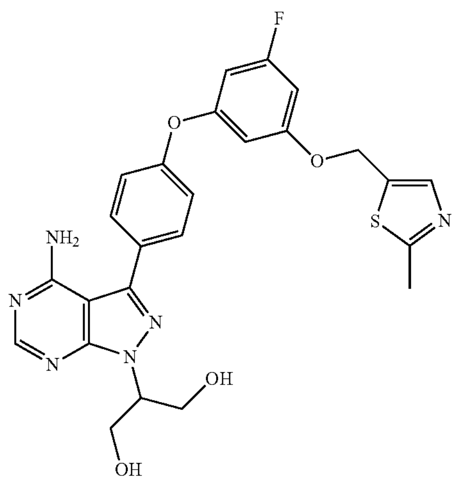 [SMILES: Cc1ncc(COc2cc(F)cc(Oc3ccc(-c4nn(C(CO)CO)c5ncnc(N)c45)cc3)c2)s1] | [M + H]⁺ = 523.2 |
| 101 | 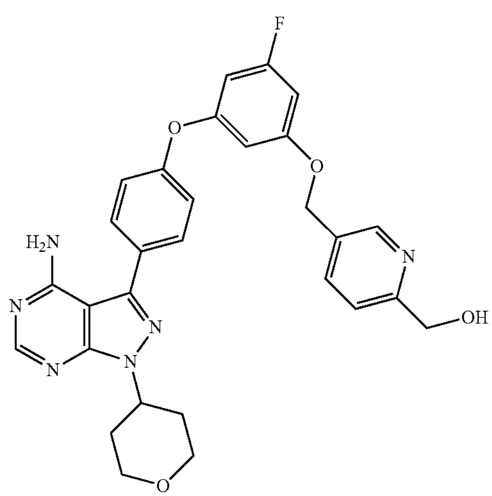 [SMILES: Nc1ncnc2c1c(-c1ccc(Oc3cc(F)cc(OCc4ccc(CO)nc4)c3)cc1)nn2C1CCOCC1] | [M + H]⁺ = 543.1 |

TABLE 1-continued

Example Compounds of Formula 1

| Compound | Structure | MS (m/z) |
|---|---|---|
| 102 | 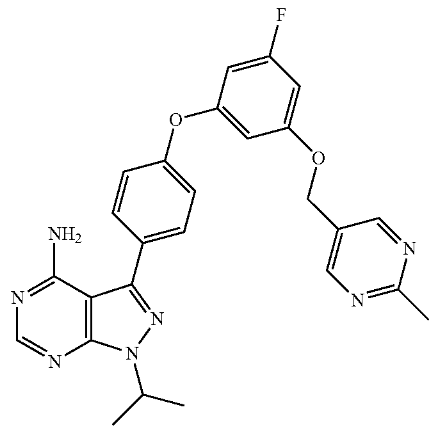 [SMILES: Cc1ncc(COc2cc(F)cc(Oc3ccc(-c4nn(C(C)C)c5ncnc(N)c45)cc3)c2)cn1] | [M + H]⁺ = 486.2 |
| 103 | 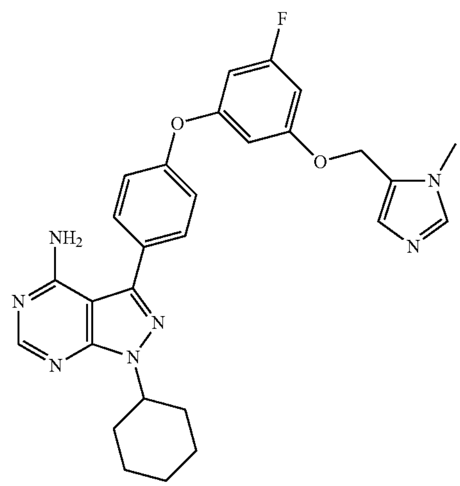 [SMILES: Cn1cncc1COc1cc(F)cc(Oc2ccc(-c3nn(C4CCCCC4)c4ncnc(N)c34)cc2)c1] | [M + H]⁺ = 514.2 |
| 104 | 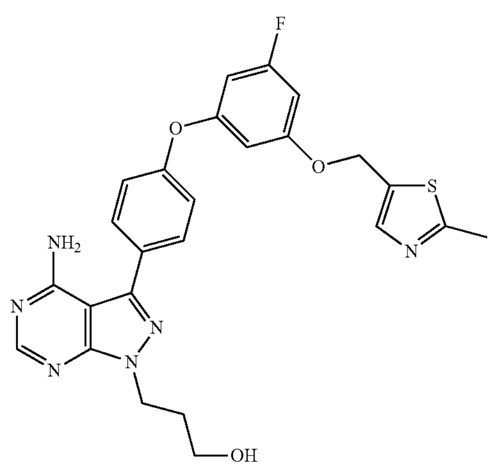 [SMILES: Cc1ncc(COc2cc(F)cc(Oc3ccc(-c4nn(CCCO)c5ncnc(N)c45)cc3)c2)s1] | [M + H]⁺ = 507.2 |

TABLE 1-continued

Example Compounds of Formula 1

| Compound | Structure | MS (m/z) |
|---|---|---|
| 105 | 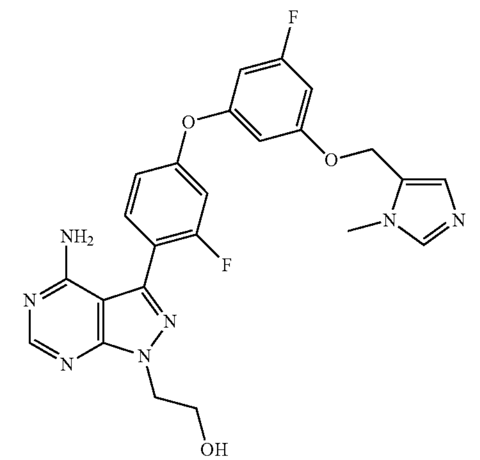 [SMILES: Cn1cncc1COc1cc(F)cc(Oc2ccc(-c3nn(CCO)c4ncnc(N)c34)c(F)c2)c1] | [M + H]+ = 494.1 |
| 106 | 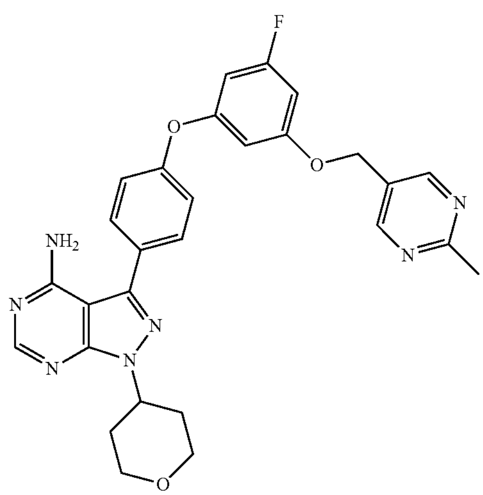 [SMILES: Cc1ncc(COc2cc(F)cc(Oc3ccc(-c4nn(C5CCOCC5)c5ncnc(N)c45)cc3)c2)cn1] | [M + H]+ = 528.1 |
| 107 | 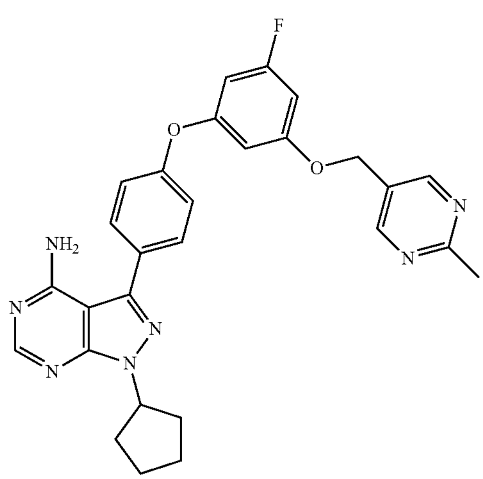 [SMILES: Cc1ncc(COc2cc(F)cc(Oc3ccc(-c4nn(C5CCCC5)c5ncnc(N)c45)cc3)c2)cn1] | [M + H]+ = 512.2 |

TABLE 1-continued
Example Compounds of Formula 1
| Compound | Structure | MS (m/z) |
|---|---|---|
| 108 | 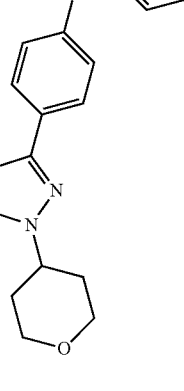 | [M + H]⁺ = 530.2 |
| 109 | 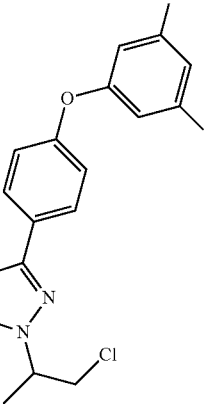 | [M + H]⁺ = 541.3 |
| 110 | 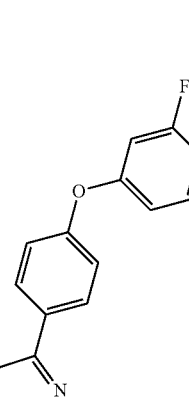 | [M + H]⁺ = 488.1 |

TABLE 1-continued
Example Compounds of Formula 1
| Compound | Structure | MS (m/z) |
|---|---|---|
| 111 | 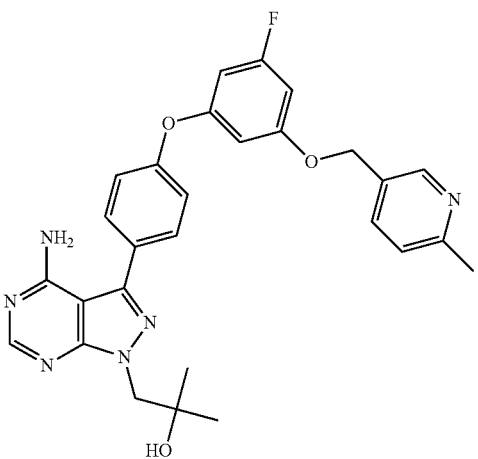 [SMILES: Cc1ccc(COc2cc(F)cc(Oc3ccc(-c4nn(CC(C)(C)O)c5ncnc(N)c45)cc3)c2)cn1] | [M + H]⁺ = 515.1 |
| 112 | 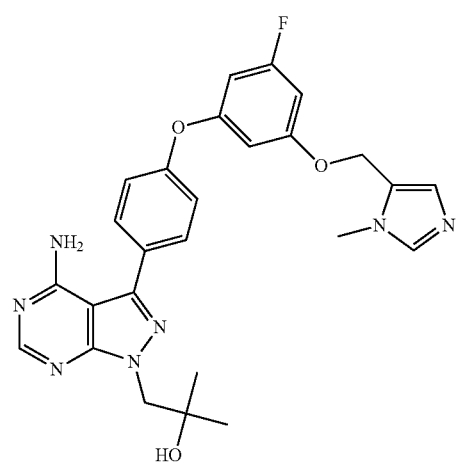 [SMILES: Cn1cncc1COc1cc(F)cc(Oc2ccc(-c3nn(CC(C)(C)O)c4ncnc(N)c34)cc2)c1] | [M + H]⁺ = 504.1 |
| 113 | 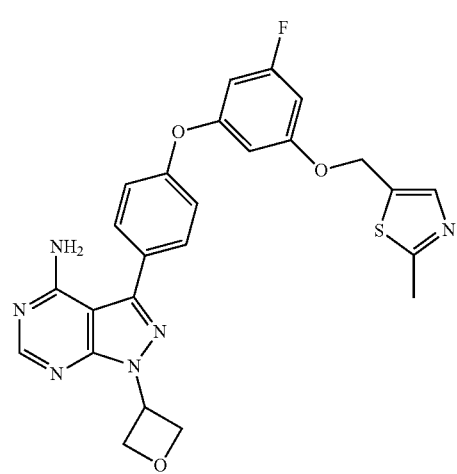 [SMILES: Cc1ncc(COc2cc(F)cc(Oc3ccc(-c4nn(C5COC5)c5ncnc(N)c45)cc3)c2)s1] | [M + H]⁺ = 505.2 |

TABLE 1-continued

Example Compounds of Formula 1

| Compound | Structure | MS (m/z) |
|---|---|---|
| 114 | 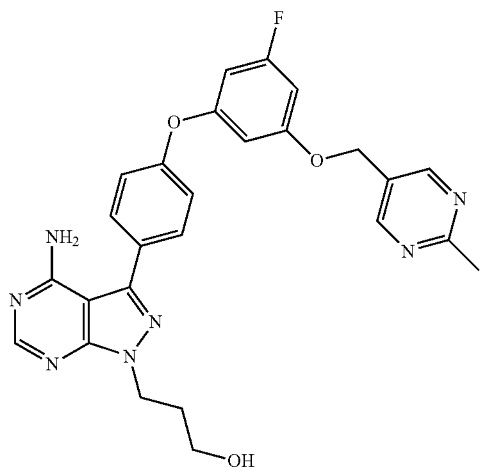 | [M + H]⁺ = 502.2 |
| 115 | 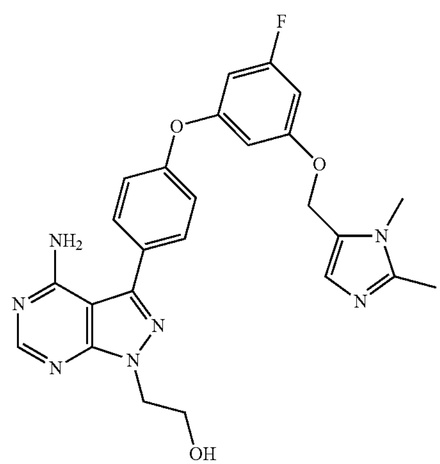 [SMILES: Cc1ncc(COc2cc(F)cc(Oc3ccc(-c4nn(CCO)c5ncnc(N)c45)cc3)c2)n1C] | [M + H]⁺ = 490.1 |
| 116 | 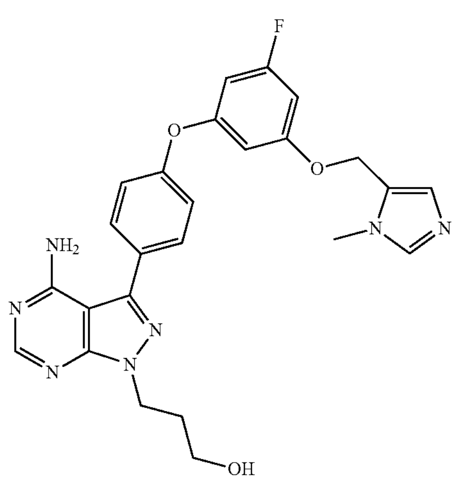 [SMILES: Cn1cncc1COc1cc(F)cc(Oc2ccc(-c3nn(CCCO)c4ncnc(N)c34)cc2)c1] | [M + H]⁺ = 490.2 |

TABLE 1-continued
Example Compounds of Formula 1
| Compound | Structure | MS (m/z) |
|---|---|---|
| 117 | 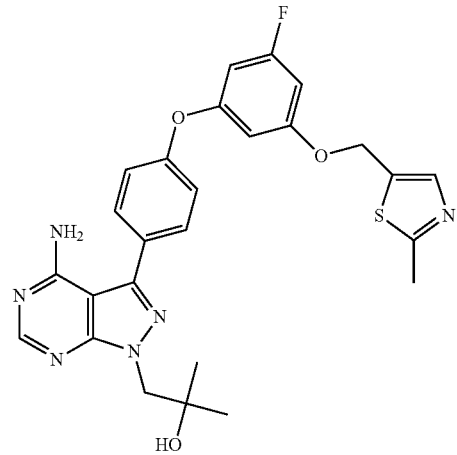 [SMILES: Cc1ncc(COc2cc(F)cc(Oc3ccc(-c4nn(CC(C)(C)O)c5ncnc(N)c45)cc3)c2)s1] | [M + H]+ = 521.1 |
| 118 | 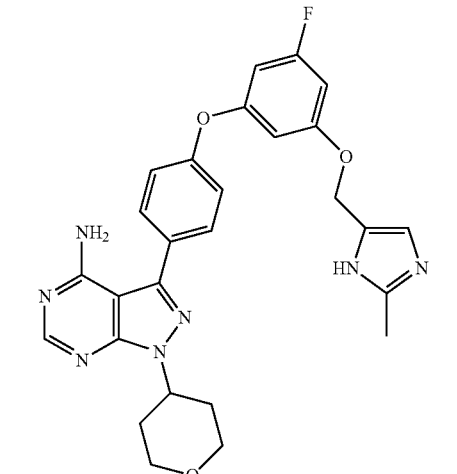 | [M + H]+ = 516.2 |
| 119 | 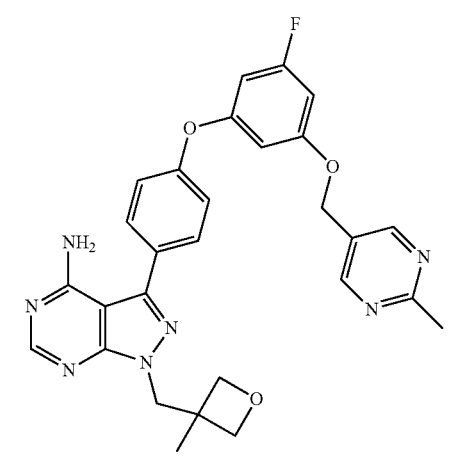 | [M + H]+ = 528.2 |

TABLE 1-continued
Example Compounds of Formula 1
| Compound | Structure | MS (m/z) |
|---|---|---|
| 120 | 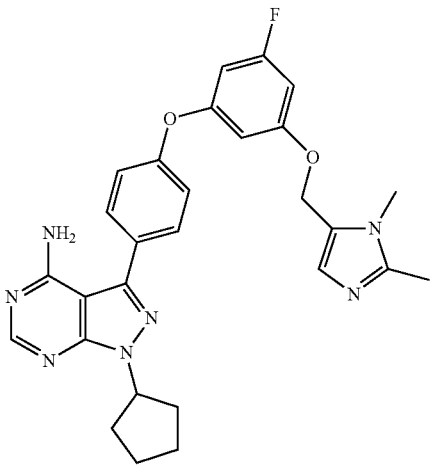 [SMILES: Cc1ncc(COc2cc(F)cc(Oc3ccc(-c4nn(C5CCCC5)c5ncnc(N)c45)cc3)c2)n1C] | [M + H]+ = 514.2 |
| 121 | 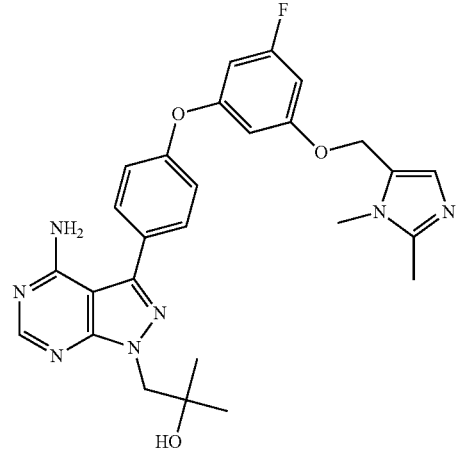 [SMILES: Cc1ncc(COc2cc(F)cc(Oc3ccc(-c4nn(CC(C)(C)O)c5ncnc(N)c45)cc3)c2)n1C] | [M + H]+ = 518.1 |
| 122 | 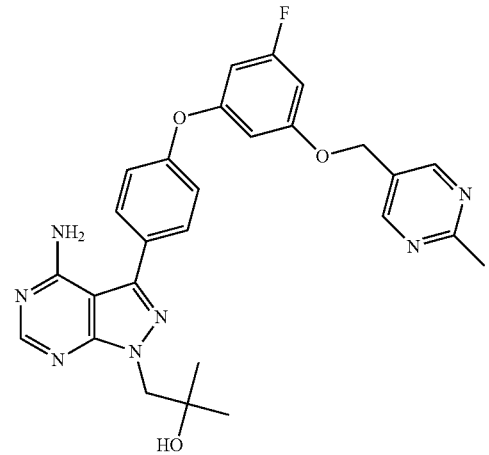 | [M + H]+ = 516.1 |

TABLE 1-continued
| Example Compounds of Formula 1 | | |
|---|---|---|
| Compound | Structure | MS (m/z) |
| 123 | 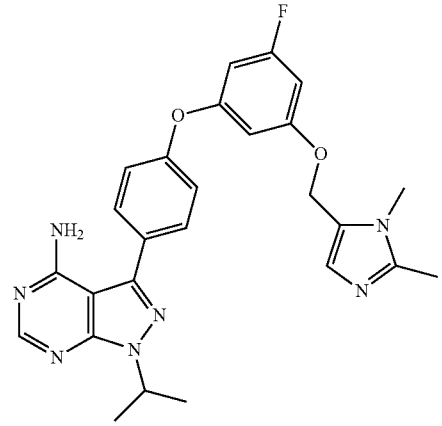 [SMILES: Cc1ncc(COc2cc(F)cc(Oc3ccc(-c4nn(C(C)C)c5ncnc(N)c45)cc3)c2)n1C] | [M + H]⁺ = 488.2 |
| 124 | 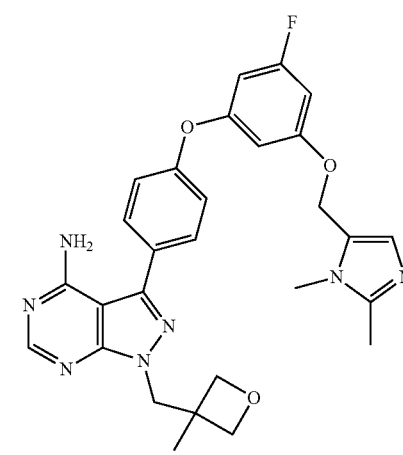 | [M + H]⁺ = 530.1 |
| 125 | 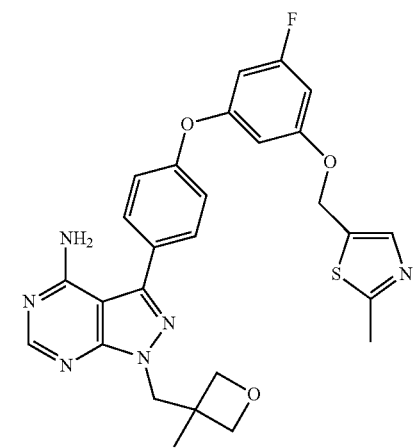 [SMILES: Cc1ncc(COc2cc(F)cc(Oc3ccc(-c4nn(CC5(C)COC5)c5ncnc(N)c45)cc3)c2)s1] | [M + H]⁺ = 533.2 |

TABLE 1-continued
Example Compounds of Formula 1
| Compound | Structure | MS (m/z) |
|---|---|---|
| 126 | 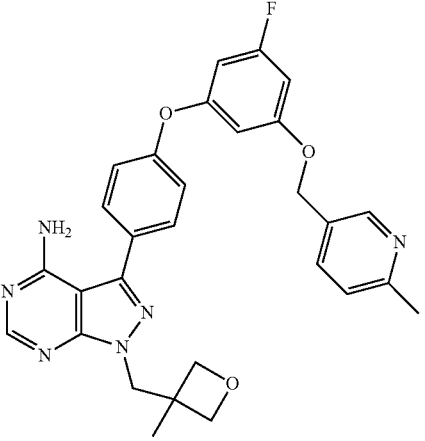 [SMILES: Cc1ccc(COc2cc(F)cc(Oc3ccc(-c4nn(CC5(C)COC5)c5ncnc(N)c45)cc3)c2)cn1] | [M + H]+ = 527.2 |
| 127 | 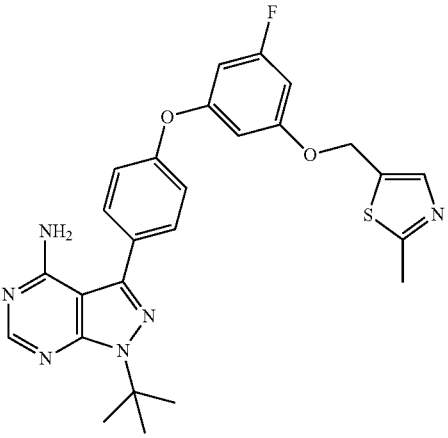 [SMILES: Cc1ncc(COc2cc(F)cc(Oc3ccc(-c4nn(C(C)(C)C)c5ncnc(N)c45)cc3)c2)s1] | [M + H]+ = 505.2 |
| 128 | 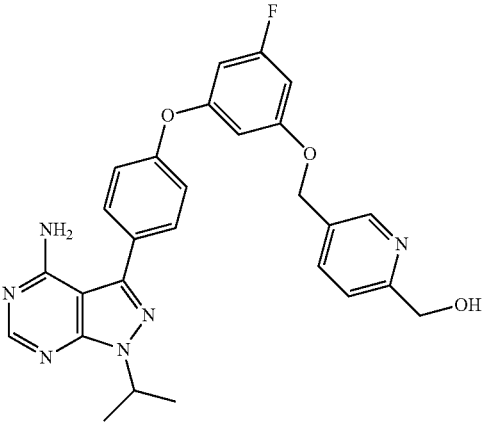 [SMILES: CC(C)n1nc(-c2ccc(Oc3cc(F)cc(OCc4ccc(CO)nc4)c3)cc2)c2c(N)ncnc21] | [M + H]+ = 501.1 |

TABLE 1-continued

Example Compounds of Formula 1

| Compound | Structure | MS (m/z) |
|----------|-----------|----------|
| 129 | 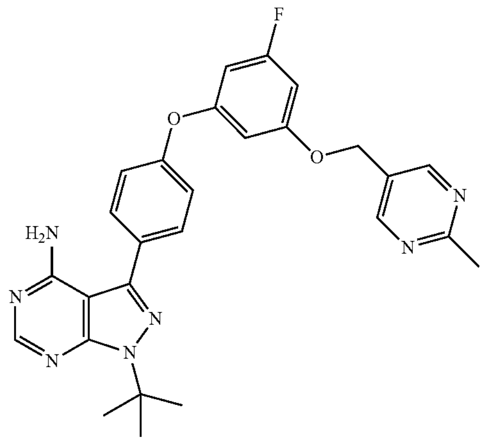 [SMILES: Cc1ncc(COc2cc(F)cc(Oc3ccc(-c4nn(C(C)(C)C)c5ncnc(N)c45)cc3)c2)cn1] | [M + H]⁺ = 500.1 |
| 130 | 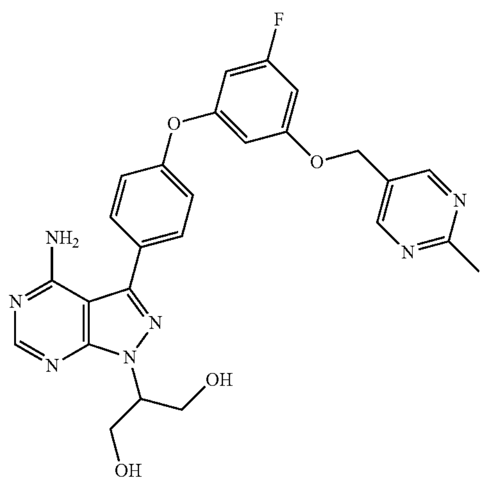 [SMILES: Cc1ncc(COc2cc(F)cc(Oc3ccc(-c4nn(C(CO)CO)c5ncnc(N)c45)cc3)c2)cn1] | [M + H]⁺ = 518.1 |
| 131 | 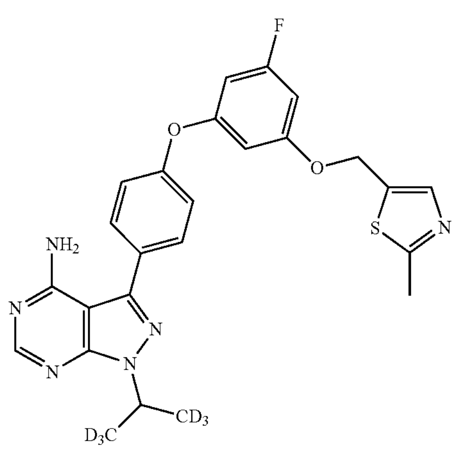 [SMILES: [2H]C([2H])([2H])C(n1nc(-c2ccc(Oc3cc(F)cc(OCc4cnc(C)s4)c3)cc2)c2c(N)ncnc21)C([2H])([2H])[2H]] | [M + H]⁺ = 497.2 |

TABLE 1-continued

Example Compounds of Formula 1

| Compound | Structure | MS (m/z) |
|---|---|---|
| 132 | 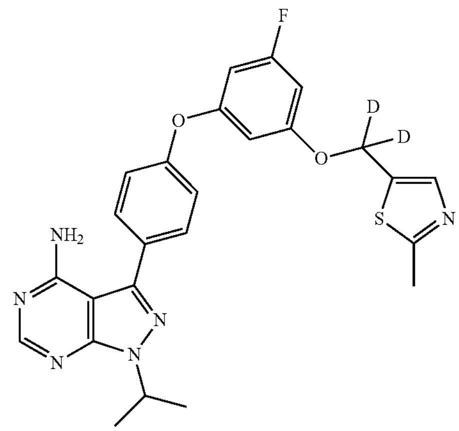 [SMILES: [2H]C([2H])(Oc1cc(F)cc(Oc2ccc(-c3nn(C(C)C)c4ncnc(N)c34)cc2)c1)c1cnc(C)s1] | [M + H]⁺ = 493.2 |
| 133 | 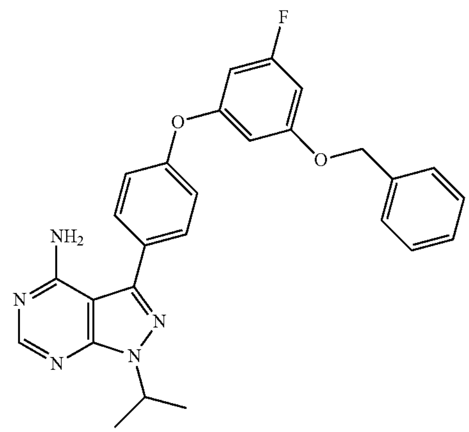 [SMILES: CC(C)n1nc(-c2ccc(Oc3cc(F)cc(OCc4ccccc4)c3)cc2)c2c(N)ncnc21] | [M + H]⁺ = 470.1 |
| 134 | 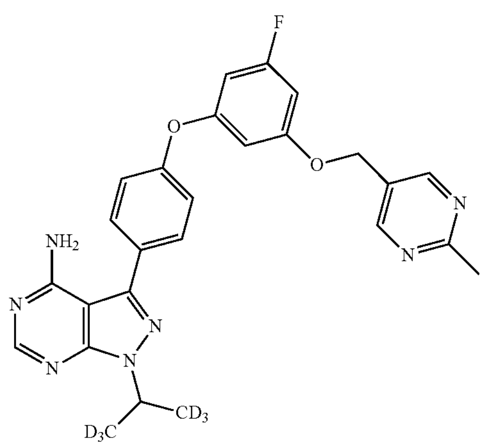 [SMILES: [2H]C([2H])([2H])C(n1nc(-c2ccc(Oc3cc(F)cc(OCc4cnc(C)nc4)c3)cc2)c2c(N)ncnc21)C([2H])([2H])[2H]] | [M + H]⁺ = 492.1 |

Kinase Binding
Btk Kinase Inhibition Assay

Fluorescence polarization-based kinase assays were performed in 384 well-plate format using histidine tagged recombinant human full-length Bruton Agammaglobulinemia Tyrosine Kinase (Btk) and a modified protocol of the KinEASE™ FP Fluorescein Green Assay supplied from Millipore. Kinase reaction were performed at room temperature for 60 minutes in presence of 250 µM substrate, 10 µM ATP and variable test article concentrations. The reaction was stopped with EDTA/kinase detection reagents and the polarization measured on a Tecan 500 instrument. From the dose-response curve obtained, the $IC_{50}$ was calculated using Graph Pad Prisms® using a non linear fit curve. The Km for ATP on each enzyme was experimentally determined and the Ki values calculated using the Cheng-Prusoff equation (see: Cheng Y, Prusoff W H. (1973) Relationship between the inhibition constant (K1) and the concentration of inhibitor which causes 50 percent inhibition ($I_{50}$) of an enzymatic reaction". *Biochem Pharmacol* 22 (23): 3099-108).

$k_i$ values are reported in Tables 2:

TABLE 2

| Inhibition of Btk | |
|---|---|
| Compound | $k_i$ (nM) |
| 1 | a |
| 2 | a |
| 3 | a |
| 4 | a |
| 5 | a |
| 6 | a |
| 7 | a |
| 8 | a |
| 9 | a |
| 10 | a |
| 11 | a |
| 12 | a |
| 13 | a |
| 14 | a |
| 15 | a |
| 16 | a |
| 17 | a |
| 18 | a |
| 19 | a |
| 20 | a |
| 21 | a |
| 22 | a |
| 23 | a |
| 24 | a |
| 25 | a |
| 26 | a |
| 27 | a |
| 28 | a |
| 29 | a |
| 30 | a |
| 31 | a |
| 32 | a |
| 33 | a |
| 34 | a |
| 35 | a |
| 36 | a |
| 37 | a |
| 38 | a |
| 39 | a |
| 40 | a |
| 41 | a |
| 42 | a |
| 43 | a |
| 44 | a |
| 45 | b |
| 46 | a |
| 47 | a |
| 48 | a |
| 49 | a |
| 50 | a |
| 51 | a |
| 52 | a |
| 53 | a |
| 54 | a |
| 55 | a |
| 56 | — |
| 57 | a |
| 58 | a |
| 59 | a |
| 60 | a |
| 61 | a |
| 62 | a |
| 63 | a |
| 64 | a |
| 65 | a |
| 66 | a |
| 67 | a |
| 68 | a |
| 69 | a |
| 70 | a |
| 71 | a |
| 72 | a |
| 73 | a |

TABLE 2-continued

| Inhibition of Btk | |
|---|---|
| Compound | $k_i$ (nM) |
| 74 | a |
| 75 | a |
| 76 | a |
| 77 | a |
| 78 | a |
| 79 | a |
| 80 | a |
| 81 | a |
| 82 | a |
| 83 | a |
| 84 | a |
| 85 | a |
| 86 | a |
| 87 | a |
| 88 | a |
| 89 | — |
| 90 | a |
| 91 | a |
| 92 | a |
| 93 | a |
| 94 | — |
| 95 | a |
| 96 | a |
| 97 | a |
| 98 | a |
| 99 | a |
| 100 | a |
| 101 | a |
| 102 | a |
| 103 | a |
| 104 | a |
| 105 | a |
| 106 | a |
| 107 | a |
| 108 | a |
| 109 | a |
| 110 | a |
| 111 | a |
| 112 | a |
| 113 | a |
| 114 | a |
| 115 | a |
| 116 | a |
| 117 | a |
| 118 | a |
| 119 | a |
| 120 | a |
| 121 | a |
| 122 | a |
| 123 | a |
| 124 | a |
| 125 | a |
| 126 | a |
| 127 | a |
| 128 | a |
| 129 | a |
| 130 | a |
| 131 | — |
| 132 | — |
| 133 | — |
| 134 | — | a - Ki < 100 nM;
b - 100 nM < Ki < 1000 nM,
c - Ki > 1000 nM

Splenic Cell Proliferation Assay

Splenocytes were obtained from 6 week old male CD1 mice (Charles River Laboratories Inc.). Mouse spleens were manually disrupted in PBS and filtered using a 70 um cell strainer followed by ammonium chloride red blood cell lysis. Cells were washed, resuspended in Splenocyte Medium (HyClone RPMI supplemented with 10% heat-inactivated FBS, 0.5× non-essential amino acids, 10 mM HEPES, 50 uM beta mercaptoethanol) and incubated at 37°

C., 5% $CO_2$ for 2 h to remove adherent cells. Suspension cells were seeded in 96 well plates at 50,000 cells per well and incubated at 37° C., 5% $CO_2$ for 1 h. Splenocytes were pre-treated in triplicate with 10,000 nM curves of Formula 1 compounds for 1 h, followed by stimulation of B cell proliferation with 2.5 ug/ml anti-IgM F(ab')$_2$ (Jackson ImmunoResearch) for 72 h. Cell proliferation was measured by Cell Titer-Glo Luminescent Assay (Promega). $EC_{50}$ values (50% proliferation in the presence of compound as compared to vehicle treated controls) were calculated from dose response compound curves using GraphPad Prism Software.

$EC_{50}$ values are reported in Table 3:

TABLE 3

Inhibition of splenic cell proliferation

| Compound | $EC_{50}$ (nM) |
| --- | --- |
| 1 | b |
| 2 | b |
| 3 | b |
| 4 | b |
| 5 | a |
| 6 | a |
| 7 | b |
| 8 | a |
| 9 | b |
| 10 | b |
| 11 | b |
| 12 | b |
| 13 | a |
| 14 | a |
| 15 | a |
| 16 | b |
| 17 | b |
| 18 | a |
| 19 | b |
| 20 | a |
| 21 | a |
| 22 | a |
| 23 | a |
| 24 | a |
| 25 | a |
| 26 | a |
| 27 | a |
| 28 | a |
| 29 | a |
| 30 | a |
| 31 | b |
| 32 | a |
| 33 | a |
| 34 | b |
| 35 | a |
| 36 | a |
| 37 | a |
| 38 | a |
| 39 | b |
| 40 | b |
| 41 | b |
| 42 | a |
| 43 | b |
| 44 | a |
| 45 | b |
| 46 | a |
| 47 | a |
| 48 | a |
| 49 | a |
| 50 | a |
| 51 | a |
| 52 | a |
| 53 | a |
| 54 | a |
| 55 | a |
| 56 | b |
| 57 | b |
| 58 | a |
| 59 | a |
| 60 | a |
| 61 | b |
| 62 | a |
| 63 | a |
| 64 | a |
| 65 | a |
| 66 | b |
| 67 | b |
| 68 | a |
| 69 | a |
| 70 | a |
| 71 | a |
| 72 | b |
| 73 | a |
| 74 | b |
| 75 | a |
| 76 | b |
| 77 | a |
| 78 | a |
| 79 | a |
| 80 | b |
| 81 | a |
| 82 | a |
| 83 | b |
| 84 | a |
| 85 | a |
| 86 | b |
| 87 | a |
| 88 | a |
| 89 | a |
| 90 | b |
| 91 | a |
| 92 | a |
| 93 | b |
| 94 | a |
| 95 | a |
| 96 | a |
| 97 | b |
| 98 | a |
| 99 | b |
| 100 | a |
| 101 | a |
| 102 | a |
| 103 | a |
| 104 | a |
| 105 | b |
| 106 | a |
| 107 | a |
| 108 | a |
| 109 | a |
| 110 | b |
| 111 | b |
| 112 | b |
| 113 | a |
| 114 | b |
| 115 | b |
| 116 | a |
| 117 | a |
| 118 | b |
| 119 | b |
| 120 | a |
| 121 | b |
| 122 | b |
| 123 | a |
| 124 | b |
| 125 | a |
| 126 | b |
| 127 | a |
| 128 | a |
| 129 | a |
| 130 | b |
| 131 | — |
| 132 | — |

TABLE 3-continued

Inhibition of splenic cell proliferation

| Compound | EC$_{50}$ (nM) |
|---|---|
| 133 | — |
| 134 | — | a - EC$_{50}$ < 100 nM;
b - 100 nM < EC$_{50}$ < 1000 nM,
c - EC$_{50}$ > 1000 nM

Methods: Mouse Arthus

Mouse Arthus studies were conducted as reported in Braselmann S, Taylor V, Zhao H, Wang S, Sylvain C, Baluom M, Qu K, Herlaar E, Lau A, Young C, Wong B R, Lovell S, Sun T, Park G, Argade A, Jurcevic S, Pine P, Singh R, Grossbard E B, Payan D G, Masuda E S: R406 an orally available spleen tyrosine kinase inhibitor blocks fc receptor signaling and reduces immune-complex mediated inflammation. *J Pharmacol Exp Ther*, 2006, 319:998-1008.

In summary, female Balb/c mice (6-7 weeks on arrival) were habituated to the animal facility for at least 4 days. On the day of the experiment, animals were pre-treated (t=minus 1 h) with compound or vehicle alone by gavage (PO). At t=0, animals were injected intravenously (IV; 0.1 mL/mouse) with saline containing chicken ovalbumin and Evan's blue (10 mg/mL of each). Ten minutes later (t=10 min), animals were anesthesized with isoflurane, the dorsal surface was shaved and rabbit anti-chicken ovalbumin antibody was then injected intradermally at one site on the right side of the animal (25 μg in 30 μL). The same amount of isotype control antibody was then injected on the left side.

The animals were then returned to their home cage and skin punches (8 mm) were collected from each injection site four hours later. The samples were placed in 1 mL formamide overnight at 80 degrees C. (1 skin biopsy per 1 mL formamide in a glass tube). The amount of Evan's blue in the formamide solution was then assessed by spectrophotometry (630 nm) as a measure of serum extravasation into the dermis.

Compounds 14, 15, 24, 46, 50, 54, 58, 59, 62, 71, 78, 79, 82, 85, 90, 100, 102, 103, 106, 107, 108, 117, and 125 demonstrated efficacy when administered by oral gavages at 30 mg/kg.

Mouse CIA model was performed using the methods described by Trentham D E, Townes A S, Kang A H. Autoimmunity to Type II Collagen: An Experimental Model of Arthritis. J Exp Med 1977; 857-868, and Bendele A M. Animal Models of Rheumatoid Arthritis. J Musculoskel Interact 2001; 377-385.

In summary, male B10R111 mice (7-9 wks on arrival) were habituated to the animal facility for at least 4 days. On experimental day 0 mice were anaesthetized with isoflurane and the dorsal surface was shaved. Collagen, emulsified in Freund's complete adjuvant (CFA) supplemented with additional mycobacterium tuberculosis (TB) H37Ra, was injected intradermally at the base of the tail (0.15 mL/animal; 2 mg/mL collagen and 2.5 mg/mL TB in CFA). This CFA treatment was repeated on day 15.

From day 15 to the end of the study animals were scored daily for signs of arthritis. On the first day of disease (RA Day 1) animals were recruited to the study and grouped using a balanced design based on arthritis score. Once recruited, animals were weighed and dosed twice daily by gavage (PO, BID). Recruited animals were then scored twice a week on RA days 1, 5, 8 and 12. At the end of the study (RA day 12) animals were weighed and scored.

Compounds 14, 58, 78, 85 and 102 demonstrated efficacy when administered by oral gavages at 30 mg/kg (BID).

The invention claimed is:
1. A compound of Formula 1:

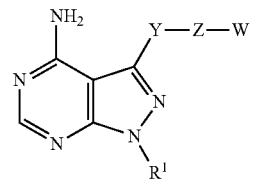

Formula 1 wherein,
$R^1$ is selected from the group consisting of hydrogen, heteroalkyl, carbocyclyl, heterocyclyl, C(O)R$^4$ and substituted and unsubstituted alkyl;
wherein the heteroalkyl, carbocyclyl and heterocyclyl may be further substituted by the groups consisting of hydroxy, alkoxy, alkyl, —OC(O)R$^4$, —OC(O)NR$^5$R$^6$, —C(O)R$^4$, —C(O)NR$^5$R$^6$, —NR$^5$R$^6$, —NR$^2$C(O)R$^4$, —NR$^2$S(O)$_n$R$^4$ and —NR$^2$C(O)NR$^5$R$^6$;
Y is

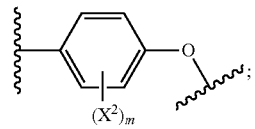

Z is

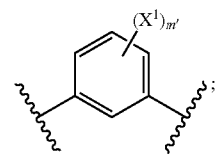

Y—Z—W is

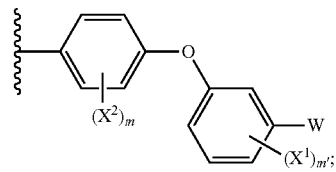

X$^1$ and X$^2$ are independently selected from the group consisting of hydrogen, halogen and cyano;
n is an integer from 0 to 2;
m is an integer from 0 to 2;
m' is an integer from 0 to 2;
W is —OR$^3$;
R$^2$ is hydrogen or alkyl;
R$^3$ is selected from the group consisting of substituted aralkyl, unsubstituted aralkyl, substituted heteroaralkyl, and unsubstituted heteroaralkyl;
R$^4$ is selected from the group consisting of substituted alkyl, unsubstituted alkyl, substituted alkenyl, unsubstituted alkenyl, substituted alkynyl, unsubstituted alkynyl, substituted heteroalkyl, unsubstituted heteroalkyl, substituted carbocyclyl, unsubstituted carbocyclyl, heterocyclyl, substituted aryl, unsubstituted aryl, substituted heteroaryl, unsubstituted heteroaryl, substituted aralkyl, unsubstituted aralkyl, substituted heteroaralkyl, and unsubstituted heteroaralkyl; and $R^5$ and $R^6$ are independently selected from the group consisting of hydrogen, alkyl, alkenyl, alkynyl, heteroalkyl, carbocyclyl, heterocyclyl, aryl, and heteroaryl; or alternatively $R^5$ and $R^6$ are fused to form a 3 to 8 membered heterocyclyl ring system; or a pharmaceutically acceptable salt, solvate, or solvate of a salt thereof.

2. The compound of claim 1, wherein W is selected from the group consisting of:

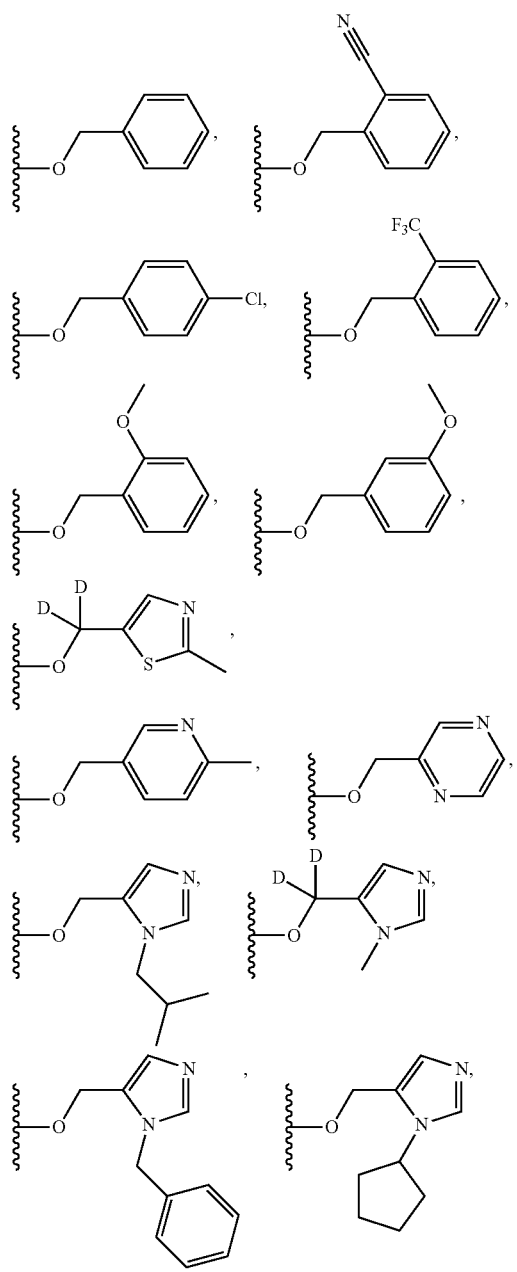

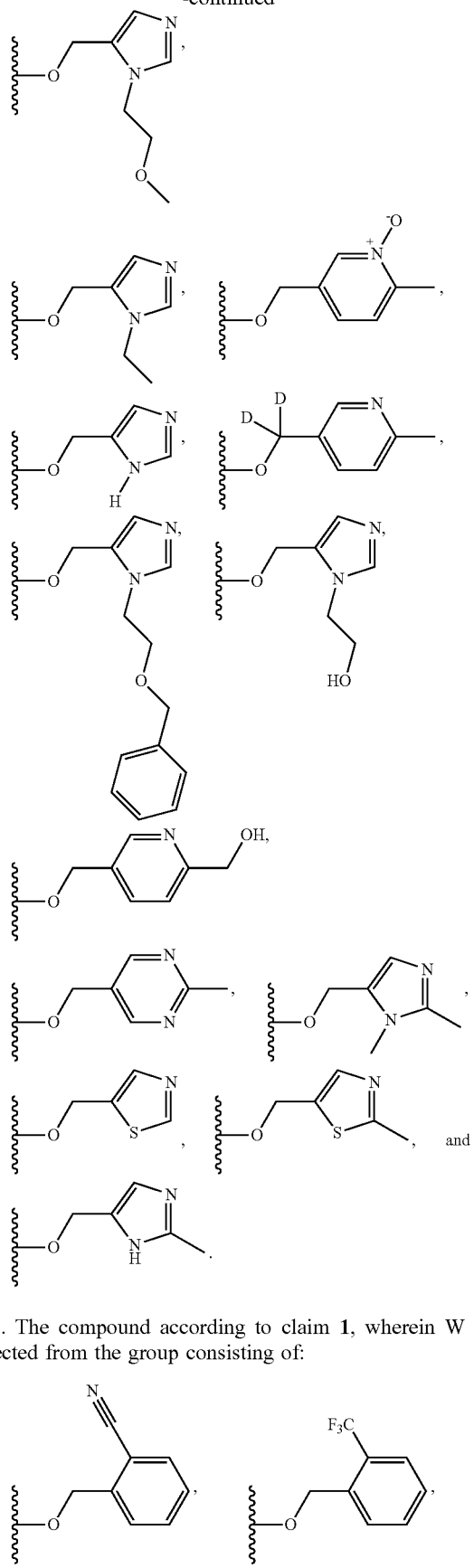

3. The compound according to claim 1, wherein W is selected from the group consisting of:

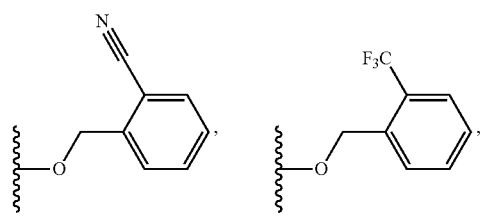

4. The compound according to claim 1, wherein $R^1$ is selected from the group consisting of:

H, CH₃, acetyl, [structures shown]

5. The compound according to claim 1, wherein $R^1$ is selected from the group consisting of:

[structures shown]

6. The compound according to claim 1, wherein Y is selected from the group consisting of:

[structures shown]

-continued
and
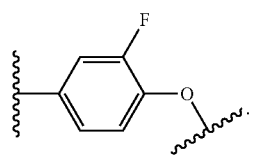
7. The compound according to claim 1, wherein Z is selected from the group consisting of:
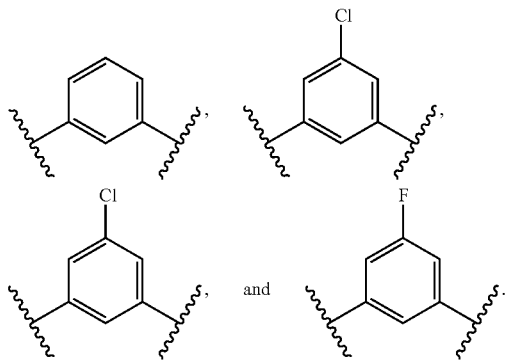
8. The compound according to claim 1, wherein Z is:
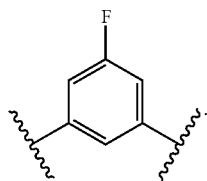
9. The compound according to claim 1, wherein Y—Z—W is selected from the group consisting of:
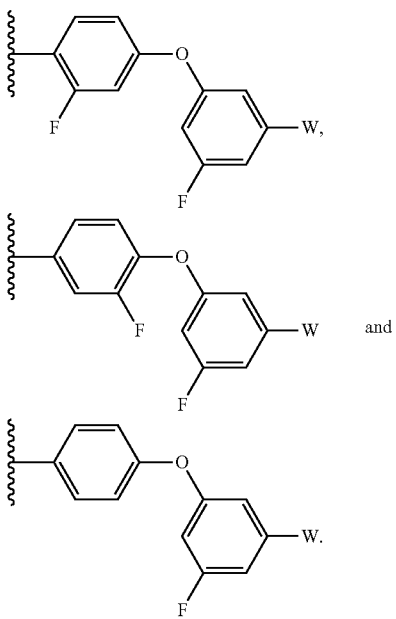
10. A compound selected from the group consisting of:
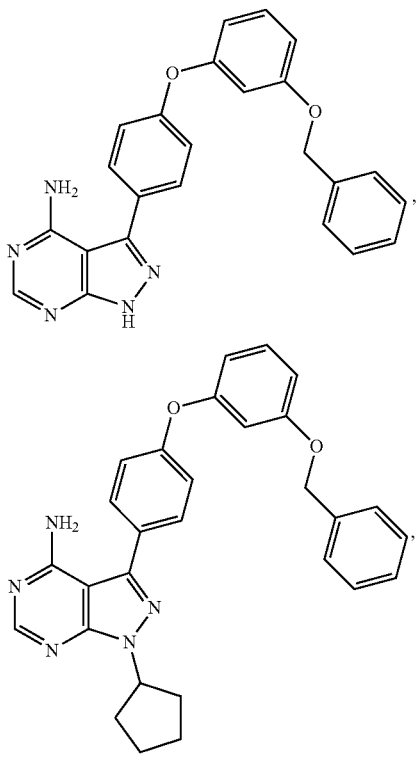
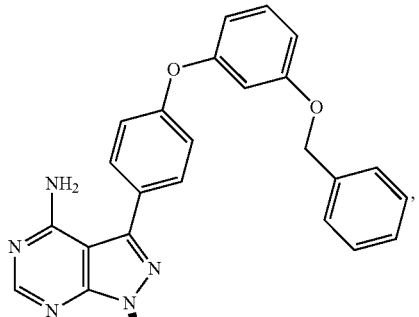
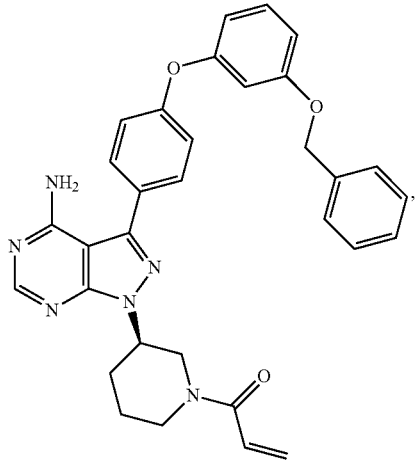

231
-continued
232
-continued
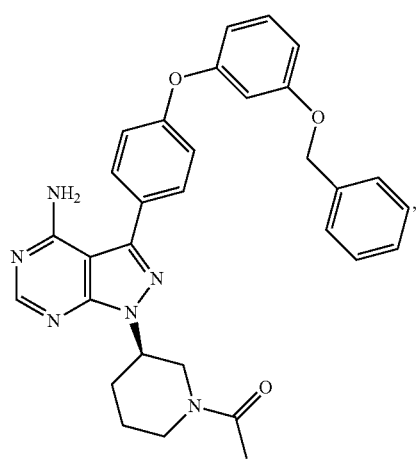
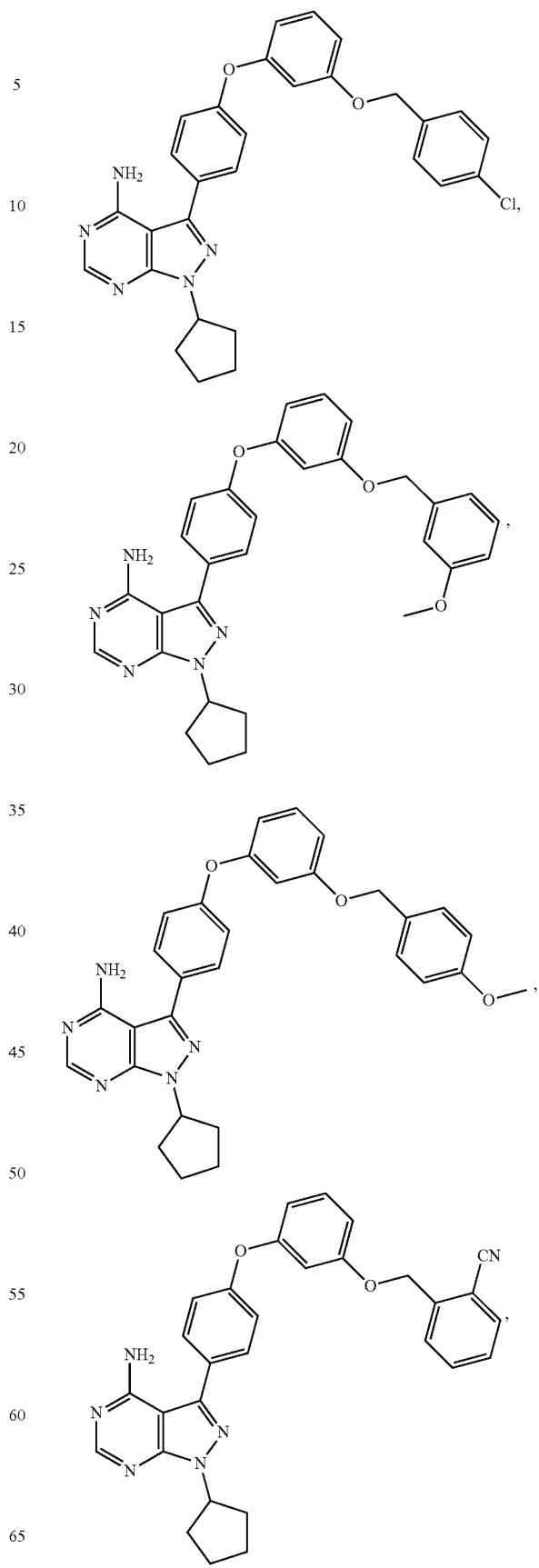

233
-continued
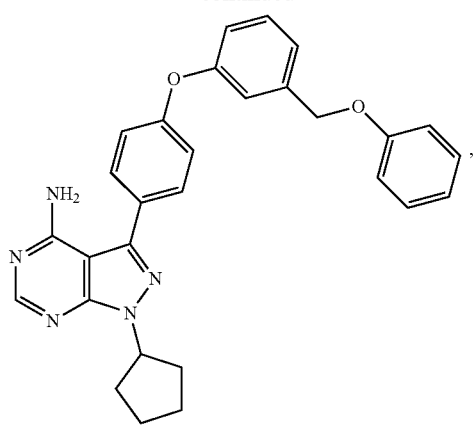
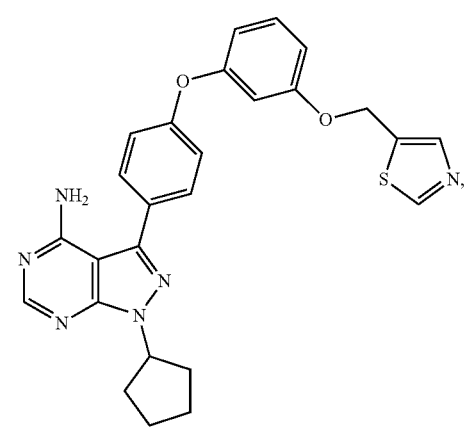
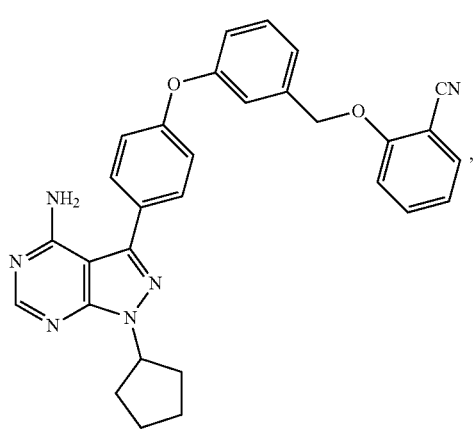
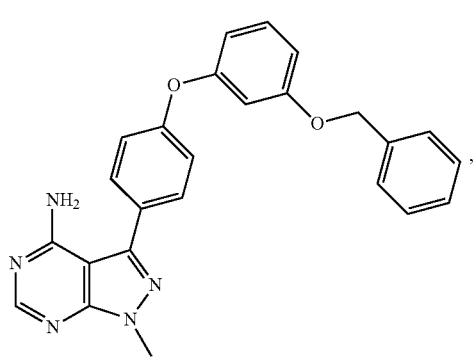
234
-continued
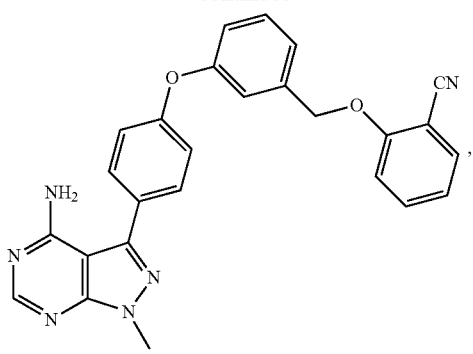
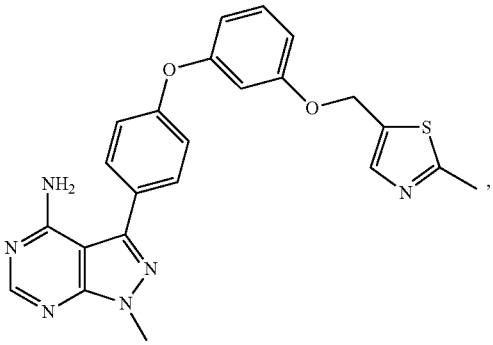
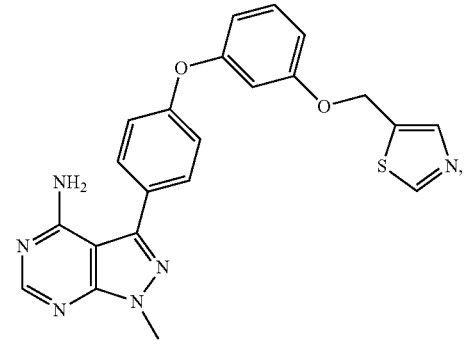
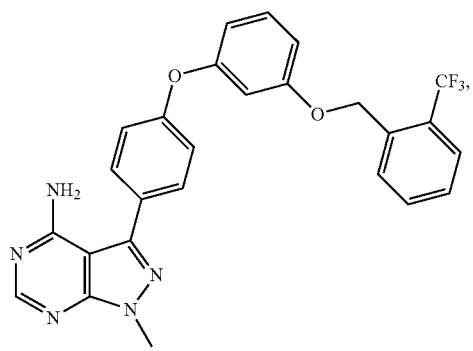

235
-continued
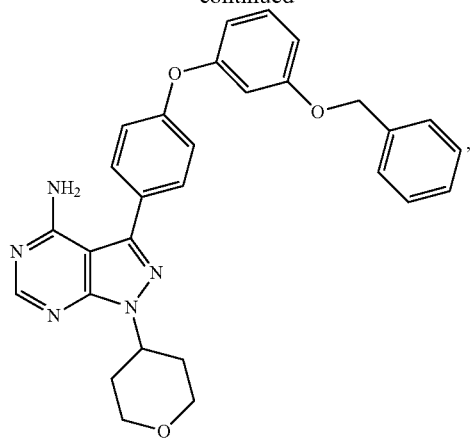
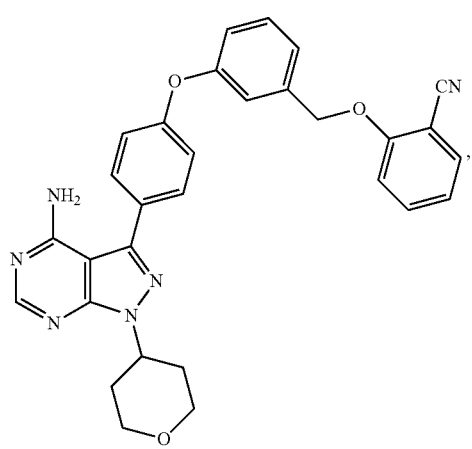
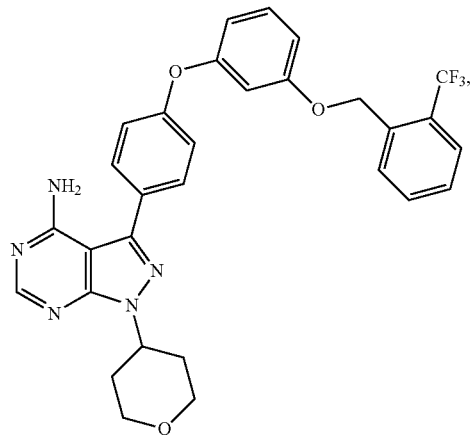
236
-continued
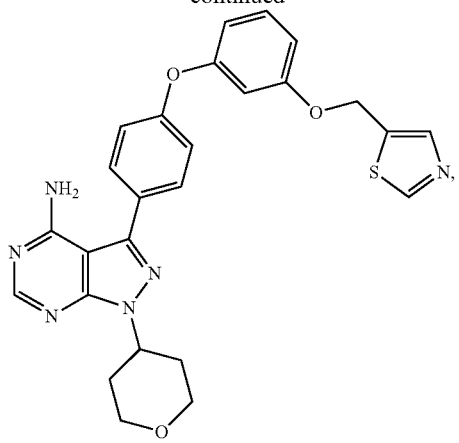
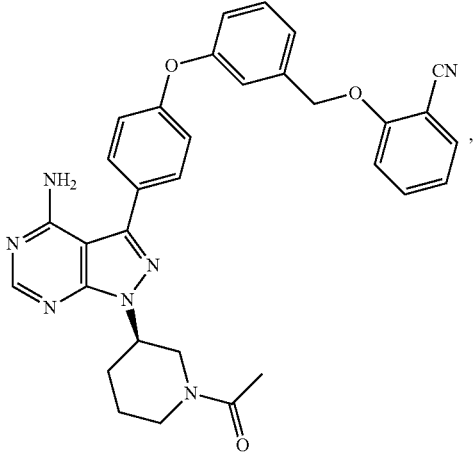
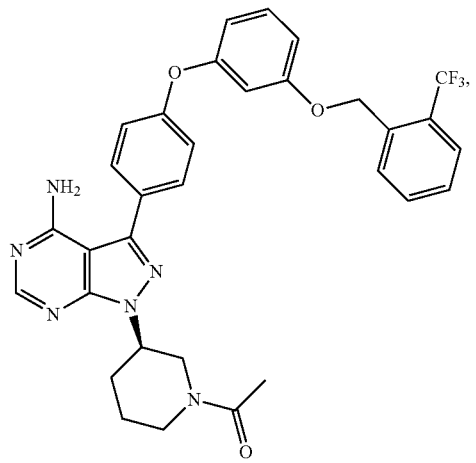

237
-continued
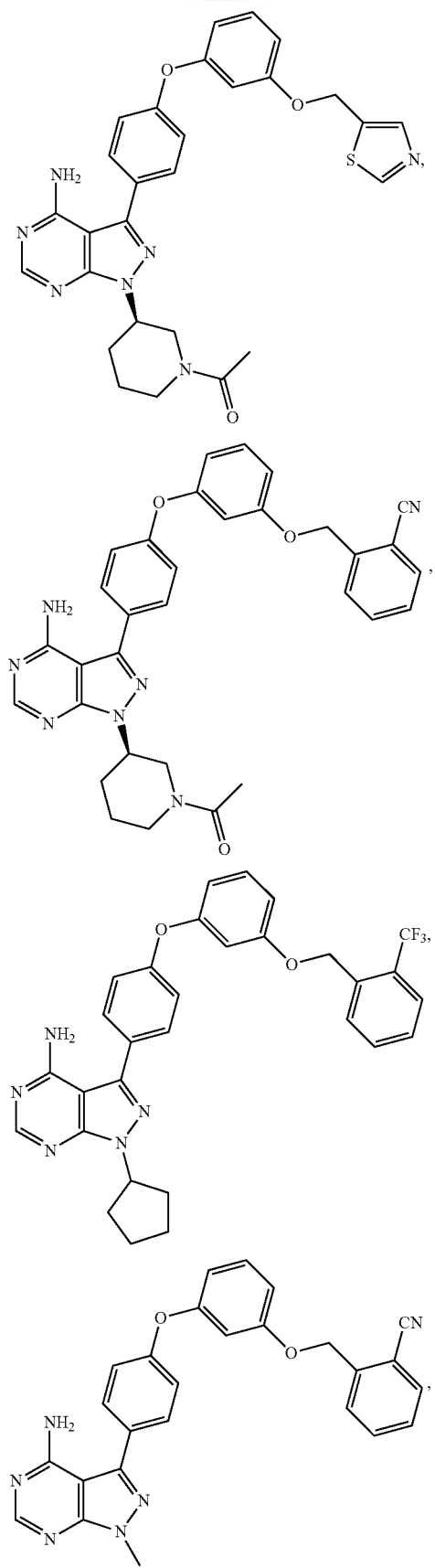
238
-continued
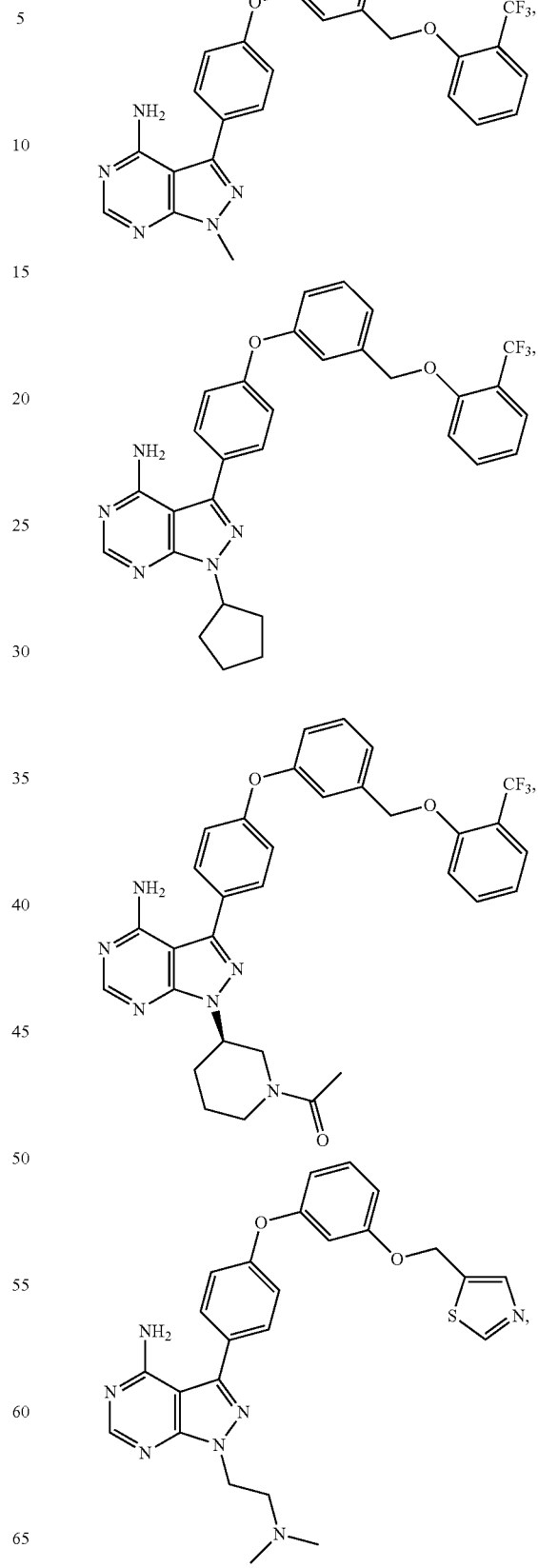

239
-continued
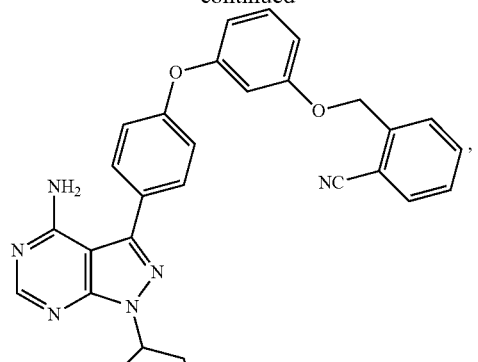
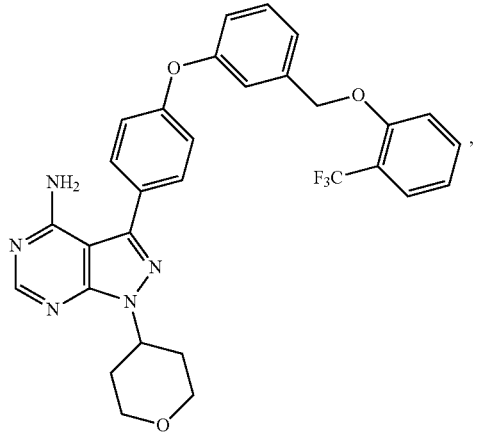
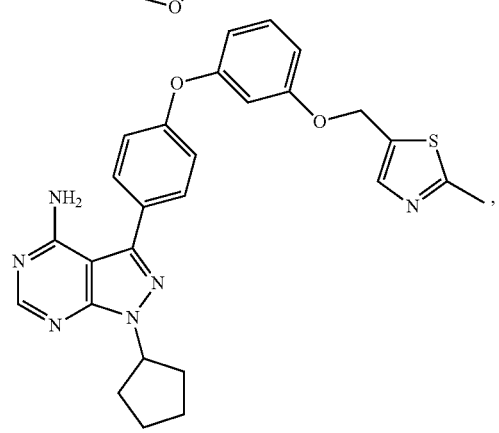
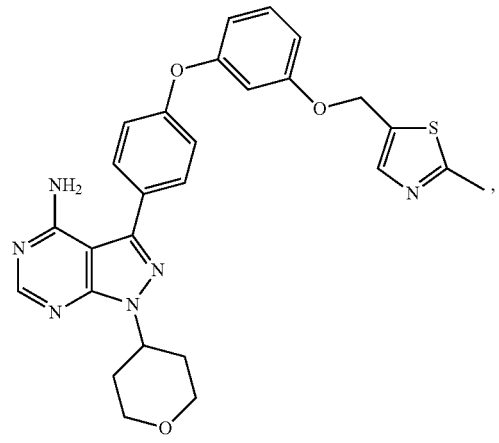
240
-continued
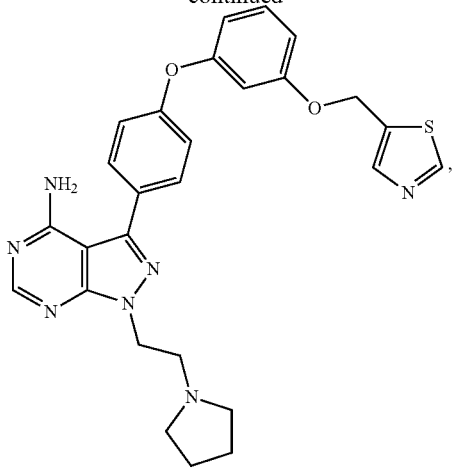
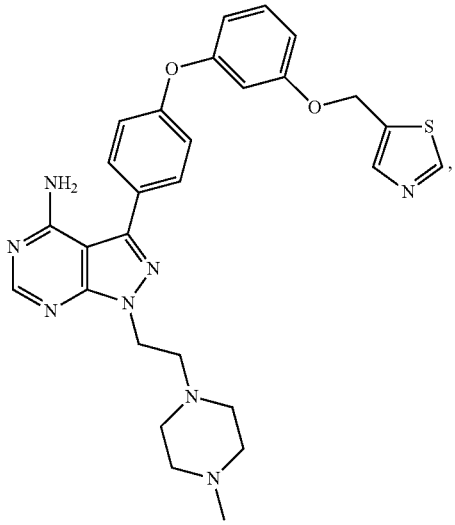
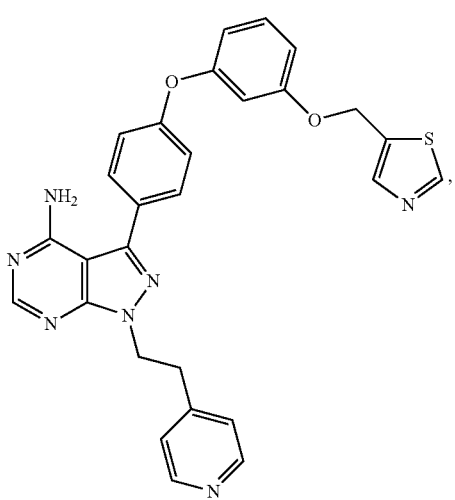

241
-continued
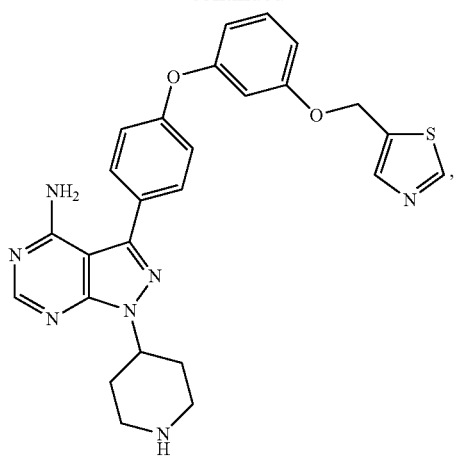
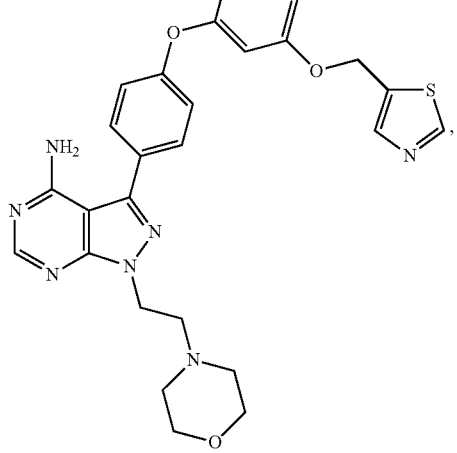
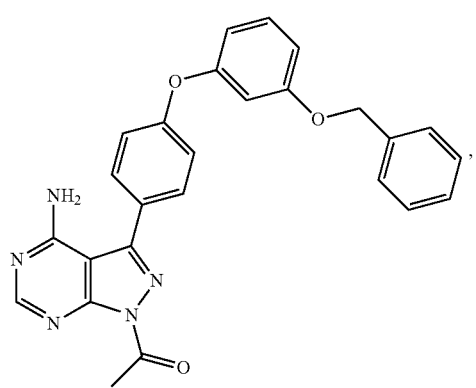
242
-continued
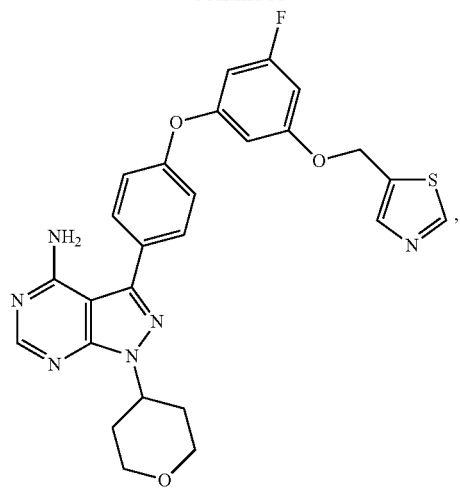
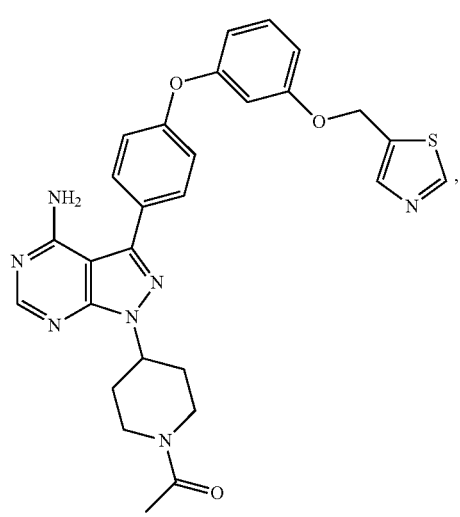
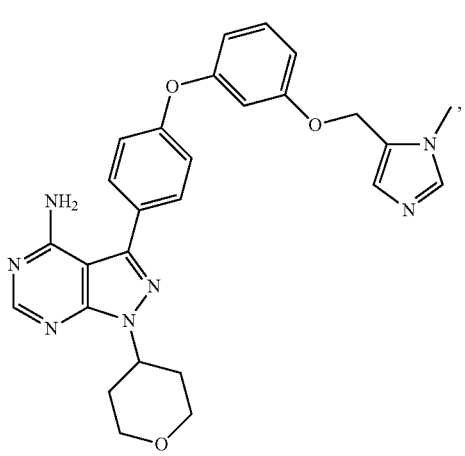

243
-continued
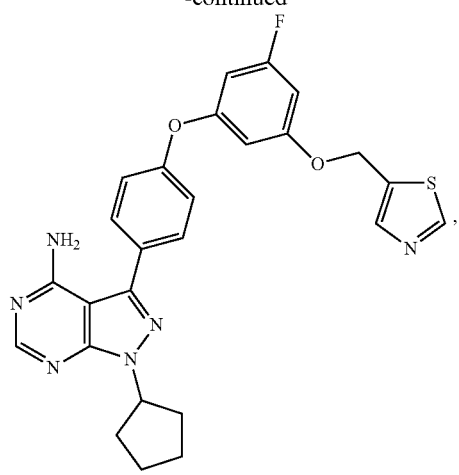
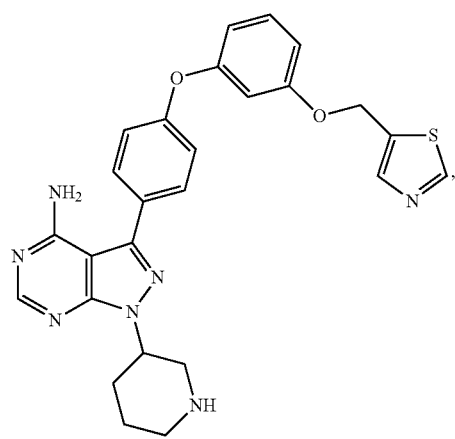
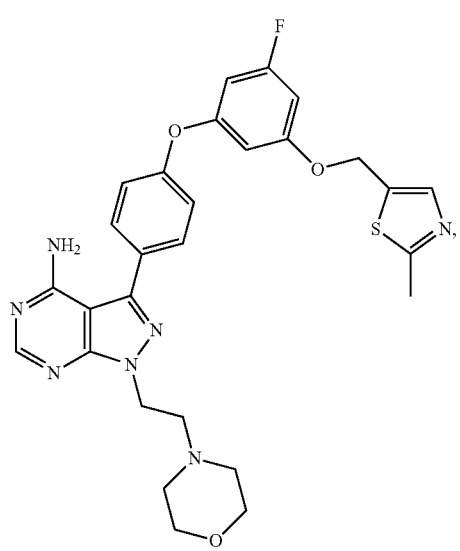
244
-continued
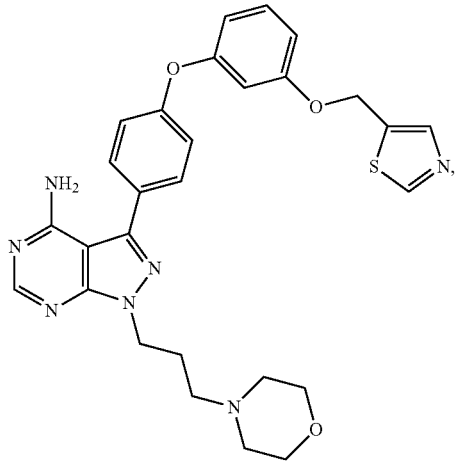
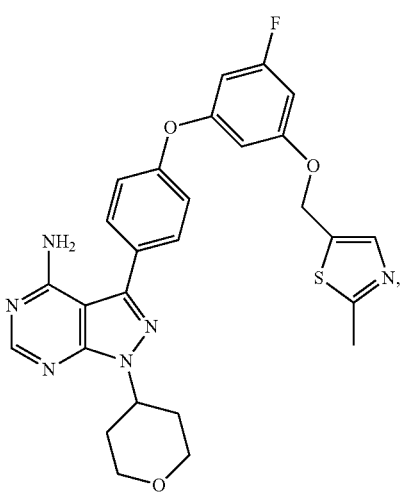
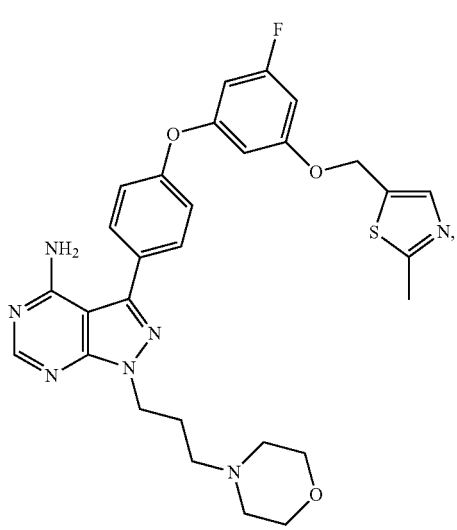

245
-continued
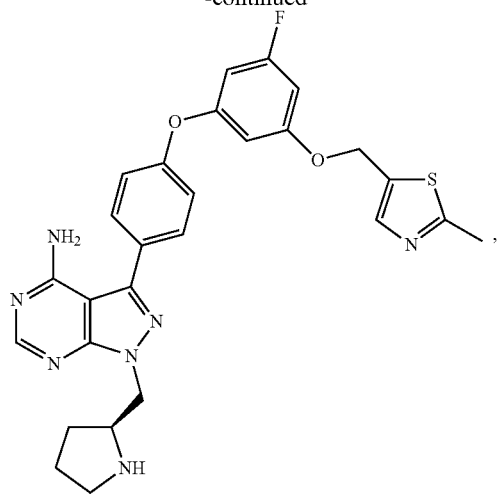
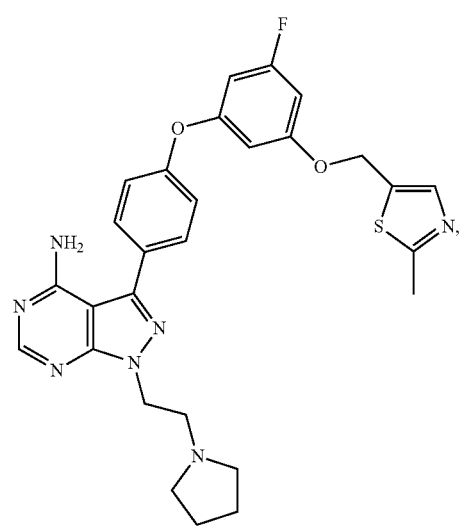
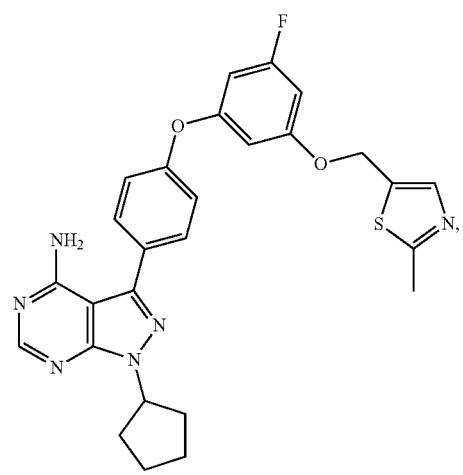
246
-continued
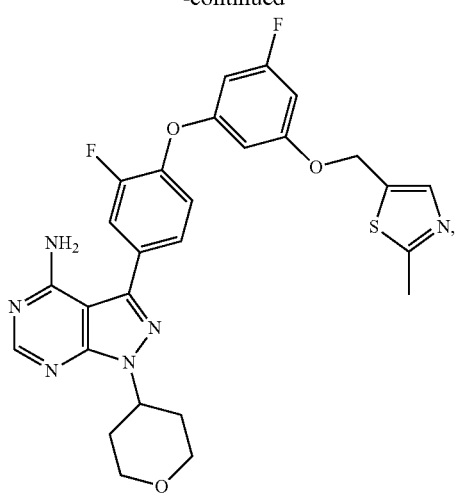
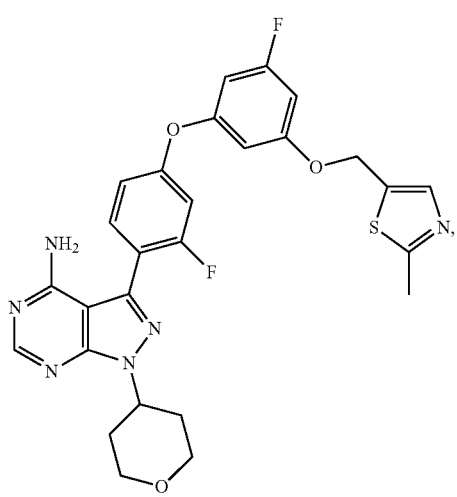
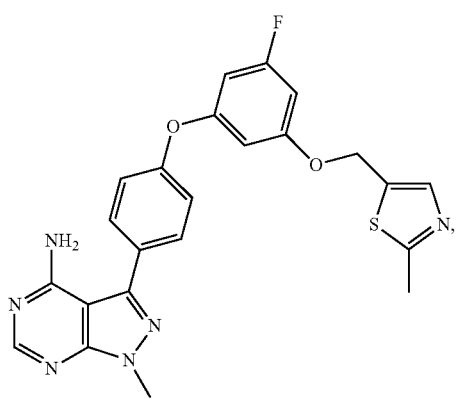

247
-continued
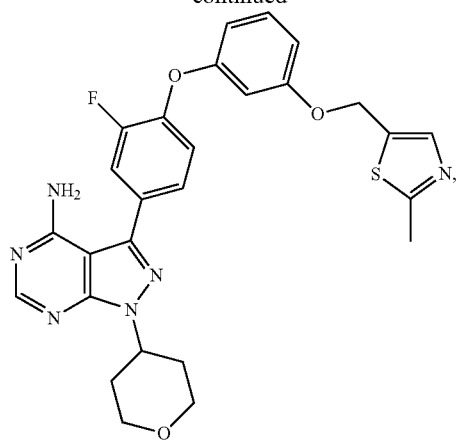
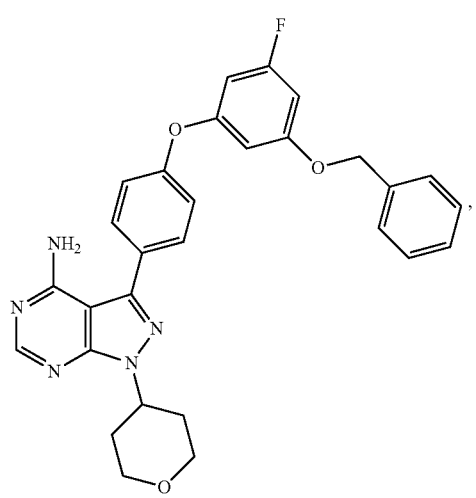
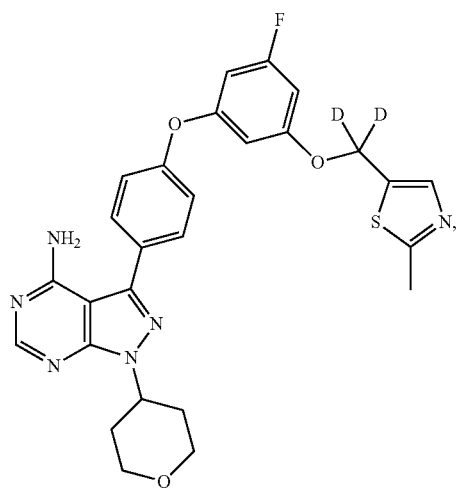
248
-continued
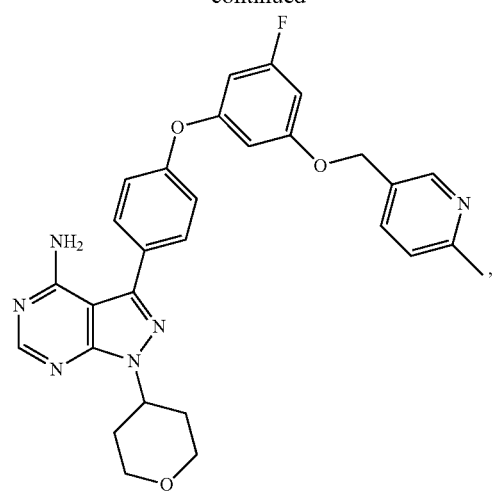
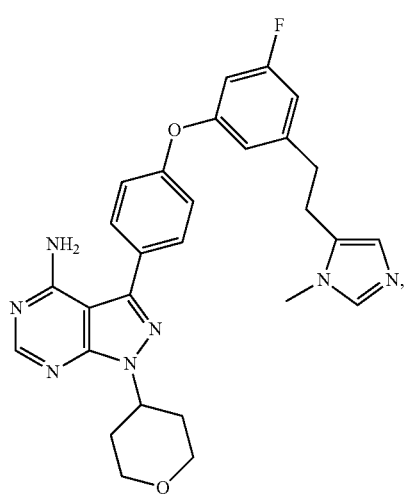

249
-continued
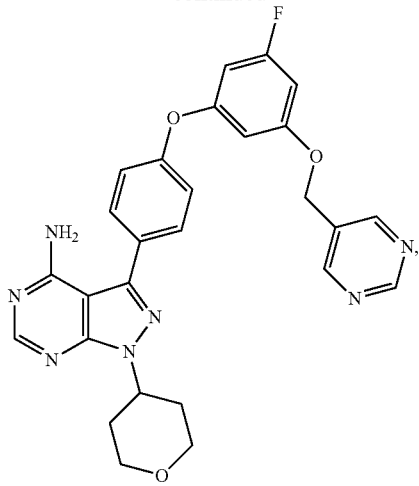
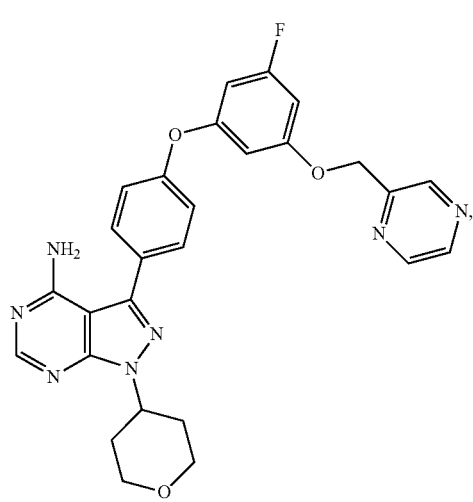
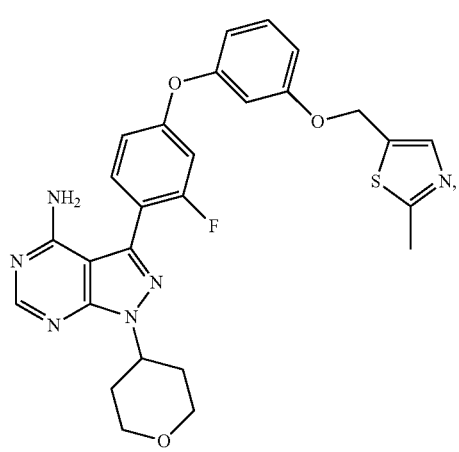
250
-continued
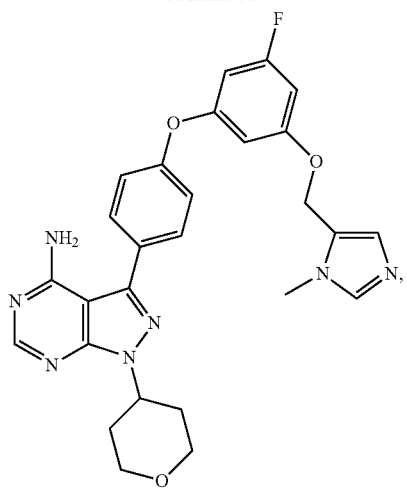
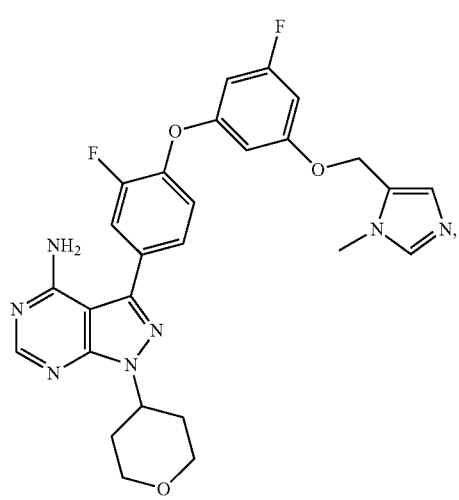
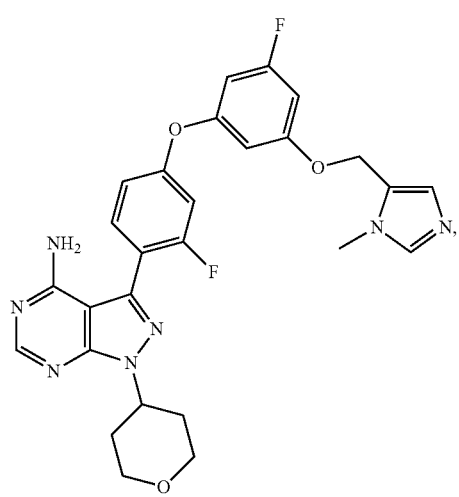

251
-continued
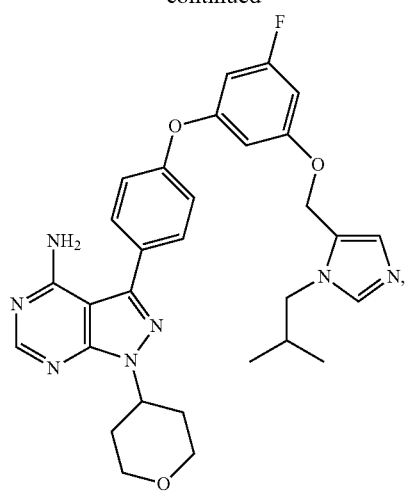
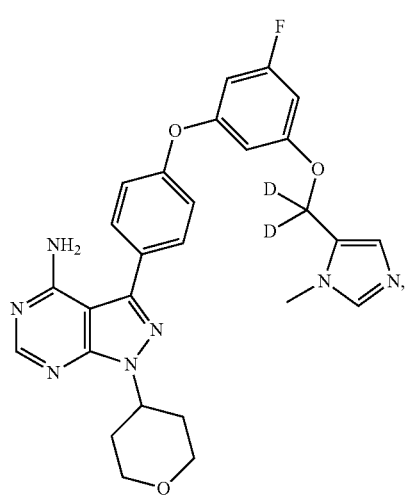
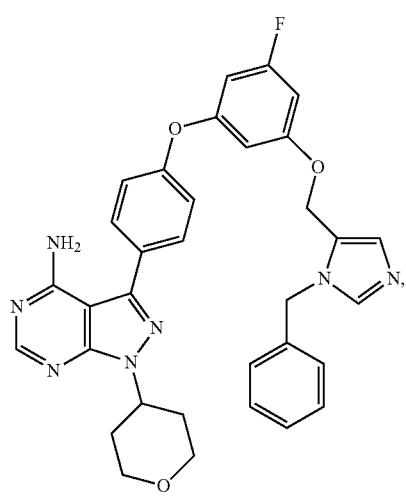
252
-continued
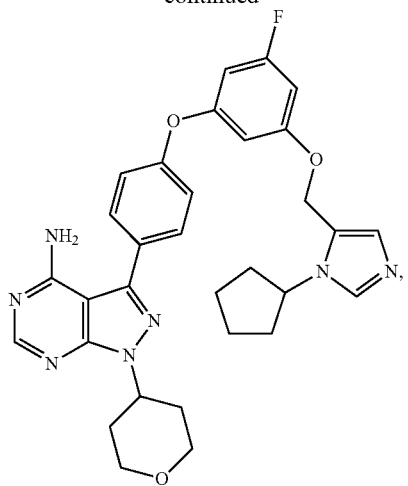
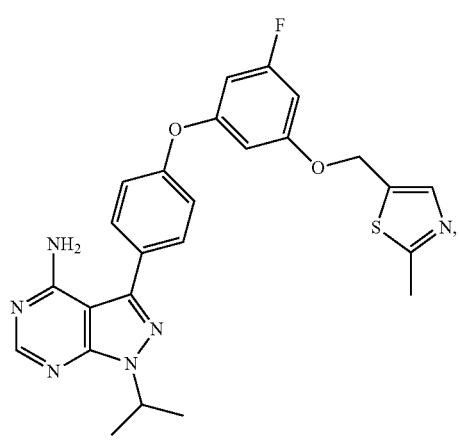
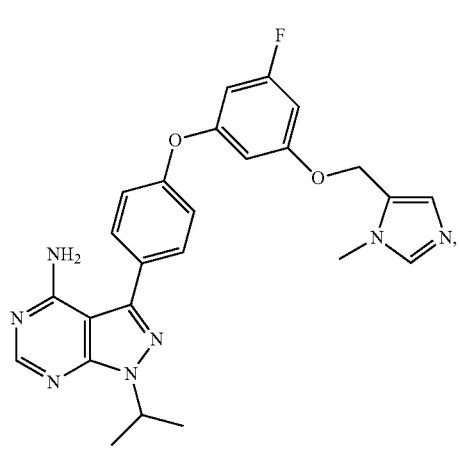

253
-continued
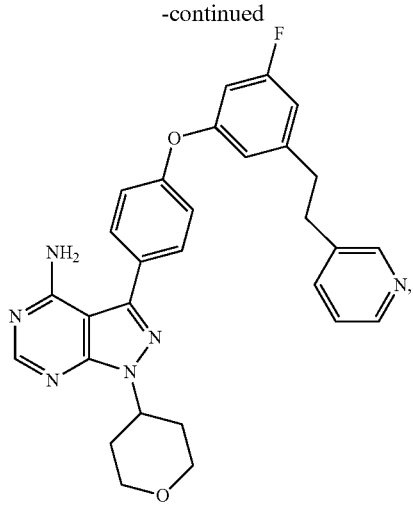
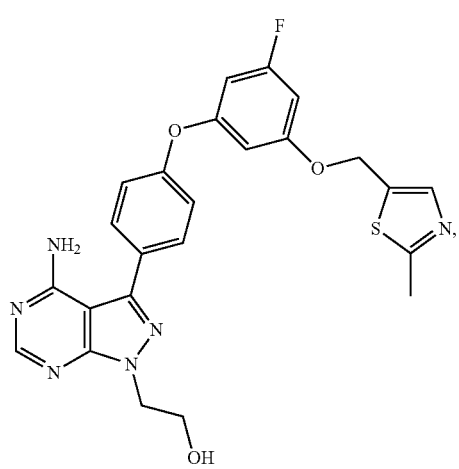
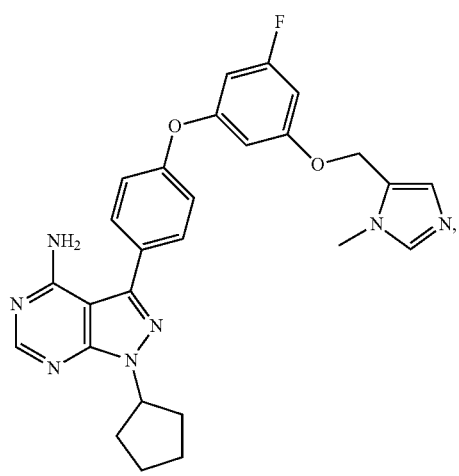
254
-continued
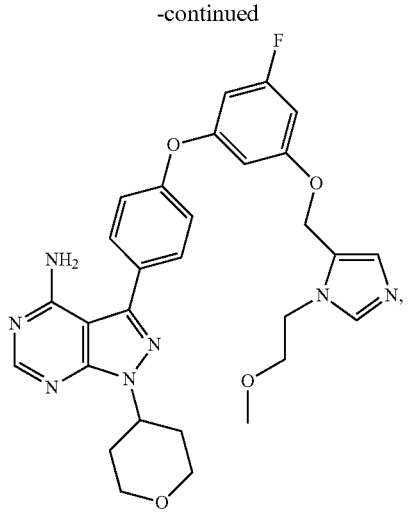
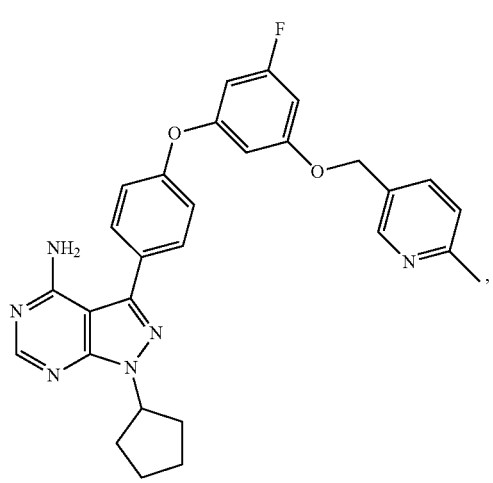
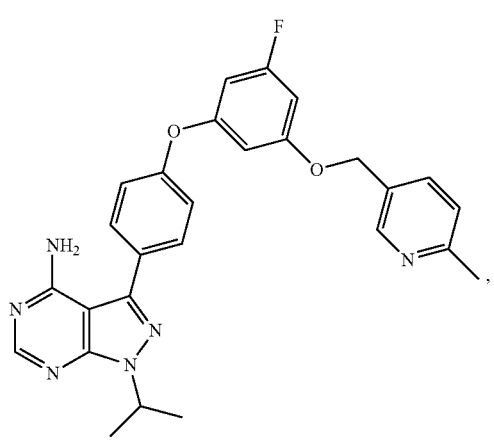

255
-continued
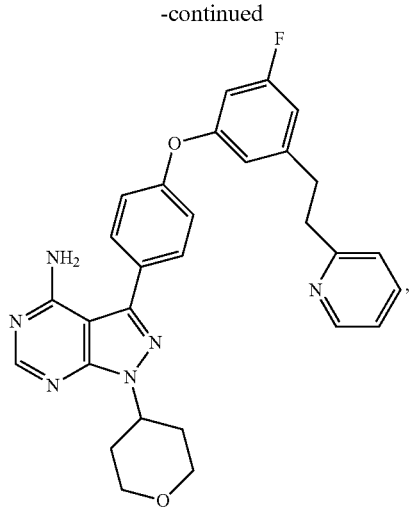
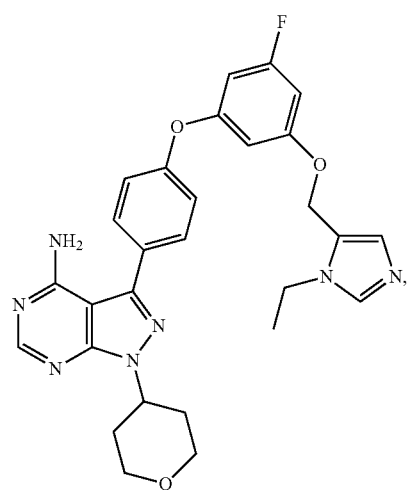
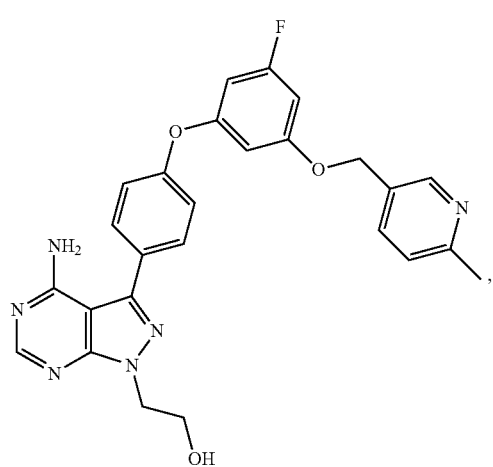
256
-continued
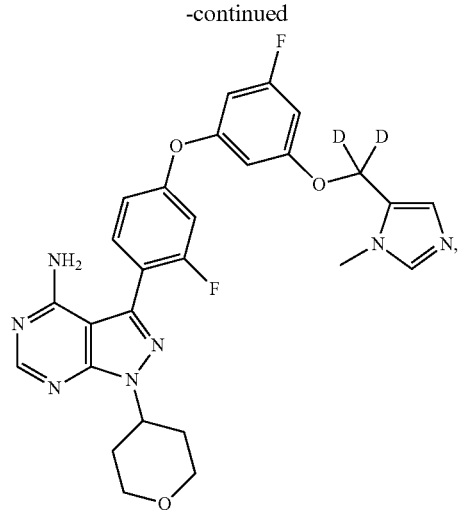
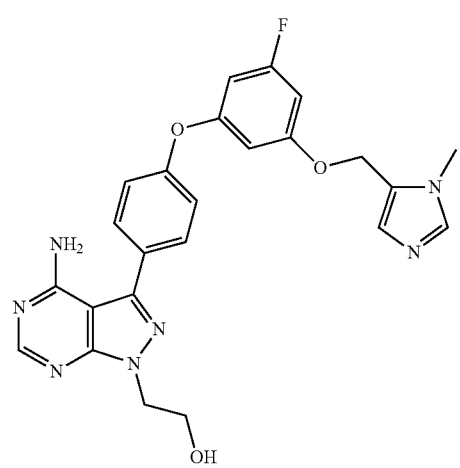
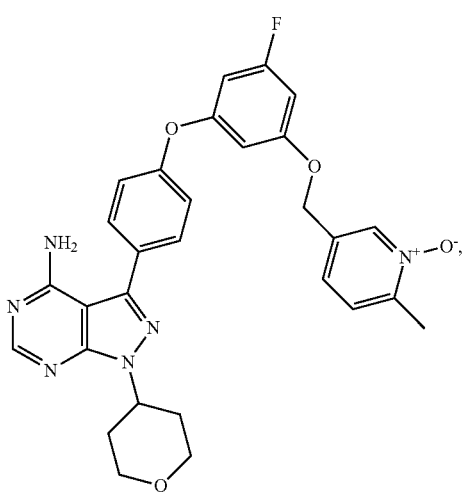

257
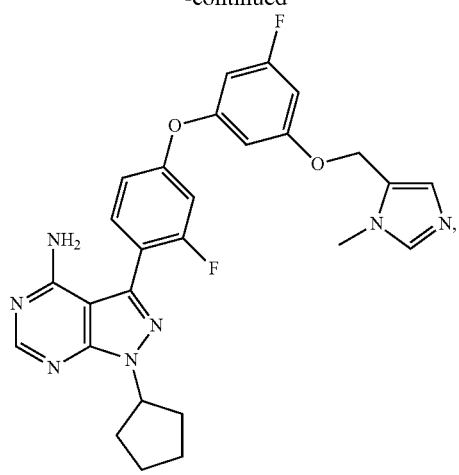
258
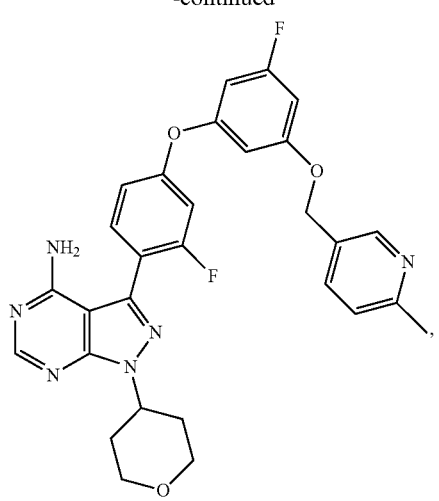
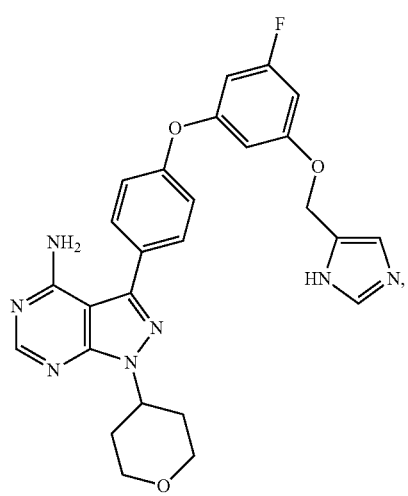
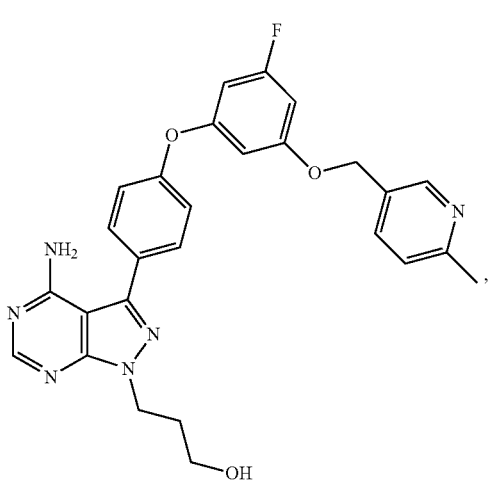
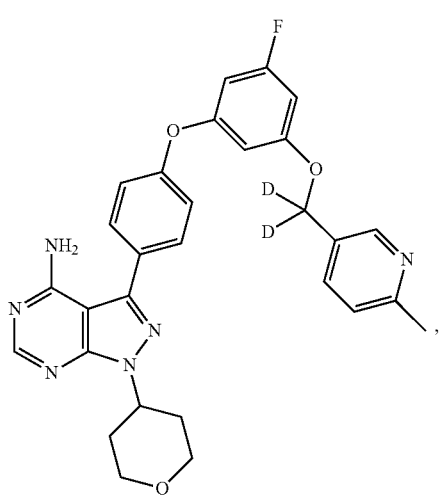
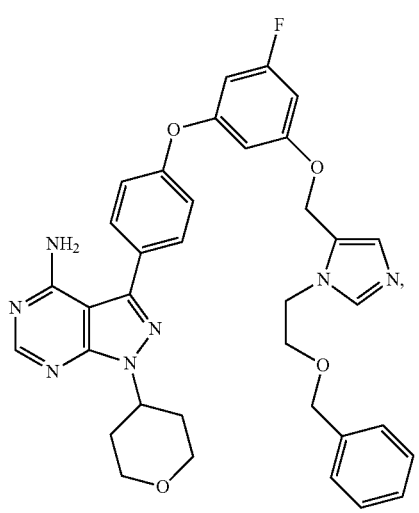

259
-continued
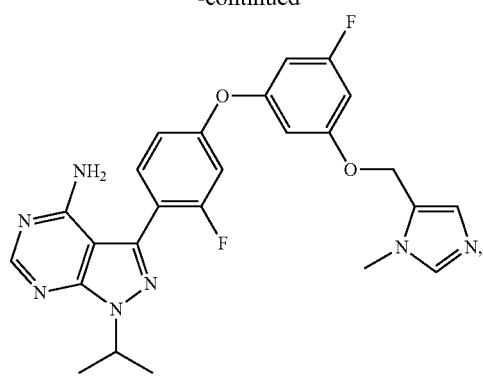
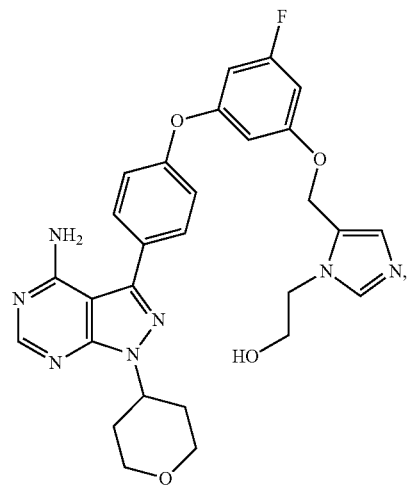
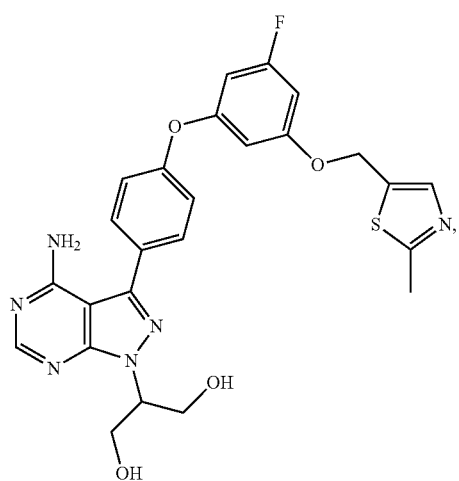
260
-continued
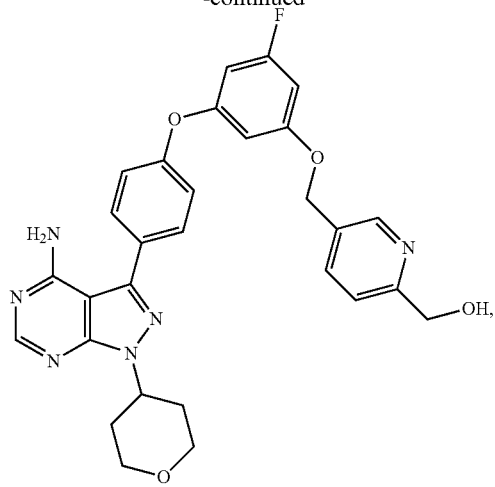
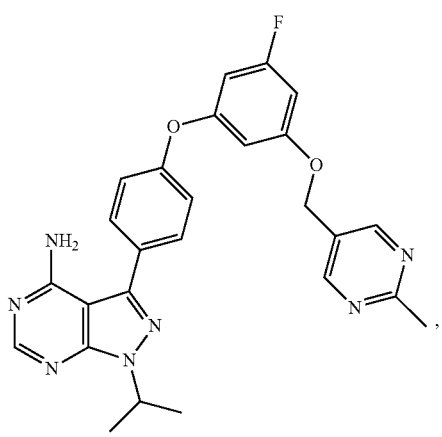
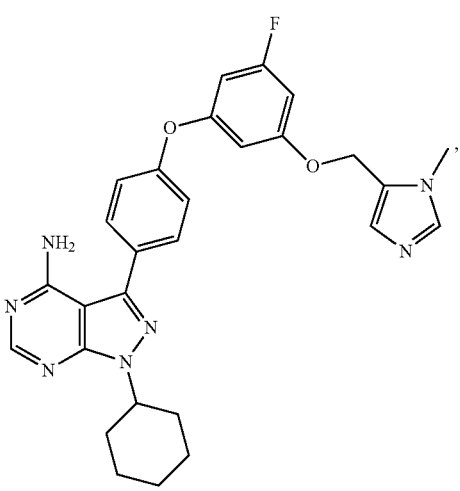

261
-continued
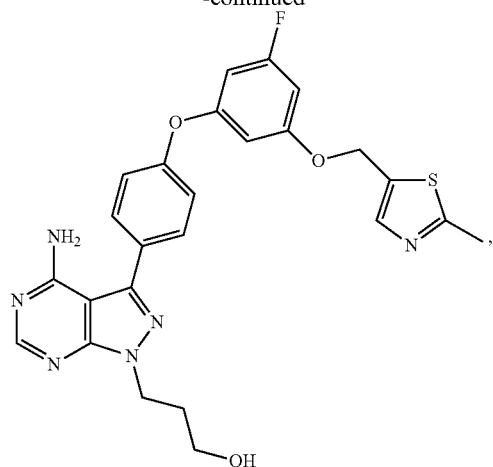
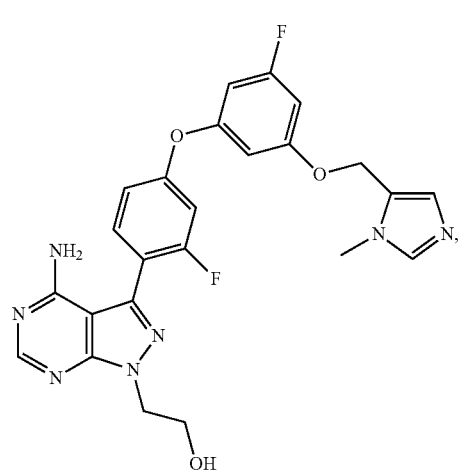
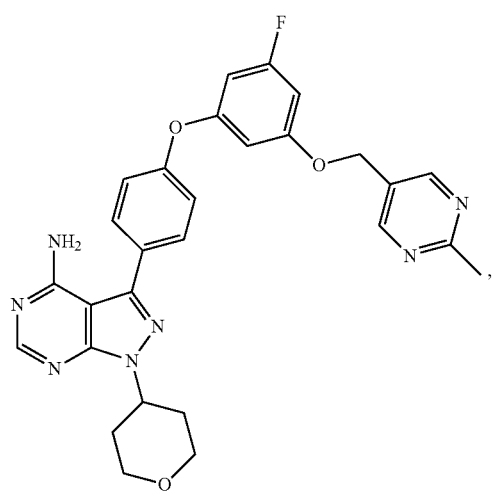
262
-continued
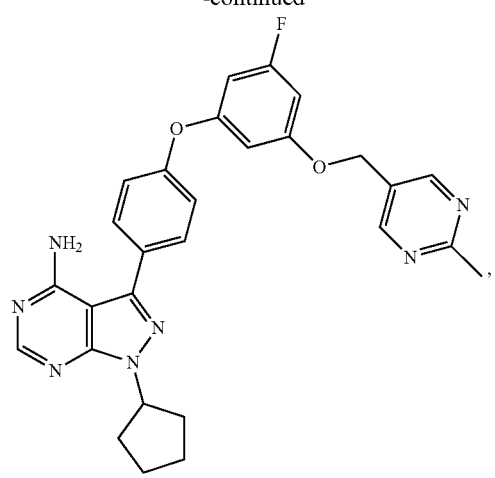
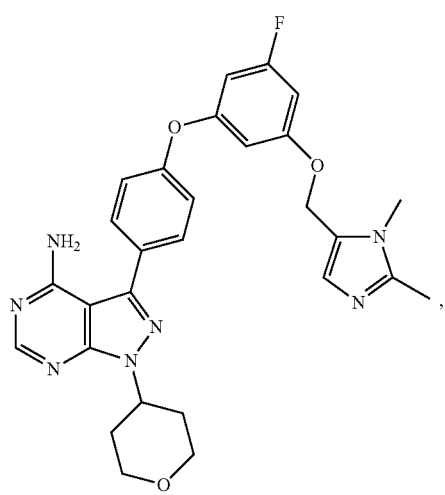
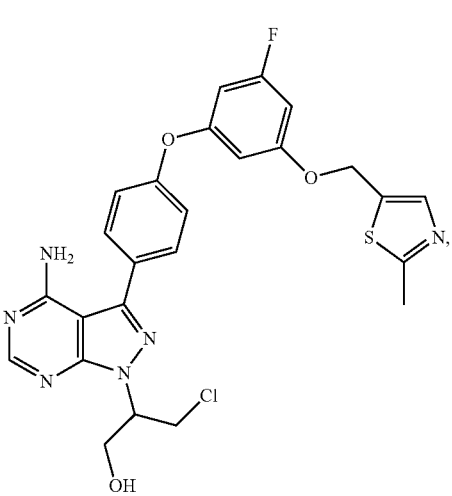

263
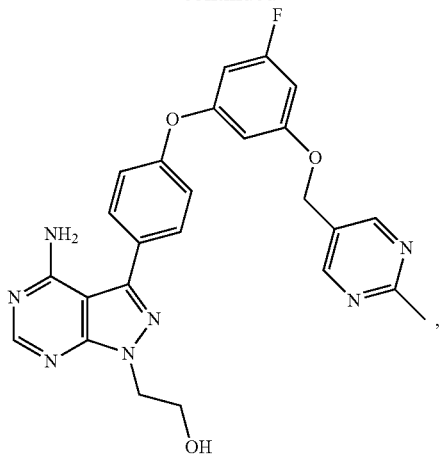
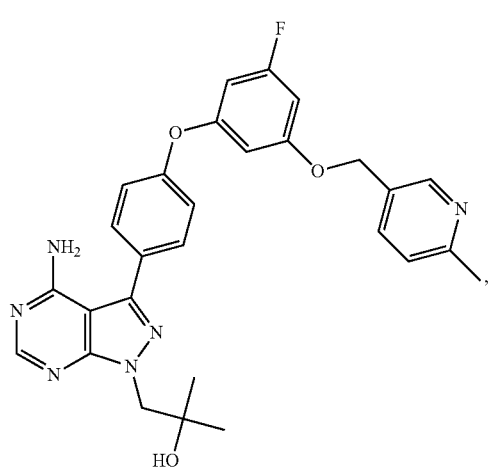
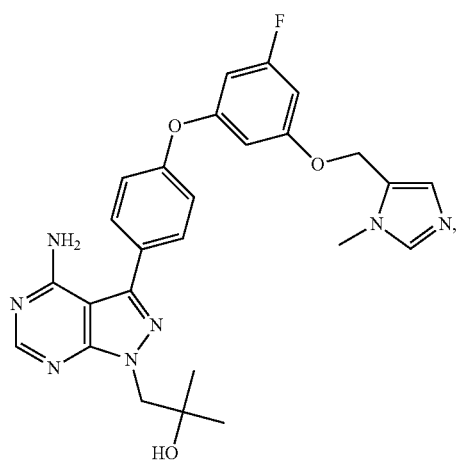
264
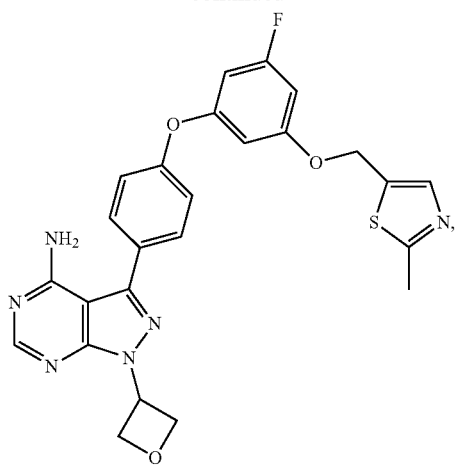
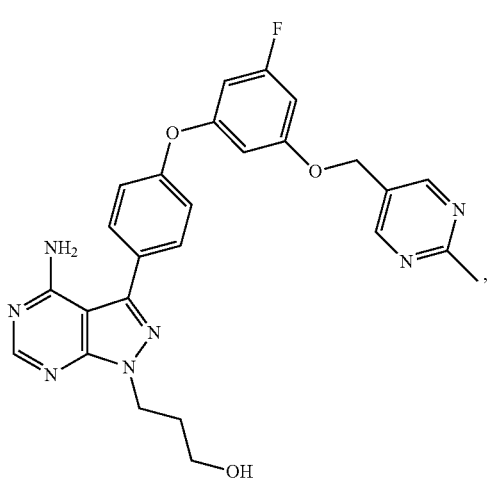
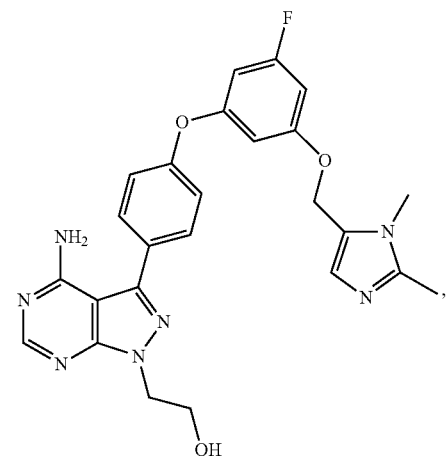

265
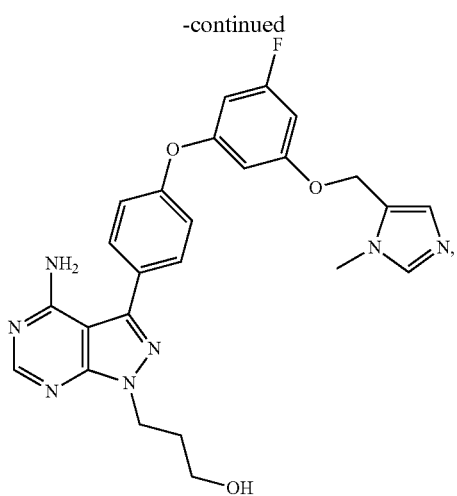
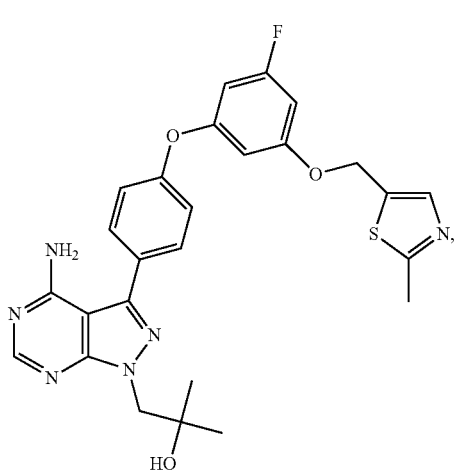
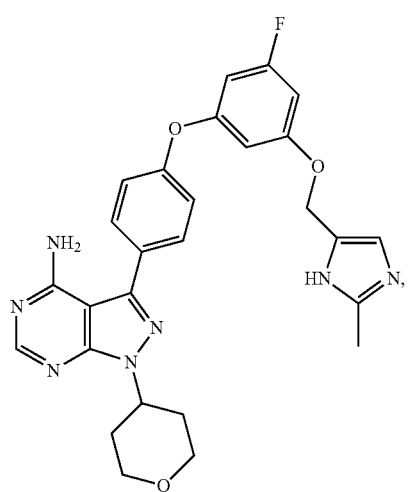
266
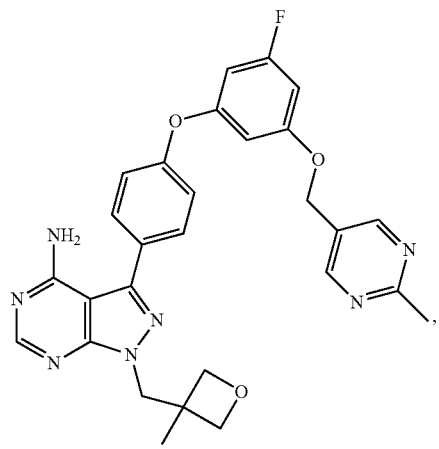
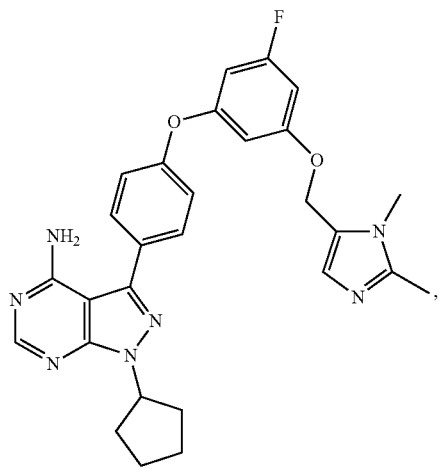
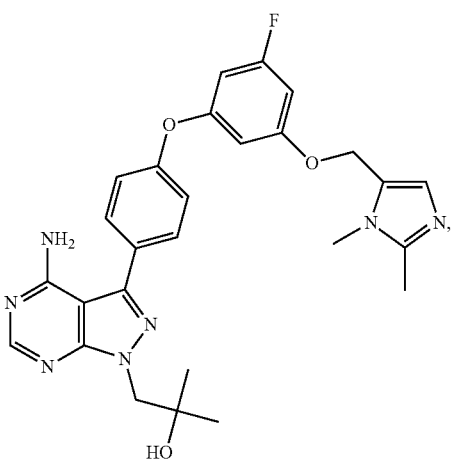

267
-continued
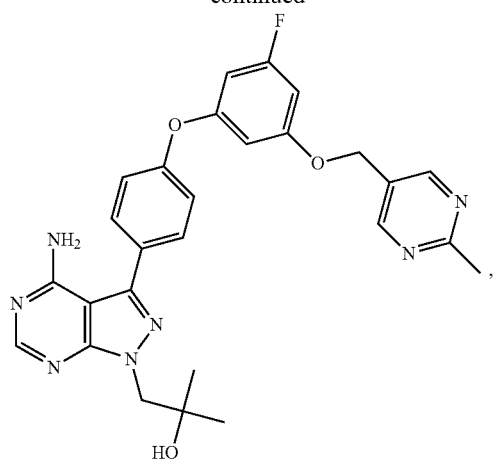
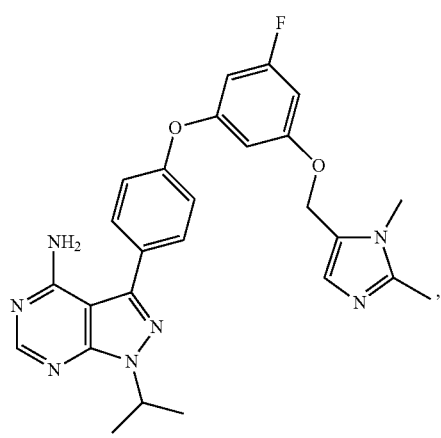
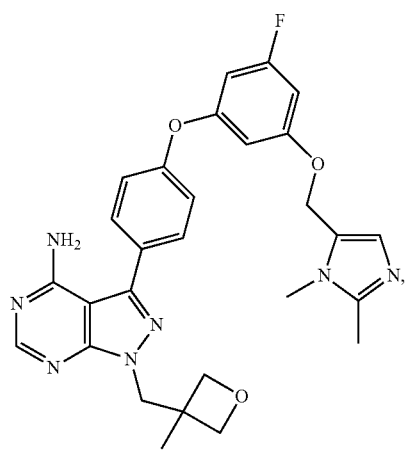
268
-continued
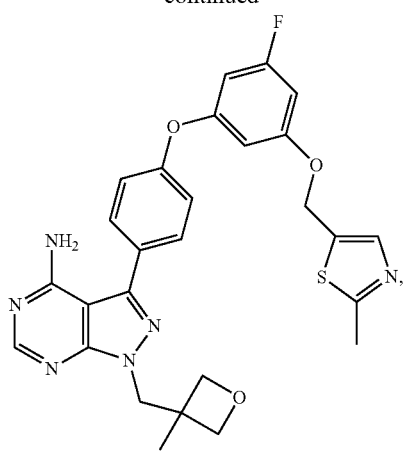
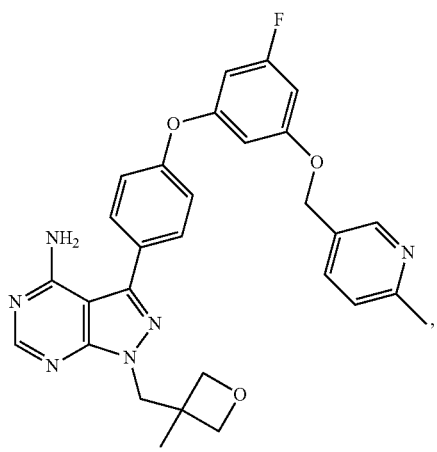
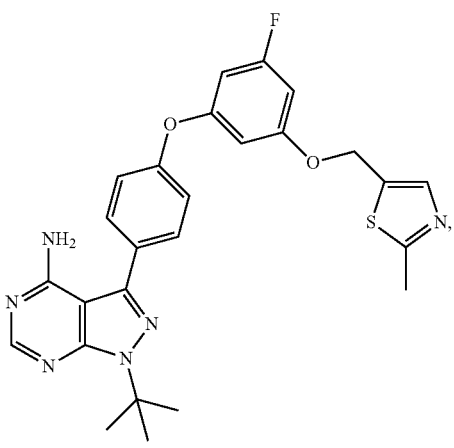

269
-continued
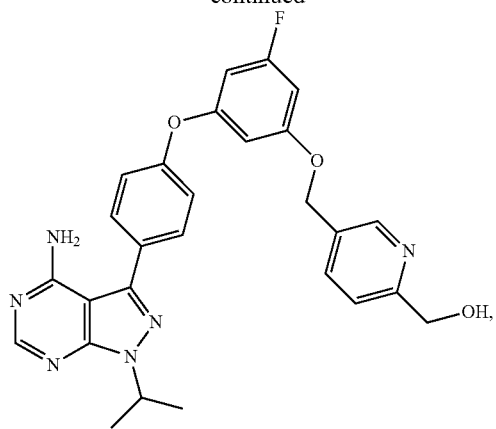
270
-continued
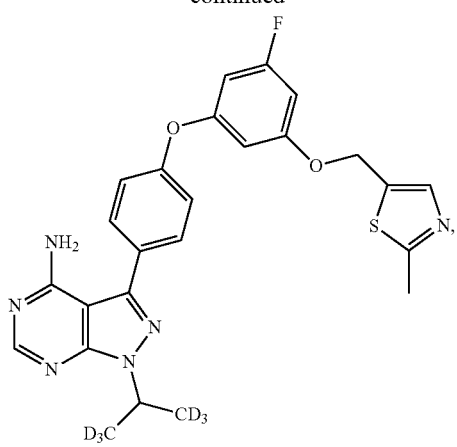
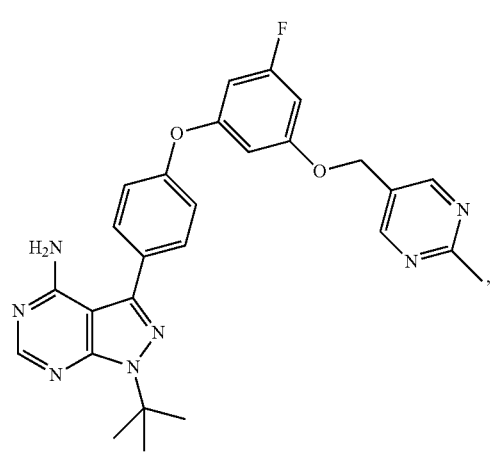
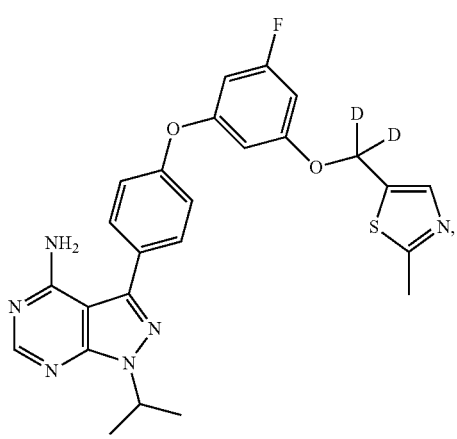
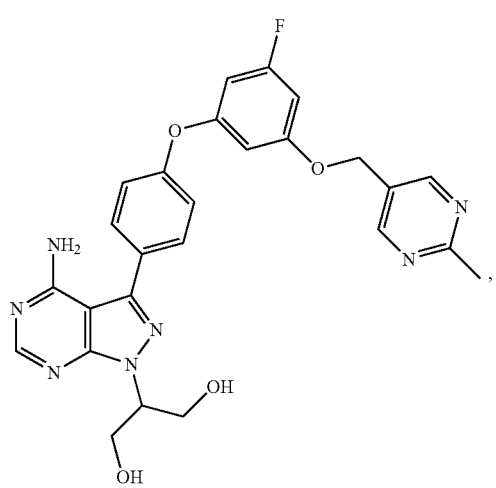
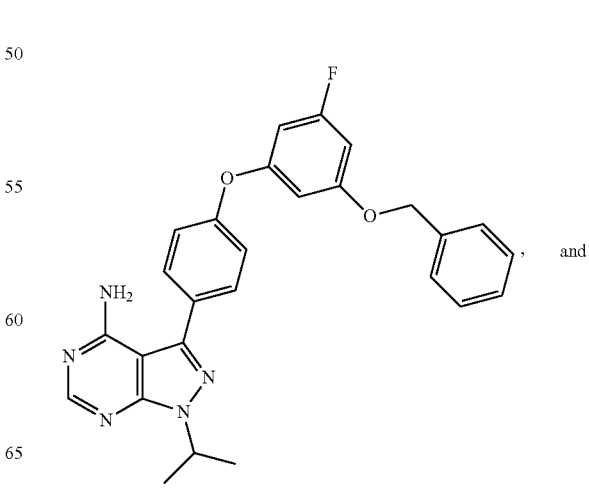, and -continued
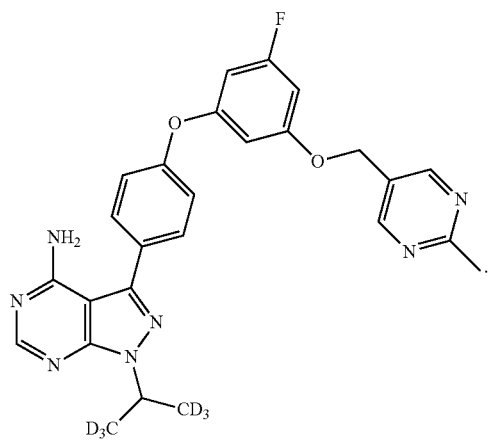
11. A pharmaceutical composition comprising a compound of claim 1 and at least one pharmaceutically acceptable excipient.
12. A compound of Formula 1:
wherein,
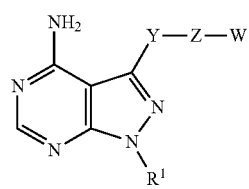
Formula 1
$R^1$ is selected from the group consisting of:
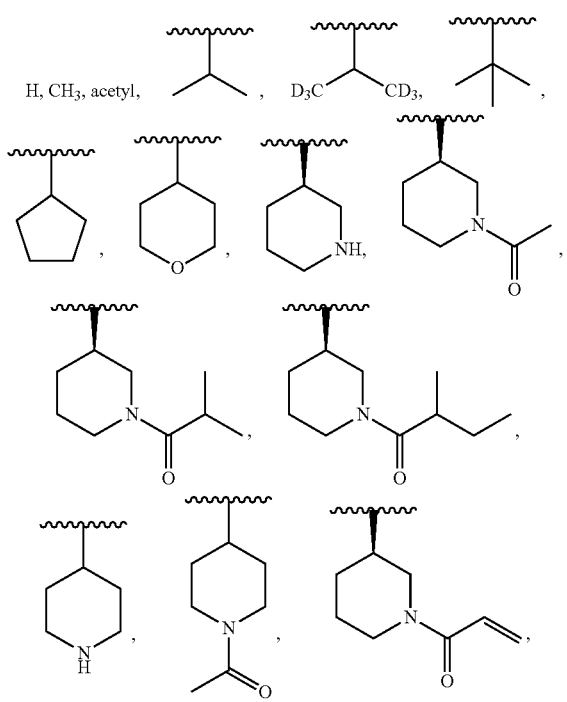
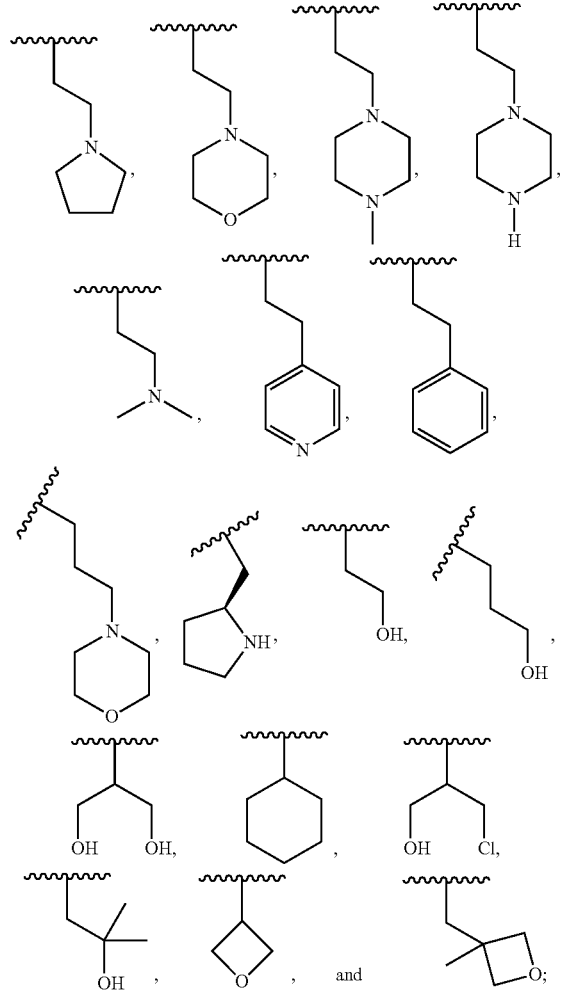
Y is
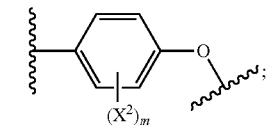
Z is
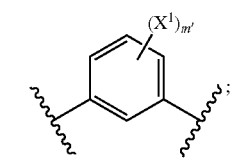
Y—Z—W is
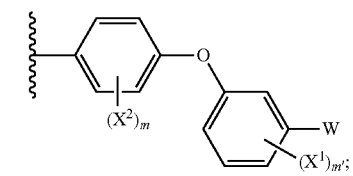

$X^1$ and $X^2$ are independently selected from the group consisting of hydrogen, halogen and cyano;

n is an integer from 0 to 2;

m is an integer from 0 to 2;

m' is an integer from 0 to 2;

W is —$OR^3$;

$R^2$ is hydrogen or alkyl;

$R^3$ is selected from the group consisting of substituted aralkyl, unsubstituted aralkyl, substituted heteroaralkyl, and unsubstituted heteroaralkyl;

$R^4$ is selected from the group consisting of substituted alkyl, unsubstituted alkyl, substituted alkenyl, unsubstituted alkenyl, substituted alkynyl, unsubstituted alkynyl, substituted heteroalkyl, unsubstituted heteroalkyl, substituted carbocyclyl, unsubstituted carbocyclyl, heterocyclyl, substituted aryl, unsubstituted aryl, substituted heteroaryl, unsubstituted heteroaryl, substituted aralkyl, unsubstituted aralkyl, substituted heteroaralkyl, and unsubstituted heteroaralkyl; and $R^5$ and $R^6$ are independently selected from the group consisting of hydrogen, alkyl, alkenyl, alkynyl, heteroalkyl, carbocyclyl, heterocyclyl, aryl, and heteroaryl; or alternatively $R^5$ and $R^6$ are fused to form a 3 to 8 membered heterocyclyl ring system; or a pharmaceutically acceptable salt, solvate, or solvate of a salt thereof.

13. The compound of claim 12, wherein W is selected from the group consisting of:

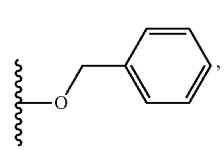
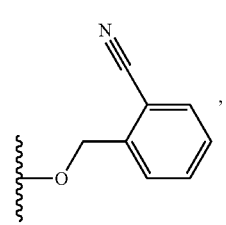
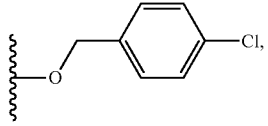
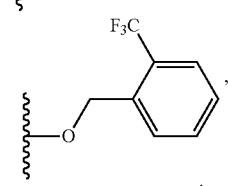
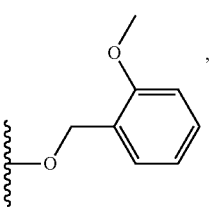
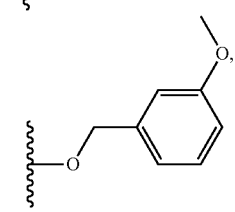
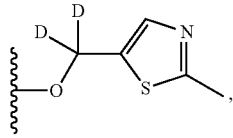
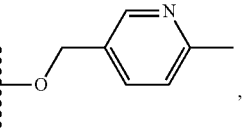
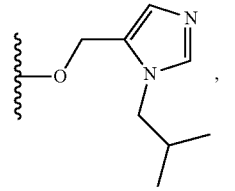

-continued

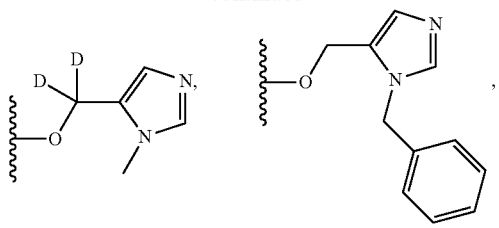
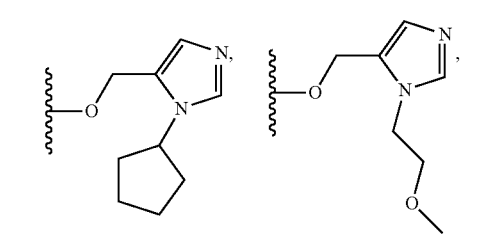
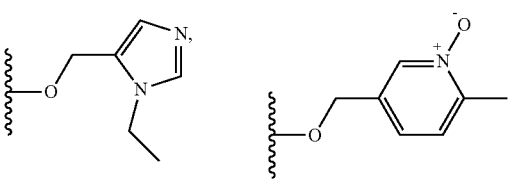
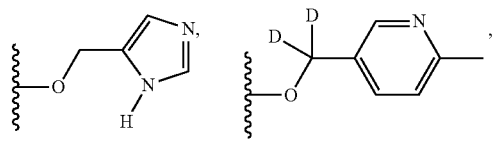
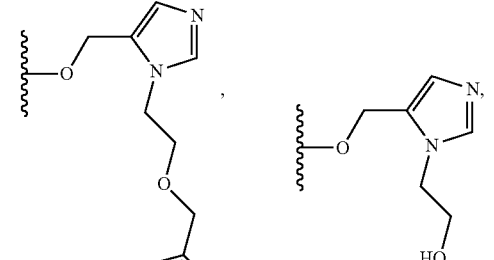
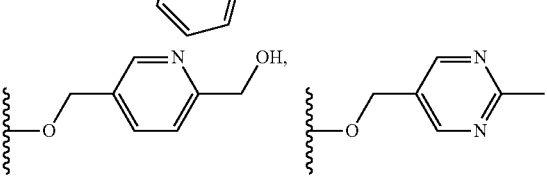
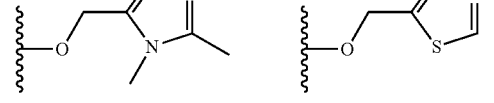
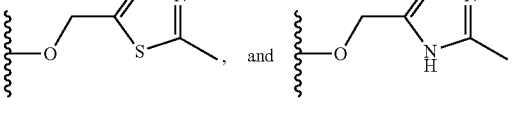

and

14. The compound according to claim 12, wherein W is selected from the group consisting of:

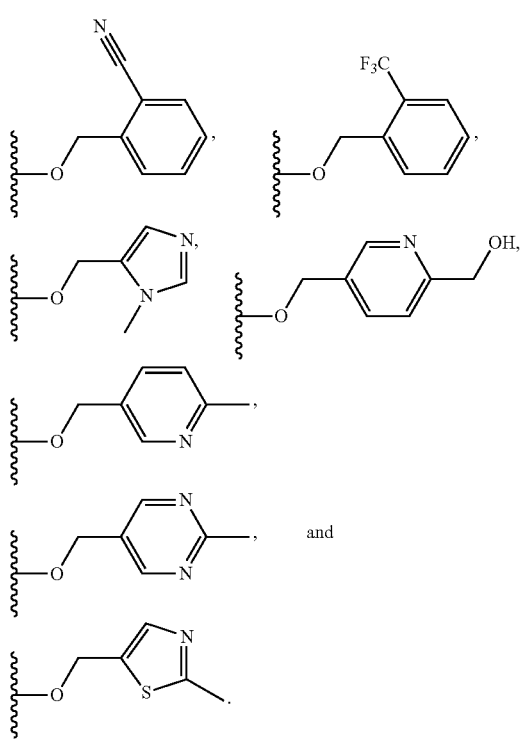

15. The compound according to claim 12, wherein $R^1$ is selected from the group consisting of:

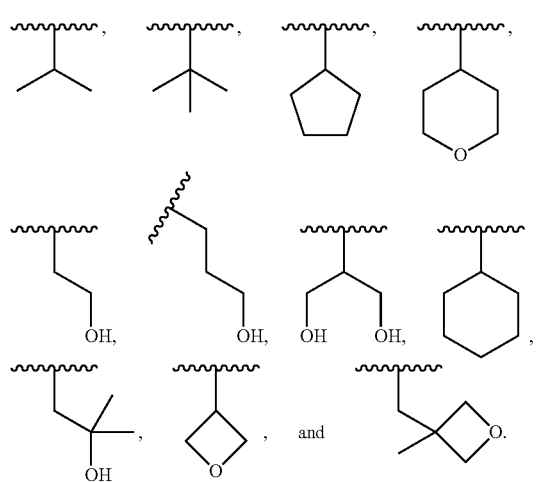

16. The compound according to claim 12, wherein Y is selected from the group consisting of:

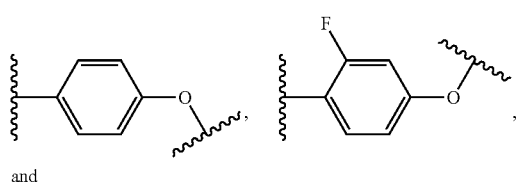

-continued

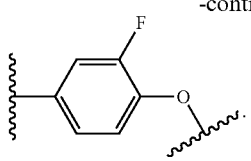

17. The compound according to claim 12, wherein Z is selected from the group consisting of:

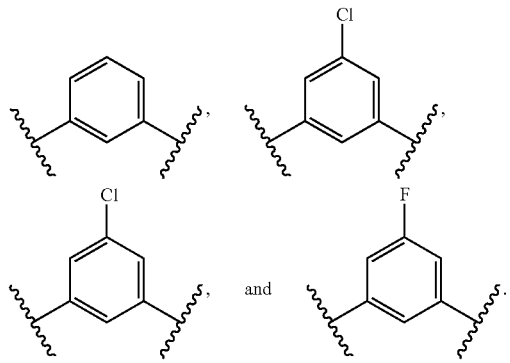

18. The compound according to claim 12, wherein Z is:

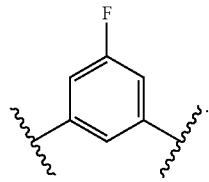 [SMILES: *c1cc(*)cc(F)c1]

19. The compound according to claim 12, wherein Y—Z—W is selected from the group consisting of:

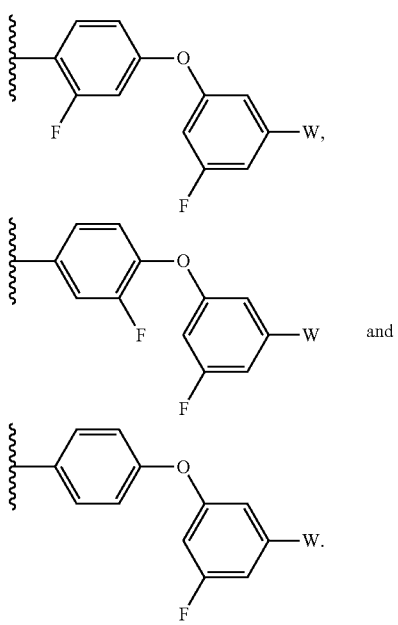

20. A pharmaceutical composition comprising a compound of claim 12 and at least one pharmaceutically acceptable excipient.

* * * * *